US010815495B2

(12) United States Patent
Gunawardena et al.

(10) Patent No.: US 10,815,495 B2
(45) Date of Patent: Oct. 27, 2020

(54) MUTATED ALLENE OXIDE SYNTHASE 2 (AOS2) GENES

(71) Applicants: CIBUS US LLC, San Diego, CA (US); CIBUS EUROPE B.V., Ad Kapelle (NL)

(72) Inventors: Uvini Gunawardena, San Diego, CA (US); Gregory F. W. Gocal, San Diego, CA (US); Peter R. Beetham, Carlsbad, CA (US); Keith A. Walker, San Diego, CA (US)

(73) Assignees: CIBUS US LLC, San Diego, CA (US); CIBUS EUROPE B.V., Ad Kapelle (NL)

( * ) Notice: Subject to any disclaimer, the term of this patent is extended or adjusted under 35 U.S.C. 154(b) by 0 days.

(21) Appl. No.: 15/785,297

(22) Filed: Oct. 16, 2017

(65) Prior Publication Data

US 2018/0051296 A1   Feb. 22, 2018

Related U.S. Application Data

(63) Continuation of application No. 14/776,647, filed as application No. PCT/US2014/029434 on Mar. 14, 2014, now Pat. No. 9,790,515.

(60) Provisional application No. 61/785,059, filed on Mar. 14, 2013.

(51) Int. Cl.
*C12N 15/82* (2006.01)
*C12N 9/88* (2006.01)

(52) U.S. Cl.
CPC .......... *C12N 15/8279* (2013.01); *C12N 9/88* (2013.01); *C12N 15/8282* (2013.01)

(58) Field of Classification Search
None
See application file for complete search history.

(56) References Cited

U.S. PATENT DOCUMENTS 6,870,075 B1 *  3/2005  Beetham ................. A01H 1/06
                                                  800/278

OTHER PUBLICATIONS

Pajerowska-Mukhtar et al, Planta, 2008, vol. 228, pp. 293-306 (Year: 2008).*
Tawty.com Website, U.S. Varieties of Potato, 2009 (Year: 2009).*
UniProt A4K3G0_SOLTU, May 1, 2007, Potato AOS2 (Year: 2007).*

* cited by examiner

*Primary Examiner* — Vinod Kumar
(74) *Attorney, Agent, or Firm* — Acuity Law Group, PC; Michael A. Whittaker

(57) ABSTRACT

Provided are compositions and methods relating to gene and/or protein mutations in plants. In certain embodiments, the disclosure relates to mutations in the allene oxide synthase 2 gene (i.e., AOS2). In some embodiments the disclosure relates to plants that are pathogen resistant.

22 Claims, 25 Drawing Sheets

Specification includes a Sequence Listing.

Figure 1: Amino Acid Sequence of Solanum tuberosum allene oxidase synthase 2 (AOS2) gene, AOS2-1 allele (StAOS2-1) (GB Accession ABD15173)

```
  1 MALTSSFSLP LPSLHQQFPS KYSTFRPIIV SLSEKPTIVV TQPTKLPTRT IPGDYGLPGI
 61 GPWKDRLDYF YNQGKDEFFE SRVVKYKSTI FRTNMPPGPF ISSNPKVIVL LDGKSFPVLF
121 DVSKVEKKDL FTGTYMPSTE LTGGYRVLSY LDPSEPNHEK LKKLMFFLLS SRRDHVIPKF
181 HETYTEFFET LDKEMAEKGT AGLNSGNDQA AFNFLARSLF GVNPVETKLG TDGPTLIGKW
241 VLLQLHPVLT LGLPKFLDDL ILHTFRLPPF LVKKDYQRLY DFFYTNSASL FAEAEKLGIS
301 KEEACHNLLF ATCFNSFGGM KIFFPNMLKS IAKAGVEVHT RLANEIRSEV KSAGGKITMS
361 AMEKMPLMKS VVYEALRVDP PVASQYGRAK QDLKIESHDA VFEVKKGEML FGYQPFATKD
421 PKIFDRPEEF VADRFVGEGE KLLKYVLWSN GPETESPTVG NKQCAGKDFV VMVSRLFVTE
481 FFLRYDTFNV DVGKSALGAS ITITSLKKA
```

Figure 2: Nucleic Acid Sequence of Solanum tuberosum allene oxidase synthase 2 (AOS2) gene, AOS2-1 allele (StAOS2-1) (GB Accession DQ369736)

```
   1 ATGGCATTAA CTTCATCTTT TTCTCTTCCT CTTCCTTCTC TTCACCAACA ATTTCCATCA
  61 AAATACTCCA CATTTCGTCC TATTATTGTT TCTTTATCGG AAAAGCCAAC AATCGTGGTA
 121 ACCCAACCTA CAAAATTACC TACTAGGACA ATACCTGGCG ACTATGGGTT GCCGGGTATT
 181 GGTCCATGGA AAGATAGGCT TGATTACTTT TACAATCAAG GGAAAGACGA ATTTTTCGAA
 241 TCAAGAGTAG TGAAATACAA ATCAACTATA TTCAGAACGA ACATGCCACC GGGACCATTC
 301 ATTTCTTCTA ACCCGAAGGT TATTGTTTTG CTCGACGGCA AGAGTTTCCC AGTCCTTTTC
 361 GATGTTTCGA AAGTCGAAAA AAAGGACCTC TTCACCGGAA CTTACATGCC GTCGACTGAA
 421 CTCACCGGTG GTTACCGTGT TCTTTCTTAT CTTGACCCAT CTGAACCAAA CCATGAAAAA
 481 TTGAAAAAAT TGATGTTCTT CCTTCTTTCT TCTCGTCGTG ATCACGTTAT ACCCAAATTC
 541 CATGAAACTT ATACAGAGTT TTTTGAAACC CTAGATAAGG AAATGGCGGA AAAAGGTACA
 601 GCTGGTTTAA ACTCCGGCAA TGATCAAGCT GCGTTTAATT TCTTAGCTAG ATCGTTGTTC
 661 GGAGTTAACC CAGTTGAAAC TAAACTCGGA ACTGATGGTC CGACATTGAT CGGAAAATGG
 721 GTTTTGCTTC AGCTTCATCC TGTACTCACT CTCGGTCTTC CGAAGTTTCT AGACGACTTA
 781 ATCCTCCATA CTTTCCGGTT ACCTCCGTTT CTGGTGAAGA AAGATTACCA GAGACTTTAC
 841 GATTTCTTTT ACACCAACTC CGCCAGTTTA TTCGCCGAAG CTGAAAAACT CGGCATTTCA
 901 AAAGAAGAAG CTTGTCATAA TCTTCTCTTC GCTACTTGCT TCAATTCCTT CGGCGGGATG
 961 AAGATTTTCT TCCCGAATAT GCTGAAATCG ATAGCGAAAG CAGGGGTGGA GGTCCATACC
1021 CGTTTAGCAA ACGAGATCCG ATCGGAAGTA AAATCCGCTG GCGGGAAGAT CACGATGTCG
1081 GCGATGGAGA AAATGCCGTT AATGAAATCA GTAGTTTATG AAGCTTTGCG AGTTGATCCT
1141 CCGGTAGCTT CACAATACGG AAGAGCCAAA CAGGACCTTA AGATCGAATC ACACGACGCC
1201 GTTTTCGAGG TGAAAAAGG TGAAATGCTA TTCGGGTACC AACCATTTGC AACGAAGGAT
1261 CCGAAAATTT TTGACCGGCC GGAAGAGTTC GTCGCCGATC GGTTCGTCGG AGAAGGAGAA
1321 AAGTTATTGA AATATGTATT ATGGTCTAAT GGACCGGAAA CGGAAAGTCC AACAGTGGGG
1381 AATAAACAGT GTGCTGGCAA AGATTTTGTA GTGATGGTTT CGAGGTTATT CGTAACGGAG
1441 TTTTTTCTCC GTTACGATAC ATTCAACGTC GACGTTGGTA AGTCGGCGTT GGGGGCTTCA
1501 ATTACTATAA CTTCTTTGAA AAAAGCTTAG
```

Figure 3: Amino Acid Sequence of Solanum tuberosum allene oxidase synthase 2 (AOS2) gene, AOS2-6 allele (StAOS2-6) (GB Accession ABD15174)

```
  1 MALTSSFSLP LPSLHQQFPS KYSTFRPIIV SLSEKPTIVV TQPTKFPTRT IPGDYGLPGI
 61 GPWKDRLDYF YNQGKDEFFE SRVVKYKSTI FRTNMPPGPF ISSNPKVIVL LDGKSFPVLF
121 DVSKVEKKDL FTGTYMPSTE LTGGYRVLSY LDPSEPNHEK LKKLMFFLLS SRRDHVIPKF
181 HETYTEFFET LDKEMADKGT AGLNSGNDQA AFNFLARSLF GVNPVETKLG TDGPTLIGKW
241 VLLQLHPVLT LGLPKVLDDL ILHTFRLPPF LVKKDYQRLY DFFYTNSASL FAEAEKLGIS
301 KEEACHNLLF ATCFNSFGGM KIFFPNMLKS IAKAGVEVHT RLANEIRSEV KSAGGKMTMS
361 AMEKMPLMKS VVYEALRVDP PVASQYGRAK QDLKIESHDA VFEVKKGEML FGYQPFATKD
421 PKIFDRPEEF VADRFVGEGE KLLKYVLWSN GPETESPTVG NKQCAGKDFV VMVSRLFVTE
481 FFLRYDTFNV DVGKSALGAS ITITSLKKA
```

Figure 4: Nucleic Acid Sequence of Solanum tuberosum allene oxidase synthase 2 (AOS2) gene, AOS2-6 allele (StAOS2-6) (GB Accession DQ369737)

```
   1 ATGGCATTAA CTTCATCTTT TTCTCTTCCT CTTCCTTCTC TTCACCAACA ATTTCCATCA
  61 AAATACTCCA CATTTCGTCC TATTATTGTT TCTTTATCGG AAAAGCCAAC AATCGTGGTA
 121 ACCCAACCTA CAAAATTTCC TACTAGGACA ATACCTGGCG ACTATGGGTT GCCGGGTATT
 181 GGTCCATGGA AAGATAGGCT TGATTACTTT TACAATCAAG GGAAAGACGA ATTTTTCGAA
 241 TCAAGAGTAG TGAAATACAA ATCAACTATA TTCAGAACGA ACATGCCACC GGGACCATTC
 301 ATTTCTTCTA ACCCGAAGGT TATTGTTTTG CTCGACGGCA AGAGTTTCCC AGTCCTTTTC
 361 GATGTTTCGA AAGTCGAAAA AAAGGACCTC TTCACCGGAA CTTACATGCC GTCGACTGAA
 421 CTCACCGGTG GTTACCGTGT TCTTTCTTAT CTTGACCCAT CTGAACCAAA CCATGAAAAA
 481 TTGAAAAAAT TGATGTTCTT CCTTCTTTCT TCTCGTCGTG ATCACGTTAT ACCCAAATTC
 541 CATGAAACTT ATACAGAGTT TTTTGAAACC CTAGATAAGG AAATGGCGGA TAAAGGTACA
 601 GCTGGTTTAA ACTCCGGCAA TGATCAAGCT GCGTTTAATT TCTTAGCTAG ATCGTTGTTC
 661 GGAGTTAACC CAGTTGAAAC TAAACTCGGA ACTGATGGTC CGACATTGAT CGGAAAATGG
 721 GTTTTGCTTC AGCTTCATCC TGTACTCACT CTCGGTCTTC CGAAAGTTCT AGACGACTTA
 781 ATCCTCCATA CTTTCCGGTT ACCTCCGTTT CTGGTGAAGA AAGATTACCA GAGACTTTAC
 841 GATTTCTTTT ACACCAACTC CGCCAGTTTA TTCGCCGAAG CTGAAAAACT CGGCATTTCA
 901 AAAGAAGAAG CTTGTCATAA TCTTCTCTTC GCTACTTGCT TCAATTCCTT CGGCGGGATG
 961 AAGATTTTCT TCCCGAATAT GCTGAAATCG ATAGCGAAAG CAGGAGTGGA GGTCCATACC
1021 CGTTTAGCAA ACGAGATCCG ATCGGAAGTA AAATCCGCTG GCGGGAAGAT GACGATGTCG
1081 GCGATGGAGA AAATGCCGTT AATGAAATCA GTAGTTTATG AAGCGTTGCG AGTTGATCCT
1141 CCGGTAGCTT CACAATACGG AAGAGCCAAA CAGGACCTTA AGATCGAATC ACACGACGCC
1201 GTTTTCGAGG TGAAAAAGG TGAAATGCTA TTCGGGTACC AACCATTTGC AACGAAGGAT
1261 CCGAAAATTT TTGACCGGCC GGAAGAGTTC GTCGCCGATC GGTTCGTCGG AGAAGGAGAA
1321 AAGTTATTGA AATATGTATT ATGGTCTAAT GGACCGGAAA CGGAAAGTCC AACAGTGGGG
1381 AATAAACAGT GTGCTGGCAA AGATTTTGTA GTGATGGTTT CGAGGTTATT CGTAACGGAG
1441 TTTTTTCTCC GTTACGATAC ATTCAACGTC GACGTTGGTA AGTCGGCGTT GGGGGCTTCA
1501 ATTACTATAA CTTCTTTGAA AAAAGCTTAG
```

Figure 5: Amino Acid Sequence of Solanum tuberosum allene oxidase synthase 2 (AOS2) gene, AOS2-7 allele (StAOS2-7) (GB Accession ABD15175)

```
  1 MALTSSFSLP LPSLHQQFPS KYSTFRPIIA SLSEKPIIVV TQPTKLPTRT MPGDYGLPGI
 61 GPWKDRLDYF YNQGKNEFFE SRVVKYKSTI FRTNMPPGPF ISSNPKVIVL LDGKSFPVLF
121 DVSKVEKKDL FTGTYMPSTE LTGGYRVLSY LDPSEPNHEK LKKLMFFLLS SRRDHVIPKF
181 HETYTELFET LDKEMAEKGT AGLNSGNDQA AFNFLARSLF GVNPVEAKLG TDGPTLIGKW
241 VLLQLHPVLT LGLPKFLDDL ILHTFRLPPF LVKKDYQRLY DFFYTNSANL FVEAEKLGIS
301 KEEACHNLLF ATCFNSFGGM KIFFPNMMKS IAKAGVEVHT RLANEIRSEV KSAGGKITMS
361 AMEKMPLMKS VVYEALRVDP PVASQYGRAK QDLKIESHDA VFEVKKGEML FGYQPFATKD
421 PKIFDRPEEL VADRFVGEEG EKLLKYVLWS NGPETESPTV GNKQCAGKDF VVMVSRLFVV
481 EFFLRYDTFN VDVGTSALGA SITITSLKKA
```

Figure 6: Nucleic Acid Sequence of Solanum tuberosum allene oxidase synthase 2 (AOS2) gene, AOS2-7 allele (StAOS2-7) (GB Accession DQ369738)

```
   1 ATGGCATTAA CTTCATCTTT TTCTCTTCCT CTTCCTTCTC TTCACCAACA ATTTCCATCA
  61 AAATACTCCA CATTTCGTCC TATTATTGCT TCGTTATCCG AAAAACCAAT AATCGTGGTA
 121 ACCCAACCTA CAAAATTACC TACCAGGACA ATGCCCGGCG ACTATGGGTT ACCGGGTATT
 181 GGTCCATGGA AAGATAGGCT TGATTACTTT TACAATCAAG GCAAAACGA ATTTTTCGAA
 241 TCAAGAGTAG TGAAATACAA ATCAACTATA TTCAGAACGA ACATGCCACC GGGACCATTC
 301 ATTTCTTCTA ACCCGAAGGT TATTGTTTTG CTCGACGGCA AGAGTTTCCC AGTCCTTTTC
 361 GATGTTTCGA AAGTCGAAAA AAAGGACCTC TTCACTGGAA CTTACATGCC GTCGACTGAA
 421 CTCACCGGTG GTTACCGTGT TCTTTCTTAT CTTGACCCAT CTGAACCAAA CCATGAAAAA
 481 TTGAAAAAAT TGATGTTCTT CCTTCTTTCT TCTCGTCGTG ATCACGTTAT ACCCAAATTC
 541 CATGAAACTT ATACAGAGTT GTTTGAAACC CTAGATAAGG AAATGGCGGA AAAAGGTACA
 601 GCTGGTTTAA ACTCCGGCAA TGATCAAGCT GCGTTTAATT TCTTAGCTAG ATCGTTGTTC
 661 GGAGTTAACC CAGTTGAAGC TAAACTCGGA ACTGATGGTC CGACATTGAT CGGAAAATGG
 721 GTTTTGCTTC AGCTTCATCC TGTGCTTACT CTCGGTCTTC CGAAGTTTCT AGACGACTTA
 781 ATCCTCCATA CTTTCCGGTT ACCTCCGTTT CTGGTGAAAA AAGATTACCA GAGACTTTAC
 841 GATTTCTTTT ACACCAATTC CGCCAATTTA TTCGTCGAAG CTGAAAAACT CGGCATTTCT
 901 AAAGAAGAAG CTTGTCATAA TCTTCTCTTC GCTACTTGCT TCAATTCCTT CGGCGGGATG
 961 AAGATTTTCT TCCCGAATAT GATGAAATCG ATAGCGAAAG CAGGGGTGGA GGTCCATACC
1021 CGTTTAGCAA ACGAGATCCG ATCGGAAGTA AAATCCGCCG GCGGGAAGAT CACGATGTCG
1081 GCGATGGAGA AAATGCCGTT AATGAAATCA GTAGTATATG AAGCTTTACG AGTTGATCCT
1141 CCGGTAGCTT CACAATACGG AAGAGCCAAA CAGGACCTTA AGATCGAATC ACACGACGCC
1201 GTTTTCGAGG TGAAAAAGG TGAAATGCTA TTCGGGTACC AACCATTTGC AACGAAGGAT
1261 CCGAAAATTT TTGACCGACC GGAAGAGCTC GTCGCCGATC GGTTCGTCGG AGAAGAAGGA
1321 GAAAGTTAT TGAAATATGT ATTATGGTCT AATGGACCGG AAACGGAAAG TCCGACAGTG
1381 GGGAATAAAC AGTGTGCTGG AAAAGATTTT GTAGTGATGG TTTCGAGGTT ATTCGTAGTG
1441 GAGTTTTTC TCCGTTACGA TACATTCAAC GTCGACGTTG GTACGTCGGC GTTGGGGCT
1501 TCAATTACTA TAACTTCTTT GAAAAAGCT TAG
```

Figure 7: Amino Acid Sequence of Solanum tuberosum allene oxidase synthase 2 (AOS2) gene, AOS2-8 allele (StAOS2-8) (GB Accession ABD15176)

```
  1 MALTSFFSLP LPSLHQQFPS KYSTFRPIIV SLSEKPTIVV TQPTKLPVRT IPGDYGLPGI
 61 GPWKDRLDYF YNQGKNEFFE SRVVKYKSTI FRTNMPPGPF ISSNPKVIVL LDGKSFPVLF
121 DVSKVEKKDL FTGTYMPSTE LTGGYRVLSY LDPSEPNHEK LKKLMFFLLS SRRDHVIPKF
181 HETYTEFFET LDKEMAEKGK AGLNSGNDQA AFNFLARSLF GVNPVETKLG IDGPTLIGKW
241 VLLQLHPVLT LGLPKFLDDL ILHAFRLPPL LVKKDYQRLY DFFYTNSANL FVEAEKLGIS
301 KEEACHNLLF ATCFNSFGGM KIFFPNMMKS IAKAGVEVHT RLANEIRSEV KSAGGKITMS
361 AMEKMPLMKS VVYEALRVDP PVASQYGRAK QDLKIESHDA VFEVKKGEML FGYQPFATKD
421 PKFFDRPEEF VADRFVGEEG EKLLKYVLWS NGPETESPTV GNKQCAGKDF VVMVSRLFVT
481 EFFLRYDTFN VDVGTSALGA SITITSLKKA
```

Figure 8: Nucleic Acid Sequence of Solanum tuberosum allene oxidase synthase 2 (AOS2) gene, AOS2-8 allele (StAOS2-8) (GB Accession DQ369739)

```
   1 ATGGCTTTAA CTTCATTTTT TTCTCTTCCT CTTCCTTCTC TTCACCAACA ATTTCCATCA
  61 AAATACTCTA CATTTCGTCC TATTATTGTT TCTTTGTCCG AAAAACCAAC AATCGTGGTA
 121 ACCCAACCTA CAAAATTACC TGTCAGGACA ATACCCGGCG ACTATGGGTT GCCGGGTATT
 181 GGTCCATGGA AAGATAGGCT TGATTACTTT TACAATCAAG GCAAAAACGA ATTTTTCGAA
 241 TCAAGAGTAG TGAAATACAA ATCAACTATA TTCAGAACTA ACATGCCACC GGGACCATTC
 301 ATTTCTTCTA ACCCGAAGGT TATTGTTTTG CTCGACGGCA AGAGTTTCCC AGTCCTTTTC
 361 GATGTTTCGA AAGTCGAAAA AAAGGACCTC TTCACCGGAA CTTACATGCC GTCGACTGAA
 421 CTCACCGGTG GTTATCGTGT TCTTTCTTAT CTTGACCCAT CTGAACCAAA CCATGAAAAA
 481 TTGAAAAAAT TGATGTTCTT CCTTCTTTCT TCTCGTCGTG ATCACGTTAT ACCCAAATTC
 541 CATGAAACTT ATACAGAGTT TTTTGAAACC CTAGATAAGG AAATGGCGGA AAAAGGTAAA
 601 GCTGGTTTAA ACTCTGGCAA TGATCAAGCT GCGTTTAATT TCTTAGCTAG ATCGTTGTTC
 661 GGAGTTAACC CAGTTGAAAC TAAACTCGGA ATTGATGGTC CGACATTGAT CGGAAAATGG
 721 GTTTTGCTTC AGCTTCATCC TGTACTCACT CTCGGTCTTC CGAAGTTTCT AGATGACTTA
 781 ATCCTCCATG CTTTCCGGTT ACCTCCGCTT CTGGTGAAGA AAGATTACCA GAGACTTTAC
 841 GATTTCTTTT ACACCAACTC CGCCAATTTA TTCGTCGAAG CTGAAAAACT CGGCATTTCT
 901 AAAGAAGAAG CTTGTCATAA TCTTCTCTTC GCTACTTGCT TCAATTCCTT CGGCGGGATG
 961 AAGATTTTCT TCCCGAATAT GATGAAATCG ATAGCGAAAG CAGGGGTGGA GGTCCATACC
1021 CGTTTAGCAA ACGAGATCCG ATCGGAAGTA AAATCCGCCG GCGGGAAGAT CACGATGTCG
1081 GCGATGGAGA AAATGCCGCT AATGAAATCA GTAGTATATG AAGCTTTACG AGTTGATCCT
1141 CCGGTAGCTT CACAATACGG AAGAGCCAAA CAGGACCTTA AGATCGAATC ACACGACGCC
1201 GTTTTCGAGG TGAAAAAGG TGAAATGCTA TTCGGGTACC AACCATTTGC AACGAAGGAT
1261 CCGAAATTTT TTGACCGGCC GGAAGAGTTC GTCGCCGATC GGTTCGTCGG AGAAGAAGGA
1321 GAAAAGTTAT TGAAATACGT ATTATGGTCT AATGGACCGG AAACGGAAAG TCCGACAGTG
1381 GGGAATAAAC AGTGTGCTGG AAAAGATTTT GTAGTGATGG TTTCGAGGTT ATTCGTAACG
1441 GAGTTTTTTC TCCGTTACGA TACATTCAAT GTCGACGTTG GTACGTCGGC ATTGGGGGCT
1501 TCAATTACTA TAACTTCTTT GAAAAAAGCT TAA
```

Figure 9: Amino Acid Sequence of Solanum tuberosum allene oxidase synthase 2 (AOS2) gene, AOS2-12 allele (StAOS2-12) (GB Accession ABD15172)

```
  1 MALTSFFSLP LPSLHQQFPS KYSTFRPIIV SLSEKPTIVV TQPTKLPTRT IPGDYGLPGI
 61 GPWKDRLDYF YNQGKNEFFE SRVVKYKSTI FRTNMPPGPF ISSNPKVIVL LDGKSFPVLF
121 DVSKVEKKDL FTGTYMPSTE LTGGFRVLSY LDPSEPNHEK LKKLMFFLLS SRRDHVIPKF
181 HETYTEFFET LDKEMAEKGK AGLNSGNDQA AFNFLARSLF GVNPVETKLG GDGPTLIGKW
241 VLLQLHPVLT LCLPKFLDDL ILHTFRLPPF LVKKDYQRLY DFFYTNSANL FVEAEKLCIS
301 KEEACHNLLF ATCFNSFGGM KIFFPNMMKS IAKAGVEVHT RLANEIRSEV KSAGGKITMS
361 AMEKMPLMKS VVYEALRVDP PVASQYGRAK QDLTIESHDA VFEVKKGEML FGYQPFATKD
421 PKIFDRPEEF VADRFVGEEG EKLLKYVLWS NGPETESPTV GNKQCAGKDF VVMVSRLFVT
481 EFFLRYDTFN VDVGTSALGA SITITSLKKA
```

Figure 10: Nucleic Acid Sequence of Solanum tuberosum allene oxidase synthase 2 (AOS2) gene, AOS2-12 allele (StAOS2-12) (GB Accession DQ369735)

```
   1 ATGGCTTTAA CTTCATTTTT TTCTCTTCCT CTTCCTTCTC TTCACCAACA ATTTCCATCA
  61 AAATACTCTA CATTTCGTCC TATTATTGTT TCTTTGTCCG AAAAACCAAC AATCGTGGTA
 121 ACCCAACCTA CAAAATTACC TACCAGGACA ATACCCGGCG ACTATGGGTT GCCGGGTATT
 181 GGTCCATGGA AGATAGGCT TGATTACTTT TACAATCAAG GCAAAACGA ATTTTTCGAA
 241 TCAAGAGTAG TGAAATACAA ATCAACTATA TTCAGAACGA ACATGCCACC GGGACCATTC
 301 ATTTCTTCTA ACCCGAAGGT TATTGTTTTG CTCGACGGCA AGAGTTTCCC AGTCCTTTTC
 361 GATGTTTCGA AAGTCGAAAA AAAGGACCTC TTCACCGGAA CTTACATGCC GTCGACTGAA
 421 CTCACCGGTG GTTTCCGTGT TCTTTCTTAT CTTGACCCAT CTGAACCAAA CCATGAAAAA
 481 TTGAAAAAAT TGATGTTCTT CCTTCTTTCT TCTCGCCGTG ATCACGTTAT ACCCAAATTC
 541 CATGAAACTT ATACAGAGTT TTTTGAAACC CTAGATAAGG AAATGGCGGA AAAAGGTAAA
 601 GCTGGTTTAA ACTCCGGCAA TGATCAAGCT GCGTTTAATT TCTTAGCTAG ATCGTTGTTC
 661 GGAGTTAACC CAGTTGAAAC TAAACTCGGA GGTGATGGTC CGACATTGAT CGGAAAATGG
 721 GTGTTGCTTC AGCTTCATCC TGTGCTTACT CTCGGTCTTC CGAAGTTTCT AGATGACTTA
 781 ATCCTCCATA CTTTCCGGTT ACCTCCGTTT CTGGTGAAGA AAGATTACCA GAGACTTTAC
 841 GATTTCTTTT ACACCAACTC CGCCAATTTA TTCGTCGAAG CTGAAAAACT CGGCATTTCA
 901 AAAGAAGAAG CTTGTCATAA TCTTCTCTTC GCTACTTGCT TCAATTCCTT CGGCGGGATG
 961 AAGATTTTCT TCCCGAATAT GATGAAATCG ATAGCGAAAG CAGGGGTGGA GGTCCATACC
1021 CGTTAGCAA ACGAGATCCG ATCGGAAGTA AAATCCGCCG GCGGGAAGAT CACGATGTCG
1081 GCGATGGAGA AAATGCCGTT AATGAAATCA GTAGTATATG AAGCTTTACG AGTTGATCCT
1141 CCGGTAGCTT CACAATACGG AAGAGCCAAA CAGGACCTTA CGATCGAATC ACACGACGCC
1201 GTTTTCGAGG TGAAAAAAGG TGAAATGCTA TTCGGGTACC AACCATTTGC AACGAAGGAT
1261 CCGAAAATTT TTGACCGGCC GGAAGAGTTC GTCGCCGATC GGTTCGTCGG AGAAGAAGGA
1321 GAAAAGTTAT TGAAATACGT ATTATGGTCT AATGGACCGG AAACGGAAAG TCCGACAGTG
1381 GGGAATAAAC AGTGTGCTGG AAAAGATTTT GTAGTGATGG TTTCGAGGTT ATTCGTAACG
1441 GAGTTTTTTC TCCGTTACGA TACATTCAAC GTCGACGTTG GTACGTCGGC GTTGGGGCT
1501 TCAATTACTA TAACTTCTTT GAAAAAGCT TAA
```

Figure 11: Amino Acid Sequence of Solanum tuberosum allene oxidase synthase 2 (AOS2) gene, StAOS2_CB1

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 12: Nucleic Acid Sequence of Solanum tuberosum allene oxidase synthase 2 (AOS2) gene, StAOS2_CB1

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTCATTGTTTTGCTCGACGGCAAGAGTTTCCCAGTCCTTTTCGATGTTTCGAAAGTCGAAAAAAGG
ACCTCTTCACCGGAACTTATATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCCGGCGGGAAGATCACGATGT
CGGCTATGGAGAAAATGCCGTTAATGAAATCAGTAGTATATGAAGCTTGCGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGCTTCAATTACTATAACTTCTTTGAAAAAGCTTAG
```

Figure 13: Amino Acid Sequence of Solanum tuberosum allene oxidase synthase 2 (AOS2) gene, StAOS2_CB2

```
MALTSSFSLPLRSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSANLFVEAEKLGISKEEACHNL
LFATCFNSFGGMKIFFPNMMKSIAKAGVDLHTRLANEIRSEVKSAGGKITMSAMEKMPLMKSVVYEALRVDPPVASQ
YGRAKQDLKIESHDAVFEVKKCEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 14: Nucleic Acid Sequence of Solanum tuberosum allene oxidase synthase 2 (AOS2) gene, StAOS2_CB2

```
ATGGCATTAACTTCATCTTTTTCTCTTCCTCTTCGTTCTCTTCACCAACAATTTCCATCAAAATACTCCACATTTCG
TCCTATTATTGTTTCTTTATCGGAAAAGCCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTCATTGTTTTGCTCGACGGCAAGAGTTTCCCAGTCCTTTTCGATGTTTCGAAAGTCGAAAAAAAGG
ACCTCTTCACCGGAACTTATATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAATCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAATTTATTCGTCGAAGCTGAAAAACTCGGCATTTCTAAAGAAGAAGCTTGTCATAATCTT
CTCTTCGCTACTTGCTTCAATTCCTTCGGCGGGATGAAGATTTTCTTCCCGAATATGATGAAATCGATAGCGAAAGC
AGGGGTGGATCTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAATGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 15: Amino Acid Sequence of Solanum tuberosum allene oxidase synthase 2 (AOS2) gene, StAOS2_CB3

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMMKSIAKAGVDLHTRLANEIRSEVKSAGGKITMSAMEKMPLMKSVVYEALRVDPPVASQ
YGRAKQDLKIESHDAVFEVKKCEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 16: Nucleic Acid Sequence of Solanum tuberosum allene oxidase synthase 2 (AOS2) gene, StAOS2_CB3

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTCATTGTTTTGCTCGACGGCAAGAGTTTCCCAGTCCTTTTCGATGTTTCGAAAGTCGAAAAAAAGG
ACCTCTTCACCGGAACTTATATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGATGAAATCGATAGCGAAAGC
AGGGGTGGATCTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAATGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 17: Amino Acid Sequence of Solanum tuberosum allene oxidase synthase 2 (AOS2) gene, StAOS2_CB4

```
MALTSSFSLPLRSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 18: Nucleic Acid Sequence of Solanum tuberosum allene oxidase synthase 2 (AOS2) gene, StAOS2_CB4

```
ATGGCATTAACTTCATCTTTTTCTCTTCCTCTTCGTTCTCTTCACCAACAATTTCCATCAAAATACTCCACATTTCG
TCCTATTATTGTTTCTTTATCGGAAAAGCCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTCATTGTTTTGCTCGACGGCAAGAGTTTCCCAGTCCTTTTCGATGTTTCGAAAGTCGAAAAAAAGG
ACCTCTTCACCGGAACTTATATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCCGGCGGGAAGATCACGATGT
CGGCTATGGAGAAAATGCCGTTAATGAAATCAGTAGTATATGAAGCTTTGCGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 19: Amino Acid Sequence of Solanum tuberosum allene oxidase synthase 2 (AOS2) gene, StAOS2_CB5

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
IFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 20: Nucleic Acid Sequence of Solanum tuberosum allene oxidase synthase 2 (AOS2) gene, StAOS2_CB5

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAGGGCAAAAACGAA
TTTTTCGAATCAAGAGTAGTAAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
ATCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 21: Amino Acid Sequence of Solanum tuberosum allene oxidase synthase 2 (AOS2) gene, StAOS2_CB6

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
IFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVDKSALGASITITSLKKA
```

Figure 22: Nucleic Acid Sequence of Solanum tuberosum allene oxidase synthase 2 (AOS2) gene, StAOS2_CB6

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAGGGCAAAAACGAA
TTTTTCGAATCAAGAGTAGTAAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
ATCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGATAAGTCGGCGTTGGGGGCTTCAATTACTATAACTTCTTTGAAAAAAGCTTAG
```

Figure 23: Amino Acid Sequence of Solanum tuberosum allene oxidase synthase 2 (AOS2) gene, StAOS2_CB7

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPNVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
IFATCFNSFGGLKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVDKSALGASITITSLKKA
```

Figure 24: Nucleic Acid Sequence of Solanum tuberosum allene oxidase synthase 2 (AOS2) gene, StAOS2_CB7

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGCAAAAACGAA
TTTTTCGAATCAAGAGTAGTGAAATACAAATCAACTATATTCAGAACGAACATGCCACCGGGACCATTCATTTCTTC
TAACCCGAATGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGATCCATCT
GAACCAAACCATGAAAAATTGAAAAAATTGATGTTCTTCCTTCTTTCTTCTCGACGTGATCACGTTATACCCAAATT
CCATGAAACTTATACAGAGTTTTTCGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
ATCTTCGCTACTTGCTTCAATTCCTTCGGCGGGTTGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGATAAGTCGGCGTTGGGGGCTTCAATTACTATAACTTCTTTGAAAAAAGCTTAG
```

Figure 25: Amino Acid Sequence of Solanum tuberosum allene oxidase synthase 2 (AOS2) gene, StAOS2_CB8

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEGEKLLKYVLWSNGPETESPTVGNK
QCAGKDFVVMVSRLFVTEFFLRYDTFNVDVGKSALGASITITSLKKA
```

Figure 26: Nucleic Acid Sequence of Solanum tuberosum allene oxidase synthase 2 (AOS2) gene, StAOS2_CB8

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGCAAAAACGAA
TTTTTCGAATCAAGAGTAGTGAAATACAAATCAACTATATTCAGAACGAACATGCCACCGGGACCATTCATTTCTTC
TAACCCGAATGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGATCCATCT
GAACCAAACCATGAAAAATTGAAAAAATTGATGTTCTTCCTTCTTTCTTCTCGACGTGATCACGTTATACCCAAATT
CCATGAAACTTATACAGAGTTTTTCGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTTGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
ATCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAATTTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 27: Amino Acid Sequence of Solanum tuberosum allene oxidase synthase 2 (AOS2) gene, StAOS2_CB9

```
MALTSSFSLPLPSLHQQFPSKYSTFRPIIVSLSEKPTIVVTQPTKLPIRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMVKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKFFDRPEEFVADRFVGEEGEKLLKYVLWSNGPETESPTVGN
KQCAGKDFVVMVSRLFVTEFFLRYDTFNVDVGKSALGASITITSLKKA
```

Figure 28: Nucleic Acid Sequence of Solanum tuberosum allene oxidase synthase 2 (AOS2) gene, StAOS2_CB9

```
ATGGCATTAACTTCATCTTTTTCTCTTCCTCTTCCTTCTCTTCACCAACAATTTCCATCAAAATACTCCACATTTCG
TCCTATTATTGTTTCTTTATCCGAAAAACCAACAATCGTGGTAACCCAACCTACAAAATTACCTATCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCTAAAGAAGAAGCTTGTCATAATCTT
CTCTTCGCTACTTGCTTCAATTCCTTCGGCGGGATGAAGATTTTCTTCCCGAATATGGTGAAATCGATAGCAAAAGC
AGGGGTGGAGGTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCAGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAATTTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 29: Amino Acid Sequence of Solanum tuberosum allene oxidase synthase 2 (AOS2) gene, StAOS2_CB10

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEGEKLLKYVLWSNGPETESPTVGNK
QCAGKDFVVMVSRLFVTEFFLRYDTFNVDVGKSALGASITITSLKKA
```

Figure 30: Nucleic Acid Sequence of Solanum tuberosum allene oxidase synthase 2 (AOS2) gene, StAOS2_CB10

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAGGGCAAAAACGAA
TTTTTCGAATCAAGAGTAGTAAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGGAGAAAAGTTATTGAAATATGTATTATGGTCTAATGGACCGGAAACGGAAAGTCCAACAGTGGGGAATAAA
CAGTGTGCTGGCAAAGATTTTGTAGTGATGGTTTCGAGGTTATTCGTAACGGAGTTTTTTCTCCGTTACGATACATT
CAACGTCGACGTTGGTAAGTCGGCGTTGGGGGCTTCAATTACTATAACTTCTTTGAAAAAAGCTTAG
```

Figure 31: Amino Acid Sequence of Solanum tuberosum allene oxidase synthase 2 (AOS2) gene, StAOS2_CB11

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEGEKLLKYVLWSNGPETESPTVGNK
QCAGKDFVVMVSRLFVTEFFLRYDTFNVDVDKSALGASITITSLKKA
```

Figure 32: Nucleic Acid Sequence of Solanum tuberosum allene oxidase synthase 2 (AOS2) gene, StAOS2_CB11

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAGGGCAAAAACGAA
TTTTTCGAATCAAGAGTAGTAAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGGAGAAAAGTTATTGAAATATGTATTATGGTCTAATGGACCGGAAACGGAAAGTCCAACAGTGGGGAATAAA
CAGTGTGCTGGCAAAGATTTTGTAGTGATGGTTTCGAGGTTATTCGTAACGGAGTTTTTCTCCGTTACGATACATT
CAACGTCGACGTTGATAAGTCGGCGTTGGGGGCTTCAATTACTATAACTTCTTTGAAAAAAGCTTAG
```

Figure 33: Amino Acid Sequence of Solanum tuberosum allene oxidase synthase 2 (AOS2) gene, StAOS2_CB12

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMVKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKFFDRPEEFVADRFVGEEGEKLLKYVLWSNGPETESPTVGN
KQCAGKDFVVMVSRLFVTEFFLRYDTFNVDVGKSALGASITITSLKKA
```

Figure 34: Nucleic Acid Sequence of Solanum tuberosum allene oxidase synthase 2 (AOS2) gene, StAOS2_CB12

```
ATGGCATTAACTTCATCTTTTTCTCTTCCTCTTCCTTCTCTTCACCAACAATTTCCATCAAAATACTCCACATTTCG
TCCTATTATTGTTTCTTTATCGGAAAAGCCAACAATCGTGGTAACCCAACCTACAAAATTACCTACTAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCTCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGGTGAAATCGATAGCAAAAGC
AGGGGTGGAGGTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCAGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAATTTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAGCTTAG
```

Figure 35: Amino Acid Sequence of Solanum tuberosum allene oxidase synthase 2 (AOS2) gene, StAOS2_CB13

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPLVASQ
YGRAKQDLKIESHDAVFEVKKGEMLFGYQPFATKDPKIFDRPEEFVADRFVGEGEKLLKYVLWSNGPETESPTVGNK
QCAGKDFVVMVSRLFVTEFFLRYDTFNVDVGKSALGASITITSLKKA
```

Figure 36: Nucleic Acid Sequence of Solanum tuberosum allene oxidase synthase 2 (AOS2) gene, StAOS2_CB13

```
ATGGCATTAACTTCATCTTTTTCTCTTCCTCTTCCTTCTCTTCACCAACAATTTCCATCAAAATACTCCACATTTCG
TCCTATTATTGTTTCTTTATCGGAAAAGCCAACAATCGTGGTAACCCAACCTACAAAATTACCTACTAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCGTCGTGATCATGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCAACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCTGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGGAGAAAAGTTATTGAAATATGTATTATGGTCTAATGGACCGGAAACGGAAAGTCCAACAGTGGGGAATAAA
CAGTGTGCTGGCAAAGATTTTGTAGTGATGGTTTCGAGGTTATTCGTAACGGAGTTTTTTCTCCGTTACGATACATT
CAACGTCGACGTTGGTAAGTCGGCGTTGGGGGCTTCAATTACTATAACTTCTTTGAAAAAAGCTTAG
```

Figure 37: Amino Acid Sequence of Solanum tuberosum allene oxidase synthase 2 (AOS2) gene, StAOS2_CB14

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEGEKLLKYVLWSNGPETESPTVGNK
QCAGKDFVVMVSRLFVTEFFLRYDTFNVDVGKSALGASITITSLKKA
```

Figure 38: Nucleic Acid Sequence of Solanum tuberosum allene oxidase synthase 2 (AOS2) gene, StAOS2_CB14

```
ATGGCATTAACTTCATCTTTTTCTCTTCCTCTTCCTTCTCTTCACCAACAATTTCCATCAAAATACTCCACATTTCG
TCCTATTATTGTTTCTTTATCGGAAAAGCCAACAATCGTGGTAACCCAACCTACAAAATTACCTACTAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCGTCGTGATCATGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCAACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGGAGAAAAGTTATTGAAATATGTATTATGGTCTAATGGACCGGAAACGGAAAGTCCAACAGTGGGGAATAAA
CAGTGTGCTGGCAAAGATTTTGTAGTGATGGTTTCGAGGTTATTCGTAACGGAGTTTTTCTCCGTTACGATACATT
CAACGTCGACGTTGGTAAGTCGGCGTTGGGGGCTTCAATTACTATAACTTCTTTGAAAAAAGCTTAG
```

Figure 39: Amino Acid Sequence of Solanum tuberosum allene oxidase synthase 2 (AOS2) gene, StAOS2_CB15

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCASKDFVVMVSRLFVTEFFLRYDTFNVDVGKSALGASITITSLKKA
```

Figure 40: Nucleic Acid Sequence of Solanum tuberosum allene oxidase synthase 2 (AOS2) gene, StAOS2_CB15

```
ATGGCATTAACTTCATCTTTTTCTCTTCCTCTTCCTTCTCTTCACCAACAATTTCCATCAAAATACTCCACATTTCG
TCCTATTATTGTTTCTTTATCGGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGATGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCTCGACGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTAGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 41: Amino Acid Sequence of Solanum tuberosum allene oxidase synthase 2 (AOS2) gene, StAOS2_CB16

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 42: Nucleic Acid Sequence of Solanum tuberosum allene oxidase synthase 2 (AOS2) gene, StAOS2_CB16

```
ATGGCATTAACTTCATCTTTTTCTCTTCCTCTTCCTTCTCTTCACCAACAATTTCCATCAAAATACTCCACATTTCG
TCCTATTATTGTTTCTTTATCGGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGATGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCTCGACGTGATCACGTTATACCCAAATT
CCATGAAACTTATACAGAGTTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 43: Amino Acid Sequence of Solanum tuberosum allene oxidase synthase 2 (AOS2) gene, StAOS2_CB17

```
MALTSSFSLPLPSLHQQFPSKYSTFRPIIVSLSEKPTIVVTQPTKLPTRTIPGDYGLPGIGPWKDRLDYFYNQGKNE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
IFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVDKSALGASITITSLKKA
```

Figure 44: Nucleic Acid Sequence of Solanum tuberosum allene oxidase synthase 2 (AOS2) gene, StAOS2_CB17

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAGGGCAAAAACGAA
TTTTTCGAATCAAGAGTAGTAAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
ATCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCTGGCGGGAAGATCACGATGT
CGGCGATGGAGAAAATGCCGTTAATGAAATCAGTAGTTTATGAAGCTTTACGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGATAAGTCGGCGTTGGGGGCTTCAATTACTATAACTTCTTTGAAAAAAGCTTAG
```

Figure 45: Amino Acid Sequence of Solanum tuberosum allene oxidase synthase 2 (AOS2) gene, StAOS2_CB18

```
MALTSSFSLPLPSLHQQFPSKYSTFRPIIVSLSEKPTIVVTQPTKLPTRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGG
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMLKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKIFDRPEEFVADRFVGEEGEKLLKYVLWSNGPETESPTVGN
KQCAGKDFVVMVSRLFVTEFFLRYDTFNVDVGKSALGASITITSLKKA
```

Figure 46: Nucleic Acid Sequence of Solanum tuberosum allene oxidase synthase 2 (AOS2) gene, StAOS2_CB18

```
ATGGCATTAACTTCATCTTTTTCTCTTCCTCTTCCTTCTCTTCACCAACAATTTCCATCAAAATACTCTACATTTCG
TCCTATTATCGTTTCTTTATCCGAAAAACCAACAATCGTGGTAACCCAACCTACAAAATTACCTACCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTCATTGTTTTGCTCGACGGCAAGAGTTTCCCAGTCCTTTTCGATGTTTCGAAAGTCGAAAAAAAGG
ACCTCTTCACCGGAACTTATATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCTTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAGGT
GATGGTCCGACATTGATCGGAAAATGGGTTTTGCTTCAGCTTCATCCTGTGCTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCAAAAGAAGAAGCTTGTCATAATCTT
CTCTTCGCTACTTGCTTCAATTCCTTCGGCGGGATGAAGATTTTCTTCCCGAATATGCTGAAATCGATAGCGAAAGC
AGGGGTGGAGGTCCATACCCGTTTAGCAAACGAGATCCGATCGGAAGTAAAATCCGCCGGCGGGAAGATCACGATGT
CGGCTATGGAGAAAATGCCGTTAATGAAATCAGTAGTATATGAAGCTTTGCGAGTTGATCCTCCGGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAAATTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 47: Amino Acid Sequence of Solanum tuberosum allene oxidase synthase 2 (AOS2) gene, StAOS2_CB19

```
MALTSSFSLPLPSLHQQFPSKYSTFRPIIVSLSEKPTIVVTQPTKLPIRTIPGDYGLPGIGPWKDRLDYFYNQGKDE
FFESRVVKYKSTIFRTNMPPGPFISSNPKVIVLLDGKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMVKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKFFDRPEEFVADRFVGEEGEKLLKYVLWSNGPETESPTVGN
KQCAGKDFVVMVSRLFVTEFFLRYDTFNVDVGKSALGASITITSLKKA
```

Figure 48: Nucleic Acid Sequence of Solanum tuberosum allene oxidase synthase 2 (AOS2) gene, StAOS2_CB19

```
ATGGCATTAACTTCATCTTTTTCTCTTCCTCTTCCTTCTCTTCACCAACAATTTCCATCAAAATACTCCACATTTCG
TCCTATTATTGTTTCTTTATCCGAAAAACCAACAATCGTGGTAACCCAACCTACAAAATTACCTATCAGGACAATAC
CCGGCGACTATGGGTTGCCGGGTATTGGTCCATGGAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGGCAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCTAAAGAAGAAGCTTGTCATAATCTT
CTCTTCGCTACTTGCTTCAATTCCTTCGGCGGGATGAAGATTTTCTTCCCGAATATGGTGAAATCGATAGCAAAAGC
AGGGGTGGAGGTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCAGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAATTTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

Figure 49: Amino Acid Sequence of Solanum tuberosum allene oxidase synthase 2 (AOS2) gene, StAOS2_CB20

```
MALTSSFSLPLPSLHQQFPSKYSTFRPIIVSLSEKPTIVVTQPTKLPIRTIPGDYGLPGIGPWKDRLDYFYNQGKDE
FFESRVVKYKSTIFRTNMPPGPFISSNPKVIVLLDDKSFPVLFDVSKVEKKDLFTGTYMPSTELTGGYRVLSYLDPS
EPNHEKLKKLMFFLLSSRRDHVIPKFHETYTEFFETLDKEMAEKGTAGLNSGNDQAAFNFLARSLFGVNPVETKLGT
DGPTLIGKWVLLQLHPVLTLGLPKFLDDLILHTFRLPPFLVKKDYQRLYDFFYTNSASLFAEAEKLGISKEEACHNL
LFATCFNSFGGMKIFFPNMVKSIAKAGVEVHTRLANEIRSEVKSAGGKITMSAMEKMPLMKSVVYEALRVDPPVASQ
YGRAKQDLKIESHDAVFEVKKGEMLFGYQPFATKDPKFFDRPEEFVADRFVGEEGEKLLKYVLWSNGPETESPTVGN
KQCAGKDFVVMVSRLFVTEFFLRYDTFNVDVGKSALGASITITSLKKA
```

Figure 50: Nucleic Acid Sequence of Solanum tuberosum allene oxidase synthase 2 (AOS2) gene, StAOS2_CB20

```
ATGGCATTAACTTCATCTTTTTCTCTTCCTCTTCCTTCTCTTCACCAACAATTTCCATCAAAATACTCCACATTTCG
TCCTATTATTGTTTCTTTATCCGAAAAACCAACAATCGTGGTAACCCAACCTACAAAATTACCTATCAGGACAATAC
CCGGCGACTATGGGTTGCCGGGTATTGGTCCATGGAAAGATAGGCTTGATTACTTTTACAATCAAGGGAAAGACGAA
TTTTTCGAATCAAGAGTAGTGAAATACAAATCAACTATATTCAGAACGAACATGCCACCGGGACCATTCATTTCTTC
TAACCCGAAGGTTATTGTTTTGCTCGACGACAAGAGTTTCCCAGTCCTTTTCGATGTTTCGAAAGTCGAAAAAAAGG
ACCTCTTCACCGGAACTTACATGCCGTCGACTGAACTCACCGGTGGTTACCGTGTTCTTTCTTATCTTGACCCATCT
GAACCAAACCATGAAAAATTGAAAAAATTGATGTTCTTCCTTCTTTCCTCCCGTCGTGATCACGTTATACCCAAATT
CCATGAAACTTATACAGAGTTTTTTGAAACCCTAGATAAGGAAATGGCGGAAAAAGGTACAGCTGGTTTAAACTCCG
GCAATGATCAAGCTGCGTTTAATTTCTTAGCTAGATCGTTGTTCGGAGTTAACCCAGTTGAAACTAAACTCGGAACT
GATGGTCCGACATTGATCGGAAAATGGGTTTTGCTTCAGCTTCATCCTGTACTCACTCTCGGTCTTCCGAAGTTTCT
AGACGACTTAATCCTCCATACTTTCCGGTTACCTCCGTTTCTGGTGAAGAAAGATTACCAGAGACTTTACGATTTCT
TTTACACCAACTCCGCCAGTTTATTCGCCGAAGCTGAAAAACTCGGCATTTCTAAAGAAGAAGCTTGTCATAATCTT
CTCTTCGCTACTTGCTTCAATTCCTTCGGCGGGATGAAGATTTTCTTCCCGAATATGGTGAAATCGATAGCAAAAGC
AGGGGTGGAGGTCCATACCCGTTTAGCAAACGAGATCCGATCGGAAGTAAAATCCGCCGGCGGGAAGATCACGATGT
CGGCGATGGAGAAAATGCCGTTAATGAAATCAGTAGTTTATGAAGCTTTACGAGTTGATCCTCCAGTAGCTTCACAA
TACGGAAGAGCCAAACAGGACCTTAAGATCGAATCACACGACGCCGTTTTCGAGGTGAAAAAAGGTGAAATGCTATT
CGGGTACCAACCATTTGCAACGAAGGATCCGAAATTTTTTGACCGGCCGGAAGAGTTCGTCGCCGATCGGTTCGTCG
GAGAAGAAGGAGAAAAGTTATTGAAATATGTATTATGGTCTAATGGACCGGAAACGGAAAGTCCGACAGTGGGGAAT
AAACAGTGTGCTGGCAAAGATTTTGTAGTGATGGTTTCGAGGTTATTCGTAACGGAGTTTTTTCTCCGTTACGATAC
ATTCAACGTCGACGTTGGTAAGTCGGCGTTGGGGGCTTCAATTACTATAACTTCTTTGAAAAAAGCTTAG
```

MUTATED ALLENE OXIDE SYNTHASE 2 (AOS2) GENES

The present invention is a continuation of U.S. patent application Ser. No. 14/776,647, filed Sep. 14, 2015, now U.S. Pat. No. 9,790,515, issued Oct. 17, 2017, which is the U.S. national phase of International Patent Application No. PCT/US2014/029434, filed Mar. 14, 2014, which designated the United States and claims priority to U.S. Provisional Application No. 61/785,059, filed Mar. 14, 2013, each of which is hereby incorporated by reference in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Oct. 16, 2017, is named CIBUS_019_CT_SeqListing.txt and is 161 kilobytes in size.

FIELD OF THE INVENTION

This disclosure relates in part to gene and/or protein mutations in plants.

BACKGROUND OF THE INVENTION

The following discussion of the background of the invention is merely provided to aid the reader in understanding the invention and is not admitted to describe or constitute prior art to the present invention.

*Phytophthora infestans* (Pi) is an organism that belongs in the phylum Oomycota and can cause devastating disease on potato (*Solanum tuberosum*), also known as Late Blight. The *Phytophthora* genus causes disease in other plant species such as tomato, soybean, pepper and tobacco. Pi has been managed by the use of chemicals such as methyl bromide and metalaxyl.

An association between the *Solanum tuberosum* Allene Oxide Synthase (StAOS2) gene and resistance to late blight has been reported. Pajerowska-Mukhtar et al., Planta 228: 293 (2008) discloses "[n]atural variation of potato allene oxide synthase 2 causes differential levels of jasmonates and pathogen resistance in *Arabidopsis*." Pajerowska-Mukhtar et al., Genetics 181:1115 (2009) discloses that "[a] major association was found at the StAOS2 locus encoding allene oxide synthase 2, a key enzyme in the biosynthesis of jasmonates . . . " and "[t]wo SNPs at the StAOS2 locus were associated with the largest effect on resistance. StAOS2_snp691 and StAOS2_snp692 . . . ."

SUMMARY OF THE INVENTION

The present disclosure relates, in part, to methods and compositions relating to gene and protein mutations in plants. In some aspects and embodiments, the present disclosure may also relate to compositions and methods for producing pathogen resistant plants. In some aspects and embodiments, the present disclosure may also relate to compositions and methods for producing a transgenic or non-transgenic plant with a normal or altered maturity rating. In some aspects and embodiments, the present disclosure may also relate to compositions and methods for producing a transgenic or non-transgenic plant with increased jasmonic acid levels. The present disclosure also relates, at least in part, to compositions and methods relating to mutations in the Allene Oxide Synthase 2 (AOS2) gene(s)/allele(s).

In one aspect, there is provided a plant or a plant cell including a mutated AOS2 gene. In certain embodiments, the mutated AOS2 gene encodes a mutated AOS2 protein. In certain embodiments, a plant having a plant cell that includes a mutated AOS2 gene may be pathogen resistant; e.g., resistant to a plant pathogen such as *Phytophthora infestans* (Pi). In certain embodiments, a plant having a plant cell that includes a mutated AOS2 gene may have an altered maturity rating. In certain embodiments, a plant having a plant cell that includes a mutated AOS2 gene may have increased jasmonic acid levels.

In conjunction with any of the various aspects, embodiments, compositions and methods disclosed herein, a plant or plant cell can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant or plant cell may be selected from a species of plant selected from the group consisting of potato, sunflower, sugar beet, maize, cotton, soybean, wheat, rye, oats, rice, canola, fruits, vegetables, tobacco, aubergine, barley, boxthane, sorghum, tomato, tomatillo, tamarillo, mango, peach, apple, pear, strawberry, banana, melon, goji berry, garden huckleberry, ground cherry, carrot, lettuce, onion, soya spp, sugar cane, pea, field beans, poplar, grape, citrus, alfalfa, rye, oats, turf and forage grasses, cucurbits, flax, oilseed rape, cucumber, squash, pumpkin, watermelon, muskmelons, morning glory, balsam, pepper, sweet pepper, bell pepper, chili pepper, paprika, pimento, habanero, cayenne, eggplant, marigold, lotus, cabbage, daisy, carnation, tulip, iris, lily, and nut-producing plants insofar as they are not already specifically mentioned. The plant or plant cell may also be of a species selected from the group consisting of *Arabidopsis thaliana, Solanum tuberosum, Solanum phureja, Oryza sativa, Amaranthus tuberculatus*, and *Zea mays*. In various embodiments, plants as disclosed herein can be of any species of the Solanaceae family.

In conjunction with any of the various aspects, embodiments, compositions and methods disclosed herein, a plant or plant cell can be a potato of any commercial variety. For example, the plant or plant cell may be selected from a potato variety selected from the group consisting of Anya, Arran Victory, Atlantic, Belle de Fontenay, BF-15, Bintje, Cabritas, Camota, Chelina, Chiloé, Cielo, Clavela Blanca, Désirée, Fianna, Fingerling, Flava, Fontana, Golden Wonder, Innovator, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, B53 (Roslin Eburu), Kiraya, Kenya Akiba, 9, Original, Gituma, Mukorino, Amin, Pimpernel, Anett, B, Gituru, Feldeslohn, C, Kigeni, Romano, Kenya Ruaka, Purplu, Njae, Suzanna, Cardinal, Kathama, Kinare-Mwene, Kibururu, Karoa-Igura, Muturu, Faraja, Kiamucove, Michiri, Rugano, Njine Giathireko, Meru Mix, Blue Baranja, Patrones, Robijn, Roslin Chania, Urgentia, Mirka, and Roslin Sasamua.

As used herein, the term "AOS2 gene" refers to a DNA sequence capable of generating an Allene Oxide Synthase 2

(AOS2) polypeptide that shares homology and/or amino acid identity with the amino acid sequence SEQ ID NO: 1, and/or encodes a protein that demonstrates AOS2 activity. In certain embodiments, the AOS2 gene has 70%; 75%; 80%; 85%; 90%; 95%; 96%; 97%; 98%; 99%; or 100% identity to a specific AOS2 gene; e.g., a *Solanum tuberosum* AOS2 gene e.g., StAOS2. In certain embodiments, the AOS2 gene has 60%; 70%; 75%; 80%; 85%; 90%; 95%; 96%; 97%; 98%; 99%; or 100% identity to a sequence selected from SEQ ID NOs: 2, 4, 6, 8, 10, 12, 14, 16, 18, 20, 22, 24, 26, 28, 30, 32, 34, 36, 38, 40, 42, 44, 46, 48 and 50.

As used herein, the term "pathogen resistance" refers to traits of plants that reduce pathogen growth once infection by a pathogenic isolate has taken place.

As used herein the term "pathogen tolerance" refers to the ability of a plant to decrease the effect of infection on plant fitness. In some embodiments, a pathogen resistant plant may have necrotic lesions that are confined and/or do not spread indeterminately. In some embodiments of a pathogen tolerant plant, little or no necrosis is observed, but water soaked lesions may exist. In some embodiments, a pathogen tolerant plant can survive infection with minimal injury or little reduction in the harvested yield of saleable material.

As used herein, the term "mutation" refers to at least a single nucleotide variation in a nucleic acid sequence and/or a single amino acid variation in a polypeptide relative to the normal sequence or wild-type sequence or a reference sequence, e.g., SEQ ID NO: 1 or SEQ ID NO: 2. In some embodiments a mutation refers to at least a single nucleotide variation in a nucleic acid sequence and/or a single amino acid variation in a polypeptide relative to a nucleotide or amino acid sequence of an AOS2 protein that does not confer an acceptable level of pathogen resistance and/or tolerance. In certain embodiments, a mutation may include a substitution, a deletion, an inversion or an insertion. In some embodiments, a substitution, deletion, insertion, or inversion may include variation of more than one nucleotide. In certain embodiments, a substitution, deletion, insertion or inversion may include variations of 1, 2, 3, 4, 5, 6, 7, 8, 9, 10, 11, 12, 13, 14, 15, 16, 17, 18, 19, 20, 21, 22, 23 or 24 nucleotides. In some embodiments, a substitution, deletion, insertion, or inversion may include a variation of 1, 2, 3, 4, 5, 6, 7, 8, 9, 10, 11 or 12 amino acid positions. The term "nucleic acid" or "nucleic acid sequence" refers to an oligonucleotide, nucleotide or polynucleotide, and fragments or portions thereof, which may be single or double stranded, and represent the sense or antisense strand. A nucleic acid may include DNA or RNA, and may be of natural or synthetic origin. For example, a nucleic acid may include mRNA or cDNA or genomic DNA. Nucleic acid may include nucleic acid that has been amplified (e.g., using polymerase chain reaction). The convention "NTwt###NTmut" is used to indicate a mutation that results in the wild-type nucleotide NTwt at position ### in the nucleic acid being replaced with mutant NTmut. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymine (uracil if RNA); "M" means adenine or cytosine; "K" means guanine or thymine; and "W" means adenine or thymine.

As used herein, the term "mutated AOS2 gene" refers to an allene oxide synthase 2 (AOS2) gene having one or more mutations at positions of nucleotides relative to a reference AOS2 nucleic acid sequence (e.g., SEQ ID NO: 2, 4, 6, 8, 10, 12, 14, 16, 18, 20, 22, 24, 26, 28, 30, 32, 34, 36, 38, 40, 42, 44, 46, 48 and/or 50). In certain embodiments a mutated AOS2 gene has one or more mutations relative to a corresponding wild type AOS2 sequence. In some embodiments a mutated AOS2 gene has one or more mutations relative to a corresponding AOS2 sequence that encodes an AOS2 protein that does not confer an acceptable level of pathogen resistance and/or tolerance. In some embodiments a mutated AOS2 gene has one or more mutations relative to, for example SEQ ID NO: 2 at homologous positions of paralogs thereof. In some embodiments, the AOS2 gene is modified with at least one mutation. In certain embodiments, the AOS2 gene is modified with at least two mutations. In certain embodiments, the AOS2 gene is modified with at least three mutations. In some embodiments, a mutated AOS2 gene encodes one or more mutated AOS2 proteins, such as describe herein. In some embodiments, a mutated AOS2 gene is a mutated *Solanum tuberosum* AOS2 gene/alleles; e.g., StAOS2. In some embodiments, a mutated AOS2 gene is a mutated Desiree AOS2 gene/allele. In some embodiments, a mutated AOS2 gene is a mutated Bintje AOS2 gene/allele. In some embodiments, a mutated AOS2 gene is a mutated Fontana AOS2 gene/allele. In some embodiments, a mutated AOS2 gene is a mutated Innovator AOS2 gene/alleles.

In some embodiments, a mutated AOS2 gene includes an A at a position corresponding to position 691 of SEQ ID NO: 2. In some embodiments, a mutated AOS2 gene includes a C at a position corresponding to position 692 of SEQ ID NO: 2. In some embodiments, a mutated AOS2 gene includes an A at a position corresponding to position 678 of SEQ ID NO: 2. In some embodiments, a mutated AOS2 gene includes a T at a position corresponding to position 681 of SEQ ID NO: 2. In some embodiments, a mutated AOS2 gene includes a C at a position corresponding to position 727 of SEQ ID NO: 2. In some embodiments, a mutated AOS2 gene includes an A at a position corresponding to position 744 of SEQ ID NO: 2. In some embodiments, a mutated AOS2 gene includes a C at a position corresponding to position 774 of SEQ ID NO: 2. In some embodiments, a mutated AOS2 gene includes an A at a position corresponding to position 879 of SEQ ID NO: 2. In some embodiments, a mutated AOS2 gene includes an A at a position corresponding to position 900 of SEQ ID NO: 2. In some embodiments, a mutated AOS2 gene includes a C at a position corresponding to position 954 of SEQ ID NO: 2.

As used herein, the term "AOS2 protein" refers to a protein that has homology and/or amino acid identity to an AOS2 protein of SEQ ID NO: 1, 3, 5, 7, 9, 11, 13, 15, 17 19, 21, 23, 25, 27, 29, 31, 33, 35, 37, 39, 41, 43, 45, 47 and/or 49 and/or demonstrates AOS2 activity. In certain embodiments, the AOS2 protein has 70%; 75%; 80%; 85%; 90%; 95%; 96%; 97%; 98%; 99%; or 100% identity to a specific AOS2 protein (e.g., SEQ ID NO: 1, 3, 5, 7, 9, 11, 13, 15, 17 19, 21, 23, 25, 27, 29, 31, 33, 35, 37, 39, 41, 43, 45, 47 or 49), such as e.g., the *Solanum tuberosum* AOS2 protein. In some embodiments, a mutated AOS2 protein is a mutated Desiree AOS2 protein. In some embodiments, a mutated AOS2 protein is a mutated Bintje AOS2 protein. In some embodiments, a mutated AOS2 protein is a mutated Fontana AOS2 protein. In some embodiments, a mutated AOS2 protein is a mutated Innovator AOS2 protein. In certain embodiments, the AOS2 protein has 70%; 75%; 80%; 85%; 90%; 95%; 96%; 97%; 98%; 99%; or 100% identity to a sequence selected from the sequences in FIGS. 1, 3, 5, 7, 9, 11, 13, 15, 17 19, 21, 23, 25, 27, 29, 31, 33, 35, 37, 39, 41, 43, 45, 47 and/or 49.

As used herein, the term "mutated AOS2 protein" refers to an AOS2 protein having one or more mutations at positions of amino acids relative to a reference AOS2 amino acid sequence, or at homologous positions of paralogs thereof. In some embodiments, a mutated AOS2 protein has one or more mutations relative to a reference AOS2 amino acid sequence, e.g., a reference AOS2 amino acid sequence having SEQ ID NO: 1, 3, 5, 7, 9, 11, 13, 15, 17 19, 21, 23, 25, 27, 29, 31, 33, 35, 37, 39, 41, 43, 45, 47 or 49, or portions thereof. In certain embodiments a mutated AOS2 protein has one or more mutations relative to a corresponding AOS2 wild type protein. In certain embodiments a mutated AOS2 protein has one or more mutations at a position corresponding to positions selected from the group consisting of 6, 12, 30, 37, 46, 48, 51, 76, 113, 145, 187, 197, 200, 227, 231, 256, 264, 270, 282, 289, 292, 309, 320, 328, 337, 338, 357, 381, 394, 407, 423, 430, 439, 467, 480, 494 and 495 of SEQ ID NO: 1. In certain embodiments a mutated AOS2 protein has one or more mutations relative to a reference AOS2 amino acid sequence wherein the reference AOS2 amino acid sequence has an F at amino acid position 6. In certain embodiments a mutated AOS2 protein has one or more mutations relative to a reference AOS2 amino acid sequence wherein the reference AOS2 amino acid sequence has an R at amino acid position 12. In certain embodiments a mutated AOS2 protein has one or more mutations relative to a reference AOS2 amino acid sequence wherein the reference AOS2 amino acid sequence has a P at amino acid position 12. In certain embodiments a mutated AOS2 protein has one or more mutations relative to a reference AOS2 amino acid sequence wherein the reference AOS2 amino acid sequence has an A at position 30. In certain embodiments a mutated AOS2 protein has one or more mutations relative to a reference AOS2 amino acid sequence wherein the reference AOS2 amino acid sequence has an I at position 37. In certain embodiments a mutated AOS2 protein has one or more mutations relative to a reference AOS2 amino acid sequence wherein the reference AOS2 amino acid sequence has an F at amino acid position 46. In certain embodiments a mutated AOS2 protein has one or more mutations relative to a reference AOS2 amino acid sequence wherein the reference AOS2 amino acid sequence has an L at amino acid position 46. In certain embodiments a mutated AOS2 protein has one or more mutations relative to a reference AOS2 amino acid sequence wherein the reference AOS2 amino acid sequence has an I at amino acid position 48. In certain embodiments a mutated AOS2 protein has one or more mutations relative to a reference AOS2 amino acid sequence wherein the reference AOS2 amino acid sequence has a V at amino acid position 48. In certain embodiments a mutated AOS2 protein has one or more mutations relative to a reference AOS2 amino acid sequence wherein the reference AOS2 amino acid sequence has a T at amino acid position 48. In certain embodiments a mutated AOS2 protein has one or more mutations relative to a reference AOS2 amino acid sequence wherein the reference AOS2 amino acid sequence has an M at amino acid position 51. In certain embodiments a mutated AOS2 protein has one or more mutations relative to a reference AOS2 amino acid sequence wherein the reference AOS2 amino acid sequence has an N at amino acid position 76. In certain embodiments a mutated AOS2 protein has one or more mutations relative to a reference AOS2 amino acid sequence wherein the reference AOS2 amino acid sequence has a D at amino acid position 76. In certain embodiments a mutated AOS2 protein has one or more mutations relative to a reference AOS2 amino acid sequence wherein the reference AOS2 amino acid sequence has a D at position 113. In certain embodiments a mutated AOS2 protein has one or more mutations relative to a reference AOS2 amino acid sequence wherein the reference AOS2 amino acid sequence has a G at position 113. n certain embodiments a mutated AOS2 protein has one or more mutations relative to a reference AOS2 amino acid sequence wherein the reference AOS2 amino acid sequence has an F at amino acid position 145. In certain embodiments a mutated AOS2 protein has one or more mutations relative to a reference AOS2 amino acid sequence wherein the reference AOS2 amino acid sequence has a L at amino acid position 187. In certain embodiments a mutated AOS2 protein has one or more mutations relative to a reference AOS2 amino acid sequence wherein the reference AOS2 amino acid sequence has a D at amino acid position 197. In certain embodiments a mutated AOS2 protein has one or more mutations relative to a reference AOS2 amino acid sequence wherein the reference AOS2 amino acid sequence has a E at amino acid position 197. In certain embodiments a mutated AOS2 protein has one or more mutations relative to a reference AOS2 amino acid sequence wherein the reference AOS2 amino acid sequence has a K at amino acid position 200. In certain embodiments a mutated AOS2 protein has one or more mutations relative to a reference AOS2 amino acid sequence wherein the reference AOS2 amino acid sequence has an A at amino acid position 227. In certain embodiments a mutated AOS2 protein has one or more mutations relative to a reference AOS2 amino acid sequence wherein the reference AOS2 amino acid sequence has an I at amino acid position 231. In certain embodiments a mutated AOS2 protein has one or more mutations relative to a reference AOS2 amino acid sequence wherein the reference AOS2 amino acid sequence has a G at amino acid position 231. In certain embodiments a mutated AOS2 protein has one or more mutations relative to a reference AOS2 amino acid sequence wherein the reference AOS2 amino acid sequence has a T at amino acid position 231. In certain embodiments a mutated AOS2 protein has one or more mutations relative to a reference AOS2 amino acid sequence wherein the reference AOS2 amino acid sequence has a V at amino acid position 256. In certain embodiments a mutated AOS2 protein has one or more mutations relative to a reference AOS2 amino acid sequence wherein the reference AOS2 amino acid sequence has a F at amino acid position 256. In certain embodiments a mutated AOS2 protein has one or more mutations relative to a reference AOS2 amino acid sequence wherein the reference AOS2 amino acid sequence has an A at amino acid position 264. In certain embodiments a mutated AOS2 protein has one or more mutations relative to a reference AOS2 amino acid sequence wherein the reference AOS2 amino acid sequence has a L at amino acid position 270. In certain embodiments a mutated AOS2 protein has one or more mutations relative to a reference AOS2 amino acid sequence wherein the reference AOS2 amino acid sequence has a S at amino acid position 282. In certain embodiments a mutated AOS2 protein has one or more mutations relative to a reference AOS2 amino acid sequence wherein the reference AOS2 amino acid sequence has a F at amino acid position 282. In certain embodiments a mutated AOS2 protein has one or more mutations relative to a reference AOS2 amino acid sequence wherein the reference AOS2 amino acid sequence has a V at amino acid position 289. In certain embodiments a mutated AOS2 protein has one or more mutations relative to a reference AOS2 amino acid sequence wherein the reference AOS2 amino acid sequence has an N at amino acid position 289. In certain embodiments a mutated AOS2 protein has one or more mutations relative to a reference AOS2 amino acid sequence wherein the reference AOS2 amino acid sequence has a S at amino acid position 289. In certain embodiments a mutated AOS2 protein has one or more mutations relative to a reference AOS2 amino acid sequence wherein the reference AOS2 amino acid sequence has a V at amino acid position 292. In certain embodiments a mutated AOS2 protein has one or more mutations relative to a reference AOS2 amino acid sequence wherein the reference AOS2 amino acid sequence has an I at amino acid position 309. In certain embodiments a mutated AOS2 protein has one or more mutations relative to a reference AOS2 amino acid sequence wherein the reference AOS2 amino acid sequence has a L at amino acid position 309. In certain embodiments a mutated AOS2 protein has one or more mutations relative to a reference AOS2 amino acid sequence wherein the reference AOS2 amino acid sequence has a L at amino acid position 320. In certain embodiments a mutated AOS2 protein has one or more mutations relative to a reference AOS2 amino acid sequence wherein the reference AOS2 amino acid sequence has a M at amino acid position 320. In certain embodiments a mutated AOS2 protein has one or more mutations relative to a reference AOS2 amino acid sequence wherein the reference AOS2 amino acid sequence has a M at amino acid position 328. In certain embodiments a mutated AOS2 protein has one or more mutations relative to a reference AOS2 amino acid sequence wherein the reference AOS2 amino acid sequence has a V at amino acid position 328. In certain embodiments a mutated AOS2 protein has one or more mutations relative to a reference AOS2 amino acid sequence wherein the reference AOS2 amino acid sequence has a L at amino acid position 328. In certain embodiments a mutated AOS2 protein has one or more mutations relative to a reference AOS2 amino acid sequence wherein the reference AOS2 amino acid sequence has a D at amino acid position 337. In certain embodiments a mutated AOS2 protein has one or more mutations relative to a reference AOS2 amino acid sequence wherein the reference AOS2 amino acid sequence has an E at amino acid position 337. In certain embodiments a mutated AOS2 protein has one or more mutations relative to a reference AOS2 amino acid sequence wherein the reference AOS2 amino acid sequence has a L at amino acid position 338. In certain embodiments a mutated AOS2 protein has one or more mutations relative to a reference AOS2 amino acid sequence wherein the reference AOS2 amino acid sequence has a V at amino acid position 338. In certain embodiments a mutated AOS2 protein has one or more mutations relative to a reference AOS2 amino acid sequence wherein the reference AOS2 amino acid sequence has a M at amino acid position 357. In certain embodiments a mutated AOS2 protein has one or more mutations relative to a reference AOS2 amino acid sequence wherein the reference AOS2 amino acid sequence has an I at amino acid position 357. In certain embodiments a mutated AOS2 protein has one or more mutations relative to a reference AOS2 amino acid sequence wherein the reference AOS2 amino acid sequence has a L at amino acid position 381. In certain embodiments a mutated AOS2 protein has one or more mutations relative to a reference AOS2 amino acid sequence wherein the reference AOS2 amino acid sequence has a P at amino acid position 381. In certain embodiments a mutated AOS2 protein has one or more mutations relative to a reference AOS2 amino acid sequence wherein the reference AOS2 amino acid sequence has a T at amino acid position 394. In certain embodiments a mutated AOS2 protein has one or more mutations relative to a reference AOS2 amino acid sequence wherein the reference AOS2 amino acid sequence has a C at amino acid position 407. In certain embodiments a mutated AOS2 protein has one or more mutations relative to a reference AOS2 amino acid sequence wherein the reference AOS2 amino acid sequence has a G at amino acid position 407. In certain embodiments a mutated AOS2 protein has one or more mutations relative to a reference AOS2 amino acid sequence wherein the reference AOS2 amino acid sequence has a F at amino acid position 423. In certain embodiments a mutated AOS2 protein has one or more mutations relative to a reference AOS2 amino acid sequence wherein the reference AOS2 amino acid sequence has a L at amino acid position 430. In certain embodiments a mutated AOS2 protein has one or more mutations relative to a reference AOS2 amino acid sequence wherein the reference AOS2 amino acid sequence has an E at position 439. In certain embodiments a mutated AOS2 protein has one or more mutations relative to a reference AOS2 amino acid sequence wherein the reference AOS2 amino acid sequence has a S at amino acid position 467. In certain embodiments a mutated AOS2 protein has one or more mutations relative to a reference AOS2 amino acid sequence wherein the reference AOS2 amino acid sequence has a G at amino acid position 467. In certain embodiments a mutated AOS2 protein has one or more mutations relative to a reference AOS2 amino acid sequence wherein the reference AOS2 amino acid sequence has a V at amino acid position 480. In certain embodiments a mutated AOS2 protein has one or more mutations relative to a reference AOS2 amino acid sequence wherein the reference AOS2 amino acid sequence has a D at amino acid position 494. In certain embodiments a mutated AOS2 protein has one or more mutations relative to a reference AOS2 amino acid sequence wherein the reference AOS2 amino acid sequence has a G at amino acid position 494. In certain embodiments a mutated AOS2 protein has one or more mutations relative to a reference AOS2 amino acid sequence wherein the reference AOS2 amino acid sequence has a T at amino acid position 495. In another embodiment, a mutated AOS2 protein may be composed of any combination of amino acid mutations at any positions in the protein relative to a reference sequence (e.g., SEQ ID NO: 1, 3, 5, 7, 9, 11, 13, 15, 17 19, 21, 23, 25, 27, 29, 31, 33, 35, 37, 39, 41, 43, 45, 47 and/or 49). In some embodiments a mutated AOS2 protein has one or more mutations relative to a corresponding AOS2 protein that confers lower than acceptable pathogen resistance and/or tolerance (e.g., resistant to *Phytophthora infestans*). In some embodiments, the AOS2 protein is modified with one or more mutations. In some embodiments, the AOS2 protein is modified with at least one mutation. In certain embodiments, the AOS2 protein is modified with at least two mutations. In certain embodiments, the AOS2 protein is modified with at least three mutations. In certain embodiments, the AOS2 protein is modified with at least four mutations. In certain embodiments, the AOS2 protein is modified with at least five mutations. In certain embodiments, the AOS2 protein is modified with at least six mutations. In certain embodiments, the AOS2 protein is modified with at least seven mutations. In certain embodiments, the AOS2 protein is modified with at least eight mutations. In certain embodiments, the AOS2 protein is modified with at least nine mutations. In certain embodiments, the AOS2 protein is modified with at least ten mutations. In certain embodiments, the AOS2 protein is modified with at least eleven mutations. In certain embodiments, the AOS2 protein is modified with at least twelve mutations. In some embodiments, a mutated AOS2 protein is one or more *Solanum* tuberosum AOS2 proteins. In some embodiments, the term mutated AOS2 protein refers to an AOS2 protein that confers increased resistance and/or tolerance to one or more pathogens as compared to a reference protein.

As used herein, the term "lower than acceptable level of pathogen resistance and/or tolerance" means that the susceptibility of a plant or crop to a pathogen impairs or destroys the commercial profitability of the plant or crop. In certain embodiments, a lower than acceptable level of pathogen resistance and/or tolerance reduces profitability of the plant or crop by at least 10%; or at least 25%; or at least 50%; or at least 75%; or at least 100% as compared to a similar plant or crop that is pathogen resistant and/or tolerant. In contrast, the profitability of a crop or plant with an "acceptable level of resistance and/or tolerance" to a pathogen is not substantially impaired or destroyed due to pathogen exposures. In certain embodiments, the profitability of a plant or crop is reduced by less than 20%; or less than 15% or less than 10% upon exposure to a pathogen. The profitability of a crop or plant with a "higher than acceptable level of resistance and/or tolerance" to a pathogen is reduced by less than 10%; or less than 5% or less than 2% upon exposure to a pathogen.

In conjunction with any of the aspects, embodiments, compositions and methods disclosed herein, a mutation refers to at least a single nucleotide variation in an AOS2 gene or a single amino acid variation in a polypeptide relative to an amino acid sequence of an AOS2 gene/protein that confers pathogen resistance and/or tolerance. In some embodiments, a mutation refers to at least a single nucleotide variation in an AOS2 gene or a single amino acid variation in a polypeptide relative to an amino acid sequence of an AOS2 protein that does not confer an acceptable level of pathogen resistance and/or tolerance. In certain embodiments, a mutation may include a substitution, a deletion, an inversion or an insertion at one or more positions in the gene and/or protein. In some embodiments, a substitution, deletion, insertion, or inversion may include a variation at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 amino acid positions.

In conjunction with any of the aspects, embodiments, compositions and methods disclosed herein, the one or more mutations in a mutated AOS2 protein includes one or more, two or more, three or more, four or more, five or more, six or more, seven or more, eight or more, nine or more, or ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, thirty or more, thirty-one or more, thirty-two or more, thirty-three or more, thirty-four or more, thirty-five or more, thirty-six or more, thirty-seven or more mutations at positions corresponding to the positions selected from the group consisting of 6, 12, 30, 37, 46, 48, 51, 76, 113, 145, 187, 197, 200, 227, 231, 256, 264, 270, 282, 289, 292, 309, 320, 328, 337, 338, 357, 381, 394, 407, 423, 430, 439, 467, 480, 494 and 495 of SEQ ID NO: 1, 3, 5, 7, 9, 11, 13, 15, 17 19, 21, 23, 25, 27, 29, 31, 33, 35, 37, 39, 41, 43, 45, 47 and/or 49.

In conjunction with any of the aspects, embodiments, compositions and methods disclosed herein, the one or more mutations in a mutated AOS2 protein includes one or more, two or more, three or more, four or more, five or more, six or more, seven or more, eight or more, nine or more, or ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more mutations at positions selected from the group consisting of S6, P12, R12, V30, T37, F46, L46, I48, T48, I51, D76, D113, G113, Y145, F187, D197, E197, T200, T227, G231, T231, F256, V256, T264, F270, F282, S282, N289, S289, A292, I309, L309, L320, M320, L328, V328, D337, E337, L338, V338, I357, M357, L381, P381, K394, C407, G407, I423, F430, Δ439 (where Δ indicates a deletion), G467, S467, T480, D494, G494 and K495 of SEQ ID NO: 1, 3, 5, 7, 9, 11, 13, 15, 17 19, 21, 23, 25, 27, 29, 31, 33, 35, 37, 39, 41, 43, 45, 47 and/or 49.

In conjunction with any of the aspects, embodiments, compositions and methods disclosed herein a mutated AOS2 gene includes a G at a position corresponding to position 231 of SEQ ID NO: 1 and a V at a position corresponding to position 328 of SEQ ID NO: 1. [0001]

In conjunction with any of the aspects, embodiments, compositions and methods disclosed herein, the one or more mutations in a mutated AOS2 protein includes one or more mutations, two or more mutations, three or more mutations, four or more mutations, five or more mutations, six or more mutations, seven or more mutations, eight or more mutations, nine or more mutations, or ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more mutations selected from the group consisting of F6S, R12P, P12R, A30V, I37T, L46F, F46L, V48T, V48I, T48I, I48T, M51I, D76N, N76D, G113D, D113G, F145Y, L187F, D197E, E197D, K200T, A227T, I231T, I231G, G231T, T231G, F256V, V256F, A264T, L270F, F282S, S282F, V289N, V289S, S289N, N289S, V292A, L309I, I309L, M320L, L320M, M328L, M328V, L328V, V328L, E337D, D337E, V338L, L338V, I357M, M357I, P381L, L381P, T394K, G407C, C407G, F423I, L430F, E439Δ, G467S, S467G, V480T, G494D, D494G and T495K. In some embodiments, the one or more mutations in a mutated AOS2 protein includes one or more mutations, two or more mutations, three or more mutations, four or more mutations, five or more mutations, six or more mutations, seven or more mutations, eight or more mutations, nine or more mutations, or ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more mutations selected from the group consisting of a phenylalanine to a serine at a position corresponding to position 6, an arginine to a proline at a position corresponding to position 12, a proline to an arginine at a position corresponding to position 12, an alanine to a valine at a position corresponding to position 30, an isoleucine to a threonine at a position corresponding to position 37, a phenylalanine to a leucine at a position corresponding to position 46, a leucine to a phenylalanine at a position corresponding to position 46, a valine to a threonine at a position corresponding to position 48, a valine to an isoleucine at a position corresponding to position 48, an isoleucine to a threonine at a position corresponding to position 48, a threonine to an isoleucine at a position corresponding to position 48, a methionine to an isoleucine at a position corresponding to position 51, an asparagine to an aspartic acid at a position corresponding to position 76, an aspartic acid to an asparagine at a position corresponding to position 76, an aspartic acid to a glycine at a position corresponding to position 113, a glycine to an aspartic acid at a position corresponding to position 113, a phenylalanine to a tyrosine at a position corresponding to position 145, a leucine to a phenylalanine at a position corresponding to position 187, an aspartic acid to a glutamic acid at a position corresponding to position 197, a glutamic acid to an aspartic acid at a position corresponding to position 197, a lysine to a threonine at a position corresponding to position 200, an alanine to a threonine at a position corresponding to position 227, an isoleucine to a threonine at a position corresponding to position 231, an isoleucine to a glycine at a position corresponding to position 231, a glycine to a threonine at a position corresponding to position 231, a threonine to a glycine at a position corresponding to position 231, a valine to a phenylalanine at a position corresponding to position 256, a phenylalanine to a valine at a position corresponding to position 256, an alanine to a threonine at a position corresponding to position 264, a leucine to a phenylalanine at a position corresponding to position 270, a serine to a phenylalanine at a position corresponding to position 282, a phenylalanine to a serine at a position corresponding to position 282, a valine to an asparagine at a position corresponding to position 289, a valine to a serine at a position corresponding to position 289, a serine to an asparagine at a position corresponding to position 289, an asparagine to a serine at a position corresponding to position 289, a valine to an alanine at a position corresponding to position 292, an isoleucine to leucine at a position corresponding to position 309, a leucine to an isoleucine at a position corresponding to position 309, a leucine to methionine at a position corresponding to position 320, a methionine to a leucine at a position corresponding to position 320, a methionine to a leucine at a position corresponding to position 328, a methionine to valine at a position corresponding to position 328, a valine to a leucine at a position corresponding to position 328, a leucine to a valine at a position corresponding to position 328, an aspartic acid to a glutamic acid at a position corresponding to position 337, a glutamic acid to an aspartic acid at a position corresponding to position 337, a leucine to a valine at a position corresponding to position 338, a valine to a leucine at a position corresponding to position 338, a methionine to an isoleucine at a position corresponding to position 357, an isoleucine to a methionine at a position corresponding to position 357, a leucine to a proline at a position corresponding to position 381, a proline to a leucine at a position corresponding to position 381, a threonine to a lysine at a position corresponding to position 394, a cysteine to a glycine at a position corresponding to position 407, a glycine to a cysteine at a position corresponding to position 407, a phenylalanine to an isoleucine at a position corresponding to position 423, a leucine to a phenylalanine at a position corresponding to position 430, a serine to a glycine at a position corresponding to position 467, a glycine to a serine at a position corresponding to position 467, a valine to a threonine at a position corresponding to position 480, an aspartic acid to a glycine at a position corresponding to position 494, a glycine to an aspartic acid at a position corresponding to position 494, a threonine to a lysine at a position corresponding to position 495 of SEQ ID NO: 1, 3, 5, 7, 9, 11, 13, 15, 17 19, 21, 23, 25, 27, 29, 31, 33, 35, 37, 39, 41, 43, 45, 47 or 49, and a deletion of a glutamic acid at a position corresponding to position 439 SEQ ID NO: 5, 7, 9, 11, 13, 15, 17, 19, 21, 23, 25, 27, 33, 39, 41, 43, 45, 47 or 49.

In conjunction with any of the aspects, embodiments, compositions and methods disclosed herein, a mutated AOS2 protein includes SEQ ID NO: 1. In conjunction with any of the aspects, embodiments, compositions and methods disclosed herein, a mutated AOS2 protein includes SEQ ID NO: 3.

In another aspect, there is provided a method for producing a plant cell. In some embodiments, the plant cell has a mutated AOS2 gene. In certain embodiments, the mutated AOS2 gene encodes a mutated AOS2 protein. In certain embodiments, the plant cell may be part of a pathogen resistant plant. The method may include introducing into a plant cell a gene repair oligonucleobase (GRON); e.g., using a GRON with a targeted mutation to produce a nucleotide change at the homologous location in an AOS2 gene. In certain embodiments, the plant cell produced by the method may include an AOS2 gene capable of expressing a mutated AOS2 protein. The method may further include identifying a plant cell or a plant including a plant cell that includes (1) a mutated AOS2 gene and/or (2) normal or altered growth, and/or AOS2 catalytic activity, enhanced AOS2 enzyme stability, signaling capability and/or (3) higher pathogen resistance and/or tolerance as compared to a corresponding wild-type plant cell. The pathogen resistant plant having a plant cell such as described herein may be identified in the presence of a pathogen. In some embodiments, the plant cell is transgenic. In some embodiments, the plant cell is non-transgenic. A plant that includes a plant cell such as described herein may be a non-transgenic pathogen resistant/tolerant plant; e.g., the plant and/or plant cell may have a mutated AOS2 gene that results in resistance and/or tolerance to at least one pathogen. In some embodiments, a plant having a plant cell as described herein may be produced asexually; e.g., from one or more plant cells or from a plant tissue made up of one or more plant cells; e.g., from a tuber or piece of a potato tuber containing at least one or two eyes (dormant buds), often referred to as seed potatoes. In certain embodiments, a plant having a plant cell such as described herein may be produced sexually yielding true genetic seed.

In another aspect, there is provided a method for producing a pathogen resistant and/or tolerant plant. The method may include introducing into a plant cell a gene repair oligonucleobase (GRON); e.g., using a GRON with a targeted mutation to produce a nucleotide change at the homologous location in to an AOS2 gene. The method may produce a plant cell with a mutated AOS2 gene. The mutated AOS2 gene may express a mutated AOS2 protein. The method may further include identifying a plant that has normal or altered growth, AOS2 protein catalytic activity, AOS2 enzyme stability and/or signaling capability as compared to a corresponding wild-type plant cell. The method may further include regenerating a pathogen resistant plant from a plant cell with a mutated AOS2 gene. The plant may be identified in the presence of pathogens. In some embodiments, the plant is transgenic. In some embodiments, the plant is non-transgenic. The plant may in some embodiments be a non-transgenic pathogen resistant plant; e.g., the plant may include a mutated AOS2 gene that results in improved resistance and/or tolerance to at least one pathogen. In some embodiments, the plant may include a mutated AOS2 gene that gives rise to a plant with altered maturity rating. In certain embodiments, the plant may include a mutated AOS2 gene that gives rise to a plant with a late maturity rating.

In another aspect, there is provided a method for producing a plant with an early, mid, mid-early or late maturity rating. The method may include introducing into a plant cell a gene repair oligonucleobase (GRON); e.g., using a GRON with a targeted mutation to produce a nucleotide change at the homologous location in an AOS2 gene. The method may produce a plant cell with a mutated AOS2 gene. The mutated AOS2 gene may express a mutated AOS2 protein. The method may further include identifying a plant cell that has normal growth and/or catalytic activity as compared to a corresponding wild-type plant cell. The method may further include regenerating a pathogen resistant plant from a plant cell with a mutated AOS2 gene. In some embodiments, the plant is non-transgenic. The plant may be a non-transgenic plant with a mid-early maturity rating. The plant may in some embodiments be a non-transgenic pathogen resistant plant; e.g., the plant may include a mutated AOS2 gene that results in resistance and/or tolerance to at least one pathogen. In some embodiments, the plant is transgenic. The plant may be a non-transgenic plant with a mid-early maturity rating. The plant may in some embodiments be a transgenic pathogen resistant plant; e.g., the plant may include a mutated AOS2 gene that results in resistance and/or tolerance to at least one pathogen.

In another aspect, there is provided a method for increasing jasmonic acid levels in a plant. The method may include introducing into a plant cell a gene repair oligonucleobase (GRON); e.g., using a GRON with a targeted mutation to produce a nucleotide change at the homologous location in an AOS2 gene. The method may produce a plant cell with a mutated AOS2 gene. The mutated AOS2 gene may express a mutated AOS2 protein. The method may further include identifying a plant that has normal or altered growth AOS2 protein catalytic activity, AOS2 enzyme stability and/or signaling capability as compared to a corresponding wild-type plant cell. The method may further include regenerating a plant with increased jasmonic acid levels from a plant cell with a mutated AOS2 gene. The plant may be identified in the presence of pathogens. In some embodiments, the plant is non-transgenic. The plant may in some embodiments be a non-transgenic pathogen resistant plant; e.g., the plant may include a mutated AOS2 gene that results in resistance and/or tolerance to at least one pathogen. In some embodiments, the plant may include a mutated AOS2 gene that gives rise to a plant with increased jasmonic acid levels. In some embodiments, the plant is transgenic. The plant may in some embodiments be a transgenic pathogen resistant plant; e.g., the plant may include a mutated AOS2 gene that results in resistance and/or tolerance to at least one pathogen. In some embodiments, the plant may include a mutated AOS2 gene that gives rise to a plant with increased jasmonic acid levels.

In another aspect, there is provided a method for increasing the pathogen-resistance and/or tolerance of a plant. The method may include introducing into a plant cell a gene repair oligonucleobase (GRON); e.g., using a GRON with a targeted mutation to produce a nucleotide change at the homologous location in an AOS2 gene. The method may produce a plant cell with a mutated AOS2 gene. The mutated AOS2 gene may express a mutated AOS2 protein. The method may further include identifying a plant that has normal or altered growth and/or AOS2 protein catalytic activity and/or AOS2 protein stability as compared to a corresponding wild-type plant cell. The method may further include regenerating a pathogen resistant plant from a plant cell with a mutated AOS2 gene. The plant may be identified in the presence of a pathogen. In some embodiments, the plant is non-transgenic. The plant may in some embodiments be a non-transgenic pathogen resistant plant; e.g., the plant may include a mutated AOS2 gene that results in resistance and/or tolerance to at least one pathogen. In some embodiments, the plant may include a mutated AOS2 gene that gives rise to a plant with a mid-early maturity rating. In certain embodiments, the plant may include a mutated AOS2 gene that gives rise to a plant with a late maturity rating. In some embodiments, the plant is transgenic. The plant may in some embodiments be a transgenic pathogen resistant plant; e.g., the plant may include a mutated AOS2 gene that results in resistance and/or tolerance to at least one pathogen. In some embodiments, the plant may include a mutated AOS2 gene that gives rise to a plant with a mid-early maturity rating. In certain embodiments, the plant may include a mutated AOS2 gene that gives rise to a plant with a late maturity rating.

In another aspect, there is provided a plant or plant cell including a mutated AOS2 gene. In certain embodiments, the mutated AOS2 gene encodes a mutated AOS2 protein. In certain embodiments, the plant or plant cell may be of the Desiree potato variety. In certain embodiments, the plant or plant cell may be of the Bintje potato variety. In certain embodiments, the plant or plant cell may be of the Fontana potato variety. In certain embodiments, the plant or plant cell may be of the Innovator potato variety. In certain embodiments, a plant having a plant cell that includes a mutated AOS2 gene may be pathogen resistant and/or tolerant. In certain embodiments, the plant or the plant cell is non-transgenic. In certain embodiments, the plant or the plant cell is transgenic.

In conjunction with any of the aspects, embodiments, compositions and methods disclosed herein, the compositions and methods may involve a plant or plant cell having multiple AOS2 genes, with each gene having two alleles, in two or more sets of chromosomes. For example; a tetraploid plant may include one, two, three, or four mutated AOS2 alleles. In some embodiments, the multiple AOS2 genes may include the same mutation or different mutations. In some embodiments, the multiple AOS2 genes may include any combination or permutation of mutations, e.g., the AOS2 mutations as disclosed herein.

In conjunction with any of the aspects, embodiments, compositions and methods disclosed herein, the plant or plant cell may include mutations in an AOS2 gene/allele/locus on one or more chromosomes. A plant or plant cell may include a plant with various multiples of chromosomes; e.g., at least one set of chromosomes, at least two sets of chromosomes, at least three sets of chromosomes, at least four sets of chromosomes, at least five sets of chromosomes, at least six sets of chromosomes, at least seven sets of chromosomes, at least eight sets of chromosomes, at least nine sets of chromosomes, at least ten sets of chromosomes, at least eleven sets of chromosomes and at least twelve sets of chromosomes. In some embodiments, a plant or plant cell includes a plant with four sets of chromosomes.

In conjunction with any of the aspects, embodiments, compositions and methods disclosed herein, the mutated AOS2 gene includes at least one mutation that confers pathogen resistance and/or tolerance or at least one mutation that confers a late maturity rating. In some embodiments, the at least one mutation that confers pathogen resistance and/or tolerance is the same mutation as the at least one mutation that confers a late maturity rating. In certain embodiments, the at least one mutation that confers pathogen resistance and/or tolerance is different from the at least one mutation that confers a late maturity rating.

In conjunction with any of the aspects, embodiments, compositions and methods disclosed herein, the mutated AOS2 gene includes at least one mutation that confers pathogen resistance and/or tolerance and at least one mutation that confers a mid-early maturity rating. In some embodiments, the at least one mutation that confers pathogen resistance and/or tolerance is the same mutation as the at least one mutation that confers a mid-early maturity rating. In certain embodiments, the at least one mutation that confers pathogen resistance and/or tolerance is different from the at least one mutation that confers a mid-early maturity rating.

In conjunction with any of the aspects, embodiments, compositions and methods disclosed herein, the mutated AOS2 gene includes at least one mutation that confers pathogen resistance and/or tolerance and at least one mutation that confers an early maturity rating. In some embodiments, the at least one mutation that confers pathogen resistance and/or tolerance is the same mutation as the at least one mutation that confers an early maturity rating. In certain embodiments, the at least one mutation that confers pathogen resistance and/or tolerance is different from the at least one mutation that confers an early maturity rating.

In conjunction with any of the aspects, embodiments, compositions and methods disclosed herein, the mutated AOS2 gene includes at least one mutation that confers pathogen resistance and/or tolerance and at least one mutation that confers a mid maturity rating. In some embodiments, the at least one mutation that confers pathogen resistance and/or tolerance is the same mutation as the at least one mutation that confers a mid maturity rating. In certain embodiments, the at least one mutation that confers pathogen resistance and/or tolerance is different from the at least one mutation that confers a mid maturity rating.

In another aspect there is provided a seed including a mutated AOS2 gene. In some embodiments, the seed has a mutated AOS2 gene. In some embodiments, the mutated AOS2 gene encodes a mutated AOS2 protein. In some embodiments, the mutated AOS2 protein may be resistant and/or tolerant to a pathogen. In some embodiments, the seed is resistant and/or tolerant to a pathogen. In some embodiments, the seed may include a mutated AOS2 gene that results in a pathogen resistant and/or tolerant plant. In some embodiments, the seed is non-transgenic. In some embodiments, the seed is transgenic. In some embodiments, the seed may include a mutated AOS2 gene that gives rise to a plant with a mid-early maturity rating. In some embodiments, the seed may include a mutated AOS2 gene that gives rise to a plant with a late maturity rating.

In another aspect there is provided vegetative plant material that can give rise to a new plant including but not limited to tubers or pieces thereof containing at least a single eye, in vitro grown shoots, rooted shoots or protoplast-derived callus having at least one mutated AOS2 allele. In some embodiments, such vegetatively propagated material has a mutated AOS2 gene. In some embodiments, the mutated AOS2 gene encodes a mutated AOS2 protein. In some embodiments, the mutated AOS2 protein may be resistant and/or tolerant to a pathogen. In some embodiments, the vegetative material is resistant and/or tolerant to a pathogen. In some embodiments, the vegetative material may include a mutated AOS2 gene that results in a pathogen resistant and/or tolerant plant. In some embodiments, the vegetative material is non-transgenic. In some embodiments, the vegetative material is transgenic. In some embodiments, the vegetative material may include a mutated AOS2 gene that gives rise to a plant with a mid-early maturity rating. In some embodiments, the vegetative material may include a mutated AOS2 gene that gives rise to a plant with a late maturity rating.

In another aspect, there is provided a method for increasing the pathogen-resistance and/or tolerance of a plant by: (a) crossing a first plant to a second plant, in which the first plant includes a mutated AOS2 gene, in which the gene encodes a mutated AOS2 protein; (b) screening a population resulting from the cross for increased pathogen-resistance and/or tolerance; (c) selecting a member resulting from the cross having increased pathogen-resistance and/or tolerance; and (d) producing seeds resulting from the cross. In some embodiments, a hybrid seed is produced by any of the above methods. In some embodiments, plants are grown from seeds produced by any of the above methods. In some embodiments, the plants and/or seeds are non-transgenic. In some embodiments, the plants and/or seeds are transgenic. In some embodiments, the first and second plants are *Solanum tuberosum* plants. In some embodiments, the plants and/or seeds have a early, mid-early, mid or late maturity rating.

In another aspect, there is provided an isolated nucleic acid of a mutated AOS2 gene. In some embodiments, the isolated nucleic acid encodes for a mutated AOS2 protein. In certain embodiments, the isolated nucleic acid encodes a mutated AOS2 protein that is pathogen resistant and/or tolerant. In some embodiments, the isolated nucleic acid encodes a mutated AOS2 protein that gives rise to a plant with early, mid, mid-early or late maturity rating.

In another aspect, there is provided an expression vector containing an isolated nucleic acid of a mutated AOS2 gene. In some embodiments, the expression vector contains an isolated nucleic acid encoding an AOS2 protein.

In conjunction with any of the aspects, embodiments, compositions and methods disclosed herein, the methods and compositions disclosed herein include one or more mutated AOS2 genes that encode one or more AOS2 proteins. In some embodiments, the methods and compositions include a mutated chloroplast targeted AOS2 gene. In some embodiments, the methods and compositions include a mutated AOS2 gene. In some embodiments, the methods and compositions include a mutated *Solanum tuberosum* AOS2 gene; for example StAOS2. In some embodiments, the methods and compositions include a mutated AOS2 gene allele StAOS2-1. In some embodiments, the methods and compositions include a mutated AOS2 gene allele StAOS2-6. In some embodiments, the methods and compositions include a mutated AOS2 gene allele StAOS2-12. In some embodiments, the methods and compositions include a mutated AOS2 gene allele StAOS2-7. In some embodiments, the methods and compositions include a mutated AOS2 gene allele StAOS2-8. In some embodiments, the methods and compositions include a mutated AOS2 gene allele StAOS2 CB1. In some embodiments, the methods and compositions include a mutated AOS2 gene allele StAOS2 CB2. In some embodiments, the methods and compositions include a mutated AOS2 gene allele StAOS2 CB3. In some embodiments, the methods and compositions include a mutated AOS2 gene allele StAOS2 CB4. In some embodiments, the methods and compositions include a mutated AOS2 gene allele StAOS2 CB5. In some embodiments, the methods and compositions include a mutated AOS2 gene allele StAOS2 CB6. In some embodiments, the methods and compositions include a mutated AOS2 gene allele StAOS2 CB7. In some embodiments, the methods and compositions include a mutated AOS2 gene allele StAOS2 CB8. In some embodiments, the methods and compositions include a mutated AOS2 gene allele StAOS2 CB9. In some embodiments, the methods and compositions include a mutated AOS2 gene allele StAOS2 CB10. In some embodiments, the methods and compositions include a mutated AOS2 gene allele StAOS2 CB11. In some embodiments, the methods and compositions include a mutated AOS2 gene allele StAOS2 CB12. In some embodiments, the methods and compositions include a mutated AOS2 gene allele StAOS2 CB13. In some embodiments, the methods and compositions include a mutated AOS2 gene allele StAOS2 CB14. In some embodiments, the methods and compositions include a mutated AOS2 gene allele StAOS2 CB15. In some embodiments, the methods and compositions include a mutated AOS2 gene allele StAOS2 CB16. In some embodiments, the methods and compositions include a mutated AOS2 gene allele StAOS2 CB17. In some embodiments, the methods and compositions include a mutated AOS2 gene allele StAOS2 CB18. In some embodiments, the methods and compositions include a mutated AOS2 gene allele StAOS2 CB19. In some embodiments, the methods and compositions include a mutated AOS2 gene allele StAOS2 CB20.

In conjunction with any of the various aspects, embodiments, compositions and methods disclosed herein, a plant or plant cell that includes a mutated AOS2 gene has at least one gene/allele having an A at position 691. In some embodiments, a plant or plant cell that includes a mutated AOS2 gene has at least two genes/alleles having an A at position 691. In some embodiments, a plant or plant cell that includes a mutated AOS2 gene has at least three genes/alleles having an A at position 691. In some embodiments, a plant or plant cell that includes a mutated AOS2 gene has at least four genes/alleles having an A at position 691. In some embodiments, the plant or plant cell is a potato. In some embodiments, the plant or plant cell is a Desiree potato. In some embodiments, the plant or plant cell is a Bintje potato. In some embodiments, the gene(s)/allele(s) are not a transgene(s). In some embodiments, the AOS2 gene is SEQ ID NO: 1, 3, 5, 7, 9, 11, 13, 15, 17, 19, 21, 23, 25, 27, 29, 31, 33, 35, 37, 39, 41, 43, 45, 47 or 49.

In conjunction with any of the various aspects, embodiments, compositions and methods disclosed herein, a plant or plant cell that includes a mutated AOS2 gene has at least one gene/allele having a C at position 692. In some embodiments, a plant or plant cell that includes a mutated AOS2 gene has at least two genes/alleles having a C at position 692. In some embodiments, a plant or plant cell that includes a mutated AOS2 gene has at least three genes/alleles having an a C at position 692. In some embodiments, a plant or plant cell that includes a mutated AOS2 gene has at least four genes/alleles having a C at position 692. In some embodiments, the plant or plant cell is a potato. In some embodiments, the plant or plant cell is a Desiree potato. In some embodiments, the plant or plant cell is a Bintje potato. In some embodiments, the gene(s)/allele(s) are not a transgene(s). In some embodiments, the AOS2 gene is SEQ ID NO: 1, 3, 5, 7, 9, 11, 13, 15, 17, 19, 21, 23, 25, 27, 29, 31, 33, 35, 37, 39, 41, 43, 45, 47 or 49.

In conjunction with any of the various aspects, embodiments, compositions and methods disclosed herein, a plant or plant cell that includes a mutated AOS2 gene has at least one gene/allele having an A at position 691 and a C at position 692. In some embodiments, a plant or plant cell that includes a mutated AOS2 gene has at least two genes/alleles having A at position 691 and a C at position 692. In some embodiments, a plant or plant cell that includes a mutated AOS2 gene has at least three genes/alleles having an A at position 691 and a C at position 692. In some embodiments, a plant or plant cell that includes a mutated AOS2 gene has at least four genes/alleles having A at position 691 and a C at position 692. In some embodiments, the plant or plant cell is a potato. In some embodiments, the plant or plant cell is a Desiree potato. In some embodiments, the plant or plant cell is a Bintje potato. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, the plant or plant cell includes a mutated AOS2 gene having an A at position 691. In some embodiments, the plant or plant cell is a polyploidy. In some embodiments, at least one mutated AOS2 gene/allele of a polyploid plant has an A at position 691. In some embodiments, at least two mutated AOS2 genes/alleles of a polyploid plant have an A at position 691. In some embodiments, at least three mutated AOS2 genes/alleles of a polyploid plant have an A at position 691. In some embodiments, at least four mutated AOS2 genes/alleles of a polyploid plant have an A at position 691. In some embodiments, at least five mutated AOS2 genes/alleles of a polyploid plant have an A at position 691. In some embodiments, at least six mutated AOS2 genes/alleles of a polyploid plant have an A at position 691. In some embodiments, at least seven mutated AOS2 genes/alleles of a polyploid plant have an A at position 691. In some embodiments, at least eight mutated AOS2 genes/alleles of a polyploid plant have an A at position 691. In some embodiments, at least nine mutated AOS2 genes/alleles of a polyploid plant have an A at position 691. In some embodiments, at least ten mutated AOS2 genes/alleles of a polyploid plant have an A at position 691. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a potato or potato cell includes a mutated AOS2 gene having an A at position 691. In some embodiments, at least one mutated AOS2 gene/allele of a potato or potato cell has an A at position 691. In some embodiments, at least two mutated AOS2 genes/alleles of a potato or potato cell have an A at position 691. In some embodiments, at least three mutated AOS2 genes/alleles of a potato or potato cell have an A at position 691. In some embodiments, at least four mutated AOS2 genes/alleles of a potato or potato cell have an A at position 691. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a Desiree potato or Desiree potato cell includes a mutated AOS2 gene having an A at position 691. In some embodiments, at least one mutated AOS2 gene/allele of a Desiree potato or Desiree potato cell has an A at position 691. In some embodiments, at least two mutated AOS2 genes/alleles of a Desiree potato or Desiree potato cell have an A at position 691. In some embodiments, at least three mutated AOS2 genes/alleles of a Desiree potato or Desiree potato cell have an A at position 691. In some embodiments, at least four mutated AOS2 genes/alleles of a Desiree potato or Desiree potato cell have an A at position 691. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a Bintje potato or Bintje potato cell includes a mutated AOS2 gene having an A at position 691. In some embodiments, at least one mutated AOS2 gene/allele of a Bintje potato or Bintje potato cell has an A at position 691. In some embodiments, at least two mutated AOS2 genes/alleles of a Bintje potato or Bintje potato cell have an A at position 691. In some embodiments, at least three mutated AOS2 genes/alleles of a Bintje potato or Bintje potato cell have an A at position 691. In some embodiments, at least four mutated AOS2 genes/alleles of a Bintje potato or Bintje potato cell have an A at position 691. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, the plant or plant cell includes a mutated AOS2 gene having an A at position 692. In some embodiments, the plant or plant cell is a polyploidy. In some embodiments, at least one mutated AOS2 gene/allele of a polyploid plant has a C at position 692. In some embodiments, at least two mutated AOS2 genes/alleles of a polyploid plant have a C at position 692. In some embodiments, at least three mutated AOS2 genes/alleles of a polyploid plant have a C at position 692. In some embodiments, at least four mutated AOS2 genes/alleles of a polyploid plant have a C at position 692. In some embodiments, at least five mutated AOS2 genes/alleles of a polyploid plant have a C at position 692. In some embodiments, at least six mutated AOS2 genes/alleles of a polyploid plant have a C at position 692. In some embodiments, at least seven mutated AOS2 genes/alleles of a polyploid plant have a C at position 692. In some embodiments, at least eight mutated AOS2 genes/alleles of a polyploid plant have a C at position 692. In some embodiments, at least nine mutated AOS2 genes/alleles of a polyploid plant have a C at position 692. In some embodiments, at least ten mutated AOS2 genes/alleles of a polyploid plant have a C at position 692. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a potato or potato cell includes a mutated AOS2 gene having a C at position 692. In some embodiments, at least one mutated AOS2 gene/allele of a potato or potato cell has a C at position 692. In some embodiments, at least two mutated AOS2 genes/alleles of a potato or potato cell have a C at position 692. In some embodiments, at least three mutated AOS2 genes/alleles of a potato or potato cell have a C at position 692. In some embodiments, at least four mutated AOS2 genes/alleles of a potato or potato cell have a C at position 692. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a Desiree potato or Desiree potato cell includes a mutated AOS2 gene having a C at position 692. In some embodiments, at least one mutated AOS2 gene/allele of a Desiree potato or Desiree potato cell has a C at position 692. In some embodiments, at least two mutated AOS2 genes/alleles of a Desiree potato or Desiree potato cell have a C at position 692. In some embodiments, at least three mutated AOS2 genes/alleles of a Desiree potato or Desiree potato cell have a C at position 692. In some embodiments, at least four mutated AOS2 genes/alleles of a Desiree potato or Desiree potato cell have a C at position 692. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, a Bintje potato or Bintje potato cell includes a mutated AOS2 gene having a C at position 692. In some embodiments, at least one mutated AOS2 gene/allele of a Bintje potato or Bintje potato cell has a C at position 692. In some embodiments, at least two mutated AOS2 genes/alleles of a Bintje potato or Bintje potato cell have a C at position 692. In some embodiments, at least three mutated AOS2 genes/alleles of a Bintje potato or Bintje potato cell have a C at position 692. In some embodiments, at least four mutated AOS2 genes/alleles of a Bintje potato or Bintje potato cell have a C at position 692. In some embodiments, the gene(s)/allele(s) are not a transgene(s). In some embodiments, the AOS2 gene is SEQ ID NO: 2, 4, 6, 8, 10, 12, 14, 16, 18, 20, 22, 24, 26, 28, 30, 32, 34, 36, 38, 40, 42, 44, 46, 48 or 50.

In conjunction with any of the various aspects, embodiments, compositions and methods disclosed herein, the plant or plant cell is tetraploid. In some embodiments, the tetraploid plant or plant cell includes mutations in AOS2 gene(s)/allele(s) that produce a genotype of AAAA/CCCC at nucleotide positions corresponding to 691/692 of SEQ ID NO: 2. In some embodiments, a tetraploid plant or plant cell includes mutations in AOS2 gene(s)/allele(s) that produce a genotype of AAAG/CCCG at nucleotide positions corresponding to 691/692 of SEQ ID NO: 2. In some embodiments, a tetraploid plant or plant cell includes mutations in AOS2 gene(s)/allele(s) that produce a genotype of AAGG/CCCG at nucleotide positions corresponding to 691/692 of SEQ ID NO: 2. In some embodiments, a tetraploid plant or plant cell includes mutations in AOS2 gene(s)/allele(s) that produce a genotype of AAAG/CCGG at nucleotide positions corresponding to 691/692 of SEQ ID NO: 2. In some embodiments, a tetraploid plant or plant cell includes mutations in AOS2 gene(s)/allele(s) that produce a genotype of AAGG/CCGG at nucleotide positions corresponding to 691/692 of SEQ ID NO: 2. In some embodiments, a tetraploid plant or plant cell includes mutations in AOS2 gene(s)/allele(s) that produce a genotype of AAAG/CCCG at nucleotide positions corresponding to 691/692 of SEQ ID NO: 2. In some embodiments, a tetraploid plant or plant cell includes mutations in AOS2 gene(s)/allele(s) that produce a genotype of AAGG/CCCG at nucleotide positions corresponding to 691/692 of SEQ ID NO: 2. In some embodiments, a tetraploid plant or plant cell includes mutations in AOS2 gene(s)/allele(s) that produce a genotype of AAAG/CCGG at nucleotide positions corresponding to 691/692 of SEQ ID NO: 2. In some embodiments, a tetraploid plant or plant cell includes mutations in AOS2 gene(s)/allele(s) that produce a genotype of AAGG/CCGG at nucleotide positions corresponding to 691/692 of SEQ ID NO: 2. In some embodiments, a tetraploid plant or plant cell includes mutations in AOS2 gene(s)/allele(s) that produce a genotype of AAAG/CGGG at nucleotide positions corresponding to 691/692 of SEQ ID NO: 2. In some embodiments, a tetraploid plant or plant cell includes mutations in AOS2 gene(s)/allele(s) that produce a genotype of AAGG/CGGG at nucleotide positions corresponding to 691/692 of SEQ ID NO: 2. In some embodiments, a tetraploid plant or plant cell includes mutations in AOS2 gene(s)/allele(s) that produce a genotype of AGGG/CGGG at nucleotide positions corresponding to 691/692 of SEQ ID NO: 2. In some embodiments, a tetraploid plant or plant cell includes mutations in AOS2 gene(s)/allele(s) that produce a genotype of AAGG/GGGG at nucleotide positions corresponding to 691/692 of SEQ ID NO: 2. In some embodiments, a tetraploid plant or plant cell includes mutations in AOS2 gene(s)/allele(s) that produce a genotype of AGGG/GGGG at nucleotide positions corresponding to 691/692 of SEQ ID NO: 2. In some embodiments, a tetraploid plant or plant cell includes mutations in AOS2 gene(s)/allele(s) that produce a genotype of GGGG/GGGG at nucleotide positions corresponding to 691/692 of SEQ ID NO: 2. In some embodiments, the plant or plant cell is non-transgenic. In some embodiments, the plant or plant cell is transgenic.

In conjunction with any of the various aspects, embodiments, compositions and methods disclosed herein, the plant or plant cell is a potato plant or plant cell. In some embodiments, the potato plant or potato cell includes mutations in AOS2 gene(s)/allele(s) that produce a genotype of AAAA/CCCC at nucleotide positions corresponding to 691/692 of SEQ ID NO: 2. In some embodiments, a potato plant or potato cell includes mutations in AOS2 gene(s)/allele(s) that produce a genotype of AAAG/CCCG at nucleotide positions corresponding to 691/692 of SEQ ID NO: 2. In some embodiments, a potato plant or potato cell includes mutations in AOS2 gene(s)/allele(s) that produce a genotype of AAGG/CCCG at nucleotide positions corresponding to 691/692 of SEQ ID NO: 2. In some embodiments, a tetraploid potato plant or potato cell includes mutations in AOS2 gene(s)/allele(s) that produce a genotype of AAAG/CCGG at nucleotide positions corresponding to 691/692 of SEQ ID NO: 2. In some embodiments, a potato plant or potato cell includes mutations in AOS2 gene(s)/allele(s) that produce a genotype of AAGG/CCGG at nucleotide positions corresponding to 691/692 of SEQ ID NO: 2. In some embodiments, a potato plant or potato cell includes mutations in AOS2 gene(s)/allele(s) that produce a genotype of AAAG/CCGG at nucleotide positions corresponding to 691/692 of SEQ ID NO: 2. In some embodiments, a potato plant or potato cell includes mutations in AOS2 gene(s)/allele(s) that produce a genotype of AAGG/CCCG at nucleotide positions corresponding to 691/692 of SEQ ID NO: 2. In some embodiments, a potato plant or potato cell includes mutations in AOS2 gene(s)/allele(s) that produce a genotype of AAAG/CCGG at nucleotide positions corresponding to 691/692 of SEQ ID NO: 2. In some embodiments, a potato plant or potato cell includes mutations in AOS2 gene(s)/allele(s) that produce a genotype of AAGG/CCGG at nucleotide positions corresponding to 691/692 of SEQ ID NO: 2. In some embodiments, a potato plant or potato cell includes mutations in AOS2 gene(s)/allele(s) that produce a genotype of AAAG/CGGG at nucleotide positions corresponding to 691/692 of SEQ ID NO: 2. In some embodiments, a potato plant or potato cell includes mutations in AOS2 gene(s)/allele(s) that produce a genotype of AAGG/CGGG at nucleotide positions corresponding to 691/692 of SEQ ID NO: 2. In some embodiments, a potato plant or potato cell includes mutations in AOS2 gene(s)/allele(s) that produce a genotype of AGGG/CGGG at nucleotide positions corresponding to 691/692 of SEQ ID NO: 2. In some embodiments, a potato plant or potato cell includes mutations in AOS2 gene(s)/allele(s) that produce a genotype of AAGG/GGGG at nucleotide positions corresponding to 691/692 of SEQ ID NO: 2. In some embodiments, a potato plant or potato cell includes mutations in AOS2 gene(s)/allele(s) that produce a genotype of AGGG/GGGG at nucleotide positions corresponding to 691/692 of SEQ ID NO: 2. In some embodiments, a potato plant or potato cell includes mutations in AOS2 gene(s)/allele(s) that produce a genotype of GGGG/GGGG at nucleotide positions corresponding to 691/692 of SEQ ID NO: 2. In certain embodiments, the potato is a Desiree potato. In certain embodiments, the potato is a Bintje potato In some embodiments, the plant or plant cell is non-transgenic. In some embodiments, the plant or plant cell is transgenic.

In conjunction with any of the various aspects, embodiments, compositions and methods disclosed herein, the plant or plant cell is a *Solanum tuberosum* potato plant or plant cell.

In conjunction with any of the aspects, embodiments, compositions and methods disclosed herein, a plant having a plant cell that includes a mutated AOS2 gene may have a early, mid, mid-early or late maturity rating. In certain embodiments, the plant or plant cell is non-transgenic. In certain embodiments, the plant or plant cell is transgenic. In certain embodiments, a plant or plant cell includes a mutation in the coding sequence of the AOS2 gene. In certain embodiments, a plant or plant cell includes a mutation in the non-coding sequence of the AOS2 gene. In certain embodiments, a plant or plant cell includes a mutation upstream of the AOS2 gene coding sequence.

As used herein, the term "gene" refers to a DNA sequence that includes control and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. The term "gene" also refers and encompasses the respective alleles of the plant cultivar or plant line.

An allele is one of several alternative forms of a gene or nucleotide sequence at a specific variation at a given position within the nucleic acid sample. An allele may be represented by one or more base changes at a given locus (e.g., a SNP). For example, at each autosomal locus a diploid individual possesses 2 alleles, one maternally inherited, the other paternally.

As used herein, the term "pathogen" refers to an infectious agent that causes disease in its host. In certain embodiments, a pathogen is *Phytophthora infestans*.

As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

As used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

A nucleobase is a base, which in certain preferred embodiments is a purine, pyrimidine, or a derivative or analog thereof. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; preferably at least a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridize by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3' end and a 5' end, and when an oligonucleobase strand is coextensive with a chain, the 3' and 5' ends of the strand are also 3' and 5' termini of the chain.

As used herein, the term "gene repair oligonucleobase" or "GRON" refers to oligonucleobases, including mixed duplex oligonucleotides, non-nucleotide containing molecules, single stranded oligodeoxynucleotides and other gene repair molecules.

As used herein, the term "isolated" when referring to a nucleic acid (e.g., an oligonucleotide such as RNA, DNA, or a mixed polymer), refers to a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, the term "amino acid sequence" refers to a polypeptide or protein sequence. The convention "AAwt###AAmut" is used to indicate a mutation that results in the wild-type amino acid AAwt at position ### in the polypeptide being replaced with mutant AAmut.

As used herein, the term "complement" refers to the complementary sequence to a nucleic acid according to standard Watson/Crick pairing rules. A complement sequence can also be a sequence of RNA complementary to the DNA sequence or its complement sequence, and can also be a cDNA.

As used herein, the term "substantially complementary" refers to two sequences that hybridize under near stringent hybridization conditions. The skilled artisan will understand that substantially complementary sequences need not hybridize along their entire length.

As used herein, the term "codon" refers to a sequence of three adjacent nucleotides (either RNA or DNA) constituting the genetic code that determines the addition of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. "Wild-type" may also refer to the sequence at a specific nucleotide position or positions, or the sequence at a particular codon position or positions, or the sequence at a particular amino acid position or positions.

As used herein, the term "mutant," or "modified" refers to a nucleic acid or protein which displays modifications in sequence and or functional properties (i.e., altered characteristics) when compared to the wild-type gene or gene product. "Mutant," or "modified" also refers to the sequence at a specific nucleotide position or positions, or the sequence at a particular codon position or positions, or the sequence at a particular amino acid position or positions which displays modifications in sequence and or functional properties (i.e., altered characteristics) when compared to the wild-type gene or gene product.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

As used herein, the term "heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, e.g., nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In certain embodiments, the smaller peak is at least about 10% of the larger peak. In certain embodiments, the smaller peak is at least about 5% of the larger peak. In certain embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, e.g., nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in a single nucleotide in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

BRIEF DESCRIPTION OF THE FIGURES

FIG. 1 is the amino acid sequence of *Solanum tuberosum* AOS2 protein, allele 1 (SEQ ID NO: 1).

FIG. 2 is the nucleic acid sequence of *Solanum tuberosum* AOS2 gene, allele 1 (SEQ ID NO: 2).

FIG. 3 is the amino acid sequence of *Solanum tuberosum* AOS2 protein, allele 6 (SEQ ID NO: 3).

FIG. 4 is the nucleic acid sequence of *Solanum tuberosum* AOS2 gene, allele 6 (SEQ ID NO: 4).

FIG. 5 is the amino acid sequence of *Solanum tuberosum* AOS2 protein, allele 7 (SEQ ID NO: 5).

FIG. 6 is the nucleic acid sequence of *Solanum tuberosum* AOS2 gene, allele 7 (SEQ ID NO: 6).

FIG. 7 is the amino acid sequence of *Solanum tuberosum* AOS2 protein, allele 8 (SEQ ID NO: 7).

FIG. 8 is the nucleic acid sequence of *Solanum tuberosum* AOS2 gene, allele 8 (SEQ ID NO: 8).

FIG. 9 is the amino acid sequence of *Solanum tuberosum* AOS2 protein, allele 12 (SEQ ID NO: 9).

FIG. 10 is the nucleic acid sequence of *Solanum tuberosum* AOS2 gene, allele 12 (SEQ ID NO: 10).

FIG. 11 is the amino acid sequence of *Solanum tuberosum* AOS2 protein, allele CB1 (SEQ ID NO: 11).

FIG. 12 is the nucleic acid sequence of *Solanum tuberosum* AOS2 gene, allele CB1 (SEQ ID NO: 12).

FIG. 13 is the amino acid sequence of *Solanum tuberosum* AOS2 protein, allele CB2 (SEQ ID NO: 13).

FIG. 14 is the nucleic acid sequence of *Solanum tuberosum* AOS2 gene, allele CB2 (SEQ ID NO: 14).

FIG. 15 is the amino acid sequence of *Solanum tuberosum* AOS2 protein, allele CB3 (SEQ ID NO: 15).

FIG. 16 is the nucleic acid sequence of *Solanum tuberosum* AOS2 gene, allele CB3 (SEQ ID NO: 16).

FIG. 17 is the amino acid sequence of *Solanum tuberosum* AOS2 protein, allele CB4 (SEQ ID NO: 17).

FIG. 18 is the nucleic acid sequence of *Solanum tuberosum* AOS2 gene, allele CB4 (SEQ ID NO: 18).

FIG. 19 is the amino acid sequence of *Solanum tuberosum* AOS2 protein, allele CB5 (SEQ ID NO: 19).

FIG. 20 is the nucleic acid sequence of *Solanum tuberosum* AOS2 gene, allele CB5 (SEQ ID NO: 20).

FIG. 21 is the amino acid sequence of *Solanum tuberosum* AOS2 protein, allele CB6 (SEQ ID NO: 21).

FIG. 22 is the nucleic acid sequence of *Solanum tuberosum* AOS2 gene, allele CB6 (SEQ ID NO: 22).

FIG. 23 is the amino acid sequence of *Solanum tuberosum* AOS2 protein, allele CB7 (SEQ ID NO: 23).

FIG. 24 is the nucleic acid sequence of *Solanum tuberosum* AOS2 gene, allele CB7 (SEQ ID NO: 24).

FIG. 25 is the amino acid sequence of *Solanum tuberosum* AOS2 protein, allele CB8 (SEQ ID NO: 25).

FIG. 26 is the nucleic acid sequence of *Solanum tuberosum* AOS2 gene, allele CB8 (SEQ ID NO: 26).

FIG. 27 is the amino acid sequence of *Solanum tuberosum* AOS2 protein, allele CB9 (SEQ ID NO: 27).

FIG. 28 is the nucleic acid sequence of *Solanum tuberosum* AOS2 gene, allele CB9 (SEQ ID NO: 28).

FIG. 29 is the amino acid sequence of *Solanum tuberosum* AOS2 protein, allele CB10 (SEQ ID NO: 29).

FIG. 30 is the nucleic acid sequence of *Solanum tuberosum* AOS2 gene, allele CB10 (SEQ ID NO: 30).

FIG. 31 is the amino acid sequence of *Solanum tuberosum* AOS2 protein, allele CB11 (SEQ ID NO: 31).

FIG. 32 is the nucleic acid sequence of *Solanum tuberosum* AOS2 gene, allele CB11 (SEQ ID NO: 32).

FIG. 33 is the amino acid sequence of *Solanum tuberosum* AOS2 protein, allele CB12 (SEQ ID NO: 33).

FIG. 34 is the nucleic acid sequence of *Solanum tuberosum* AOS2 gene, allele CB12 (SEQ ID NO: 34).

FIG. 35 is the amino acid sequence of *Solanum tuberosum* AOS2 protein, allele CB13 (SEQ ID NO: 35).

FIG. 36 is the nucleic acid sequence of *Solanum tuberosum* AOS2 gene, allele CB13 (SEQ ID NO: 36).

FIG. 37 is the amino acid sequence of *Solanum tuberosum* AOS2 protein, allele CB14 (SEQ ID NO: 37).

FIG. 38 is the nucleic acid sequence of *Solanum tuberosum* AOS2 gene, allele CB14 (SEQ ID NO: 38).

FIG. 39 is the amino acid sequence of *Solanum tuberosum* AOS2 protein, allele CB15 (SEQ ID NO: 39).

FIG. 40 is the nucleic acid sequence of *Solanum tuberosum* AOS2 gene, allele CB15 (SEQ ID NO: 40).

FIG. 41 is the amino acid sequence of *Solanum tuberosum* AOS2 protein, allele CB16 (SEQ ID NO: 41).

FIG. 42 is the nucleic acid sequence of *Solanum tuberosum* AOS2 gene, allele CB16 (SEQ ID NO: 42).

FIG. 43 is the amino acid sequence of *Solanum tuberosum* AOS2 protein, allele CB17 (SEQ ID NO: 43).

FIG. 44 is the nucleic acid sequence of *Solanum tuberosum* AOS2 gene, allele CB17 (SEQ ID NO: 44).

FIG. 45 is the amino acid sequence of *Solanum tuberosum* AOS2 protein, allele CB18 (SEQ ID NO: 45).

FIG. 46 is the nucleic acid sequence of *Solanum tuberosum* AOS2 gene, allele CB18 (SEQ ID NO: 46).

FIG. 47 is the amino acid sequence of *Solanum tuberosum* AOS2 protein, allele CB19 (SEQ ID NO: 47).

FIG. 48 is the nucleic acid sequence of *Solanum tuberosum* AOS2 gene, allele CB19 (SEQ ID NO: 48).

FIG. 49 is the amino acid sequence of *Solanum tuberosum* AOS2 protein, allele CB20 (SEQ ID NO: 49).

FIG. 50 is the nucleic acid sequence of *Solanum tuberosum* AOS2 gene, allele CB20 (SEQ ID NO: 50).

DETAILED DESCRIPTION OF THE INVENTION

Allene Oxidase Synthase Proteins

Allene oxide synthase 2 (A052) proteins belong to cytochrome P450 superfamily and comprise the CYP74 group specialized in the metabolism of hydroperoxides. These proteins act in the plant oxylipin biosynthesis pathway which is important for generating substances that play important roles in a variety of plant stress and developmental processes including pathogen/insect attack as well as plant fertility. Hughes et al., Chembiochem 10:1122 (2009). These enzymes are coded by three distinct genes AOS1, 2 and 3, which catalyze the respective production of C6 aldehydes, Jasmonic acid (JA) and C9 aldehydes. AOS1 and AOS2 are chloroplast located enzymes while the expression of AOS3 is reported to be confined to below ground organs in potato. Stumpe et al., Plant J 47: 883 (2006). All three are unusual cytochrome P450 proteins, which do not bind molecular oxygen but use already oxygenated fatty acid hydroperoxide substrates as the oxygen donor. Schaller and Stintzi, Phytochemistry 70:1532 (2009). AOS2 protein catalyzes the determinate step in Jasmonic acid (JA) formation in plants. Jasmonic acid is well known for its important role in plant defense induction in response to plant wounding and pathogen attack.

Allene Oxidase Synthase 2 (AOS2) Alleles and SNPs Associated with Pathogen Resistance and/or Tolerance AOS2 gene product is known as Allene Oxide Synthase 2 and catalyzes the conversion of hydroperoxides to allene oxide, the committed step in jasmonic acid (JA) biosynthesis. Jasmonic acid and its derivatives collectively known as jasmonates are key signaling molecules involved in the induction of plant defense reactions in response to pathogen attack or wounding. Loss of JA production or sensitivity to it, results in the enhanced disease susceptibility of plants—e.g., *Arabidopsis* coi1 mutants (Feys et al., Plant Cell. 6(5):751-759 (1994)). In potato, JA application inhibits sporangial germination and mycelial growth of *Phytophthora infestans* (Pi). The *Solanum tuberosum* AOS2 (StAOS2) gene is mapped to a quantitative resistance locus (QRL) on the potato chromosome XI that harbors the R3a resistance gene that acts in the race specific disease resistance against Pi. Pajerowska et al., Planta 228:293 (2008). In addition, silencing of the AOS2 gene in potato led to highly reduced levels of jasmonic acid in wounded plants and increased lesion development when infected with Pi. (Pajerowska-Mukhtar et al., 2008, Planta 228:293 (2008). StAOS2 gene complemented an AOS2 gene knock out line of *Arabidopsis thaliana* which lacked JA and this complemented plant line, when compared to the gene deleted line, exhibited enhanced resistance to a bacterial pathogen of *Arabidopsis*. (Pajerowska-Mukhtar et al., 2008).

Sequences of five AOS2 alleles originating from diploid potato utilized in pre-breeding populations are known. Pajerowska et al., (2008); Pajerowska-Mukhtar et al., Genetics 181:1115 (2009). These five different alleles are categorized into three groups, "resistant" (StAOS2-1, StAOS2-6), "neutral" (StAOS2-12) and "susceptible" (StAOS2-7, StAOS2-8). In the above mentioned published studies, two populations of F1 progenies of heterozygous parent lines were categorized as quantitative resistant, quantitative neutral and quantitative susceptible according to late blight development. Later, these categories were linked with the specific alleles of StAOS2 gene listed above. Complementation analyses of the *Arabidopsis* JA deficient mutant with the StAOS2 alleles resulted in restoring JA production (and 12-oxo-phytodienoate (OPDA) reductase, an intermediate in JA biosynthesis). Additionally, complementation by "resistant" alleles led to a 10-fold increase in JA production compared to the levels produced by the "susceptible" alleles. The "neutral" allele had intermediate levels of JA and OPDA. Additionally, a pathogen assay utilizing *Erwinia carotovora* ssp. *carotovora* on these complemented *Arabidopsis* lines corroborated the JA production profile by exhibiting 10 times more bacterial growth in plants complemented with the "susceptible" alleles than by the "resistant" alleles.

Comparison of the amino acid sequence of the five different alleles revealed the presence of multiple amino acid differences along the otherwise highly conserved sequence of the AOS2 gene alleles. Twenty five amino acid variations and one InDel (insertion/deletion polymorphism) are present in the five alleles with five amino acids (N76D, V289S, V292A, M328L and T495K) and the InDel being specific to the "resistant" alleles based on numbering of the susceptible allele StAOS2-7 (SEQ ID NO: 5). No amino acid variation was specific to the "susceptible" alleles. Three substitutions (Y145F, T231I/G and K394T) occurred in the neutral allele. Pajerowska et al., Planta 228:293 (2008).

The amino acid changes T495K and N76D are in close proximity to the active site. F256V polymorphism between StAOS2-1 and StAOS2-6 is proposed to explain the slight inferior performance of StAOS2-6 based on its location relative to the substrate binding pocket. In addition, Y145F of the neutral allele may contribute towards its intermediary activity profile since this residue is adjacent to the active site Pajerowska-Mukhtar et al., Planta 228:293 (2008).

An evaluation of the field resistance of potato cultivars to Pi revealed the AOS2 gene to be an important locus that governs the resistance phenotype of certain cultivars Pajerowska-Mukhtar et al., Genetics 181:1115 (2009). Two SNPs, StAOS2_SNP691(A) and StAOS2_SNP692(C) are correlated with field resistance (rAUDPC value of 0.15 which indicates very low disease establishment). In this study, the most resistant genotype to late blight had the homozygous AAAA/CCCC genotype and a positive correlation was observed with the degree of deviation from this and the severity of late blight development. These two SNPs are also reported to be associated with plant maturity (PM). In general, a positive correlation exists between potato maturity rating (early vs. late maturing cultivars) and Pi resistance. Wastie R L, Adv Plant Pathology 7: 193 (1999). However, those individuals homozygous for the A and C alleles fall into the mid-early maturity class thus separating them from the highly undesired late maturity phenotype. Pajerowska-Mukhtar et al., Genetics 181:1115 (2009).

*Solanum tuberosum* is a quite heterozygous tetraploid, which makes it difficult to transfer desirable traits between cultivars for expression in progeny. In addition, some species of *Solanum* with natural resistance to insect pests and diseases, such as several found in Peru and Central America, are diploid and are not easily bred with the tetraploid *Solanum tuberosum*. The autotetraploid genome and asexual propagation used to breed potatoes creates challenges in developing new cultivars with desired traits. Resistance traits demonstrated in diploid species, e.g., *Solanum bulbocastanum*, are inaccessible for breeding because the species has an endosperm balance number of 1 compared to *S. tuberosum* has an endosperm balance number of 4.

The use of RTDS™ in potatoes has some of the advantages of transgenic genetic engineering over traditional breeding. RTDS™ allows manipulation of the endogenous AOS2 genes, eliminating the need for backcrossing required to remove undesirable traits in traditional breeding. RTDS™ allows introduction of mutations in genes conferring resistance and/or tolerance demonstrated by other species that do not have a compatible ploidy with *S. tuberosum*. In addition, RTDS™ has advantages over transgenic genetic engineering. RTDS™ is capable of manipulating the endogenous genes, as opposed to introducing a foreign transgene.

Rapid Trait Development System (RTDS™)

In any of the various aspects and embodiments of the compositions and methods disclosed herein, mutations in genes and proteins may be made using, e.g., the Rapid Trait Development System (RTDS™) technology developed by Cibus. In combination or alone, plants containing any of the mutations disclosed herein can form the basis of new pathogen resistant and/or tolerant products. Also provided are seeds/vegetative material produced from the mutated plants in which the AOS2 genes are either homozygous or heterozygous for the mutations. The mutations disclosed herein can be in combination with any other mutation known or with mutations discovered in the future.

In some embodiments, RTDS™ is based on altering a targeted gene by utilizing the cell's own gene repair system to specifically modify the gene sequence in situ and not insert foreign DNA and gene expression control sequences. This procedure may effect a precise change in the genetic sequence while the rest of the genome is left unaltered. In contrast to conventional transgenic GMOs, there is no integration of foreign genetic material, nor is any foreign genetic material left in the plant. In many embodiments, the changes in the genetic sequence introduced by RTDS™ are not randomly inserted. Since affected genes remain in their native location, no random, uncontrolled or adverse pattern of expression occurs.

The RTDS™ process is carried out using a chemically synthesized oligonucleotide (a gene repair oligonucleobase (GRON)) which may be composed of both DNA and modified RNA bases as well as other chemical moieties, and is designed to hybridize at the targeted gene location to create a mismatched base-pair(s). This mismatched base-pair acts as a signal to attract the cell's own natural gene repair system to that site and correct (replace, insert or delete) the designated nucleotide(s) within the gene. Once the correction process is complete the GRON molecule is degraded and the now-modified or repaired gene continues to be expressed under that gene's normal endogenous control mechanisms.

Gene Repair Oligonucleobases ("GRON")

The methods and compositions disclosed herein can be practiced or made with "gene repair oligonucleobases" for example, having the conformations and chemistries as described in detail below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "single stranded oligodeoxynucleotide mutational vectors" (SSOMVs); "duplex mutational vectors;" and "heteroduplex mutational vectors."

Oligonucleobases having the conformations and chemistries described in U.S. Pat. No. 5,565,350 by Kmiec (Kmiec I) and U.S. Pat. No. 5,731,181 by Kmiec (Kmiec II), hereby incorporated by reference, are suitable for use as "gene repair oligonucleobases" of the present disclosure. The gene repair oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Additional gene repair molecules that can be used for the present invention are described in U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789, which are each hereby incorporated in their entirety.

In one embodiment, the gene repair oligonucleobase is a mixed duplex oligonucleotide (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a gene repair oligonucleobase by an unsubstituted phosphodiester linkage or any of the non-natural linkages taught by Kmiec I or Kmiec II.

In a particular embodiment of the present invention, the gene repair oligonucleobase is a mixed duplex oligonucleotides (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides (MDONs) having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three or more mismatched nucleotides. The mismatched nucleotides can be contiguous or alternatively can be separated by one, two, three, four, five, six, seven, eight, nine, ten, eleven, twelve, thirteen, fourteen or fifteen nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present disclosure, the gene repair oligonucleobase (GRON) is a single stranded oligodeoxynucleotide mutational vector (SSOMV), for example, such as disclosed in International Patent Application PCT/US2000/23457; U.S. Pat. Nos. 6,271,360; 6,479,292; and 7,060,500 which are incorporated by reference in their entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

In addition to the oligodeoxynucleotide, the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred reagents to make SSOMVs are the reagents sold as Cy3™ and Cy5™ by Glen Research, Sterling Va. (now GE Healthcare), which are blocked phosphoramidites that upon incorporation into an oligonucleotide yield 3,3,3',3'-tetramethyl N,N'-isopropyl substituted indomonocarbocyanine and indodicarbocyanine dyes, respectively. Cy3™ is particularly preferred. When the indocarbocyanine is N-oxyalkyl substituted it can be conveniently linked to the 5' terminal of the oligodeoxynucleotide as a phosphodiester with a 5' terminal phosphate. The chemistry of the dye linker between the dye and the oligodeoxynucleotide is not critical and is chosen for synthetic convenience. When the commercially available Cy3™ phosphoramidite is used as directed, the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical. The SSOMV can in addition have a 3' blocking substituent. Again the chemistry of the 3' blocking substituent is not critical.

The mutations herein described might also be obtained by mutagenesis (random, somatic or directed) and other DNA editing or recombination technologies including, but not limited to, gene targeting using site-specific homologous recombination by zinc finger nucleases, meganucleases or other nucleases.

Delivery of Gene Repair Oligonucleobases into Plant Cells

Any commonly known method used to transform a plant cell can be used for delivering the gene repair oligonucleobases. Illustrative methods are described below.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods of the present invention are described in International Publication WO 99/07865. In an illustrative technique, ice cold microcarriers (60 mg/mL), mixed duplex oligonucleotide (60 mg/mL) 2.5 M $CaCl_2$ and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 μg/μL microcarriers, 14-17 μg/mL mixed duplex oligonucleotide, 1.1-1.4 M $CaCl_2$ and 18-22 mM spermidine. Optimal results were observed under the conditions of 8 μg/μL microcarriers, 16.5 μg/mL mixed duplex oligonucleotide, 1.3 M $CaCl_2$ and 21 mM spermidine.

Gene repair oligonucleobases can also be introduced into plant cells for the practice of the present invention using microfibers to penetrate the cell wall and cell membrane. U.S. Pat. No. 5,302,523 to Coffee et al. describes the use of 30×0.5 μm and 10×0.3 μm silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2 μg) are suspended in 150 μL of plant culture medium containing about 10 μg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 h as is appropriate for the particular trait.

Protoplast Electroporation

In an alternative embodiment, the gene repair oligonucleobases can be delivered to the plant cell by electroporation of a protoplast derived from a plant part or suspension of plant cells. The protoplasts are formed by enzymatic treatment of a plant part, particularly a leaf, according to techniques well known to those skilled in the art. See, e.g., Gallois et al., 1996, Methods in Molecular Biology 55:89-107, Humana Press, Totowa, N.J.; Kipp et al., 1999, Methods in Molecular Biology 133:213-221, Humana Press, Totowa, N.J. The protoplasts need not be cultured in growth media prior to electroporation. Illustrative conditions for electroporation are $3 \times 10^5$ protoplasts in a total volume of 0.3 mL with a concentration of gene repair oligonucleobase of between 0.6-4 μg/mL.

Protoplast PEG-Mediated DNA Uptake

In an alternative embodiment, nucleic acids are taken up by plant protoplasts in the presence of the membrane-modifying agent polyethylene glycol, according to techniques well known to those skilled in the art (see, e.g., Gharti-Chhetri et al., Physiol. Plant. 85:345-351 (1992); Datta et al., Plant Molec. Biol. 20:619-629 (1992)).

Microinjection

In an alternative embodiment, the gene repair oligonucleobases can be delivered by injecting it with a microcapillary into plant cells or into protoplasts (see, e.g., Miki B. et al., Meth. Cell Science 12:139-144 (1989); Schnorf M., et al., Transgen. Res. 1:23-30 (1991)).

Transgenics

In any of the various aspects and embodiments of the compositions and methods disclosed herein, mutations in genes and proteins may be made using, e.g., transgenic technology. In some embodiments, the compositions and methods include a plant or plant cell having a transformed nucleic acid construct including a promoter operably linked to an AOS2 nucleotide disclosed herein. The methods disclosed herein may include introducing an AOS2 nucleic acid construct disclosed herein into at least one plant cell and regenerating a transformed plant therefrom. The nucleic acid construct comprises at least one nucleotide sequence that encodes a pathogen resistant and/or tolerant AOS2 protein as disclosed herein, particularly the nucleotide sequences of set forth in FIGS. 2 and 4, and fragments and variants thereof. The methods further involve the use of a promoter that is capable of driving gene expression in a plant cell. In one embodiment, such a promoter is a constitutive promoter or a tissue-preferred promoter. A plant produced by these methods may have increased or stabilized AOS2 activity and/or elevated jasmonic acid and/or 12-oxo-phytodienoic acid (OPDA) levels leading to enhanced resistance and/or tolerance to pathogens when compared to an untransformed plant. Thus, the methods find use in enhancing or increasing the resistance and/or tolerance of a plant to at least one pathogen.

In one embodiment, the methods for producing a pathogen resistant and/or tolerant plant include transforming a plant cell with a nucleic acid construct comprising a nucleotide sequence operably linked to a promoter that drives expression in a plant cell and regenerating a transformed plant from said transformed plant cell. The nucleotide sequence is selected from those nucleotide sequences that encode the pathogen resistant and/or tolerant AOS2 disclosed herein, particularly the nucleotide sequences set forth in FIGS. 2 and 4, and fragments and variants thereof. A pathogen resistant and/or tolerant plant produced by this method comprises enhanced resistance and/or tolerance, compared to an untransformed plant, to at least one pathogen, e.g., *Phytophthora infestans*.

The disclosed nucleic acid molecules can be used in nucleic acid constructs for the transformation of plants, for example, crop plants, such as *Solanum tuberosum*. In one embodiment, such nucleic acid constructs containing the nucleic acid molecules of the present disclosure can be used to produce transgenic plants to provide for resistance and/or tolerance to pathogens, such as *Phytophthora infestans*. The nucleic acid constructs can be used in expression cassettes, expression vectors, transformation vectors, plasmids and the like. The transgenic plants obtained following transformation with such constructs demonstrate increased resistance and/or tolerance to pathogens such as, e.g., *Phytophthora infestans*.

Constructs

The nucleic acid molecules disclosed herein (e.g., mutated AOS2 genes) can be used in the production of recombinant nucleic acid constructs. In one embodiment, the nucleic acid molecules of the invention can be used in the preparation of nucleic acid constructs, for example, expression cassettes for expression in the plant of interest.

Expression cassettes may include regulatory sequences operably linked to the AOS2 nucleic acid sequences disclosed herein. The cassette may additionally contain at least one additional gene to be co-transformed into the organism. Alternatively, the additional gene(s) can be provided on multiple expression cassettes.

The nucleic acid constructs may be provided with a plurality of restriction sites for insertion of the AOS2 nucleic acid sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant host and/or to the AOS2 nucleic acid sequences disclosed herein. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the AOS2 nucleic acid sequences disclosed herein, it is intended that the promoter is not the native or naturally occurring promoter for the operably linked AOS2 nucleic acid sequences disclosed herein. As used herein, a chimeric gene comprises a coding sequence operably linked to a transcription initiation region that is heterologous to the coding sequence.

In some embodiments, the AOS2 nucleic acid sequences disclosed herein are expressed using heterologous promoters, the native promoter sequences may be used in the preparation of the constructs. Such constructs would change expression levels of the AOS2 protein in the plant or plant cell. Thus, the phenotype of the plant or plant cell is altered.

Any promoter can be used in the preparation of constructs to control the expression of the AOS2 coding sequence, such as promoters providing for constitutive, tissue-preferred, inducible, or other promoters for expression in plants. Constitutive promoters include, for example, the core promoter of the Rsyn7 promoter and other constitutive promoters disclosed in WO 99/43 838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct AOS2 expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254 (3):337-343; Russell et al. (1997) Transgenic Res. 6(2):157-168; Rinehart et al. (1996) Plant Physiol. 1 12(3):1331-1341; Van Camp et al. (1996) Plant Physiol. 1 12(2):525-535; Canevascini et al. (1996) Plant Physiol. 112(2): 513-524; Yamamoto et al. (1994) Plant Cell Physiol. 35(5):773-778; Lam (1994) Results Probl. Cell Differ. 20:181-196; Orozco et al. (1993) Plant Mol Biol. 23(6):1129-1138; Matsuoka et al. (1993) Proc Natl. Acad. Sci. USA 90(20): 9586-9590; and Guevara-Garcia et al. (1993) Plant J. 4(3): 495-505.

The nucleic acid constructs may also include transcription termination regions. Where transcription terminations regions are used, any termination region may be used in the preparation of the nucleic acid constructs. For example, the termination region may be native to the transcriptional initiation region, may be native to the operably linked AOS2 sequence of interest, may be native to the plant host, or may be derived from another source (i.e., foreign or heterologous to the promoter, the AOS2 nucleic acid molecule of interest, the plant host, or any combination thereof). Examples of termination regions that are available for use in the constructs of the present invention include those from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

In some embodiments, the nucleic acids may be optimized for increased expression in the transformed plant. That is, the nucleic acids encoding the mutant AOS2 proteins can be synthesized using plant-preferred codons for improved expression. See, e.g., Campbell and Gowri (1990) Plant Physiol. 92:1-11 for a discussion of host-preferred codon usage. Methods are available in the art for synthesizing plant-preferred genes. See, e.g., U.S. Pat. Nos. 5,380,831, and 5,436,391, and Murray et al. (1989) Nucleic Acids Res. 17:477-498.

In addition, other sequence modifications can be made to the nucleic acid sequences disclosed herein. For example, additional sequence modifications enhance gene expression in a cellular host. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present invention, for example to enhance the expression of the AOS2 coding sequence. Such nucleic acid sequences include intron 1 of the maize Adh1 gene (Callis et al. (1987) Genes and Development 1:1183-1200), and leader sequences, (W-sequence) from the Tobacco Mosaic virus (TMV), Maize Chlorotic Mottle Virus and Alfalfa Mosaic Virus (Gallie et al., (1987) Nucleic Acid Res. 15:8693-8711, and Skuzeski et al., (1990) Plant Mol. Biol. 15:65-79). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al., Plant Physiol. 106:929-939 (1994)) have also shown that introns are useful for regulating gene expression on a tissue specific basis. To further enhance or to optimize AOS2 gene expression, the plant expression vectors disclosed herein may also contain DNA sequences containing matrix attachment regions (MARs). Plant cells transformed with such modified expression systems, then, may exhibit overexpression or constitutive expression of a nucleotide sequence of the invention.

The expression constructs disclosed herein can also include nucleic acid sequences capable of directing the expression of the AOS2 sequence to the chloroplast. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences, "operably linked" means that the nucleic acid sequence encoding a transit peptide (i.e., the chloroplast-targeting sequence) is linked to the AOS2 nucleic acid molecule of the invention such that the two sequences are contiguous and in the same reading frame. See, e.g., Von Heijne et al. (1991) Plant Mol. Biol. Rep. 9:104-126; Clark et al. (1989) J. Biol. Chem. 264: 17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the AOS2 proteins disclosed herein may include a native chloroplast transit peptide, any chloroplast transit peptide known in the art can be fused to the amino acid sequence of a mature AOS2 protein of the invention by operably linking a choloroplast-targeting sequence to the 5'-end of a nucleotide sequence encoding a mature AOS2 protein of the invention.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(1 1):6081-6087); plastocyanin (Lawrence et al. (1997) J. Biol. Chem. 272 (33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263:14996-14999). See also Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

In another embodiment, the nucleic acid constructs may be prepared to direct the expression of the mutant AOS2 coding sequence from the plant cell chloroplast. Methods for transformation of chloroplasts are known in the art. See, e.g., Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, e.g., U.S. Pat. No. 5,380,831, herein incorporated by reference.

The nucleic acid constructs can be used to transform plant cells and regenerate transgenic plants comprising the mutant AOS2 coding sequences. Numerous plant transformation vectors and methods for transforming plants are available. See, e.g., U.S. Pat. No. 6,753,458; An, G. et al. (1986) Plant Physiol., 81:301-305; Fry, J. et al. (1987) Plant Cell Rep. 6:321-325; Block, M. (1988) Theor. Appl Genet. 76:767-774; Hinchee et al. (1990) Stadler. Genet. Symp. 203212.203-212; Cousins et al. (1991) Aust. J. Plant Physiol. 18:481-494; Chee, P. P. et al. (1992) Gene. 118: 255-260; Christou et al. (1992) Trends. Biotechnol. 10:239-246; D'Halluin et al. (1992) Bio/Technol. 10:309-3 14; Dhir et al. (1992) Plant Physiol. 99:81-88; Casas et al. (1993) Proc. Nat. Acad. Sci. USA 90:11212-11216; Christou, P. (1993) In Vitro Cell. Dev. Biol.-Plant; 29P:1 19-124; Davies et al. (1993) Plant Cell Rep. 12:180-183; Dong, J. A. et al. (1993) Plant Sci. 91:139-148; Franklin, C. I. et al. (1993) Plant. Physiol. 102:167; Golovkin et al. (1993) Plant Sci. 90:41-52; Guo Chin Sci. Bull. 38:2072-2078; Asano et al. (1994) Plant Cell Rep. 13; Ayeres, N. M. et al. (1994) Crit. Rev. Plant. Sci. 13:219-239; Barcelo et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman et al. (1994) Bio-Technology 12: 919923; Ritala et al. (1994) Plant. Mol. Biol. 24:317-325; and Wan, Y. C. et al. (1994) Plant Physiol. 104:3748. The constructs may also be transformed into plant cells using homologous recombination.

The disclosed constructs comprising the AOS2 nucleic acid sequences disclosed herein can be used in various methods to produce transgenic host cells, such as bacteria, yeast, and to transform plant cells and in some cases regenerate transgenic plants. For example, methods of producing a transgenic crop plant containing the AOS2 mutant proteins disclosed herein, where expression of the nucleic acid(s) in the plant results in pathogen resistance and/or tolerance as compared to wild-type plants or to known AOS2 mutant type plants comprising: (a) introducing into a plant cell an expression vector comprising nucleic acid encoding a mutant AOS2 protein, and (b) generating from the plant cell a transgenic plant which is pathogen resistant and/or tolerant.

AOS2 Mutations

The compositions and methods may relate at least in part to mutations in an AOS2 gene, for example mutations that render a plant resistant or tolerant to a pathogen. The compositions and methods also in certain embodiments relate to the use of a gene repair oligonucleobase to make a desired mutation in the chromosomal or episomal sequences of a plant in the gene encoding for an AOS2 protein. The mutated protein, which may in some embodiments substantially maintain the catalytic activity of the wild-type protein, allowing for increased resistance and/or tolerance of the plant to a pathogen, and thus in some embodiments allowing for substantially normal or altered growth or development of the plant, its organs, tissues, or cells as compared to the wild-type plant irrespective of the presence or absence of the pathogen. The compositions and methods also relate to a non-transgenic plant cell in which an AOS2 gene has been mutated, a non-transgenic plant regenerated therefrom, as well as a plant resulting from a cross using a regenerated non-transgenic plant to a plant having a mutation in a different AOS2 gene or in the same AOS2 gene, for example. The compositions and methods also relate to a transgenic plant cell in which an AOS2 gene has been mutated, a transgenic plant regenerated therefrom, as well as a plant resulting from a cross using a regenerated transgenic plant to a plant having a mutation in a different AOS2 gene or in the same AOS2 gene, for example.

In conjunction with any of the aspects, embodiments, compositions and methods disclosed herein, a mutated AOS2 protein has one or more mutations at a position corresponding to positions selected from the group consisting of 6, 12, 30, 37, 46, 48, 51, 76, 113, 145, 187, 197, 200, 227, 231, 256, 264, 270, 282, 289, 292, 309, 320, 328, 337, 338, 357, 381, 394, 407, 423, 430, 439, 467, 480, 494 and 495 of SEQ ID NO: 5. In some embodiments, a mutated AOS2 protein has one or more mutations at a position corresponding to position 6 of SEQ ID NO: 5. In some embodiments, a mutated AOS2 protein has one or more mutations at a position corresponding to position 12 of SEQ ID NO: 5. In some embodiments, a mutated AOS2 protein has one or more mutations at a position corresponding to position 30 of SEQ ID NO: 5. In some embodiments, a mutated AOS2 protein has one or more mutations at a position corresponding to position 37 of SEQ ID NO: 5. In some embodiments, a mutated AOS2 protein has one or more mutations at a position corresponding to position 46 of SEQ ID NO: 5. In some embodiments, a mutated AOS2 protein has one or more mutations at a position corresponding to position 48 of SEQ ID NO: 5. In some embodiments, a mutated AOS2 protein has one or more mutations at a position corresponding to position 51 of SEQ ID NO: 5. In some embodiments, a mutated AOS2 protein has one or more mutations at a position corresponding to position 76 of SEQ ID NO: 5. In some embodiments, a mutated AOS2 protein has one or more mutations at a position corresponding to position 113 of SEQ ID NO: 5. In some embodiments, a mutated AOS2 protein has one or more mutations at a position corresponding to position 145 of SEQ ID NO: 5. In some embodiments, a mutated AOS2 protein has one or more mutations at a position corresponding to position 187 of SEQ ID NO: 5. In some embodiments, a mutated AOS2 protein has one or more mutations at a position corresponding to position 197 of SEQ ID NO: 5. In some embodiments, a mutated AOS2 protein has one or more mutations at a position corresponding to position 200 of SEQ ID NO: 5. In some embodiments, a mutated AOS2 protein has one or more mutations at a position corresponding to position 227 of SEQ ID NO: 5. In some embodiments, a mutated AOS2 protein has one or more mutations at a position corresponding to position 231 of SEQ ID NO: 5. In some embodiments, a mutated AOS2 protein has one or more mutations at a position corresponding to position 256 of SEQ ID NO: 5. In some embodiments, a mutated AOS2 protein has one or more mutations at a position corresponding to position 264 of SEQ ID NO: 5. In some embodiments, a mutated AOS2 protein has one or more mutations at a position corresponding to position 270 of SEQ ID NO: 5. In some embodiments, a mutated AOS2 protein has one or more mutations at a position corresponding to position 282 of SEQ ID NO: 5. In some embodiments, a mutated AOS2 protein has one or more mutations at a position corresponding to position 289 of SEQ ID NO: 5. In some embodiments, a mutated AOS2 protein has one or more mutations at a position corresponding to position 292 of SEQ ID NO: 5. In some embodiments, a mutated AOS2 protein has one or more mutations at a position corresponding to position 309 of SEQ ID NO: 5. In some embodiments, a mutated AOS2 protein has one or more mutations at a position corresponding to position 320 of SEQ ID NO: 5. In some embodiments, a mutated AOS2 protein has one or more mutations at a position corresponding to position 328 of SEQ ID NO: 5. In some embodiments, a mutated AOS2 protein has one or more mutations at a position corresponding to position 337 of SEQ ID NO: 5. In some embodiments, a mutated AOS2 protein has one or more mutations at a position corresponding to position 338 of SEQ ID NO: 5. In some embodiments, a mutated AOS2 protein has one or more mutations at a position corresponding to position 357 of SEQ ID NO: 5. In some embodiments, a mutated AOS2 protein has one or more mutations at a position corresponding to position 381 of SEQ ID NO: 5. In some embodiments, a mutated AOS2 protein has one or more mutations at a position corresponding to position 394 of SEQ ID NO: 5. In some embodiments, a mutated AOS2 protein has one or more mutations at a position corresponding to position 407 of SEQ ID NO: 5. In some embodiments, a mutated AOS2 protein has one or more mutations at a position corresponding to position 423 of SEQ ID NO: 5. In some embodiments, a mutated AOS2 protein has one or more mutations at a position corresponding to position 430 of SEQ ID NO: 5. In some embodiments, a mutated AOS2 protein has one or more mutations at a position corresponding to position 439 of SEQ ID NO: 5. In some embodiments, a mutated AOS2 protein has one or more mutations at a position corresponding to position 467 of SEQ ID NO: 5. In some embodiments, a mutated AOS2 protein has one or more mutations at a position corresponding to position 480 of SEQ ID NO: 5. In some embodiments, a mutated AOS2 protein has one or more mutations at a position corresponding to position 494 of SEQ ID NO: 5. In some embodiments, a mutated AOS2 protein has one or more mutations at a position corresponding to position 495 of SEQ ID NO: 5.

In conjunction with any of the aspects, embodiments, compositions and methods disclosed herein, a mutated AOS2 protein includes one or more mutations relative to an AOS2 amino acid sequence having a F at amino acid position 6 of SEQ ID NO: 7; a P at amino acid position 12 of SEQ ID NO: 5; a R at amino acid position 12 of SEQ ID NO: 11; an A at amino acid position 30 of SEQ ID NO: 5; an I at amino acid position 37 of SEQ ID NO: 5; a L at amino acid position 46 of SEQ ID NO: 5; a F at amino acid position 46 of SEQ ID NO: 3; a T at amino acid position 48 of SEQ ID NO: 5; an I at amino acid position 48 of SEQ ID NO: 27; a V at amino acid position 48 of SEQ ID NO: 7; a M at amino acid position 51 of SEQ ID NO: 5; a D at amino acid position 76 of SEQ ID NO: 5; an N at amino acid position 76 of SEQ ID NO: 5; a G at position 113 of SEQ ID NO: 5; an D at position 113 of SEQ ID NO: 49; a F at amino acid position 145 of SEQ ID NO: 9; a L at amino acid position 187 of SEQ ID NO: 5 an E at amino acid position 197 of SEQ ID NO: 5; an D at amino acid position 197 of SEQ ID NO: 3; a K at amino acid position 200 of SEQ ID NO: 7; an A at amino acid position 227 of SEQ ID NO: 5; a T at amino acid position 231 of SEQ ID NO: 5; an I at amino acid position 231 of SEQ ID NO: 7; a G at amino acid position 231 of SEQ ID NO: 9; a F at amino acid position 256 of SEQ ID NO: 5; a V at amino acid position 256 of SEQ ID NO: 3; an A at amino acid position 264 of SEQ ID NO: 7; a L at amino acid position 270 of SEQ ID NO: 7; a F at amino acid position 282 of SEQ ID NO: 5; a S at amino acid position 282 of SEQ ID NO: 41; a V at amino acid position 289 of SEQ ID NO: 5; a S at amino acid position 289 of SEQ ID NO: 11; an N at amino acid position 289 of SEQ ID NO: 13; a V at amino acid position 292 of SEQ ID NO: 5; an L at amino acid position 309 of SEQ ID NO: 5; an I at amino acid position 309 of SEQ ID NO: 19; a M at amino acid position 320 of SEQ ID NO: 5; a L at amino acid position 320 of SEQ ID NO: 23; a M at amino acid position 328 of SEQ ID NO: 5; a L at amino acid position 328 of SEQ ID NO: 19; a V at amino acid position 328 of SEQ ID NO: 27; an E at amino acid position 337 of SEQ ID NO: 5; an D at amino acid position 337 of SEQ ID NO: 13; a V at amino acid position 338 of SEQ ID NO: 5; a L at amino acid position 338 of SEQ ID NO: 13; an I at amino acid position 357 of SEQ ID NO: 5; a M at amino acid position 357 of SEQ ID NO: 3; a P at amino acid position 381 of SEQ ID NO: 5; a L at amino acid position 381 of SEQ ID NO: 35; a T at amino acid position 394 of SEQ ID NO: 9; a G at amino acid position 407 of SEQ ID NO: 5; a C at amino acid position 407 of SEQ ID NO: 13; a F at amino acid position 423 of SEQ ID NO: 7; a L at amino acid position 430 of SEQ ID NO: 5; a deletion of an amino acid E at position 439 of SEQ ID NO: 5; a G at amino acid position 467 of SEQ ID NO: 5; a S at amino acid position 467 of SEQ ID NO: 39; a V at amino acid position 480 of SEQ ID NO: 5, a G at amino acid position 494 of SEQ ID NO: 5; a D at amino acid position 494 of SEQ ID NO: 21; and/or a T at amino acid position 495 of SEQ ID NO: 5. In some embodiments, a mutated AOS2 protein includes one or more mutations relative to an AOS2 amino acid sequence having a F at amino acid position 6 of SEQ ID NO: 7. In some embodiments, a mutated AOS2 protein includes one or more mutations relative to an AOS2 amino acid sequence having a P at amino acid position 12 of SEQ ID NO: 5. In some embodiments, a mutated AOS2 protein includes one or more mutations relative to an AOS2 amino acid sequence having an R at amino acid position 12 of SEQ ID NO: 11. In some embodiments, a mutated AOS2 protein includes one or more mutations relative to an AOS2 amino acid sequence having an A at amino acid position 30 of SEQ ID NO: 5. In some embodiments, a mutated AOS2 protein includes one or more mutations relative to an AOS2 amino acid sequence having an I at amino acid position 37 of SEQ ID NO: 5. In some embodiments, a mutated AOS2 protein includes one or more mutations relative to an AOS2 amino acid sequence having a L at amino acid position 46 of SEQ ID NO: 5. In some embodiments, a mutated AOS2 protein includes one or more mutations relative to an AOS2 amino acid sequence having a F at amino acid position 46 of SEQ ID NO: 3. In some embodiments, a mutated AOS2 protein includes one or more mutations relative to an AOS2 amino acid sequence having a T at amino acid position 48 of SEQ ID NO: 5. In some embodiments, a mutated AOS2 protein includes one or more mutations relative to an AOS2 amino acid sequence having an I at amino acid position 48 of SEQ ID NO: 27. In some embodiments, a mutated AOS2 protein includes one or more mutations relative to an AOS2 amino acid sequence having a V at amino acid position 48 of SEQ ID NO: 7. In some embodiments, a mutated AOS2 protein includes one or more mutations relative to an AOS2 amino acid sequence having a M at amino acid position 51 of SEQ ID NO: 5. In some embodiments, a mutated AOS2 protein includes one or more mutations relative to an AOS2 amino acid sequence having an N at amino acid position 76 of SEQ ID NO: 5. In some embodiments, a mutated AOS2 protein includes one or more mutations relative to an AOS2 amino acid sequence having a D at amino acid position 76 of SEQ ID NO: 5. In some embodiments, a mutated AOS2 protein includes one or more mutations relative to an AOS2 amino acid sequence having a G at position 113 of SEQ ID NO: 5. In some embodiments, a mutated AOS2 protein includes one or more mutations relative to an AOS2 amino acid sequence having an D at position 113 of SEQ ID NO: 49. In some embodiments, a mutated AOS2 protein includes one or more mutations relative to an AOS2 amino acid sequence having a F at amino acid position 145 of SEQ ID NO: 9. In some embodiments, a mutated AOS2 protein includes one or more mutations relative to an AOS2 amino acid sequence having a L at amino acid position 187 of SEQ ID NO: 5. In some embodiments, a mutated AOS2 protein includes one or more mutations relative to an AOS2 amino acid sequence having an E at amino acid position 197 of SEQ ID NO: 5. In some embodiments, a mutated AOS2 protein includes one or more mutations relative to an AOS2 amino acid sequence having an D at amino acid position 197 of SEQ ID NO: 3. In some embodiments, a mutated AOS2 protein includes one or more mutations relative to an AOS2 amino acid sequence having a K at amino acid position 200 of SEQ ID NO: 7. In some embodiments, a mutated AOS2 protein includes one or more mutations relative to an AOS2 amino acid sequence having an A at amino acid position 227 of SEQ ID NO: 5. In some embodiments, a mutated AOS2 protein includes one or more mutations relative to an AOS2 amino acid sequence having a T at amino acid position 231 of SEQ ID NO: 5. In some embodiments, a mutated AOS2 protein includes one or more mutations relative to an AOS2 amino acid sequence having an I at amino acid position 231 of SEQ ID NO: 7. In some embodiments, a mutated AOS2 protein includes one or more mutations relative to an AOS2 amino acid sequence having a G at amino acid position 231 of SEQ ID NO: 9. In some embodiments, a mutated AOS2 protein includes one or more mutations relative to an AOS2 amino acid sequence having a F at amino acid position 256 of SEQ ID NO: 5. In some embodiments, a mutated AOS2 protein includes one or more mutations relative to an AOS2 amino acid sequence having a V at amino acid position 256 of SEQ ID NO: 3. In some embodiments, a mutated AOS2 protein includes one or more mutations relative to an AOS2 amino acid sequence having an A at amino acid position 264 of SEQ ID NO: 7. In some embodiments, a mutated AOS2 protein includes one or more mutations relative to an AOS2 amino acid sequence having a L at amino acid position 270 of SEQ ID NO: 7. In some embodiments, a mutated AOS2 protein includes one or more mutations relative to an AOS2 amino acid sequence having a F at amino acid position 282 of SEQ ID NO: 5. In some embodiments, a mutated AOS2 protein includes one or more mutations relative to an AOS2 amino acid sequence having a S at amino acid position 282 of SEQ ID NO: 41. In some embodiments, a mutated AOS2 protein includes one or more mutations relative to an AOS2 amino acid sequence having a V at amino acid position 289 of SEQ ID NO: 5. In some embodiments, a mutated AOS2 protein includes one or more mutations relative to an AOS2 amino acid sequence having a S at amino acid position 289 of SEQ ID NO: 11. In some embodiments, a mutated AOS2 protein includes one or more mutations relative to an AOS2 amino acid sequence having an N at amino acid position 289 of SEQ ID NO: 13. In some embodiments, a mutated AOS2 protein includes one or more mutations relative to an AOS2 amino acid sequence having a V at amino acid position 292 of SEQ ID NO: 5. In some embodiments, a mutated AOS2 protein includes one or more mutations relative to an AOS2 amino acid sequence having a L at amino acid position 309 of SEQ ID NO: 5. In some embodiments, a mutated AOS2 protein includes one or more mutations relative to an AOS2 amino acid sequence having an I at amino acid position 309 of SEQ ID NO: 19. In some embodiments, a mutated AOS2 protein includes one or more mutations relative to an AOS2 amino acid sequence having a M at amino acid position 320 of SEQ ID NO: 5. In some embodiments, a mutated AOS2 protein includes one or more mutations relative to an AOS2 amino acid sequence having a L at amino acid position 320 of SEQ ID NO: 23. In some embodiments, a mutated AOS2 protein includes one or more mutations relative to an AOS2 amino acid sequence having a M at amino acid position 328 of SEQ ID NO: 5. In some embodiments, a mutated AOS2 protein includes one or more mutations relative to an AOS2 amino acid sequence having a L at amino acid position 328 of SEQ ID NO: 19. In some embodiments, a mutated AOS2 protein includes one or more mutations relative to an AOS2 amino acid sequence having a V at amino acid position 328 of SEQ ID NO: 27. In some embodiments, a mutated AOS2 protein includes one or more mutations relative to an AOS2 amino acid sequence having an E at amino acid position 337 of SEQ ID NO: 5. In some embodiments, a mutated AOS2 protein includes one or more mutations relative to an AOS2 amino acid sequence having an D at amino acid position 337 of SEQ ID NO: 13. In some embodiments, a mutated AOS2 protein includes one or more mutations relative to an AOS2 amino acid sequence having a V at amino acid position 338 of SEQ ID NO: 5. In some embodiments, a mutated AOS2 protein includes one or more mutations relative to an AOS2 amino acid sequence having a L at amino acid position 338 of SEQ ID NO: 13. In some embodiments, a mutated AOS2 protein includes one or more mutations relative to an AOS2 amino acid sequence having an I at amino acid position 357 of SEQ ID NO: 5. In some embodiments, a mutated AOS2 protein includes one or more mutations relative to an AOS2 amino acid sequence having a M at amino acid position 357 of SEQ ID NO: 3. In some embodiments, a mutated AOS2 protein includes one or more mutations relative to an AOS2 amino acid sequence having a P at amino acid position 381 of SEQ ID NO: 5. In some embodiments, a mutated AOS2 protein includes one or more mutations relative to an AOS2 amino acid sequence having a L at amino acid position 381 of SEQ ID NO: 35. In some embodiments, a mutated AOS2 protein includes one or more mutations relative to an AOS2 amino acid sequence having a T at amino acid position 394 of SEQ ID NO: 9. In some embodiments, a mutated AOS2 protein includes one or more mutations relative to an AOS2 amino acid sequence having a G at amino acid position 407 of SEQ ID NO: 5. In some embodiments, a mutated AOS2 protein includes one or more mutations relative to an AOS2 amino acid sequence having a C at amino acid position 407 of SEQ ID NO: 13. In some embodiments, a mutated AOS2 protein includes one or more mutations relative to an AOS2 amino acid sequence having a F at amino acid position 423 of SEQ ID NO: 7. In some embodiments, a mutated AOS2 protein includes one or more mutations relative to an AOS2 amino acid sequence having a L at amino acid position 430 of SEQ ID NO: 5. In some embodiments, a mutated AOS2 protein includes one or more mutations relative to an AOS2 amino acid sequence having a deletion of an amino acid E at position 439 of SEQ ID NO: 5. In some embodiments, a mutated AOS2 protein includes one or more mutations relative to an AOS2 amino acid sequence having a G at amino acid position 467 of SEQ ID NO: 5. In some embodiments, a mutated AOS2 protein includes one or more mutations relative to an AOS2 amino acid sequence having a S at amino acid position 467 of SEQ ID NO: 39. In some embodiments, a mutated AOS2 protein includes one or more mutations relative to an AOS2 amino acid sequence having a V at amino acid position 480 of SEQ ID NO: 5. In some embodiments, a mutated AOS2 protein includes one or more mutations relative to an AOS2 amino acid sequence having a G at amino acid position 494 of SEQ ID NO: 5. In some embodiments, a mutated AOS2 protein includes one or more mutations relative to an AOS2 amino acid sequence having an D at amino acid position 494 of SEQ ID NO: 21. In some embodiments, a mutated AOS2 protein includes one or more mutations relative to an AOS2 amino acid sequence having and/or a T at amino acid position 495 of SEQ ID NO: 5.

In conjunction with any of the aspects, embodiments, compositions and methods disclosed herein, a mutated AOS2 gene encodes a mutated AOS2 protein. In some embodiments, a mutated AOS2 gene includes an A at a position corresponding to position 691 of SEQ ID NO: 2. In some embodiments, a mutated AOS2 gene includes a C at a position corresponding to position 692 of SEQ ID NO: 2. In some embodiments, a mutated AOS2 gene includes an A at a position corresponding to position 678 of SEQ ID NO: 2. In some embodiments, a mutated AOS2 gene includes a T at a position corresponding to position 681 of SEQ ID NO: 2. In some embodiments, a mutated AOS2 gene includes a C at a position corresponding to position 727 of SEQ ID NO: 2. In some embodiments, a mutated AOS2 gene includes an A at a position corresponding to position 744 of SEQ ID NO: 2. In some embodiments, a mutated AOS2 gene includes a C at a position corresponding to position 774 of SEQ ID NO: 2. In some embodiments, a mutated AOS2 gene includes an A at a position corresponding to position 879 of SEQ ID NO: 2. In some embodiments, a mutated AOS2 gene includes an A at a position corresponding to position 900 of SEQ ID NO: 2. In some embodiments, a mutated AOS2 gene includes a C at a position corresponding to position 954 of SEQ ID NO: 2.

In conjunction with any of the aspects, embodiments, compositions and methods disclosed herein, a mutated AOS2 gene may encode a mutated AOS2 protein. In some embodiments, the mutated AOS2 gene encodes a mutated AOS2 protein that includes one or more mutations relative to an AOS2 amino acid sequence having a F at amino acid position 6 of SEQ ID NO: 7; a P at amino acid position 12 of SEQ ID NO: 5; an R at amino acid position 12 of SEQ ID NO: 11; an A at amino acid position 30 of SEQ ID NO: 5; an I at amino acid position 37 of SEQ ID NO: 5; a L at amino acid position 46 of SEQ ID NO: 5; a F at amino acid position 46 of SEQ ID NO: 3; a T at amino acid position 48 of SEQ ID NO: 5; an I at amino acid position 48 of SEQ ID NO: 27; a V at amino acid position 48 of SEQ ID NO: 7; a M at amino acid position 51 of SEQ ID NO: 5; a D at amino acid position 76 of SEQ ID NO: 5; an N at amino acid position 76 of SEQ ID NO: 5; a G at position 113 of SEQ ID NO: 5; an D at position 113 of SEQ ID NO: 49; a F at amino acid position 145 of SEQ ID NO: 9; a L at amino acid position 187 of SEQ ID NO: 5; an E at amino acid position 197 of SEQ ID NO: 5; an D at amino acid position 197 of SEQ ID NO: 3; a K at amino acid position 200 of SEQ ID NO: 7; an A at amino acid position 227 of SEQ ID NO: 5; a T at amino acid position 231 of SEQ ID NO: 5; an I at amino acid position 231 of SEQ ID NO: 7; a G at amino acid position 231 of SEQ ID NO: 9; a F at amino acid position 256 of SEQ ID NO: 5; a V at amino acid position 256 of SEQ ID NO: 3; an A at amino acid position 264 of SEQ ID NO: 7; a L at amino acid position 270 of SEQ ID NO: 7; a F at amino acid position 282 of SEQ ID NO: 5; a S at amino acid position 282 of SEQ ID NO: 41; a V at amino acid position 289 of SEQ ID NO: 5; a S at amino acid position 289 of SEQ ID NO: 11; an N at amino acid position 289 of SEQ ID NO: 13; a V at amino acid position 292 of SEQ ID NO: 5; a L at amino acid position 309 of SEQ ID NO: 5; an I at amino acid position 309 of SEQ ID NO: 19; a M at amino acid position 320 of SEQ ID NO: 5; a L at amino acid position 320 of SEQ ID NO: 23; a M at amino acid position 328 of SEQ ID NO: 5; a L at amino acid position 328 of SEQ ID NO: 19; a V at amino acid position 328 of SEQ ID NO: 27; an E at amino acid position 337 of SEQ ID NO: 5; an D at amino acid position 337 of SEQ ID NO: 13; a V at amino acid position 338 of SEQ ID NO: 5; a L at amino acid position 338 of SEQ ID NO: 13; an I at amino acid position 357 of SEQ ID NO: 5; a M at amino acid position 357 of SEQ ID NO: 3; a P at amino acid position 381 of SEQ ID NO: 5; a L at amino acid position 381 of SEQ ID NO: 35; a T at amino acid position 394 of SEQ ID NO: 9; a G at amino acid position 407 of SEQ ID NO: 5; a C at amino acid position 407 of SEQ ID NO: 13; a F at amino acid position 423 of SEQ ID NO: 7; a L at amino acid position 430 of SEQ ID NO: 5; a deletion of an amino acid E at position 439 of SEQ ID NO: 5; a G at amino acid position 467 of SEQ ID NO: 5; a S at amino acid position 467 of SEQ ID NO: 39; a V at amino acid position 480 of SEQ ID NO: 5, a G at amino acid position 494 of SEQ ID NO: 5; an D at amino acid position 494 of SEQ ID NO: 21; and/or a T at amino acid position 495 of SEQ ID NO: 5. In some embodiments, the mutated AOS2 gene encodes a mutated AOS2 protein that includes one or more mutations relative to an AOS2 amino acid sequence having a F at amino acid position 6 of SEQ ID NO: 7. In some embodiments, a mutated AOS2 gene encodes a mutated AOS2 protein that includes one or more mutations relative to an AOS2 amino acid sequence having a P at amino acid position 12 of SEQ ID NO: 5. In some embodiments, a mutated AOS2 gene encodes a mutated AOS2 protein that includes one or more mutations relative to an AOS2 amino acid sequence having an R at amino acid position 12 of SEQ ID NO: 11. In some embodiments, a mutated AOS2 gene encodes a mutated AOS2 protein that includes one or more mutations relative to an AOS2 amino acid sequence having an A at amino acid position 30 of SEQ ID NO: 5. In some embodiments, a mutated AOS2 gene encodes a mutated AOS2 protein that includes one or more mutations relative to an AOS2 amino acid sequence having an I at amino acid position 37 of SEQ ID NO: 5. In some embodiments, a mutated AOS2 gene encodes a mutated AOS2 protein that includes one or more mutations relative to an AOS2 amino acid sequence having a L at amino acid position 46 of SEQ ID NO: 5. In some embodiments, a mutated AOS2 gene encodes a mutated AOS2 protein that includes one or more mutations relative to an AOS2 amino acid sequence having a F at amino acid position 46 of SEQ ID NO: 3. In some embodiments, a mutated AOS2 gene encodes a mutated AOS2 protein that includes one or more mutations relative to an AOS2 amino acid sequence having a T at amino acid position 48 of SEQ ID NO: 5. In some embodiments, a mutated AOS2 gene encodes a mutated AOS2 protein that includes one or more mutations relative to an AOS2 amino acid sequence having an I at amino acid position 48 of SEQ ID NO: 27. In some embodiments, a mutated AOS2 gene encodes a mutated AOS2 protein that includes one or more mutations relative to an AOS2 amino acid sequence having a V at amino acid position 48 of SEQ ID NO: 7. In some embodiments, a mutated AOS2 gene encodes a mutated AOS2 protein that includes one or more mutations relative to an AOS2 amino acid sequence having a M at amino acid position 51 of SEQ ID NO: 5. In some embodiments, a mutated AOS2 gene encodes a mutated AOS2 protein that includes one or more mutations relative to an AOS2 amino acid sequence having a D at amino acid position 76 of SEQ ID NO: 5. In some embodiments, a mutated AOS2 gene encodes a mutated AOS2 protein that includes one or more mutations relative to an AOS2 amino acid sequence having an N at amino acid position 76 of SEQ ID NO: 5. In some embodiments, a mutated AOS2 gene encodes a mutated AOS2 protein that includes one or more mutations relative to an AOS2 amino acid sequence having a G at position 113 of SEQ ID NO: 5. In some embodiments, a mutated AOS2 gene encodes a mutated AOS2 protein that includes one or more mutations relative to an AOS2 amino acid sequence having an D at position 113 of SEQ ID NO: 49. In some embodiments, a mutated AOS2 gene encodes a mutated AOS2 protein that includes one or more mutations relative to an AOS2 amino acid sequence having a F at amino acid position 145 of SEQ ID NO: 9. In some embodiments, a mutated AOS2 gene encodes a mutated AOS2 protein that includes one or more mutations relative to an AOS2 amino acid sequence having a L at amino acid position 187 of SEQ ID NO: 5. In some embodiments, a mutated AOS2 gene encodes a mutated AOS2 protein that includes one or more mutations relative to an AOS2 amino acid sequence having an E at amino acid position 197 of SEQ ID NO: 5. In some embodiments, a mutated AOS2 gene encodes a mutated AOS2 protein that includes one or more mutations relative to an AOS2 amino acid sequence having an D at amino acid position 197 of SEQ ID NO: 3. In some embodiments, a mutated AOS2 gene encodes a mutated AOS2 protein that includes one or more mutations relative to an AOS2 amino acid sequence having a K at amino acid position 200 of SEQ ID NO: 7. In some embodiments, a mutated AOS2 gene encodes a mutated AOS2 protein that includes one or more mutations relative to an AOS2 amino acid sequence having an A at amino acid position 227 of SEQ ID NO: 5. In some embodiments, a mutated AOS2 gene encodes a mutated AOS2 protein that includes one or more mutations relative to an AOS2 amino acid sequence having a T at amino acid position 231 of SEQ ID NO: 5. In some embodiments, a mutated AOS2 gene encodes a mutated AOS2 protein that includes one or more mutations relative to an AOS2 amino acid sequence having an I at amino acid position 231 of SEQ ID NO: 7. In some embodiments, a mutated AOS2 gene encodes a mutated AOS2 protein that includes one or more mutations relative to an AOS2 amino acid sequence having a G at amino acid position 231 of SEQ ID NO: 9. In some embodiments, a mutated AOS2 gene encodes a mutated AOS2 protein that includes one or more mutations relative to an AOS2 amino acid sequence having a F at amino acid position 256 of SEQ ID NO: 5. In some embodiments, a mutated AOS2 gene encodes a mutated AOS2 protein that includes one or more mutations relative to an AOS2 amino acid sequence having a V at amino acid position 256 of SEQ ID NO: 3. In some embodiments, a mutated AOS2 gene encodes a mutated AOS2 protein that includes one or more mutations relative to an AOS2 amino acid sequence having an A at amino acid position 264 of SEQ ID NO: 7. In some embodiments, a mutated AOS2 gene encodes a mutated AOS2 protein that includes one or more mutations relative to an AOS2 amino acid sequence having a L at amino acid position 270 of SEQ ID NO: 7. In some embodiments, a mutated AOS2 gene encodes a mutated AOS2 protein that includes one or more mutations relative to an AOS2 amino acid sequence having a F at amino acid position 282 of SEQ ID NO: 5. In some embodiments, a mutated AOS2 gene encodes a mutated AOS2 protein that includes one or more mutations relative to an AOS2 amino acid sequence having a S at amino acid position 282 of SEQ ID NO: 41. In some embodiments, a mutated AOS2 gene encodes a mutated AOS2 protein that includes one or more mutations relative to an AOS2 amino acid sequence having a V at amino acid position 289 of SEQ ID NO: 5. In some embodiments, a mutated AOS2 gene encodes a mutated AOS2 protein that includes one or more mutations relative to an AOS2 amino acid sequence having a S at amino acid position 289 of SEQ ID NO: 11. In some embodiments, a mutated AOS2 gene encodes a mutated AOS2 protein that includes one or more mutations relative to an AOS2 amino acid sequence having an N at amino acid position 289 of SEQ ID NO: 13. In some embodiments, a mutated AOS2 gene encodes a mutated AOS2 protein that includes one or more mutations relative to an AOS2 amino acid sequence having a V at amino acid position 292 of SEQ ID NO: 5. In some embodiments, a mutated AOS2 gene encodes a mutated AOS2 protein that includes one or more mutations relative to an AOS2 amino acid sequence having a L at amino acid position 309 of SEQ ID NO: 5. In some embodiments, a mutated AOS2 gene encodes a mutated AOS2 protein that includes one or more mutations relative to an AOS2 amino acid sequence having an I at amino acid position 309 of SEQ ID NO: 19. In some embodiments, a mutated AOS2 gene encodes a mutated AOS2 protein that includes one or more mutations relative to an AOS2 amino acid sequence having a M at amino acid position 320 of SEQ ID NO: 5. In some embodiments, a mutated AOS2 gene encodes a mutated AOS2 protein that includes one or more mutations relative to an AOS2 amino acid sequence having a L at amino acid position 320 of SEQ ID NO: 23. In some embodiments, a mutated AOS2 gene encodes a mutated AOS2 protein that includes one or more mutations relative to an AOS2 amino acid sequence having a M at amino acid position 328 of SEQ ID NO: 5. In some embodiments, a mutated AOS2 gene encodes a mutated AOS2 protein that includes one or more mutations relative to an AOS2 amino acid sequence having a L at amino acid position 328 of SEQ ID NO: 19. In some embodiments, a mutated AOS2 gene encodes a mutated AOS2 protein that includes one or more mutations relative to an AOS2 amino acid sequence having a V at amino acid position 328 of SEQ ID NO: 27. In some embodiments, a mutated AOS2 gene encodes a mutated AOS2 protein that includes one or more mutations relative to an AOS2 amino acid sequence having an E at amino acid position 337 of SEQ ID NO: 5. In some embodiments, a mutated AOS2 gene encodes a mutated AOS2 protein that includes one or more mutations relative to an AOS2 amino acid sequence having an D at amino acid position 337 of SEQ ID NO: 13. In some embodiments, a mutated AOS2 gene encodes a mutated AOS2 protein that includes one or more mutations relative to an AOS2 amino acid sequence having a V at amino acid position 338 of SEQ ID NO: 5. In some embodiments, a mutated AOS2 gene encodes a mutated AOS2 protein that includes one or more mutations relative to an AOS2 amino acid sequence having a L at amino acid position 338 of SEQ ID NO: 13. In some embodiments, a mutated AOS2 gene encodes a mutated AOS2 protein that includes one or more mutations relative to an AOS2 amino acid sequence having an I at amino acid position 357 of SEQ ID NO: 5. In some embodiments, a mutated AOS2 gene encodes a mutated AOS2 protein that includes one or more mutations relative to an AOS2 amino acid sequence having a M at amino acid position 357 of SEQ ID NO: 3. In some embodiments, a mutated AOS2 gene encodes a mutated AOS2 protein that includes one or more mutations relative to an AOS2 amino acid sequence having a P at amino acid position 381 of SEQ ID NO: 5. In some embodiments, a mutated AOS2 gene encodes a mutated AOS2 protein that includes one or more mutations relative to an AOS2 amino acid sequence having a L at amino acid position 381 of SEQ ID NO: 35. In some embodiments, a mutated AOS2 gene encodes a mutated AOS2 protein that includes one or more mutations relative to an AOS2 amino acid sequence having a T at amino acid position 394 of SEQ ID NO: 9. In some embodiments, a mutated AOS2 gene encodes a mutated AOS2 protein that includes one or more mutations relative to an AOS2 amino acid sequence having a G at amino acid position 407 of SEQ ID NO: 5. In some embodiments, a mutated AOS2 gene encodes a mutated AOS2 protein that includes one or more mutations relative to an AOS2 amino acid sequence having a C at amino acid position 407 of SEQ ID NO: 13. In some embodiments, a mutated AOS2 gene encodes a mutated AOS2 protein that includes one or more mutations relative to an AOS2 amino acid sequence having a F at amino acid position 423 of SEQ ID NO: 7. In some embodiments, a mutated AOS2 gene encodes a mutated AOS2 protein that includes one or more mutations relative to an AOS2 amino acid sequence having a L at amino acid position 430 of SEQ ID NO: 5. In some embodiments, a mutated AOS2 gene encodes a mutated AOS2 protein that includes one or more mutations relative to an AOS2 amino acid sequence having a deletion of an amino acid E at position 439 of SEQ ID NO: 5. In some embodiments, a mutated AOS2 gene encodes a mutated AOS2 protein that includes one or more mutations relative to an AOS2 amino acid sequence having a G at amino acid position 467 of SEQ ID NO: 5. In some embodiments, a mutated AOS2 gene encodes a mutated AOS2 protein that includes one or more mutations relative to an AOS2 amino acid sequence having a S at amino acid position 467 of SEQ ID NO: 39. In some embodiments, a mutated AOS2 gene encodes a mutated AOS2 protein that includes one or more mutations relative to an AOS2 amino acid sequence having a V at amino acid position 480 of SEQ ID NO: 5. In some embodiments, a mutated AOS2 gene encodes a mutated AOS2 protein that includes one or more mutations relative to an AOS2 amino acid sequence having a G at amino acid position 494 of SEQ ID NO: 5. In some embodiments, a mutated AOS2 gene encodes a mutated AOS2 protein that includes one or more mutations relative to an AOS2 amino acid sequence having an D at amino acid position 494 of SEQ ID NO: 21. In some embodiments, a mutated AOS2 gene encodes a mutated AOS2 protein that includes one or more mutations relative to an AOS2 amino acid sequence having and/or a T at amino acid position 495 of SEQ ID NO: 5.

In conjunction with any of the aspects, embodiments, compositions and methods disclosed herein, the mutated AOS2 protein includes one or more, two or more, three or more, four or more, five or more, six or more, seven or more, eight or more, nine or more, or ten or more, or eleven or more, or twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more mutations at positions selected from the group consisting of S6, P12, R12, V30, T37, F46, L46, I48, T48, I51, D76, N76, D113, G113, Y145, F187, D197, E197, T200, T227, G231, T231, F256, V256, T264, F270, F282, S282, N289, S289, A292, I309, L309, L320, M320, L328, V328, D337, E337, L338, V338, I357, M357, L381, P381, K394, C407, G407, I423, F430, Δ439 (where Δ indicates a deletion), G467, S467, T480, D494, G494 and K495 of SEQ ID NO: 1, 3, 5, 7, 9, 11, 13, 15, 17, 19, 21, 23, 25, 27, 29, 31, 33, 35, 37, 39, 41, 43, 45, 47 and/or 49. In some embodiments, a mutated AOS2 protein includes two or more mutations, at least one mutation of which is at the amino acid position corresponding to a position selected from the group consisting of S6, P12, R12, V30, T37, F46, L46, I48, T48, I51, D76, D113, G113, Y145, F187, D197, E197, T200, T227, G231, T231, F256, V256, T264, F270, F282, S282, N289, S289, A292, I309, L309, L320, M320, L328, V328, D337, E337, L338, V338, I357, M357, L381, P381, K394, C407, G407, I423, F430, Δ439 (where Δ indicates a deletion), G467, S467, T480, D494, G494 and K495 of SEQ ID NO: 1, 3, 5, 7, 9, 11, 13, 15, 17, 19, 21, 23, 25, 27, 29, 31, 33, 35, 37, 39, 41, 43, 45, 47 and/or 49. In some embodiments, a mutated AOS2 gene includes three or more mutations, at least one mutation of which is at the amino acid position corresponding to a position selected from the group consisting of S6, P12, R12, V30, T37, F46, L46, I48, T48, I51, D76, D113, G113, Y145, F187, D197, E197, T200, T227, G231, T231, F256, V256, T264, F270, F282, S282, N289, S289, A292, I309, L309, L320, M320, L328, V328, D337, E337, L338, V338, I357, M357, L381, P381, K394, C407, G407, I423, F430, Δ439 (where Δ indicates a deletion), G467, S467, T480, D494, G494 and K495 of SEQ ID NO: 1, 3, 5, 7, 9, 11, 13, 15, 17, 19, 21, 23, 25, 27, 29, 31, 33, 35, 37, 39, 41, 43, 45, 47 and/or 49.

In conjunction with any of the aspects, embodiments, compositions and methods disclosed herein, a mutated AOS2 protein includes a mutation at the amino acid position corresponding to position F6 of SEQ ID NO: 7 or 9. In conjunction with any of the aspects, embodiments, compositions and methods disclosed herein, a mutated AOS2 protein includes a mutation at the amino acid position corresponding to position R12 of SEQ ID NO: 1, 3, 7, 9, 13, 15, 17, 19, 21, 23, 25, 27, 29, 31, 33, 35, 37, 39, 41, 43, 45, 47 or 49. In conjunction with any of the aspects, embodiments, compositions and methods disclosed herein, a mutated AOS2 protein includes a mutation at the amino acid position corresponding to position P12 of SEQ ID NO: 11. In conjunction with any of the aspects, embodiments, compositions and methods disclosed herein, a mutated AOS2 protein includes a mutation at the amino acid position corresponding to position A30 of SEQ ID NO: 5. In conjunction with any of the aspects, embodiments, compositions and methods disclosed herein, a mutated AOS2 protein includes a mutation at the amino acid position corresponding to position V30 of SEQ ID NO: 1, 3, 7, 9, 11, 13, 15, 17, 19, 21, 23, 25, 27, 29, 31, 33, 35, 37, 39, 41, 43, 45, 47 or 49. In conjunction with any of the aspects, embodiments, compositions and methods disclosed herein, a mutated AOS2 protein includes a mutation at the amino acid position corresponding to position I37 of SEQ ID NO: 5. In conjunction with any of the aspects, embodiments, compositions and methods disclosed herein, a mutated AOS2 protein includes a mutation at the amino acid position corresponding to position F46 of SEQ ID NO: 3. In conjunction with any of the aspects, embodiments, compositions and methods disclosed herein, a mutated AOS2 protein includes a mutation at the amino acid position corresponding to position L46 of SEQ ID NO: 1, 5, 7, 9, 11, 13, 15, 17, 19, 21, 23, 25, 27, 29, 31, 33, 35, 37, 39, 41, 43, 45, 47 or 49. In conjunction with any of the aspects, embodiments, compositions and methods disclosed herein, a mutated AOS2 protein includes a mutation at the amino acid position corresponding to position I48 of SEQ ID NO: 27, 47 or 49. In conjunction with any of the aspects, embodiments, compositions and methods disclosed herein, a mutated AOS2 protein includes a mutation at the amino acid position corresponding to position V48 of SEQ ID NO: 7. In conjunction with any of the aspects, embodiments, compositions and methods disclosed herein, a mutated AOS2 protein includes a mutation at the amino acid position corresponding to position T48 of SEQ ID NO: 1, 3, 5, 9, 11, 13, 15, 17, 19, 21, 23, 25, 29, 31, 33, 35, 37, 39, 41, 43 or 45. In conjunction with any of the aspects, embodiments, compositions and methods disclosed herein, a mutated AOS2 protein includes a mutation at the amino acid position corresponding to position M51 of SEQ ID NO: 5. In conjunction with any of the aspects, embodiments, compositions and methods disclosed herein, a mutated AOS2 protein includes a mutation at the amino acid position corresponding to position N76 of SEQ ID NO: 5, 7, 9, 19, 21, 23, 25, 29, 31 or 43. In some embodiments, a mutated AOS2 protein includes a mutation at the amino acid position corresponding to position G113 of SEQ ID NO: 1, 3, 5, 7, 9, 11, 13, 15, 17, 19, 21, 23, 25, 27, 29, 31, 33, 35, 37, 39, 41, 43, 45 or 47. In some embodiments, a mutated AOS2 protein includes a mutation at the amino acid position corresponding to position D113 of SEQ ID NO: 49. In some embodiments, a mutated AOS2 protein includes a mutation at the amino acid position corresponding to position F145 of SEQ ID NO: 9. In some embodiments, a mutated AOS2 protein includes a mutation at the amino acid position corresponding to position L187 of SEQ ID NO: 5. In some embodiments, a mutated AOS2 protein includes a mutation at the amino acid position corresponding to position E197 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position D197 of SEQ ID NO: 3. In some embodiments, a mutated AOS2 protein includes a mutation at the amino acid position corresponding to position K200 of SEQ ID NO: 7 or 9. In some embodiments, a mutated AOS2 protein includes a mutation at the amino acid position corresponding to position A227 of SEQ ID NO: 5. In some embodiments, a mutated AOS2 protein includes a mutation at the amino acid position corresponding to position I231 of SEQ ID NO: 7. In some embodiments, a mutated AOS2 protein includes a mutation at the amino acid position corresponding to position G231 of SEQ ID NO: 9, 11, 13, 15, 17, 19, 21, 29, 43 or 45. In some embodiments, a mutated AOS2 protein includes a mutation at the amino acid position corresponding to position T231 of SEQ ID NO: 1, 3, 5, 23, 25, 27, 31, 33, 35, 37, 39, 41, 47 or 49. In some embodiments, a mutated AOS2 protein includes a mutation at the amino acid position corresponding to position F256 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position V256 of SEQ ID NO: 3. In some embodiments, a mutated AOS2 protein includes a mutation at the amino acid position corresponding to position A264 of SEQ ID NO: 7. In some embodiments, a mutated AOS2 protein includes a mutation at the amino acid position corresponding to position L270 of SEQ ID NO: 7. In some embodiments, a mutated AOS2 protein includes a mutation at the amino acid position corresponding to position F282 of SEQ ID NO: 1, 3, 5, 7, 9, 11, 13, 15, 17, 19, 21, 23, 25, 27, 29, 31, 33, 35, 37, 39, 43, 45, 47 or 49. In some embodiments, a mutated AOS2 protein includes a mutation at the amino acid position corresponding to position 5282 of SEQ ID NO: 41. In some embodiments, a mutated AOS2 protein includes a mutation at the amino acid position corresponding to position N289 of SEQ ID NO: 13. In some embodiments, a mutated AOS2 protein includes a mutation at the amino acid position corresponding to position V289 of SEQ ID NO: 5, 7 or 9. In some embodiments, a mutated AOS2 protein includes a mutation at the amino acid position corresponding to position 5289 of SEQ ID NO: 1, 3, 11, 15, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position V292 of SEQ ID NO: 5, 7, 9 or 13. In some embodiments, a mutated AOS2 protein includes a mutation at the amino acid position corresponding to position L309 of SEQ ID NO: 1, 3, 5, 7, 9, 11, 13, 15, 17, 27, 29, 31, 33, 35, 37, 39, 41, 45, 47 or 49. In some embodiments, a mutated AOS2 protein includes a mutation at the amino acid position corresponding to position 1309 of SEQ ID NO: 19, 21, 23, 25 or 43. In some embodiments, a mutated AOS2 protein includes a mutation at the amino acid position corresponding to position M320 of SEQ ID NO: 1, 3, 5, 7, 9, 11, 13, 15, 17 19, 21, 25, 27, 29, 31, 33, 35, 37, 39, 41, 43, 45, 47 or 49. In some embodiments, a mutated AOS2 protein includes a mutation at the amino acid position corresponding to position L320 of SEQ ID NO: 23. In some embodiments, a mutated AOS2 protein includes a mutation at the amino acid position corresponding to position V328 of SEQ ID NO: 27, 33, 47 or 49. In some embodiments, a mutated AOS2 protein includes a mutation at the amino acid position corresponding to position M328 of SEQ ID NO: 5, 7, 9, 13 or 15. In some embodiments, a mutated AOS2 protein includes a mutation at the amino acid position corresponding to position L328 of SEQ ID NO: 1, 3, 11, 17, 19, 21, 23, 25, 29, 31, 35, 37, 39, 41, 43 or 45. In some embodiments, a mutated AOS2 protein includes a mutation at the amino acid position corresponding to position E337 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position D337 of SEQ ID NO: 13 or 15. In some embodiments, a mutated AOS2 protein includes a mutation at the amino acid position corresponding to position V338 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position L338 of SEQ ID NO: 13 or 15. In some embodiments, a mutated AOS2 protein includes a mutation at the amino acid position corresponding to position 1357 of SEQ ID NO: 1, 7, 9, 11, 13, 15, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position M357 of SEQ ID NO: 3. In some embodiments, a mutated AOS2 protein includes a mutation at the amino acid position corresponding to position P381 of SEQ ID NO: 1, 3, 5, 7, 9, 11, 13, 15, 17, 19, 21, 23, 25, 27, 29, 31, 33, 37, 39, 41, 43, 45, 47 or 49. In some embodiments, a mutated AOS2 protein includes a mutation at the amino acid position corresponding to position L381 of SEQ ID NO: 35. In some embodiments, a mutated AOS2 protein includes a mutation at the amino acid position corresponding to position T394 of SEQ ID NO: 9. In some embodiments, a mutated AOS2 protein includes a mutation at the amino acid position corresponding to position C407 of SEQ ID NO: 13 or 15. In some embodiments, a mutated AOS2 protein includes a mutation at the amino acid position corresponding to position G407 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 protein includes a mutation at the amino acid position corresponding to position F423 of SEQ ID NO: 7, 25, 27, 33, 47 or 49. In some embodiments, a mutated AOS2 protein includes a mutation at the amino acid position corresponding to position L430 of SEQ ID NO: 5. In some embodiments, a mutated AOS2 protein includes a mutation at the amino acid position corresponding to position 5467 of SEQ ID NO: 39. In some embodiments, a mutated AOS2 protein includes a mutation at the amino acid position corresponding to position G467 of SEQ ID NO: 1, 3, 5, 7, 9, 11, 13, 15, 17, 19, 21, 23, 25, 27, 29, 31, 33, 35, 37, 41, 43, 45, 47 or 49. In some embodiments, a mutated AOS2 protein includes a mutation at the amino acid position corresponding to position V480 of SEQ ID NO: 5. In some embodiments, a mutated AOS2 protein includes a mutation at the amino acid position corresponding to position D494 of SEQ ID NO: 21, 23, 31 or 43. In some embodiments, a mutated AOS2 protein includes a mutation at the amino acid position corresponding to position G494 of SEQ ID NO: 1, 3, 5, 7, 9, 11, 13, 15, 17, 19, 25, 27, 29, 33, 35, 37, 39, 41, 45, 47 or 49. In some embodiments, a mutated AOS2 protein includes a mutation at the amino acid position corresponding to position T495 of SEQ ID NO: 5, 7 or 9. In some embodiments, a mutated AOS2 protein includes a deletion of the amino acid at position corresponding to position E439 of SEQ ID NO: 5, 7, 9, 11, 13, 15, 17, 19, 21, 23, 25, 27, 33, 39, 41, 43, 45, 47 or 49.

In conjunction with any of the aspects, embodiments, compositions and methods disclosed herein, a mutated AOS2 protein includes the amino acid serine at a position corresponding to position 6 of SEQ ID NO: 1 or SEQ ID NO: 3. In conjunction with any of the aspects, embodiments, compositions and methods disclosed herein, a mutated AOS2 protein includes the amino acid proline at a position corresponding to position 12 of SEQ ID NO: 1 or SEQ ID NO: 3. In conjunction with any of the aspects, embodiments, compositions and methods disclosed herein, a mutated AOS2 protein includes the amino acid arginine at a position corresponding to position 12 of SEQ ID NO: 11. In conjunction with any of the aspects, embodiments, compositions and methods disclosed herein, a mutated AOS2 protein includes the amino acid valine at a position corresponding to position 30 of SEQ ID NO: 1 or SEQ ID NO: 3. In conjunction with any of the aspects, embodiments, compositions and methods disclosed herein, a mutated AOS2 protein includes the amino acid threonine at a position corresponding to position 37 of SEQ ID NO: 1 or SEQ ID NO: 3. In conjunction with any of the aspects, embodiments, compositions and methods disclosed herein, a mutated AOS2 protein includes the amino acid leucine at a position corresponding to position 46 of SEQ ID NO: 1. In conjunction with any of the aspects, embodiments, compositions and methods disclosed herein, a mutated AOS2 protein includes the amino acid phenylalanine at a position corresponding to position 46 of SEQ ID NO: 3. In conjunction with any of the aspects, embodiments, compositions and methods disclosed herein, a mutated AOS2 protein includes the amino acid isoleucine at a position corresponding to position 48 of SEQ ID NO: 27, SEQ ID NO: 47 or SEQ ID NO: 49. In conjunction with any of the aspects, embodiments, compositions and methods disclosed herein, a mutated AOS2 protein includes the amino acid threonine at a position corresponding to position 48 of SEQ ID NO: 1 or SEQ ID NO: 3. In conjunction with any of the aspects, compositions and methods disclosed herein, a mutated AOS2 protein includes the amino acid isoleucine at a position corresponding to position 51 of SEQ ID NO: 1 or SEQ ID NO: 3. In conjunction with any of the aspects, embodiments, compositions and methods disclosed herein, a mutated AOS2 protein includes the amino acid aspartic acid at a position corresponding to position 76 of SEQ ID NO: 1 or SEQ ID NO: 3. In conjunction with any of the aspects, embodiments, compositions and methods disclosed herein, a mutated AOS2 protein includes the amino acid asparagine at a position corresponding to position 76 of SEQ ID NO: 1 or SEQ ID NO: 3. In conjunction with any of the aspects, embodiments, compositions and methods disclosed herein, a mutated AOS2 protein includes the amino acid glycine at a position corresponding to position 113 of SEQ ID NO: 1 or SEQ ID NO: 3. In conjunction with any of the aspects, embodiments, compositions and methods disclosed herein, a mutated AOS2 protein includes the amino acid aspartic acid at a position corresponding to position 113 of SEQ ID NO: 49. In some embodiments, a mutated AOS2 protein includes the amino acid tyrosine at a position corresponding to position 145 of SEQ ID NO: 1 or SEQ ID NO: 3. In conjunction with any of the aspects, embodiments, compositions and methods disclosed herein, a mutated AOS2 protein includes the amino acid phenylalanine at a position corresponding to position 187 of SEQ ID NO: 1 or SEQ ID NO: 3. In conjunction with any of the aspects, embodiments, compositions and methods disclosed herein, a mutated AOS2 protein includes the amino acid glutamic acid at a position corresponding to position 197 of SEQ ID NO: 1. In conjunction with any of the aspects, embodiments, compositions and methods disclosed herein, a mutated AOS2 protein includes the amino acid aspartic acid at a position corresponding to position 197 of SEQ ID NO: 3. In conjunction with any of the aspects, embodiments, compositions and methods disclosed herein, a mutated AOS2 protein includes the amino acid threonine at a position corresponding to position 200 of SEQ ID NO: 1 or SEQ ID NO: 3. In conjunction with any of the aspects, embodiments, compositions and methods disclosed herein, a mutated AOS2 protein includes the amino acid threonine at a position corresponding to position 227 of SEQ ID NO: 1 or SEQ ID NO: 3. In conjunction with any of the aspects, embodiments, compositions and methods disclosed herein, a mutated AOS2 protein includes the amino acid threonine at a position corresponding to position 231 of SEQ ID NO: 1 or SEQ ID NO: 3. In conjunction with any of the aspects, embodiments, compositions and methods disclosed herein, a mutated AOS2 protein includes the amino acid glycine at a position corresponding to position 231 of SEQ ID NO: 9. In some embodiments, a mutated AOS2 protein includes the amino acid phenylalanine at a position corresponding to position 256 of SEQ ID NO: 1. In some embodiments, a mutated AOS2 protein includes the amino acid valine at a position corresponding to position 256 of SEQ ID NO: 3. In conjunction with any of the aspects, embodiments, compositions and methods disclosed herein, a mutated AOS2 protein includes the amino acid threonine at a position corresponding to position 264 of SEQ ID NO: 1 or SEQ ID NO: 3. In conjunction with any of the aspects, embodiments, compositions and methods disclosed herein, a mutated AOS2 protein includes the amino acid phenylalanine at a position corresponding to position 270 of SEQ ID NO: 1 or SEQ ID NO: 3. In conjunction with any of the aspects, embodiments, compositions and methods disclosed herein, a mutated AOS2 protein includes the amino acid phenylalanine at a position corresponding to position 282 of SEQ ID NO: 1 or SEQ ID NO: 3. In conjunction with any of the aspects, embodiments, compositions and methods disclosed herein, a mutated AOS2 protein includes the amino acid serine at a position corresponding to position 282 of SEQ ID NO: 41. In some embodiments, a mutated AOS2 protein includes the amino acid serine at a position corresponding to position 289 of SEQ ID NO: 1 or SEQ ID NO: 3. In some embodiments, a mutated AOS2 protein includes the amino acid asparagine at a position corresponding to position 289 of SEQ ID NO: 13. In some embodiments, a mutated AOS2 protein includes the amino acid alanine at a position corresponding to position 292 of SEQ ID NO: 1 or SEQ ID NO: 3. In conjunction with any of the aspects, embodiments, compositions and methods disclosed herein, a mutated AOS2 protein includes the amino acid leucine at a position corresponding to position 309 of SEQ ID NO: 1 or SEQ ID NO: 3. In conjunction with any of the aspects, embodiments, compositions and methods disclosed herein, a mutated AOS2 protein includes the amino acid isoleucine at a position corresponding to position 309 of SEQ ID NO: 19. In conjunction with any of the aspects, embodiments, compositions and methods disclosed herein, a mutated AOS2 protein includes the amino acid methonine at a position corresponding to position 320 of SEQ ID NO: 1 or SEQ ID NO: 3. In conjunction with any of the aspects, embodiments, compositions and methods disclosed herein, a mutated AOS2 protein includes the amino acid leucine at a position corresponding to position 320 of SEQ ID NO: 23. In conjunction with any of the aspects, embodiments, compositions and methods disclosed herein, a mutated AOS2 protein includes the amino acid leucine at a position corresponding to position 328 of SEQ ID NO: 1 or SEQ ID NO: 3. In conjunction with any of the aspects, embodiments, compositions and methods disclosed herein, a mutated AOS2 protein includes the amino acid valine at a position corresponding to position 328 of SEQ ID NO: 27. In conjunction with any of the aspects, embodiments, compositions and methods disclosed herein, a mutated AOS2 protein includes the amino acid glutamic acid at a position corresponding to position 337 of SEQ ID NO: 1 or SEQ ID NO: 3. In conjunction with any of the aspects, embodiments, compositions and methods disclosed herein, a mutated AOS2 protein includes the amino acid aspartic acid at a position corresponding to position 337 of SEQ ID NO: 13 or SEQ ID NO: 15. In conjunction with any of the aspects, embodiments, compositions and methods disclosed herein, a mutated AOS2 protein includes the amino acid valine at a position corresponding to position 338 of SEQ ID NO: 1 or SEQ ID NO: 3. In conjunction with any of the aspects, embodiments, compositions and methods disclosed herein, a mutated AOS2 protein includes the amino acid leucine at a position corresponding to position 338 of SEQ ID NO: 13 or SEQ ID NO: 15. In conjunction with any of the aspects, embodiments, compositions and methods disclosed herein, a mutated AOS2 protein includes the amino acid isoleucine at a position corresponding to position 357 of SEQ ID NO: 1. In conjunction with any of the aspects, embodiments, compositions and methods disclosed herein, a mutated AOS2 protein includes the amino acid methionine at a position corresponding to position 357 of SEQ ID NO: 3. In conjunction with any of the aspects, embodiments, compositions and methods disclosed herein, a mutated AOS2 protein includes the amino acid proline at a position corresponding to position 381 of SEQ ID NO: 1 or SEQ ID NO: 3. In conjunction with any of the aspects, embodiments, compositions and methods disclosed herein, a mutated AOS2 protein includes the amino acid leucine at a position corresponding to position 381 of SEQ ID NO: 35. In conjunction with any of the aspects, embodiments, compositions and methods disclosed herein, a mutated AOS2 protein includes the amino acid lysine at a position corresponding to position 394 of SEQ ID NO: 1 or SEQ ID NO: 3. In conjunction with any of the aspects, embodiments, compositions and methods disclosed herein, a mutated AOS2 protein includes the amino acid glycine at a position corresponding to position 407 of SEQ ID NO: 1 or SEQ ID NO: 3. In conjunction with any of the aspects, embodiments, compositions and methods disclosed herein, a mutated AOS2 protein includes the amino acid cysteine at a position corresponding to position 407 of SEQ ID NO: 13 or SEQ ID NO: 15. In conjunction with any of the aspects, embodiments, compositions and methods disclosed herein, a mutated AOS2 protein includes the amino acid isoleucine at a position corresponding to position 423 of SEQ ID NO: 1 or SEQ ID NO: 3. In conjunction with any of the aspects, embodiments, compositions and methods disclosed herein, a mutated AOS2 protein includes the amino acid phenylalanine at a position corresponding to position 430 of SEQ ID NO: 1 or SEQ ID NO: 3. In conjunction with any of the aspects, embodiments, compositions and methods disclosed herein, a mutated AOS2 protein includes the deletion of the amino acid glutamic acid at a position corresponding to position 439 of SEQ ID NO: 5. In conjunction with any of the aspects, embodiments, compositions and methods disclosed herein, a mutated AOS2 protein includes the amino acid glycine at a position corresponding to position 466 of SEQ ID NO: 1 or SEQ ID NO: 3. In conjunction with any of the aspects, embodiments, compositions and methods disclosed herein, a mutated AOS2 protein includes the amino acid serine at a position corresponding to position 467 of SEQ ID NO: 39. In conjunction with any of the aspects, embodiments, compositions and methods disclosed herein, a mutated AOS2 protein includes the amino acid threonine at a position corresponding to position 479 of SEQ ID NO: 1 or SEQ ID NO: 3. In conjunction with any of the aspects, embodiments, compositions and methods disclosed herein, a mutated AOS2 protein includes the amino acid glycine at a position corresponding to position 493 of SEQ ID NO: 1 or SEQ ID NO: 3. In conjunction with any of the aspects, embodiments, compositions and methods disclosed herein, a mutated AOS2 protein includes the amino acid aspartic acid at a position corresponding to position 494 of SEQ ID NO: 21. In some embodiments, a mutated AOS2 protein includes the amino acid lysine at a position corresponding to position 494 of SEQ ID NO: 1 or SEQ ID NO: 3.

In conjunction with any of the aspects, embodiments, compositions and methods disclosed herein, a mutated AOS2 gene encodes a mutated AOS2 protein having one or more mutations, two or more mutations, three or more mutations, four or more mutations, five or more mutations, six or more mutations, seven or more, eight or more, nine or more, or ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more mutations selected from the group consisting of a phenylalanine to a serine at a position corresponding to position 6, an arginine to a proline at a position corresponding to position 12, a proline to an arginine at a position corresponding to position 12, an alanine to a valine at a position corresponding to position 30, an isoleucine to a threonine at a position corresponding to position 37, a phenylalanine to a leucine at a position corresponding to position 46, a leucine to a phenylalanine at a position corresponding to position 46, a valine to a threonine at a position corresponding to position 48, a valine to an isoleucine at a position corresponding to position 48, an isoleucine to a threonine at a position corresponding to position 48, a threonine to an isoleucine at a position corresponding to position 48, a methionine to an isoleucine at a position corresponding to position 51, an asparagine to an aspartic acid at a position corresponding to position 76, an aspartic acid to an asparagine at a position corresponding to position 76, an aspartic acid to a glycine at a position corresponding to position 113, a glycine to an aspartic acid at a position corresponding to position 113, a phenylalanine to a tyrosine at a position corresponding to position 145, a leucine to a phenylalanine at a position corresponding to position 187, an aspartic acid to a glutamic acid at a position corresponding to position 197, a glutamic acid to an aspartic acid at a position corresponding to position 197, a lysine to a threonine at a position corresponding to position 200, an alanine to a threonine at a position corresponding to position 227, an isoleucine to a threonine at a position corresponding to position 231, an isoleucine to a glycine at a position corresponding to position 231, a glycine to a threonine at a position corresponding to position 231, a threonine to a glycine at a position corresponding to position 231, a valine to a phenylalanine at a position corresponding to position 256, a phenylalanine to a valine at a position corresponding to position 256, an alanine to a threonine at a position corresponding to position 264, a leucine to a phenylalanine at a position corresponding to position 270, a serine to a phenylalanine at a position corresponding to position 282, a phenylalanine to a serine at a position corresponding to position 282, a valine to an asparagine at a position corresponding to position 289, a valine to a serine at a position corresponding to position 289, a serine to an asparagine at a position corresponding to position 289, an asparagine to a serine at a position corresponding to position 289, a valine to an alanine at a position corresponding to position 292, an isoleucine to leucine at a position corresponding to position 309, a leucine to an isoleucine at a position corresponding to position 309, a leucine to methionine at a position corresponding to position 320, a methionine to a leucine at a position corresponding to position 320, a methionine to a leucine at a position corresponding to position 328, a methionine to valine at a position corresponding to position 328, a valine to a leucine at a position corresponding to position 328, a leucine to a valine at a position corresponding to position 328, an aspartic acid to a glutamic acid at a position corresponding to position 337, a glutamic acid to an aspartic acid at a position corresponding to position 337, a leucine to a valine at a position corresponding to position 338, a valine to a leucine at a position corresponding to position 338, a methionine to an isoleucine at a position corresponding to position 357, an isoleucine to a methionine at a position corresponding to position 357, a leucine to a proline at a position corresponding to position 381, a proline to a leucine at a position corresponding to position 381, a threonine to lysine at a position corresponding to position 394, a cysteine to a glycine at a position corresponding to position 407, a glycine to a cysteine at a position corresponding to position 407, a phenylalanine to an isoleucine at a position corresponding to position 423, a leucine to a phenylalanine at a position corresponding to position 430, a serine to a glycine at a position corresponding to position 467, a glycine to a serine at a position corresponding to position 467, a valine to a threonine at a position corresponding to position 480, an aspartic acid to a glycine at a position corresponding to position 494, a glycine to an aspartic acid at a position corresponding to position 494, a threonine to a lysine at a position corresponding to position 495 of SEQ ID NO: 1, 3, 5, 7, 9, 11, 13, 15, 17, 19, 21, 23, 25, 27, 29, 31, 33, 35, 37, 39, 41, 43, 45, 47 or 49, and a deletion of a glutamic acid at a position corresponding to position 439 SEQ ID NO: 5, 7, 9, 11, 13, 15, 17, 19, 21, 23, 25, 27, 33, 39, 41, 43, 45, 47 or 49.

In conjunction with any of the aspects, embodiments, compositions and methods disclosed herein, a mutated AOS2 gene encodes a mutated AOS2 protein that includes an amino acid mutation from a phenylalanine to serine at a position corresponding to position 6 of SEQ ID NO: 1, 3, 5, 11, 13, 15, 17 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an arginine to proline at a position corresponding to position 12 of SEQ ID NO: 1, 3, 5, 7, 9, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a proline to an arginine at a position corresponding to position 12 of SEQ ID NO: 11. In some embodiments, a mutated AOS2 gene encodes a mutated AOS2 protein that includes an amino acid mutation from an alanine to a valine at a position corresponding to position 30 of SEQ ID NO: 1, 3, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an isoleucine to a threonine at a position corresponding to position 37 of SEQ ID NO: 1, 3, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a phenylalanine to leucine at a position corresponding to position 46 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a leucine to a phenylalanine at a position corresponding to position 46 of SEQ ID NO: 3. In some embodiments, a mutated AOS2 gene encodes a mutated AOS2 protein that includes an amino acid mutation from a valine to a threonine at a position corresponding to position 48 of SEQ ID NO: 1, 3, 5, 9, 11, 13, 15, 17, 19, 21, 23, 25, 29, 31, 33, 35, 37, 39, 41, 43 or 45. In some embodiments, a mutated AOS2 gene encodes a mutated AOS2 protein that includes an amino acid mutation from an isoleucine to a threonine at a position corresponding to position 48 of SEQ ID NO: 1, 3, 5, 9, 11, 13, 15, 17, 19, 21, 23, 25, 29, 31, 33, 35, 37, 39, 41, 43 or 45. In some embodiments, a mutated AOS2 gene encodes a mutated AOS2 protein that includes an amino acid mutation from a threonine to a isoleucine at a position corresponding to position 48 of SEQ ID NO: 27, 47 or 49. In some embodiments, a mutated AOS2 gene encodes a mutated AOS2 protein that includes an amino acid mutation from a valine to an isoleucine at a position corresponding to position 48 of SEQ ID NO: 27, 47 or 49. In some embodiments, a mutated AOS2 gene encodes a mutated AOS2 protein that includes an amino acid mutation from a methionine to an isoleucine at a position corresponding to position 51 of SEQ ID NO: 1, 3, 7, 9, 11, 13, 15, 17 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an asparagine to an aspartic acid at a position corresponding to position 76 of SEQ ID NO: 1, 3, 11, 13, 15, 17, 27, 33, 35, 37, 39, 41, 45, 47 or 49. In some embodiments, a mutated AOS2 gene encodes a mutated AOS2 protein that includes an amino acid mutation from an aspartic acid to an asparagine at a position corresponding to position 76 of SEQ ID NO: 1, 3, 11, 13, 15, 17, 27, 33, 35, 37, 39, 41, 45, 47 or 49. In some embodiments, a mutated AOS2 gene encodes a mutated AOS2 protein that includes an amino acid mutation from an aspartic acid to a glycine at a position corresponding to position 113 of SEQ ID NO: 1, 3, 5, 7, 9, 11, 13, 15, 17, 19, 21, 23, 25, 27, 29, 31, 33, 35, 37, 39, 41, 43, 45 or 47. In some embodiments, a mutated AOS2 gene encodes a mutated AOS2 protein that includes an amino acid mutation from a glycine to an aspartic acid at a position corresponding to position 113 of SEQ ID NO: 49. In some embodiments, a mutated AOS2 gene encodes a mutated AOS2 protein that includes an amino acid mutation from a phenylalanine to a tyrosine at a position corresponding to position 145 of SEQ ID NO: 1, 3, 5, 7, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a leucine to a phenylalanine at a position corresponding to position 187 of SEQ ID NO: 1, 3, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a glutamic acid to an aspartic acid at a position corresponding to position 197 of SEQ ID NO: 3. In some embodiments, a mutated AOS2 gene encodes a mutated AOS2 protein that includes an amino acid mutation from an aspartic acid to a glutamic acid at a position corresponding to position 197 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a lysine to a threonine at a position corresponding to position 200 of SEQ ID NO: 1, 3, 5, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an alanine to a threonine at a position corresponding to position 227 of SEQ ID NO: 1, 3, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an isoleucine to a threonine at a position corresponding to position 231 of SEQ ID NO: 1, 3, 5, 23, 25, 27, 31, 33, 35, 37, 39, 41, 47 or 49. In some embodiments, a mutated AOS2 gene encodes a mutated AOS2 protein that includes an amino acid mutation from an isoleucine to a glycine at a position corresponding to position 231 of SEQ ID NO: 9, 11, 13, 15, 17, 19, 21, 29, 43 or 45. In some embodiments, a mutated AOS2 gene encodes a mutated AOS2 protein that includes an amino acid mutation from a threonine to a glycine at a position corresponding to position 231 of SEQ ID NO: 9, 11, 13, 15, 17, 19, 21, 29 43 or 45. In some embodiments, a mutated AOS2 gene encodes a mutated AOS2 protein that includes an amino acid mutation from a glycine to a threonine at a position corresponding to position 231 of SEQ ID NO: 1, 3, 5, 23, 25, 27, 31, 33, 35, 37, 39, 41, 47 or 49. In some embodiments, a mutated AOS2 gene encodes a mutated AOS2 protein that includes an amino acid mutation from a phenylalanine to a valine at a position corresponding to position 256 of SEQ ID NO: 3. In some embodiments, a mutated AOS2 gene encodes a mutated AOS2 protein that includes an amino acid mutation from a valine to a phenylalanine at a position corresponding to position 256 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an alanine to a threonine at a position corresponding to position 264 of SEQ ID NO: 1, 3, 5, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a leucine to a phenylalanine at a position corresponding to position 270 of SEQ ID NO: 1, 3, 5, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a phenylalanine to a serine at a position corresponding to position 282 of SEQ ID NO: 41. In some embodiments, a mutated AOS2 gene encodes a mutated AOS2 protein that includes an amino acid mutation from a serine to a phenylalanine at a position corresponding to position 282 of SEQ ID NO: 1, 3, 5, 7, 9, 11, 13, 15, 17, 19, 21, 23, 25, 27, 29, 31, 33, 35, 37, 39, 43, 45, 47 or 49. In some embodiments, a mutated AOS2 gene encodes a mutated AOS2 protein that includes an amino acid mutation from a valine to an asparagine at a position corresponding to position 289 of SEQ ID NO: 13. In some embodiments, a mutated AOS2 gene encodes a mutated AOS2 protein that includes an amino acid mutation from a valine to a serine at a position corresponding to position 289 of SEQ ID NO: 1, 3, 11, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an asparagine to a serine at a position corresponding to position 289 of SEQ ID NO: 1, 3, 11, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a serine to an asparagine at a position corresponding to position 289 of SEQ ID NO: 13. In some embodiments, a mutated AOS2 gene encodes a mutated AOS2 protein that includes an amino acid mutation from a valine to an alanine at a position corresponding to position 292 of SEQ ID NO: 1, 3, 11, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a leucine to an isoleucine at a position corresponding to position 309 of SEQ ID NO: 19, 21, 23, 25, or 43. In some embodiments, a mutated AOS2 gene encodes a mutated AOS2 protein that includes an amino acid mutation from an isoleucine to a leucine at a position corresponding to position 309 of SEQ ID NO: 1, 3, 5, 7, 9, 11, 13, 15, 17, 27, 29, 31, 33, 35, 37, 39, 41, 45, 47 or 49. In some embodiments, a mutated AOS2 gene encodes a mutated AOS2 protein that includes an amino acid mutation from a leucine to a methionine at a position corresponding to position 320 of SEQ ID NO: 1, 3, 5, 7, 9, 11, 13, 15, 17, 19, 21, 25, 27, 29, 31, 33, 35, 37, 39, 41, 43, 45, 47 or 49. In some embodiments, a mutated AOS2 gene encodes a mutated AOS2 protein that includes an amino acid mutation from a methinone to a leucine at a position corresponding to position 320 of SEQ ID NO: 23. In some embodiments, a mutated AOS2 gene encodes a mutated AOS2 protein that includes an amino acid mutation from a methionine to a valine at a position corresponding to position 328 of SEQ ID NO: 27, 33, 47 or 49. In some embodiments, a mutated AOS2 gene encodes a mutated AOS2 protein that includes an amino acid mutation from a methionine to a leucine at a position corresponding to position 328 of SEQ ID NO: 1, 3, 11, 17, 19, 21, 23, 25, 29, 31, 35, 37, 39, 41, 43 or 45. In some embodiments, a mutated AOS2 gene encodes a mutated AOS2 protein that includes an amino acid mutation from a leucine to a valine at a position corresponding to position 328 of SEQ ID NO: 27, 33, 47 or 49. In some embodiments, a mutated AOS2 gene encodes a mutated AOS2 protein that includes an amino acid mutation from a valine to a leucine at a position corresponding to position 328 of SEQ ID NO: 1, 3, 11, 17, 19, 21, 23, 25, 29, 31, 35, 37, 39, 41, 43 or 45. In some embodiments, a mutated AOS2 gene encodes a mutated AOS2 protein that includes an amino acid mutation from an aspartic acid to a glutamic acid at a position corresponding to position 337 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a glutamic acid to an aspartic acid at a position corresponding to position 337 of SEQ ID NO: 13 or 15. In some embodiments, a mutated AOS2 gene encodes a mutated AOS2 protein that includes an amino acid mutation from a leucine to a valine at a position corresponding to position 338 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a valine to a leucine at a position corresponding to position 338 of SEQ ID NO: 13 or 15. In some embodiments, a mutated AOS2 gene encodes a mutated AOS2 protein that includes an amino acid mutation from a methionine to an isoleucine at a position corresponding to position 357 of SEQ ID NO: 1, 5, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from an isoleucine to a methionine at a position corresponding to position 357 of SEQ ID NO: 3. In some embodiments, a mutated AOS2 gene encodes a mutated AOS2 protein that includes an amino acid mutation from a leucine to a proline at a position corresponding to position 381 of SEQ ID NO: 1, 3, 5, 7, 9, 11, 13, 15, 17, 19, 21, 23, 25, 27, 29, 31, 33, 37, 39, 41, 43, 45, 47 or 49. In some embodiments, a mutated AOS2 gene encodes a mutated AOS2 protein that includes an amino acid mutation from a proline to a leucine at a position corresponding to position 381 of SEQ ID NO: 35. In some embodiments, a mutated AOS2 gene encodes a mutated AOS2 protein that includes an amino acid mutation from a threonine to a lysine at a position corresponding to position 394 of SEQ ID NO: 1, 3, 5, 7, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a cysteine to a glycine at a position corresponding to position 407 of SEQ ID NO: 1, 3, 5, 7, 9, 11, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a glycine to a cysteine to at a position corresponding to position 407 of SEQ ID NO: 13 or 15. In some embodiments, a mutated AOS2 gene encodes a mutated AOS2 protein that includes an amino acid mutation from a phenylalanine to an isoleucine at a position corresponding to position 423 of SEQ ID NO: 1, 3, 5, 9, 11, 13, 15, 17 19, 21, 23, 29, 31, 35, 37, 39, 41, 43 or 45. In some embodiments, a mutated AOS2 gene encodes a mutated AOS2 protein that includes an amino acid mutation from a leucine to a phenylalanine at a position corresponding to position 430 of SEQ ID NO: 1, 3, 7, 9, 11, 13, 15, 17, 19, 21, 23, 25, 27, 29, 31, 33, 35, 37, 39, 41, 43, 45, 47 or 49. In some embodiments, a mutated AOS2 gene encodes a mutated AOS2 protein that includes an amino acid mutation from a serine to a glycine at a position corresponding to position 467 of SEQ ID NO: 5, 7, 9, 11, 13, 15, 17, 19, 21, 23, 25, 27, 33, 41, 43, 45, 47 or 49 or position 466 of SEQ ID NO: 1, 3, 29, 31, 35 or 37. In some embodiments, a mutated AOS2 gene encodes a mutated AOS2 protein that includes an amino acid mutation from a glycine to a serine at a position corresponding to position 467 of SEQ ID NO: 39. In some embodiments, a mutated AOS2 gene encodes a mutated AOS2 protein that includes an amino acid mutation from a valine to a threonine at a position corresponding to position 480 of SEQ ID NO: 7, 9, 11, 13, 15, 17, 19, 21, 23, 25, 27, 29, 31, 33, 35, 37, 39, 41, 43, 45, 47 or 49 or position 479 of SEQ ID NO: 1, 3, 29, 31, 35 or 37. In some embodiments, a mutated AOS2 gene encodes a mutated AOS2 protein that includes an amino acid mutation from an aspartic acid to a glycine at a position corresponding to position 494 of SEQ ID NO: 5, 7, 9, 11, 13, 15, 17, 19, 25, 27, 29, 33, 35, 37, 39, 41, 45, 47 or 49 or position 493 of SEQ ID NO: 1, 3, 29, 35 or 37. In some embodiments, a mutated AOS2 gene encodes a mutated AOS2 protein that includes an amino acid mutation from a glycine to an aspartic acid at a position corresponding to position 494 of SEQ ID NO: 21, 23 or 43 or position 493 of SEQ ID NO: 31. In some embodiments, a mutated AOS2 gene encodes a mutated AOS2 protein that includes an amino acid mutation from a threonine to a lysine at a position corresponding to position 495 of SEQ ID NO: 11, 13, 15, 17, 19, 21, 23, 25, 27, 29, 31, 33, 35, 37, 39, 41, 43, 45, 47 or 49 or position 494 of SEQ ID NO: 1, 3, 29, 31, 35 or 37. In some embodiments, a mutated AOS2 gene encodes a mutated AOS2 protein that includes an amino acid mutation where a glutamic acid is deleted at a position corresponding to position 439 of SEQ ID NO: 1, 3, 29, 31, 35 or 37.

In conjunction with any of the aspects, embodiments, compositions and methods disclosed herein, a mutated AOS2 gene includes at least one mutation, at least two mutations, at least three mutations, at least four mutations, at least five mutations, at least six mutations, at least seven mutations at least eight mutations, at least nine mutations, at least ten mutations, at least eleven mutations, at least twelve mutations, at least thirteen mutations, at least fourteen mutations, at least fifteen mutations, at least sixteen mutations, at least seventeen mutations, at least eighteen mutations, at least nineteen mutations, at least twenty mutations, at least twenty-one mutations, at least twenty-two mutations, at least twenty-three mutations, at least twenty-four mutations, at least twenty-five mutations, at least twenty-six mutations, at least twenty-seven mutations, at least twenty-eight mutations, at least twenty-nine mutations, at least thirty mutations, at least thirty-one mutations, at least thirty-two mutations, at least thirty-three mutations, at least thirty-four mutations, at least thirty-five mutations, at least thirty-six mutations, or at least thirty-seven mutations.

Paralogs

The subject mutations in the AOS2 gene are generally described herein using the selected *Solanum tuberosum* AOS2 genes and proteins with amino acids referenced to positions in SEQ ID NOs: 1, 3, 5, 7, 9, 11, 13, 15, 17 19, 21, 23, 25, 27, 29, 31, 33, 35, 37, 39, 41, 43, 45, 47 and 49 and nucleic acid positions referenced to positions in SEQ ID NOs: 2, 4, 6, 8, 10, 12, 14, 16, 18, 20, 22, 24, 26, 28, 30, 32, 34, 36, 38, 40, 42, 44, 46, 48 and 50. The compositions and methods also encompass mutant AOS2 genes and proteins of other potato cultivars as well as other plant species (paralogs). However, due to variations in the AOS2 genes of different species, the number of the amino acid residue to be changed in one species may be different in another species. Nevertheless, the analogous position is readily identified by one of skill in the art by sequence homology. Thus, analogous positions in paralogs can be identified and mutated.

Pathogens

The compositions and methods provided herein include AOS2 genes and AOS2 proteins that confer resistance and/or tolerance to pathogens. In some embodiments, the pathogen is a *Phytophthora* pathogen. In particular embodiments, the pathogen is *Phytophthora infestans*. In particular embodiments, the pathogen is a virus, bacteria, nematode, fungi and like. Viral pathogens include any plant virus, for example, tobacco or cucumber mosaic virus, potato virus Y, ringspot virus, necrosis virus, maize dwarf mosaic virus, and the like. Fungal, oomycete and viral pathogens for major crops include, but are not limited to, *Phytophthora*, *Fusarium* ssp, *Alternaria, Pythium* spp., Soybean mosaic virus, Tobacco Ring spot virus, Tobacco Streak virus, Tomato spotted wilt virus, *Sclerotinia, Peronospora, Cladosporium, Erysiphe, Aspergillus, Puccinia* spp., *Botrytis* spp., *Blumeria* spp., and *Trichoderma*. Bacterial plant pathogens include any bacterial species that infect plant and include, but are not limited to, *Xanthomonas* (e.g., *Xanthomonas axonopodis* pv. *aurantifolii*, *Xanthomonas campestris* pv. *campestris*, *Xanthomonas campestris* pv. *vesicatoria*), *Pseudomonas* (*Pseudomonas syringae* pv. tomato, *Pseudomonas syringae* pv. *phaseolicola*, *Pseudomonas syringae* pv. *syringae*), *Erwinia* (e.g., *Erwinia carotovora* subsp. *atroseptica*), *Ralstonia* (e.g., *Ralstonia solanacearum*), *Clavibacter michiganensis* and *Xylella fastidiosa*.

Also provided is a transgenic or non-transgenic plant or plant cell having one or more mutations in the AOS2 gene, for example, such as disclosed herein. In certain embodiments, the plant or plant cell having one or more mutations in an AOS2 gene has increased resistance and/or tolerance to a pathogen. In certain embodiments, the plant or plant cell having one or more mutations in an AOS2 gene may exhibit substantially normal growth or development of the plant, its organs, tissues or cells, as compared to the corresponding wild-type plant or cell. In particular aspects and embodiments provided are non-transgenic plants having a mutation in an AOS2 gene, for example, such as disclosed herein, which in certain embodiments has increased resistance and/or tolerance to *Phytophthora infestans*.

Further provided are methods for producing a plant having a mutated AOS2 gene, for example, having one or more mutations as described herein; preferably the plant substantially maintains the catalytic activity of the wild-type protein irrespective of the presence or absence of a relevant pathogen. In certain embodiments, the methods include introducing into a plant cell a gene repair oligonucleobase with one or more targeted mutations in the AOS2 gene (e.g., such as disclosed herein) and identifying a cell, seed, or plant having a mutated AOS2 gene.

Plant Species

In conjunction with any of the various aspects, embodiments, compositions and methods disclosed herein, a plant or plant cell can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant or plant cell may be selected from a species of plant selected from the group consisting of potato, sunflower, sugar beet, maize, cotton, soybean, wheat, rye, oats, rice, canola, fruits, vegetables, tobacco, aubergine, barley, boxthane, sorghum, tomato, tomatillo, tamarillo, mango, peach, apple, pear, strawberry, banana, melon, goji berry, garden huckleberry, ground cherry, carrot, lettuce, onion, soya spp, sugar cane, pea, field beans, poplar, grape, citrus, alfalfa, rye, oats, turf and forage grasses, cucurbits, flax, oilseed rape, cucumber, squash, pumpkin, watermelon, muskmelons, morning glory, balsam, pepper, sweet pepper, bell pepper, chili pepper, paprika, pimento, habanero, cayenne, eggplant, marigold, lotus, cabbage, daisy, carnation, tulip, iris, lily, and nut-producing plants insofar as they are not already specifically mentioned. The plant or plant cell may also be of a species selected from the group consisting of *Arabidopsis thaliana, Solanum tuberosum, Solanum phureja, Oryza sativa, Amaranthus tuberculatus*, and *Zea mays*. In various embodiments, plants as disclosed herein can be of any species of the Solanaceae family.

In some embodiments, plants or plant cells may be a tomato. In some embodiments, plants or plant cells may be an eggplant. In some embodiments, plants or plant cells may be a pepper. In some embodiments, plants or plant cells may be a soybean. In some embodiments, plants or plant cells may be tobacco.

In conjunction with any of the aspects, embodiments, compositions and methods disclosed herein, plants can be a potato of any commercial variety. For example, the plant or plant cell may be selected from a potato variety selected from the group consisting of Anya, Arran Victory, Atlantic, Belle de Fontenay, BF-15, Bintje, Cabritas, Camota, Chelina, Chiloé, Cielo, Clavela Blanca, Désirée, Fianna, Fingerling, Fontana, Flava, Golden Wonder, Innovator, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, B53 (Roslin Eburu), Kiraya, Kenya Akiba, 9, Original, Gituma, Mukorino, Amin, Pimpernel, Anett, B, Gituru, Feldeslohn, C, Kigeni, Romano, Kenya Ruaka, Purplu, Njae, Suzanna, Cardinal, Kathama, Kinare-Mwene, Kibururu, Karoa-Igura, Muturu, Faraja, Kiamucove, Michiri, Rugano, Njine Giathireko, Meru Mix, Blue Baranja, Patrones, Robijn, Roslin Chania, Urgentia, Mirka, and Roslin Sasamua.

In various embodiments, plants or plant cells as disclosed herein can be a potato of any commercial variety. In some embodiments, the plant or plant cell may be of the potato variety Anya. In some embodiments, the plant or plant cell may be of the potato variety Arran Victory. In some embodiments, the plant or plant cell may be of the potato variety Atlantic. In some embodiments, the plant or plant cell may be of the potato variety Belle de Fontenay. In some embodiments, the plant or plant cell may be of the potato variety BF-15. In some embodiments, the plant or plant cell may be of the potato variety Bintje. In some embodiments, the plant or plant cell may be of the potato variety Cabritas. In some embodiments, the plant or plant cell may be of the potato variety Camota. In some embodiments, the plant or plant cell may be of the potato variety Chelina. In some embodiments, the plant or plant cell may be of the potato variety Chiloé, Cielo. In some embodiments, the plant or plant cell may be of the potato variety Clavela Blanca. In some embodiments, the plant or plant cell may be of the potato variety Désirée. In some embodiments, the plant or plant cell may be of the potato variety Fianna. In some embodiments, the plant or plant cell may be of the potato variety Fingerling. In some embodiments, the plant or plant cell may be of the potato variety Flava. In some embodiments, the plant or plant cell may be of the potato variety Fontana. In some embodiments, the plant or plant cell may be of the potato variety Golden Wonder. In some embodiments, the plant or plant cell may be of the potato variety Innovator. In some embodiments, the plant or plant cell may be of the potato variety Jersey Royal. In some embodiments, the plant or plant cell may be of the potato variety Kerr's Pink. In some embodiments, the plant or plant cell may be of the potato variety Kestrel. In some embodiments, the plant or plant cell may be of the potato variety King Edward. In some embodiments, the plant or plant cell may be of the potato variety Kipfler. In some embodiments, the plant or plant cell may be of the potato variety Lady Balfour. In some embodiments, the plant or plant cell may be of the potato variety Maris Piper. In some embodiments, the plant or plant cell may be of the potato variety Nicola. In some embodiments, the plant or plant cell may be of the potato variety Pachacoña. In some embodiments, the plant or plant cell may be of the potato variety Pink Eye. In some embodiments, the plant or plant cell may be of the potato variety Pink Fir Apple. In some embodiments, the plant or plant cell may be of the potato variety Primura. In some embodiments, the plant or plant cell may be of the potato variety Red Norland. In some embodiments, the plant or plant cell may be of the potato variety Red Pontiac. In some embodiments, the plant or plant cell may be of the potato variety Rooster. In some embodiments, the plant or plant cell may be of the potato variety Russet Burbank. In some embodiments, the plant or plant cell may be of the potato variety Russet Norkotah. In some embodiments, the plant or plant cell may be of the potato variety Shepody. In some embodiments, the plant or plant cell may be of the potato variety Spunta. In some embodiments, the plant or plant cell may be of the potato variety Vivaldi. In some embodiments, the plant or plant cell may be of the potato variety Yukon Gold. In some embodiments, the plant or plant cell may be of the potato variety Nyayo. In some embodiments, the plant or plant cell may be of the potato variety Mukori. In some embodiments, the plant or plant cell may be of the potato variety Roslin Tana. In some embodiments, the plant or plant cell may be of the potato variety Kerrs's Pink/Meru. In some embodiments, the plant or plant cell may be of the potato variety Golof. In some embodiments, the plant or plant cell may be of the potato variety Kinongo. In some embodiments, the plant or plant cell may be of the potato variety Ngure. In some embodiments, the plant or plant cell may be of the potato variety Kenya Baraka. In some embodiments, the plant or plant cell may be of the potato variety Maritta. In some embodiments, the plant or plant cell may be of the potato variety Kihoro. In some embodiments, the plant or plant cell may be of the potato variety Americar. In some embodiments, the plant or plant cell may be of the potato variety Roslin Bvumbwe. In some embodiments, the plant or plant cell may be of the potato variety Njine. In some embodiments, the plant or plant cell may be of the potato variety Roslin Gucha. In some embodiments, the plant or plant cell may be of the potato variety Arka. In some embodiments, the plant or plant cell may be of the potato variety B53 (Roslin Eburu). In some embodiments, the plant or plant cell may be of the potato variety Kiraya. In some embodiments, the plant or plant cell may be of the potato variety Kenya Akiba. In some embodiments, the plant or plant cell may be of the potato variety 9. In some embodiments, the plant or plant cell may be of the potato variety Original. In some embodiments, the plant or plant cell may be of the potato variety Gituma. In some embodiments, the plant or plant cell may be of the potato variety Mukorino. In some embodiments, the plant or plant cell may be of the potato variety Amin. In some embodiments, the plant or plant cell may be of the potato variety Pimpernel. In some embodiments, the plant or plant cell may be of the potato variety Anett. In some embodiments, the plant or plant cell may be of the potato variety B. In some embodiments, the plant or plant cell may be of the potato variety Gituru. In some embodiments, the plant or plant cell may be of the potato variety Feldeslohn. In some embodiments, the plant or plant cell may be of the potato variety C. In some embodiments, the plant or plant cell may be of the potato variety Kigeni. In some embodiments, the plant or plant cell may be of the potato variety Romano. In some embodiments, the plant or plant cell may be of the potato variety Kenya Ruaka. In some embodiments, the plant or plant cell may be of the potato variety Purplu. In some embodiments, the plant or plant cell may be of the potato variety Njae. In some embodiments, the plant or plant cell may be of the potato variety Suzanna. In some embodiments, the plant or plant cell may be of the potato variety Cardinal. In some embodiments, the plant or plant cell may be of the potato variety Kathama. In some embodiments, the plant or plant cell may be of the potato variety Kinare-Mwene. In some embodiments, the plant or plant cell may be of the potato variety Kibururu. In some embodiments, the plant or plant cell may be of the potato variety Karoa-Igura. In some embodiments, the plant or plant cell may be of the potato variety Muturu. In some embodiments, the plant or plant cell may be of the potato variety Faraja. In some embodiments, the plant or plant cell may be of the potato variety Kiamucove. In some embodiments, the plant or plant cell may be of the potato variety Michiri. In some embodiments, the plant or plant cell may be of the potato variety Rugano. In some embodiments, the plant or plant cell may be of the potato variety Njine Giathireko. In some embodiments, the plant or plant cell may be of the potato variety Meru Mix. In some embodiments, the plant or plant cell may be of the potato variety Blue Baranja. In some embodiments, the plant or plant cell may be of the potato variety Patrones. In some embodiments, the plant or plant cell may be of the potato variety Robijn. In some embodiments, the plant or plant cell may be of the potato variety Roslin Chania. In some embodiments, the plant or plant cell may be of the potato variety Urgentia. In some embodiments, the plant or plant cell may be of the potato variety Mirka. In some embodiments, the plant or plant cell may be of the potato variety Roslin Sasamua.

The gene repair oligonucleobase can be introduced into a plant cell using any method commonly used in the art, including but not limited to, microcarriers (biolistic delivery), microfibers, polyethylene glycol (PEG)-mediated uptake, electroporation, and microinjection.

Also provided are methods and compositions related to the culture of cells mutated according to methods as disclosed herein in order to obtain a plant that produces seeds, henceforth a "fertile plant," and the production of seeds and additional plants from such a fertile plant.

Also provided are methods and compositions related to the culture of cells mutated according to methods as disclosed herein in order to obtain a plant that produces substantially normal tubers with substantially normal yield such that substantially normal plants arise from a tuber or piece of a potato tuber containing at least one or two eyes (dormant buds), often referred to as seed potatoes.

Also provided are mutations in the AOS2 gene that confer resistance and/or tolerance to a relevant pathogen to a plant or wherein the mutated AOS2 gene has substantially the same or altered enzymatic activity as compared to wild-type AOS2.

Selection of Pathogen Resistant Plants and Application of Pathogens

Plants and plant cells can be tested for resistance and/or tolerance to a pathogen using commonly known methods in the art, e.g., by growing the plant or plant cell in the presence of a pathogen and measuring the rate of growth as compared to the growth rate in the absence of the pathogen. Pathogen challenge for selection of resistant and/or tolerant plants may be achieved by using either sporangial or zoospore application of the pathogen. Resistance levels of the plant with these challenges can be rated according various methods such as determining the rate of increase in pathogen DNA from infected plant material, the rate of lesion size progression etc.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type AOS2 protein.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type AOS2 protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant pathogen when they are subjected to it and provide a dose/response curve which is shifted to the right when compared with that provided by similarly subjected non-tolerant like plant. Such dose/response curves have "dose" plotted on the X-axis and "percentage kill", "pathogenic effect", etc., plotted on the y-axis. Tolerant plants will require more pathogen than non-tolerant like plants in order to produce a given pathogenic effect. Plants that are substantially "resistant" to the pathogen exhibit few, if any, necrotic, lytic, chlorotic or other lesions, when subjected to a pathogen at concentrations and rates which are typical of pathogen exposure in the field. Plants which are resistant to a pathogen are also tolerant of the pathogen.

Polymerase Chain Reaction Methods for Detecting and Quantifying Pathogens in Plants Host resistance to a pathogen can be determined utilizing methods already established and known to those skilled in the art. Generally, diverse methods are commonly utilized for diverse pathogens but in general, the following can be utilized for application toward fungal and bacterial pathogens.

Pathogen resistance and/or tolerance may be determined by monitoring the presence and amount of pathogen specific nucleic acid in a plant. For example, leaflets in a plant are inoculated with 10 µL droplets of sporangial suspension (30-40 sporangia/µL) on both sides of the midrib. Oberhagemann, P., et al. Mol. Breed. Vol. 5, p. 399-415 (1999). Disease symptoms may be scored 7 days post infection. DNA is extracted from infected plant material. Pathogen growth is monitored using *Phytophthora infestans*-ribosomal DNA specific primers as described in (exemplary forward primer sequence: 5'-GAAAGGCATAGAAGG-TAGA-3' (SEQ ID NO: 53) and exemplary reverse primer sequence: 5'-TAACCGACCAAGTAGTAAA-3' (SEQ ID NO: 54)). Intensities of *Phytophthora infestans* amplicons are calibrated relative to potato tubulin DNA bands. Band intensities are quantified and converted to arbitrary units relative to the absolute values obtained from control plants. Judelson, H S, et al. Phytopathology, vol. 90, p. 1112-1119 (2000).

Pathogen resistance levels on the potato plants of interest can be assessed by the challenge of the plants with *Phytophthora infestans* or other pathogen of interest. For *Phytophthora infestans*, leaves of 6-8 week old plants will be detached and placed with the abaxial side facing upward on 4% water agar plates. Leaves are inoculated with a drop of sporangial suspension (at 40,000-100,000 sporangia/mL) using a Pasteur pipette on the abaxial side of the leaf. Plates will be placed in an 18° C. incubator with 12 h photoperiod.

Disease development will be scored 6 days post inoculation and as necessary according to published methods as in Vleeshouwers et al. (2000) Physiol and Mol Plant Pathology, vol. 57, p. 35-42; Vleeshouwers et al. (1999) Europ J of Plant Pathology, vol. 105, p. 241-250; Oberhagemann et al. (1999) Molecular Breeding, vol. 5, p. 399-415.

For fungal infection assays, infection level assessment will be carried out according to published methods for each fungal-host interactions. References include Rogers et al. (1994) Plant Cell, vol. 6, p. 935-945; Valent et al. (1991) Genetics, vol. 127, p. 87-101; Thomas et al. (1997) Plant Cell, vol. 9, p. 2209-2224.

Typically, for a sporulating fungus, inoculations are carried out utilizing an inoculum containing spores of fungus of interest at a desired concentration. This inoculum will be sprayed on a plant at a specific developmental stage (ex: prior to $4^{th}$ leaf emergence/6-8 week old etc.). The inoculated plants will be incubated under high humidity conditions for 24 h post inoculation and then will be transferred to desired growth conditions under day-night cycles appropriate for the host plant growth. The infection intensity will be assessed typically 3-4 days after infection and scored according to established methods for the host-pathogen system. Typically, non-sporulating lesions will be assessed as "resistant" reactions while sporulating lesions are considered as "susceptible" reactions. The latter are rated for infection severity according to size and appearance of the lesions.

For assessment of disease severity related to bacterial pathogens, published methods for each bacterial species will be utilized as mentioned in Elibox, W., et al. (2008) Phytopathology, vol. 98, p. 421-426; Chaudhry et al. (2006)—Pakistan J of Botany, vol. 38 (1), p. 193-203; Zhao et al. (2005) J of Bacteriology, vol. 187, p. 8088. Typically, for bacterial pathogens, a bacterial suspension at a pre-determined density (ex: $5\times10^4$ colony forming units) will be infiltrated into leaves of host plant at a particular developmental stage (ex: 3 week old plants). Inoculated plants are maintained at high humidity for 3-4 days and the infection severity is assessed by sampling two to three leaf discs that are ground up and resulting supernatant plated on bacterial growth media to enumerate the bacterial colony forming units arising from the infected plant material.

Infection severity of the converted plant will be assessed by evaluating the colony forming units arising from the infected tissue of the converted plant compared with those arising from the infected tissue of the wildtype plants.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

EXAMPLES

The following are examples, which illustrate procedures for practicing the invention. These examples should not be construed as limiting. All percentages are by weight and all solvent mixture proportions are by volume unless otherwise noted.

Example 1

Increase of Plant Pathogen Resistance Using RTDS™ Technology

Evaluation of Cultivars of Interest for Genotype at the AOS2 Gene Loci

Utilizing skills of the trade that are known to those trained in the art, potato cultivars of interest are subjected to genotyping as follows: Genomic DNA of plant cultivars of interest were extracted with known methods and was subjected to Polymerase Chain Reaction (PCR) mediated gene amplification to isolate all AOS2 alleles present within the said genomic DNA samples. PCR primers used for the amplification are as follows: Forward primer 5'-CACCTTTGTATCACTAACATTACCCATCC-3' (SEQ ID NO: 51) and Reverse primer 5'-GCATGTGTTGCTTGTTCTTATAATTTCAG-3' (SEQ ID NO: 52). The amplified fragments were cloned into TOPO 2.1 vector (Invitrogen Corporation, Carlsbad, Calif.) and subjected to sequencing at 12 clones per amplification. Utilizing Vector NTI software analysis package (Invitrogen Corporation, Carlsbad, Calif.), the resulting sequences were aligned with the reference sequence (SEQ ID NO 2) and polymorphic sites were determined. Translation of the said nucleic acid sequences to protein coding sequence was also carried out utilizing the Vector NTI sequence analysis software and the resulting sequences were compared with the reference protein sequence (SEQ ID NO 1) to identify polymorphic amino acids. The amino acid positions are designated in accordance to the amino acid positions of the reference protein sequence given by SEQ ID NO 1.

Characterization of the Biochemical Activities of AOS2 Alleles (In Vitro)

The nucleic acid of the identified AOS2 alleles were PCR amplified with the primers as described earlier but with added Xma I and Pst I sites to the Forward and Reverse primers, respectively, to introduce Xma I and Pst I sites at the 5' and 3' ends respectively of the alleles to facilitate cloning of the amplified products into the pQE30 vector for heterologous expression in *E. coli* (M15 strain, Qiagen Inc., Valencia, Calif.). The PCR amplified fragments were digested with Xma I and Pst I restriction enzymes and were cloned into similarly digested pQE30b vector (subjected to Site Directed Mutagenesis to insert a nucleotide 5' to the Xma I site such that any gene fragment cloned into the Xma I site is in frame with the coding sequence of the pQE30 vector) and clones were selected by transformation into E. coli strain XL-1 Blue. The resulting expression plasmids were extracted from XL-1 Blue cells and subjected to colony PCR and sequencing to verify cloning and absence of any frameshifts. The verified clones were transformed into M15 cells (Qiagen Inc., Valencia, Calif.) and used for protein expression analysis.

For protein expression analyses, 500 µL of overnight 5 mL cultures of strains of interest (e.g. vector only strain harboring a plasmid without an AOS2 gene and strain of interest harboring a single allele of AOS2 gene,) were each inoculated into a 10 mL of LB medium supplemented with carbenicillin (100 µg/mL) and Kanamycin (25 µg/mL). The cultures were incubated at 37° C. with 250 rpm agitation until the absorbance at 600 nm (A600) reached desired OD units (e.g., 0.6-0.8 OD units). Then the cells were induced for protein expression with 1 mM of IPTG and incubated at desired temperature (e.g., 12° C.) with 100 rpm agitation for the desired time period (e.g., 3-7 days). Protein expression was monitored with SDS PAGE gel electrophoresis and by spectral analysis for the expression of a Type I cytochrome P450 protein. AOS2 protein purification is carried out utilizing commercially available Ni NTA binding columns according to manufacturer instructions (Thermo Scientific, Rockford, Ill.).

Biochemical Assay for the Characterization of the Catalytic Activity of the AOS2 Proteins The purified proteins expressed in E. coli are used to assay for the catalytic activity of the proteins encoded by the identified different alleles of the AOS2 gene. The assay is carried out according to published protocols (Schreier and Lorenz (1982) Z. Naturforsch, Vol. 37° C., p. 165). In general, 13S-hydroperoxy-9Z,11E-octadecadienoic acid (13-HPODE) and 13S-hydroperoxy-9Z,11E,15Z-octadecatrienoic acid (HPOTrE) act as the substrate for the enzyme assay and a reference sample with no added enzyme serves as negative control. To assess the catalytic activity of the different proteins encoded by the different AOS2 alleles, a known amount of purified protein normalized by spectral analysis or other means is determined with 3-13 µM solution of substrate in 0.1 M Phosphate buffer pH 6.0. The rate of decrease in absorbance at A234 is monitored over time and resulting kinetic data is used to calculate the specific activity of each of the proteins of interest. Enzymes with the highest specific activities are considered as those of interest and the amino acid sequences of such enzymes are compared to those with lower specific activities to identify the specific amino acid positions that confer superior catalytic activity to the AOS2 proteins.

To evaluate the effect of the G231T mutation, the 691/692 nucleotides (nt) of StAOS2 alleles StAOS2_CB17 and StAOS2_CB18 of Bintje were converted from G/G to A/C using site directed mutagenesis (SDM) leading to a G231T transition in the respective AOS2 proteins. The amino acid (aa) polymorphisms found throughout these AOS2 proteins are given in Table 2. Those clones were subjected to biochemical assay as described above and the specific activities of those proteins and those altered at the 231 aa position are given in Table 3.

TABLE 2

The genotype differences among amino acid positions 48, 76, 231, 328, 423 and 494 of StAOS2 alleles of Bintje subjected to the biochemical activity assay.

|  | 48 | 76 | 231 | 328 | 423 | 494 |
|---|---|---|---|---|---|---|
| StAOS2_CB17 | T | N | G | L | I | D |
| StAOS2_CB17_G231T | T | N | T | L | I | D |
| StAOS2_CB18 | T | D | G | L | I | G |
| StAOS2_CB18_G231T | T | D | T | L | I | G |

TABLE 3

Specific activities of the proteins encoding StAOS2 alleles, StAOS2_CB18 and StAOS2_CB17 and their derivatives. The genotype at the 691/692 nt positions as G/G and A/C respectively correspond to G and T at the 231 aa in the encoded proteins.

| Allele Name | 691/692 Genotype (231 aa) | Normalized StAOS2 specific activity Trial 1 (µM/min/mg protein) | Normalized StAOS2 specific activity Trial 2 (µM/min/mg protein) | Average StAOS2 specific activity (µM/min/mg protein) | Fold Change (compared to the wildtype allele) | Percentage |
|---|---|---|---|---|---|---|
| StAOS2_CB18 | GG (G) | 14.55 | 9.66 | 12.11 | | |
| StAOS2_CB18_G231T | AC (T) | 17.73 | 13.19 | 15.46 | 1.3x | 30% |
| StAOS2_CB17 | GG (G) | 7.64* | 5.83 | 6.74 | | |
| StAOS2_CB17_G231T | AC (T) | 16.88* | 12.8 | 14.84 | 2.2x | 120% |

As shown in Table 3, when specific activities of the isogenic proteins that only differ at the 231 aa position are compared to each other, conversion of the genotype at 691/692 nt positions of the StAOS2 gene alleles from G/G to A/C results in increasing the specific activity of the encoded proteins.

Further evaluations of the effect of the amino acid profile at the 231 and 328 positions of the protein encoded by the StAOS2_CB18 indicates that the combination of the amino acid make up at these two positions increase the specific activity of the AOS2 protein. The data is provided in Table 4.

TABLE 4

The specific activities of the proteins encoded by StAOS2_CB18 allele and its derivatives differing at the 231 and 328 aa residues.

| | 231 aa | 328 aa | AOS2 specific activity Trial 1 (μM/min/mg) | AOS2 specific activity Trial 2 (μM/min/mg) | AOS2 specific activity Average (μM/min/mg) |
|---|---|---|---|---|---|
| StAOS2_CB18_L328V | G | V | 9.147982 | 9.982926 | 9.565454 |
| StAOS2_CB18_G231T_L328V | T | V | 6.738131 | 6.950514 | 6.844323 |
| StAOS2_CB18 | G | L | 7.355882 | 9.447077 | 8.40148 |
| StAOS2_CB18_G231T | T | L | 9.190796 | 10.25108 | 9.72094 |

The alteration of the amino acid (aa) profile of the AOS2 protein encoded by StAOS2_CB18 allele at the 328 aa position from L to V (StAOS2_CB1_L328V) increased activity when combined with G at 231 aa position but decreased activity when combined with T at the 231 aa position (StAOS2_CB18_G231_L328V). The data provides that a G231T transition when combined with L328V mutation leads to a decrease in AOS2 protein specific activity and is indicative that the interplay between the aa profiles at these two positions impact the activity of the AOS2 protein.

In vitro activity assays were also utilized to test the effect of D76N mutation in StAOS2_CB19. StAOS2_CB19 was subjected to SDM to yield StAOS2_CB19_D76N allele with the 76th residue in AOS2 protein converted to an Asparagine (N) from Aspartic acid (D). These were evaluated for specific activity differences utilizing the methods described above. Data collected from three independent trials indicated that the D76N mutation led to an approximately 30% decrease in enzyme activity.

Those alleles with superior catalytic activity are chosen for in planta assays.

Characterization of the Biochemical Activities of AOS2 Alleles (In Vivo)

To evaluate the hypothesis that those AOS2 proteins with superior in vitro biochemical activity will also have superior in planta biochemical activity, those AOS2 alleles that exhibit superior specific activities are cloned into a plant binary vector under a constitutive or Arabidopsis AOS2 promoter. Utilizing Agrobacterium tumefaciens mediated transformation method, these constructs are transformed into Arabidopsis thaliana AOS2 gene disrupted plant line CS6149 (TAIR, www.arabidopsis.org/) via established methods (Bent et al. (2000) Plant Physiol, vol. 124, p. 1540). Transformants are identified by appropriate selection (dependent on the selectable marker present in the binary vector—i.e., kanamycin for the nptII gene as the selectable marker), molecular means, as well as the ability of the introduced AOS2 genes to complement the AOS2 deficient phenotype of abnormal pollination/silique development as a result of male sterility caused by the absence of a functional AOS2 gene. The AOS2 gene complemented plant lines are assessed for JA and/or OPDA levels at basal and inducing conditions using established methods (Chebab et al. (2008), PLoS ONE, vol 3: p.e1904; Schmelz et al. (2003) Plant Physiol, vol 133: p 295; Engelberth et al. (2003) Anal Biochem, vol. 312, p 242.). Alternatively, complemented lines are utilized for plant disease assays utilizing pathogens of Arabidopsis such as Erwinia carotovora or ssp. carotovora or Hyaloperonospora arabidopsidis and/or others to test the hypothesis that higher JA levels or AOS2 catalytic activity leads to enhanced resistance and/or tolerance to pathogens.

To evaluate the impact of aa polymorphisms of AOS2 protein on in planta jasmonic acid (JA) accumulation, two alleles of Bintje potato cultivar, StAOS2_CB18_G231T, driven by the Arabidopsis thaliana AtAOS2 promoter were used to complement the null mutant phenotype of the A. thaliana aos2 mutant plants. The resulting transgenics were advanced to the T3 generation to obtain homozygotes and resulting plants were subjected to JA quantification studies as per described methods (Chebab et al. (2008), PLoS ONE, vol 3: p.e1904; Schmelz et al. (2003) Plant Physiol, vol 133: p 295; Engelberth et al. (2003) Anal Biochem, vol. 312, p 242). The results are shown in Table 5.

TABLE 5

The JA accumulation pattern in the Arabidopsis thaliana transgenic lines harboring StAOS2_CB19 or StAOS2_Cb18_G231T alleles. Average JA amounts shown represent JA levels present in Arabidopsis leaf tissue under basal expression levels at ng per gram fresh weight. The results shown are averages of two replicate samples containing multiple leaves.

| StAOS2 Allele | Plant Line | Average JA | StError |
|---|---|---|---|
| StAOS2_CB19 | 1001-13-6 | 32.34 | 4.25 |
| | 1001-14-6 | 29.94 | 5.69 |
| | 1001-14-7 | 59.91 | 1.96 |
| | 1001-19-4 | 107.21 | 22.59 |
| | 1001-4-6 | 16.04 | 1.63 |
| | 1001-9-1 | 20.48 | 7.47 |
| StAOS2_CB18_G231T | 1003-10-8 | 20.90 | 6.26 |
| | 1003-16-6 | 84.20 | 24.58 |
| | 1003-17-1 | 97.60 | 18.37 |
| | 1003-17-2 | 81.08 | 1.81 |
| | 1003-4-4 | 95.50 | 3.61 |
| | 1003-7-9 | 67.66 | 30.93 |
| | aos2 | 0.16 | 0.02 |
| | Col-0 | 74.17 | 7.53 |

The experiments provided that, on the whole, A. thaliana transgenics harboring StAOS2_CB18_G231T with a T and L aa profile at 231 and 328 aa positions respectively accumulated a higher level of JA (with an average of 44.32 ng of JA/g. f.w.) than those harboring StAOS2_CB19 with a T and V aa profile (with an average of 74.45 ng of JA/g. f.w.) at the said positions, respectively. This data is consistent with that presented in Table 3 providing that the interplay between the 231 and 328 aa of the AOS2 protein play a role in modulating the AOS2 protein activity. This data also validates the in vitro collected data in planta described herein, indicating that the 231 and 328 positions of the AOS2 protein plays a role in modulating the JA levels in planta.

To evaluate the effect of the StAOS2 genotype and subsequent aa profile of the AOS2 protein on disease tolerance, the A. thaliana transgenic plants harboring the StAOS2 Alleles, StAOS2_CB18_G231T and StAOS2_CB19 of Bintje potato cultivar were inoculated with Erwinia carotovora ssp. carotovora (Ecc) at 5×10$^4$ cfu/ml according to established methods (Kariola et al., (2003) Arabidopsis, 16: MPMI, 179-187). At various time points post inoculation, leaf samples were recovered and bacterial titer was quantified. Bacterial growth was significantly lower in *A. thaliana* transgenics harboring StAOS2_CB18_G231T than those with the StAOS2_CB19 allele.

Evaluation of the Effect of the 231 Aa Profile on the Tolerance of Potato to *Phytophthora infestans*

To correlate a functional distinction to the genotype differences in StAOS2 gene alleles and test the hypothesis that StAOS2 gene alleles with A/C at the 691/692 nt confers increased tolerance when compared to those that contain G/G at these positions, two variants of the StAOS2 allele, StAOS2_CB18 and StAOS2_CB18_G231T, with G/G and A/C at the 691/692 nt positions, respectively, were over expressed in potato under the 35S promoter. Some of the resulting lines were tested for tolerance to *Phytophthora infestans* using the standard detached leaf assay. In short, for each tested allele, leaves from approximately six independent 4-8 week old transgenic potato plants grown in soil were detached and inoculated with 300 spores at 4 locations on the abaxial side of the leaf. The leaves were kept in dark for 24 hours post inoculation and then incubated with 12 hours of dark and with light at 18° C. for 8 days. The experiment was repeated with identical results using independent detached leaf assays. While leaves from plants with over-expression of the StAOS2_CB18 developed lesions similar to the wildtype Bintje potato plants and the empty vector control transgenic, leaves from transgenic plants with StAOS2_CB18_G231T show markedly decreased or no lesion development. Therefore, this supports that over-expression of the StAOS2 gene allele with the A/C genotype at the 691/692 nt results in increased tolerance to *Phytophthora infestans* in potato plants.

Similarly, these two gene constructs were also expressed in potato plants under the native promoter of the StAOS2 gene. Potato cultivar Bintje is the parent line to the transgenics while Bintje_pjIHoon is the vector only control transgenic line. The resulting plant lines were also subjected to infection with *Phytophthora infestans* utilizing the standard detached leaf assay (described herein). Similar to the results obtained for the transgene over-expression plants, while those leaves from plants with over-expression of the StAOS2_CB18 developed lesions similar to the empty vector control transgenic, leaves from plants with StAOS2_CB1_G231T show markedly decreased or no lesion development.

RTDS™ Mediated Conversion of the AOS2 Alleles

To convert AOS2 alleles of interest via the RTDS™ technology, AOS2 GRON is delivered to plant protoplasts (i.e., via PEG mediated uptake of nucleic acids, by electroporation, etc.) carrying a specific change at the targeted nucleic acid residue of interest. For example, to obtain desired A/C conversions at the 691/692 position of the AOS2 gene, respectively, the GRON carries a sequence identical to the upstream and downstream of the 691/692 positions of the target AOS2 allele but with AC at the 691/692 positions. The GRON treated cells are developed into calli using established methods.

Selection of Plants/Calli with Desired Genotypic Alterations

Those plants/calli with the desired alterations are selected by selection with pathogen challenge (in the potato late blight pathosystem, pathogen challenge will constitute *Phytophthora* sporangial or zoospore application). Alternatively, the plants/calli with desired alterations are chosen based on non-selection methods such as sequencing of the calli/plant material, e.g., primer-mediated specific amplification of the desired targets to identify those with the desired alterations.

Evaluation and Application of Multiple Rounds of RTDS™

Once plant material with the desired alterations in the AOS2 gene are identified, genotypic analysis of the AOS2 gene locus is repeated to completely evaluate the nature of the AOS2 allele diversity. If "susceptible" or "intermediary" type alleles still exist, those plants/calli are again subjected to RTDS manipulations to produce desired alterations at the allele. If needed, such iterative rounds of RTDS and selection are repeated as necessary until the desired genotype at the AOS2 locus/loci is obtained.

Final assessment of cultivars with desired alterations.

Once calli with the targeted changes are identified, those are regenerated into plants. Such plants are subjected to evaluations utilizing pathogen assays, JA/OPDA level assessment, protein expression analyses. For these efforts, the wildtype plant are utilized as a control to assess the extent of the intended changes such as higher pathogen resistance, higher JA/OPDA levels in the plants containing the desired conversions.

Example 2

Identification of Novel Mutations of the AOS2 Gene Enhancing AOS2 Activity and in Planta Functional Assay Generation of Novel Alleles of StAOS2 Gene To find those amino acids that can enhance the catalytic activity or the stability of the AOS2 protein that are not observed in nature or those that are not detected by such genotyping analyses (see above), a random mutagenesis effort or a more directed effort at targeted mutagenesis of specific target residues of the AOS2 protein are undertaken utilizing error prone PCR or Site Directed Mutagenesis (SDM). For site directed mutagenesis, the target sites could constitute sites in the AOS2 gene identified by the genotyping efforts described above (e.g., N76D and T495K), other sites such as those that are predicted to be in the vicinity of the enzyme active site that can have an effect on substrate binding or catalytic activity or others that may affect catalytic activity at a distance.

For such efforts a plasmid DNA of a construct containing a reference gene such as that given by SEQ ID NO: 2 is utilized and is subjected to the mutagenesis using established methods (Diversify Random PCR mutagenesis Kit, Clonetech, Mountain view, CA); Error prone refs; QuikChange XL Site-Directed Mutagenesis Kit; Stratagene, San Diego, Calif.). The mutated clones are selected and subjected to sequence analysis to identify the mutations and those of interest are selected for heterologous protein expression utilizing the pQE30 expression system of Qiagen Inc., Valencia, Calif. (see below).

Alternatively, a library of such mutagenized constructs are cloned into a binary vector and transformed into plant protoplasts and transformants are developed into calli and are regenerated into plants. The resulting calli are subjected to JA/OPDA levels quantification with established methods (see e.g., Chebab et al., (2008), PLoS ONE, vol 3: p.e1904; Schmelz (2003) Plant Physiol, vol 133: p 295; Engelberth et al. (2003) Anal Biochem, vol. 312, p 242.) and the tolerance of these lines are assessed using a pathogen of interest (e.g. *Phytophthora infestans*).

Example 3

Identification of Novel Mutations of the AOS2 Gene Enhancing AOS2 Activity and Complementation Analysis in *Arabidopsis*

The AOS2 gene variants that are collected via genotyping analyses or the mutagenesis procedures described above are transformed into the *Arabidopsis thaliana* aos2 mutant line CS6149 (TAIR, www.arabidopsis.org/) and AOS2 alleles of interest are selected by JA/OPDA levels or by pathogen assays as described above.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method for producing a non-transgenic plant cell with a mutated AOS2 gene, comprising
introducing into a plant cell a gene repair oligonucleobase (GRON) with a targeted mutation in an allene oxide synthase (AOS2) gene to produce a plant cell with an AOS2 gene that expresses an AOS2 protein comprising a leucine to valine mutation at a position corresponding to position L328 and a glycine at a position corresponding to position G231 of SEQ ID NO: 1, 3, 5, 7, 9, 11, 13, 15, 17, 19, 21, 23, 25, 27, 29, 31, 33, 35, 37, 39, 41, 43, 45, 47 and/or 49.

2. The method of claim 1, wherein said non-transgenic plant cell is cell from a plant selected from the group consisting of sunflower, sugar beet, maize, cotton, wheat, rye, oats, rice, canola, fruits, vegetables, barley, sorghum, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, eggplant, marigold, lotus, cabbage, daisy, carnation, tulip, iris, lily, and nut-producing plants.

3. The method of claim 2, wherein said non-transgenic plant cell is a cell from a plant species selected from the group consisting of potato, tomato, soybean, pepper and tobacco.

4. The method of claim 3, wherein said non-transgenic plant cell is a plant cell from the species *Solanum tuberosum*.

5. The method of claim 4, wherein said non-transgenic plant cell is of a potato variety selected from the group consisting of Anya, Arran Victory, Atlantic, Belle de Fontenay, BF-15, Bintje, Cabritas, Camota, Chelina, Chiloe, Cielo, Clavela Blanca, Desiree, Fianna, Fingerling, Flava, Fontana, Golden Wonder, Innovator, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, Anett, Pimpernel, B53 (Roslin Eburu), Patrones, Robijn, Roslin Chania, Urgentia, Feldeslohn, Kenya Akiba, Mirka, and Roslin Sasamua.

6. The method of claim 3, further comprising
identifying a plant cell having substantially normal growth and normal AOS2 catalytic activity as compared to a corresponding wild-type plant cell in the presence of a pathogen; and
regenerating a non-transgenic pathogen resistant plant having a mutated AOS2 gene from said plant cell.

7. The method of claim 6, wherein the pathogen is one or more species selected from the group consisting of bacterial, fungal, viral, prion and mycoplasma species.

8. The method of claim 7, wherein the pathogen species is one or more selected from the group consisting of *Phytophthora infestans Fusarium spp., Botrytis spp., Alternarial spp., Pythium spp., Personospora spp., Cladosporim spp., Erysiphe spp., Aspergillus spp., Puccinia spp., Blumeria spp., and/or Trichoderma spp., Xanthomonas* (e.g., *Xanthomonas axonopodis* pv. aurantifolii, *Xanthomonas campestris* pv. campestris, *Xanthomonas campestris* pv. vesicatoria), Pseudomonas (*Pseudomonas syringae* pv. tomato, *Pseudomonas syringae* pv. phaseolicola, *Pseudomonas syringae* pv. syringae), *Erwinia* (e.g., *Erwinia carotovora* subsp. atroseptica), *Ralstonia* (e.g., *Ralstonia solanacearum*), *Clavibacter michiganensis*, *Xylella fastidiosa*, Soybean mosaic virus, Tobacco Ring spot virus, Tobacco Streak virus, Tomato spotted wilt virus and others.

9. The method of claim 8, wherein said non-transgenic plant is selected from the group consisting of sunflower, sugar beet, maize, cotton, wheat, rye, oats, rice, canola, fruits, vegetables, barley, sorghum, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, eggplant, marigold, lotus, cabbage, daisy, carnation, tulip, iris, lily, potato, tomato, soybean, pepper, tobacco and nut-producing plants.

10. The method of claim 9, wherein said non-transgenic plant is a species selected from the group consisting of potato, tomato, soybean, pepper and tobacco.

11. The method of claim 10, wherein said non-transgenic plant is of the species *Solanum tuberosum*.

12. The method of claim 11, wherein said non-transgenic plant is of a potato variety selected from the group consisting of Anya, Arran Victory, Atlantic, Belle de Fontenay, BF-15, Bintje, Cabritas, Camota, Chelina, Chiloe, Cielo, Clavela Blanca, Desiree, Fianna, Fingerling, Flava, Golden Wonder, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, Anett, Pimpernel, B53 (Roslin Eburu), Patrones, Robijn, Roslin Chania, Urgentia, Feldeslohn, Kenya Akiba, Mirka, and Roslin Sasamua.

13. The method of claim 3, further comprising
identifying a plant cell having substantially normal growth and normal AOS2 catalytic activity as compared to a corresponding wild-type plant cell of a mid-early maturing plant; and
regenerating a non-transgenic mid-early maturing plant having a mutated AOS2 gene from said plant cell.

14. The method of claim 13, wherein said non-transgenic plant is selected from the group consisting of sunflower, sugar beet, maize, cotton, wheat, rye, oats, rice, canola, fruits, vegetables, barley, sorghum, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, eggplant, marigold, lotus, cabbage, daisy, carnation, tulip, iris, lily, and nut-producing plants.

15. The method of claim 14, wherein said non-transgenic plant is a species selected from the group consisting of potato, tomato, soybean, pepper and tobacco.

16. The method of claim 15, wherein said non-transgenic plant is of the species *Solanum tuberosum*.

17. The method of claim 16, wherein said non-transgenic plant is of a potato variety selected from the group consisting of Anya, Arran Victory, Atlantic, Belle de Fontenay, BF-15, Bintje, Cabritas, Camota, Chelina, Chiloe, Cielo, Clavela Blanca, Desiree, Fianna, Fingerling, Flava, Golden Wonder, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, Anett, Pimpernel, B53 (Roslin Eburu), Patrones, Robijn, Roslin Chania, Urgentia, Feldeslohn, Kenya Akiba, Mirka, and Roslin Sasamua.

18. A non-transgenic plant with a mutated AOS2 gene, comprising
an allene oxide synthase (AOS2) that expresses an AOS2 protein comprising a leucine to valine mutation at a position corresponding to position L328 and a glycine at a position corresponding to position G231 of SEQ ID NO: 1, 3, 5, 7, 9, 11, 13, 15, 17 19, 21, 23, 25, 27, 29, 31, 33, 35, 37, 39, 41, 43, 45, 47 and/or 49.

19. The plant of claim 18, wherein said non-transgenic plant is selected from the group consisting of sunflower, sugar beet, maize, cotton, wheat, rye, oats, rice, canola, fruits, vegetables, barley, sorghum, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, eggplant, marigold, lotus, cabbage, daisy, carnation, tulip, iris, lily, potato, tomato, soybean, pepper, tobacco and nut-producing plants.

20. The plant of claim 19, wherein said non-transgenic plant is a species selected from the group consisting of potato, tomato, soybean, pepper and tobacco.

21. The plant of claim 20, wherein said non-transgenic plant is of the species *Solanum tuberosum*.

22. The plant of claim 21, wherein said non-transgenic plant is of a potato variety selected from the group consisting of Anya, Arran Victory, Atlantic, Belle de Fontenay, BF-15, Bintje, Cabritas, Camota, Chelina, Chiloe, Cielo, Clavela Blanca, Desiree, Fianna, Fingerling, Flava, Golden Wonder, Jersey Royal, Kerr's Pink, Kestrel, King Edward, Kipfler, Lady Balfour, Maris Piper, Nicola, Pachacoña, Pink Eye, Pink Fir Apple, Primura, Red Norland, Red Pontiac, Rooster, Russet Burbank, Russet Norkotah, Shepody, Spunta, Vivaldi, Yukon Gold, Nyayo, Mukori, Roslin Tana, Kerrs's Pink/Meru, Golof, Kinongo, Ngure, Kenya Baraka, Maritta, Kihoro, Americar, Roslin Bvumbwe, Njine, Roslin Gucha, Arka, Anett, Pimpernel, B53 (Roslin Eburu), Patrones, Robijn, Roslin Chania, Urgentia, Feldeslohn, Kenya Akiba, Mirka, and Roslin Sasamua.

* * * * *

SEQUENCE LISTING

```
<160> NUMBER OF SEQ ID NOS: 54

<210> SEQ ID NO 1
<211> LENGTH: 509
<212> TYPE: PRT
<213> ORGANISM: Solanum tuberosum

<400> SEQUENCE: 1

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175
```

-continued

```
Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
            420                 425                 430

Asp Arg Phe Val Gly Glu Gly Glu Lys Leu Leu Lys Tyr Val Leu Trp
        435                 440                 445

Ser Asn Gly Pro Glu Thr Glu Ser Pro Thr Val Gly Asn Lys Gln Cys
    450                 455                 460

Ala Gly Lys Asp Phe Val Val Met Val Ser Arg Leu Phe Val Thr Glu
465                 470                 475                 480

Phe Phe Leu Arg Tyr Asp Thr Phe Asn Val Asp Val Gly Lys Ser Ala
                485                 490                 495

Leu Gly Ala Ser Ile Thr Ile Thr Ser Leu Lys Lys Ala
            500                 505
```

<210> SEQ ID NO 2
<211> LENGTH: 1530
<212> TYPE: DNA
<213> ORGANISM: Solanum tuberosum

<400> SEQUENCE: 2

```
atggcattaa cttcatcttt ttctcttcct cttccttctc ttcaccaaca atttccatca    60
aaatactcca catttcgtcc tattattgtt tctttatcgg aaaagccaac aatcgtggta   120
acccaaccta caaaattacc tactaggaca tacctggcg actatgggtt gccgggtatt   180
ggtccatgga agataggct tgattacttt tacaatcaag ggaaagacga attttttcgaa   240
```

```
tcaagagtag tgaaatacaa atcaactata ttcagaacga acatgccacc gggaccattc    300
atttcttcta acccgaaggt tattgttttg ctcgacggca agagtttccc agtccttttc    360
gatgtttcga aagtcgaaaa aaaggacctc ttcaccggaa cttacatgcc gtcgactgaa    420
ctcaccggtg gttaccgtgt tcttcttat cttgacccat ctgaaccaaa ccatgaaaaa     480
ttgaaaaaat tgatgttctt ccttctttct tctcgtcgtg atcacgttat acccaaattc    540
catgaaactt atacagagtt ttttgaaacc ctagataagg aaatggcgga aaaaggtaca    600
gctggtttaa actccggcaa tgatcaagct gcgtttaatt tcttagctag atcgttgttc    660
ggagttaacc cagttgaaac taaactcgga actgatggtc cgacattgat cggaaaatgg    720
gttttgcttc agcttcatcc tgtactcact ctcggtcttc gaagtttct agacgactta     780 atcctccata ctttccggtt acctccgttt ctggtgaaga agattacca gagacttttac   840 gatttctttt acaccaactc cgccagttta ttcgccgaag ctgaaaaact cggcatttca    900
aaagaagaag cttgtcataa tcttctcttc gctacttgct tcaattcctt cggcgggatg    960 aagatttct tcccgaatat gctgaaatcg atagcgaaag caggggtgga ggtccatacc    1020
cgtttagcaa acgagatccg atcggaagta aaatccgctg gcgggaagat cacgatgtcg   1080
gcgatggaga aaatgccgtt aatgaaatca gtagtttatg aagctttgcg agttgatcct   1140
ccggtagctt cacaatacgg aagagccaaa caggacctta agatcgaatc acgacgcc     1200 gttttcgagg tgaaaaaagg tgaaatgcta ttcgggtacc aaccatttgc aacgaaggat   1260
ccgaaaattt ttgaccggcc ggaagagttc gtcgccgatc ggttcgtcgg agaaggagaa   1320
aagttattga aatatgtatt atggtctaat ggaccggaaa cggaaagtcc aacagtgggg   1380
aataaacagt gtgctggcaa agattttgta gtgatggttt cgaggttatt cgtaacggag   1440
ttttttctcc gttacgatac attcaacgtc gacgttggta agtcggcgtt gggggcttca   1500
attactataa cttctttgaa aaaagcttag                                    1530

<210> SEQ ID NO 3
<211> LENGTH: 509
<212> TYPE: PRT
<213> ORGANISM: Solanum tuberosum

<400> SEQUENCE: 3

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Phe Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140
```

```
Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
            165                 170                 175

Ile Pro Lys Phe His Glu Thr Tyr Thr Glu Phe Phe Glu Thr Leu Asp
            180                 185                 190

Lys Glu Met Ala Asp Lys Gly Thr Ala Gly Leu Asn Ser Gly Asn Asp
            195                 200                 205

Gln Ala Ala Phe Asn Phe Leu Ala Arg Ser Leu Phe Gly Val Asn Pro
            210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Val
            245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
            275                 280                 285

Ser Leu Phe Ala Glu Ala Glu Lys Leu Gly Ile Ser Lys Glu Glu Ala
            290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
            325                 330                 335

Glu Val His Thr Arg Leu Ala Asn Glu Ile Arg Ser Glu Val Lys Ser
            340                 345                 350

Ala Gly Gly Lys Met Thr Met Ser Ala Met Glu Lys Met Pro Leu Met
            355                 360                 365

Lys Ser Val Val Tyr Glu Ala Leu Arg Val Asp Pro Pro Val Ala Ser
            370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
            405                 410                 415

Ala Thr Lys Asp Pro Lys Ile Phe Asp Arg Pro Glu Glu Phe Val Ala
            420                 425                 430

Asp Arg Phe Val Gly Glu Gly Glu Lys Leu Leu Lys Tyr Val Leu Trp
            435                 440                 445

Ser Asn Gly Pro Glu Thr Glu Ser Pro Thr Val Gly Asn Lys Gln Cys
            450                 455                 460

Ala Gly Lys Asp Phe Val Val Met Val Ser Arg Leu Phe Val Thr Glu
465                 470                 475                 480

Phe Phe Leu Arg Tyr Asp Thr Phe Asn Val Asp Val Gly Lys Ser Ala
            485                 490                 495

Leu Gly Ala Ser Ile Thr Ile Thr Ser Leu Lys Lys Ala
            500                 505

<210> SEQ ID NO 4
<211> LENGTH: 1530
<212> TYPE: DNA
<213> ORGANISM: Solanum tuberosum

<400> SEQUENCE: 4
atggcattaa cttcatcttt ttctcttcct cttccttctc ttcaccaaca atttccatca      60
```

-continued

| | |
|---|---|
| aaatactcca catttcgtcc tattattgtt tctttatcgg aaaagccaac aatcgtggta | 120 |
| acccaaccta caaaatttcc tactaggaca atacctggcg actatgggtt gccgggtatt | 180 |
| ggtccatgga agataggct tgattacttt tacaatcaag ggaaagacga attttttcgaa | 240 |
| tcaagagtag tgaaatacaa atcaactata ttcagaacga acatgccacc gggaccattc | 300 |
| atttcttcta acccgaaggt tattgttttg ctcgacggca agagtttccc agtcctttc | 360 |
| gatgtttcga aagtcgaaaa aaaggacctc ttcaccggaa cttacatgcc gtcgactgaa | 420 |
| ctcaccggtg ttaccgtgt tctttcttat cttgacccat ctgaaccaaa ccatgaaaaa | 480 |
| ttgaaaaaat tgatgttctt ccttctttct tctcgtcgtg atcacgttat acccaaattc | 540 |
| catgaaactt atacagagtt ttttgaaacc ctagataagg aaatggcgga taaaggtaca | 600 |
| gctggtttaa actccggcaa tgatcaagct gcgtttaatt tcttagctag atcgttgttc | 660 |
| ggagttaacc cagttgaaac taaactcgga actgatggtc cgacattgat cggaaaatgg | 720 |
| gttttgcttc agcttcatcc tgtactcact ctcggtcttc cgaaagttct agacgactta | 780 |
| atcctccata cttccggtt acctccgttt ctggtgaaga aagattacca gagactttac | 840 |
| gatttctttt acaccaactc cgccagttta ttcgccgaag ctgaaaaact cggcatttca | 900 |
| aaagaagaag cttgtcataa tcttctcttc gctacttgct tcaattcctt cggcgggatg | 960 |
| aagattttct tcccgaatat gctgaaatcg atagcgaaag caggagtgga ggtccatacc | 1020 |
| cgtttagcaa acgagatccg atcggaagta aaatccgctg gcgggaagat gacgatgtcg | 1080 |
| gcgatggaga aaatgccgtt aatgaaatca gtagtttatg aagcgttgcg agttgatcct | 1140 |
| ccggtagctt cacaatacgg aagagccaaa caggacctta agatcgaatc acacgacgcc | 1200 |
| gttttcgagg tgaaaaaagg tgaaatgcta ttcgggtacc aaccatttgc aacgaaggat | 1260 |
| ccgaaaattt ttgaccggcc ggaagagttc gtcgccgatc ggttcgtcgg agaaggagaa | 1320 |
| aagttattga aatatgtatt atggtctaat ggaccggaaa cggaaagtcc aacagtgggg | 1380 |
| aataaacagt gtgctggcaa agattttgta gtgatggttt cgaggttatt cgtaacggag | 1440 |
| ttttttctcc gttacgatac attcaacgtc gacgttggta agtcggcgtt gggggcttca | 1500 |
| attactataa cttcttttgaa aaaagcttag | 1530 |

<210> SEQ ID NO 5
<211> LENGTH: 510
<212> TYPE: PRT
<213> ORGANISM: Solanum tuberosum

<400> SEQUENCE: 5

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Ala Ser Leu
            20                  25                  30

Ser Glu Lys Pro Ile Ile Val Val Thr Gln Pro Thr Lys Leu Pro Thr
        35                  40                  45

Arg Thr Met Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110
```

Gly Lys Ser Phe Pro Val Leu Phe Asp Val Ser Lys Glu Lys Lys
            115                 120                 125

Asp Leu Phe Thr Gly Thr Tyr Met Pro Ser Thr Glu Leu Thr Gly Gly
130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
                165                 170                 175

Ile Pro Lys Phe His Glu Thr Tyr Thr Glu Leu Phe Glu Thr Leu Asp
            180                 185                 190

Lys Glu Met Ala Glu Lys Gly Thr Ala Gly Leu Asn Ser Gly Asn Asp
            195                 200                 205

Gln Ala Ala Phe Asn Phe Leu Ala Arg Ser Leu Phe Gly Val Asn Pro
210                 215                 220

Val Glu Ala Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
            275                 280                 285

Asn Leu Phe Val Glu Ala Glu Lys Leu Gly Ile Ser Lys Glu Glu Ala
            290                 295                 300

Cys His Asn Leu Leu Phe Ala Thr Cys Phe Asn Ser Phe Gly Gly Met
305                 310                 315                 320

Lys Ile Phe Phe Pro Asn Met Met Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
            355                 360                 365

Lys Ser Val Val Tyr Glu Ala Leu Arg Val Asp Pro Pro Val Ala Ser
370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Leu Val Ala
            420                 425                 430

Asp Arg Phe Val Gly Glu Gly Glu Lys Leu Leu Lys Tyr Val Leu
            435                 440                 445

Trp Ser Asn Gly Pro Glu Thr Glu Ser Pro Thr Val Gly Asn Lys Gln
450                 455                 460

Cys Ala Gly Lys Asp Phe Val Val Met Val Ser Arg Leu Phe Val Val
465                 470                 475                 480

Glu Phe Phe Leu Arg Tyr Asp Thr Phe Asn Val Asp Val Gly Thr Ser
                485                 490                 495

Ala Leu Gly Ala Ser Ile Thr Ile Thr Ser Leu Lys Lys Ala
            500                 505                 510

<210> SEQ ID NO 6
<211> LENGTH: 1533
<212> TYPE: DNA

<213> ORGANISM: Solanum tuberosum

<400> SEQUENCE: 6

```
atggcattaa cttcatcttt ttctcttcct cttccttctc ttcaccaaca atttccatca      60
aaatactcca catttcgtcc tattattgct tcgttatccg aaaaaccaat aatcgtggta     120
acccaaccta caaaattacc taccaggaca atgcccggcg actatgggtt accgggtatt     180
ggtccatgga agataggct tgattacttt tacaatcaag gcaaaaacga atttttcgaa      240
tcaagagtag tgaaatacaa atcaactata ttcagaacga acatgccacc gggaccattc     300
atttcttcta acccgaaggt tattgttttg ctcgacggca agagtttccc agtccttttc     360
gatgtttcga agtcgaaaa aaaggacctc ttcactggaa cttacatgcc gtcgactgaa      420
ctcaccggtg ttaccgtgt tcttcttat cttgacccat ctgaaccaaa ccatgaaaaa       480
ttgaaaaaat tgatgttctt ccttctttct tctcgtcgtg atcacgttat acccaaattc     540
catgaaactt atacagagtt gtttgaaacc ctagataagg aaatggcgga aaaaggtaca     600
gctggtttaa actccggcaa tgatcaagct gcgtttaatt tcttagctag atcgttgttc     660
ggagttaacc cagttgaagc taaactcgga actgatggtc cgacattgat cggaaaatgg     720
gttttgcttc agcttcatcc tgtgcttact ctcggtcttc cgaagtttct agacgactta     780
atcctccata ctttccggtt acctccgttt ctggtgaaaa aagattacca gagactttac     840
gatttctttt acaccaattc cgccaattta ttcgtcgaag ctgaaaaact cggcatttct     900
aaagaagaag cttgtcataa tcttctcttc gctacttgct tcaattcctt cggcgggatg     960
aagattttct tcccgaatat gatgaaatcg atagcgaaag caggggtgga ggtccatacc    1020
cgtttagcaa acgagatccg atcggaagta aaatccgccg gcgggaagat cacgatgtcg    1080
gcgatggaga aaatgccgtt aatgaaatca gtagtatatg aagctttacg agttgatcct    1140
ccggtagctt cacaatacgg aagagccaaa caggaccttta agatcgaatc acacgacgcc    1200
gttttcgagg tgaaaaaagg tgaaatgcta ttcgggtacc aaccatttgc aacgaaggat    1260
ccgaaaattt ttgaccgacc ggaagagctc gtcgccgatc ggttcgtcgg agaagaagga    1320
gaaaagttat tgaaatatgt attatggtct aatggaccgg aaacggaaag tccgacagtg    1380
gggaataaac agtgtgctgg aaaagatttt gtagtgatgg tttcgaggtt attcgtagtg    1440
gagttttttc tccgttacga tacattcaac gtcgacgttg gtacgtcggc gttgggggct    1500
tcaattacta aacttctttt gaaaaaagct tag                                 1533
```

<210> SEQ ID NO 7
<211> LENGTH: 510
<212> TYPE: PRT
<213> ORGANISM: Solanum tuberosum

<400> SEQUENCE: 7

```
Met Ala Leu Thr Ser Phe Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Val
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80
```

```
Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Lys Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Ile Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Ala Phe Arg Leu Pro Pro Leu Leu Val
            260                 265                 270

Lys Lys Asp Tyr Gln Arg Leu Tyr Asp Phe Phe Tyr Thr Asn Ser Ala
        275                 280                 285

Asn Leu Phe Val Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Met Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Phe Phe Asp Arg Pro Glu Glu Phe Val Ala
            420                 425                 430

Asp Arg Phe Val Gly Glu Gly Glu Lys Leu Leu Lys Tyr Val Leu
        435                 440                 445

Trp Ser Asn Gly Pro Glu Thr Glu Ser Pro Thr Val Gly Asn Lys Gln
    450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Thr Ser
                485                 490                 495

Ala Leu Gly Ala Ser Ile Thr Ile Thr Ser Leu Lys Lys Ala
```

<210> SEQ ID NO 8
<211> LENGTH: 1533
<212> TYPE: DNA
<213> ORGANISM: Solanum tuberosum

<400> SEQUENCE: 8

| | | | | | |
|---|---|---|---|---|---|
| atggctttaa | cttcattttt | ttctcttcct | cttccttctc | ttcaccaaca | atttccatca | 60 |
| aaatactcta | catttcgtcc | tattattgtt | tctttgtccg | aaaaaccaac | aatcgtggta | 120 |
| acccaaccta | caaaattacc | tgtcaggaca | atacccggcg | actatgggtt | gccgggtatt | 180 |
| ggtccatgga | agataggct | tgattacttt | tacaatcaag | gcaaaaacga | attttttcgaa | 240 |
| tcaagagtag | tgaaatacaa | atcaactata | ttcagaacta | acatgccacc | gggaccattc | 300 |
| atttcttcta | acccgaaggt | tattgttttg | ctcgacggca | agagtttccc | agtccttttc | 360 |
| gatgtttcga | agtcgaaaa | aaaggacctc | ttcaccggaa | cttacatgcc | gtcgactgaa | 420 |
| ctcaccggtg | gttatcgtgt | tctttcttat | cttgacccat | ctgaaccaaa | ccatgaaaaa | 480 |
| ttgaaaaaat | tgatgttctt | ccttctttct | tctcgtcgtg | atcacgttat | acccaaattc | 540 |
| catgaaactt | atacagagtt | ttttgaaacc | ctagataagg | aaatggcgga | aaaaggtaaa | 600 |
| gctggtttaa | actctggcaa | tgatcaagct | gcgtttaatt | tcttagctag | atcgttgttc | 660 |
| ggagttaacc | cagttgaaac | taaactcgga | attgatggtc | cgacattgat | cggaaaatgg | 720 |
| gttttgcttc | agcttcatcc | tgtactcact | ctcggtcttc | cgaagtttct | agatgactta | 780 |
| atcctccatg | ctttccggtt | acctccgctt | ctggtgaaga | aagattacca | gagactttac | 840 |
| gatttctttt | acaccaactc | cgccaattta | ttcgtcgaag | ctgaaaaact | cggcatttct | 900 |
| aaagaagaag | cttgtcataa | tcttctcttc | gctacttgct | tcaattcctt | cggcgggatg | 960 |
| aagattttct | tcccgaatat | gatgaaatcg | atagcgaaag | caggggtgga | ggtccatacc | 1020 |
| cgtttagcaa | acgagatccg | atcggaagta | aaatccgccg | gcgggaagat | cacgatgtcg | 1080 |
| gcgatggaga | aaatgccgct | aatgaaatca | gtagtatatg | aagctttacg | agttgatcct | 1140 |
| ccggtagctt | cacaatacgg | aagagccaaa | caggacctta | agatcgaatc | acacgacgcc | 1200 |
| gttttcgagg | tgaaaaaagg | tgaaatgcta | ttcgggtacc | aaccatttgc | aacgaaggat | 1260 |
| ccgaaatttt | tgaccggcc | ggaagagttc | gtcgccgatc | ggttcgtcgg | agaagaagga | 1320 |
| gaaaagttat | tgaaatacgt | attatggtct | aatggaccgg | aaacggaaag | tccgacagtg | 1380 |
| gggaataaac | agtgtgctgg | aaaagatttt | gtagtgatgg | tttcgaggtt | attcgtaacg | 1440 |
| gagttttttc | tccgttacga | tacattcaat | gtcgacgttg | gtacgtcggc | attgggggct | 1500 |
| tcaattacta | taacttcttt | gaaaaaagct | taa | | | 1533 |

<210> SEQ ID NO 9
<211> LENGTH: 510
<212> TYPE: PRT
<213> ORGANISM: Solanum tuberosum

<400> SEQUENCE: 9

Met Ala Leu Thr Ser Phe Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Pro Trp Lys
 50              55              60

Asp Arg Leu Asp Tyr Phe Tyr Asn Gln Gly Lys Asn Glu Phe Glu
 65              70              75              80

Ser Arg Val Val Lys Tyr Lys Ser Thr Ile Phe Arg Thr Asn Met Pro
             85              90              95

Pro Gly Pro Phe Ile Ser Ser Asn Pro Lys Val Ile Val Leu Leu Asp
             100             105             110

Gly Lys Ser Phe Pro Val Leu Phe Asp Val Ser Lys Val Glu Lys Lys
             115             120             125

Asp Leu Phe Thr Gly Thr Tyr Met Pro Ser Thr Glu Leu Thr Gly Gly
 130             135             140

Phe Arg Val Leu Ser Tyr Leu Asp Pro Ser Glu Pro Asn His Glu Lys
 145             150             155             160

Leu Lys Lys Leu Met Phe Phe Leu Leu Ser Ser Arg Arg Asp His Val
             165             170             175

Ile Pro Lys Phe His Glu Thr Tyr Thr Glu Phe Phe Glu Thr Leu Asp
             180             185             190

Lys Glu Met Ala Glu Lys Gly Lys Ala Gly Leu Asn Ser Gly Asn Asp
             195             200             205

Gln Ala Ala Phe Asn Phe Leu Ala Arg Ser Leu Phe Gly Val Asn Pro
 210             215             220

Val Glu Thr Lys Leu Gly Gly Asp Gly Pro Thr Leu Ile Gly Lys Trp
 225             230             235             240

Val Leu Leu Gln Leu His Pro Val Leu Thr Leu Gly Leu Pro Lys Phe
             245             250             255

Leu Asp Asp Leu Ile Leu His Thr Phe Arg Leu Pro Pro Phe Leu Val
             260             265             270

Lys Lys Asp Tyr Gln Arg Leu Tyr Asp Phe Phe Tyr Thr Asn Ser Ala
             275             280             285

Asn Leu Phe Val Glu Ala Glu Lys Leu Gly Ile Ser Lys Glu Glu Ala
 290             295             300

Cys His Asn Leu Leu Phe Ala Thr Cys Phe Asn Ser Phe Gly Gly Met
 305             310             315             320

Lys Ile Phe Phe Pro Asn Met Met Lys Ser Ile Ala Lys Ala Gly Val
             325             330             335

Glu Val His Thr Arg Leu Ala Asn Glu Ile Arg Ser Glu Val Lys Ser
             340             345             350

Ala Gly Gly Lys Ile Thr Met Ser Ala Met Glu Lys Met Pro Leu Met
             355             360             365

Lys Ser Val Val Tyr Glu Ala Leu Arg Val Asp Pro Pro Val Ala Ser
 370             375             380

Gln Tyr Gly Arg Ala Lys Gln Asp Leu Thr Ile Glu Ser His Asp Ala
 385             390             395             400

Val Phe Glu Val Lys Lys Gly Glu Met Leu Phe Gly Tyr Gln Pro Phe
             405             410             415

Ala Thr Lys Asp Pro Lys Ile Phe Asp Arg Pro Glu Glu Phe Val Ala
             420             425             430

Asp Arg Phe Val Gly Glu Gly Glu Lys Leu Leu Lys Tyr Val Leu
             435             440             445

Trp Ser Asn Gly Pro Glu Thr Glu Ser Pro Thr Val Gly Asn Lys Gln
 450             455             460

Cys Ala Gly Lys Asp Phe Val Val Met Val Ser Arg Leu Phe Val Thr

|  |  | 465 |  |  | 470 |  |  | 475 |  |  | 480 |  |
| --- | --- | --- | --- | --- | --- | --- | --- | --- | --- | --- | --- | --- |
| Glu | Phe | Phe | Leu | Arg | Tyr | Asp | Thr | Phe | Asn | Val | Asp | Val | Gly | Thr | Ser |

|  | 485 |  |  |  | 490 |  |  |  | 495 |  |
| --- | --- | --- | --- | --- | --- | --- | --- | --- | --- | --- |
| Ala | Leu | Gly | Ala | Ser | Ile | Thr | Ile | Thr | Ser | Leu | Lys | Lys | Ala |

|  |  | 500 |  |  |  | 505 |  |  |  | 510 |  |

<210> SEQ ID NO 10
<211> LENGTH: 1533
<212> TYPE: DNA
<213> ORGANISM: Solanum tuberosum

<400> SEQUENCE: 10

```
atggctttaa cttcattttt ttctcttcct cttccttctc ttcaccaaca atttccatca      60
aaatactcta catttcgtcc tattattgtt tctttgtccg aaaaaccaac aatcgtggta     120
acccaaccta caaaattacc taccaggaca atacccggcg actatgggtt gccgggtatt     180
ggtccatgga agataggct tgattacttt tacaatcaag caaaaacga atttttcgaa       240
tcaagagtag tgaaatacaa atcaactata ttcagaacga acatgccacc gggaccattc     300
atttcttcta acccgaaggt tattgttttg ctcgacggca agagtttccc agtccttttc     360
gatgtttcga agtcgaaaa aaaggacctc ttcaccggaa cttacatgcc gtcgactgaa      420
ctcaccggtg gtttccgtgt tctttcttat cttgacccat ctgaaccaaa ccatgaaaaa     480
ttgaaaaaat tgatgttctt ccttctttct ctcgccgtg atcacgttat acccaaattc      540
catgaaactt atacagagtt ttttgaaacc ctagataagg aaatggcgga aaaaggtaaa     600
gctggtttaa actccggcaa tgatcaagct gcgtttaatt tcttagctag atcgttgttc     660
ggagttaacc cagttgaaac taaactcgga ggtgatggtc cgacattgat cggaaaatgg     720
gtgttgcttc agcttcatcc tgtgcttact ctcggtcttc cgaagtttct agatgactta    780
atcctccata ctttccggtt acctccgttt ctggtgaaga aagattacca gagactttac    840
gatttctttt acaccaactc cgccaattta ttcgtcgaag ctgaaaaact cggcatttca    900
aaagaagaag cttgtcataa tcttctcttc gctacttgct tcaattcctt cggcgggatg    960
aagattttct tcccgaatat gatgaaatcg atagcgaaag caggggtgga ggtccatacc   1020
cgtttagcaa acgagatccg atcggaagta aaatccgccg gcgggaagat cacgatgtcg   1080
gcgatggaga aaatgccgtt aatgaaatca gtagtatatg aagctttacg agttgatcct   1140
ccggtagctt cacaatacgg aagagccaaa caggaccta cgatcgaatc acacgacgcc    1200
gttttcgagg tgaaaaaagg tgaaatgcta ttcgggtacc aaccatttgc aacgaaggat   1260
ccgaaaattt ttgaccggcc ggaagagttc gtcgccgatc ggttcgtcgg agaagaagga   1320
gaaaagttat tgaaatacgt attatggtct aatggaccgg aaacggaaag tccgacagtg   1380
gggaataaac agtgtgctgg aaaagatttt gtagtgatgg tttcgaggtt attcgtaacg   1440
gagttttttc tccgttacga tacattcaac gtcgacgttg gtacgtcggc gttgggggct   1500
tcaattacta aacttctttt gaaaaaagct taa                                1533
```

<210> SEQ ID NO 11
<211> LENGTH: 510
<212> TYPE: PRT
<213> ORGANISM: Solanum tuberosum

<400> SEQUENCE: 11

|  |  |  |  | 5 |  |  |  |  | 10 |  |  |  |  | 15 |
| --- | --- | --- | --- | --- | --- | --- | --- | --- | --- | --- | --- | --- | --- | --- |
| Met | Ala | Leu | Thr | Ser | Ser | Phe | Ser | Leu | Pro | Leu | Pro | Ser | Leu | His | Gln |
| 1 |  |  |  |  |  |  |  |  |  |  |  |  |  |  |  |

-continued

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
            35                  40                  45

Arg Thr Ile Pro Gly Asp Tyr Gly Leu Pro Gly Ile Gly Pro Trp Lys
50                      55                  60

Asp Arg Leu Asp Tyr Phe Tyr Asn Gln Gly Lys Asp Glu Phe Phe Glu
65                      70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
            115                 120                 125

Asp Leu Phe Thr Gly Thr Tyr Met Pro Ser Thr Glu Leu Thr Gly Gly
            130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
            195                 200                 205

Gln Ala Ala Phe Asn Phe Leu Ala Arg Ser Leu Phe Gly Val Asn Pro
            210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
            275                 280                 285

Ser Leu Phe Ala Glu Ala Glu Lys Leu Gly Ile Ser Lys Glu Glu Ala
            290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
            355                 360                 365

Lys Ser Val Val Tyr Glu Ala Leu Arg Val Asp Pro Pro Val Ala Ser
            370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
            420                 425                 430

Asp Arg Phe Val Gly Glu Glu Gly Glu Lys Leu Leu Lys Tyr Val Leu

```
       435                 440                 445
Trp Ser Asn Gly Pro Glu Thr Glu Ser Pro Thr Val Gly Asn Lys Gln
    450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
            500                 505                 510

<210> SEQ ID NO 12
<211> LENGTH: 1533
<212> TYPE: DNA
<213> ORGANISM: Solanum tuberosum

<400> SEQUENCE: 12
```

| | | | | | |
|---|---|---|---|---|---|
| atggcattaa | cttcatcttt | ttctcttcct | cttccttctc | ttcaccaaca | atttccatca | 60 |
| aaatactcta | catttcgtcc | tattatcgtt | tctttatccg | aaaaaccaac | aatcgtggta | 120 |
| acccaaccta | caaaattacc | taccaggaca | atacccggcg | actatgggtt | gccgggtatt | 180 |
| ggtccatgga | aagataggct | tgattacttt | tacaatcaag | gaaagacga | attttcgaa | 240 |
| tcaagagtag | tgaaatacaa | atcaactata | ttcagaacga | acatgccacc | gggaccattc | 300 |
| atttcttcta | acccgaaggt | cattgttttg | ctcgacggca | agagtttccc | agtccttttc | 360 |
| gatgtttcga | agtcgaaaaa | aaaggacctc | ttcaccggaa | cttatatgcc | gtcgactgaa | 420 |
| ctcaccggtg | gttaccgtgt | tcttctttat | cttgacccat | ctgaaccaaa | ccatgaaaaa | 480 |
| ttgaaaaaat | tgatgttctt | ccttcttct | tcccgtcgtg | atcacgttat | acccaaattc | 540 |
| catgaaactt | atacagagtt | ttttgaaacc | ctagataagg | aaatggcgga | aaaaggtaca | 600 |
| gctggtttaa | actccggcaa | tgatcaagct | gcgtttaatt | tcttagctag | atcgttgttc | 660 |
| ggagttaacc | cagttgaaac | taaactcgga | ggtgatggtc | cgacattgat | cggaaaatgg | 720 |
| gttttgcttc | agcttcatcc | tgtgctcact | ctcggtcttc | cgaagtttct | agacgactta | 780 |
| atcctccata | ctttccggtt | acctccgttt | ctggtgaaga | aagattacca | gagactttac | 840 |
| gatttctttt | acaccaactc | cgccagttta | ttcgccgaag | ctgaaaaact | cggcatttca | 900 |
| aaagaagaag | cttgtcataa | tcttctcttc | gctacttgct | tcaattcctt | cggcgggatg | 960 |
| aagattttct | tcccgaatat | gctgaaatcg | atagcgaaag | caggggtgga | ggtccatacc | 1020 |
| cgtttagcaa | acgagatccg | atcggaagta | aaatccgccg | gcgggaagat | cacgatgtcg | 1080 |
| gctatggaga | aaatgccgtt | aatgaaatca | gtagtatatg | aagctttgcg | agttgatcct | 1140 |
| ccggtagctt | cacaatacgg | aagagccaaa | caggacctta | agatcgaatc | acacgacgcc | 1200 |
| gttttcgagg | tgaaaaaagg | tgaaatgcta | ttcgggtacc | aaccatttgc | aacgaaggat | 1260 |
| ccgaaaattt | ttgaccggcc | ggaagagttc | gtcgccgatc | ggttcgtcgg | agaagaagga | 1320 |
| gaaaagttat | tgaaatatgt | attatggtct | aatggaccgg | aaacggaaag | tccgacagtg | 1380 |
| gggaataaac | agtgtgctgg | caaagatttt | gtagtgatgg | tttcgaggtt | attcgtaacg | 1440 |
| gagttttttc | tccgttacga | tacattcaac | gtcgacgttg | gtaagtcggc | gttgggggct | 1500 |
| tcaattacta | taacttcttt | gaaaaaagct | tag | | | 1533 |

```
<210> SEQ ID NO 13
<211> LENGTH: 510
<212> TYPE: PRT
<213> ORGANISM: Solanum tuberosum
```

<400> SEQUENCE: 13

```
Met Ala Leu Thr Ser Ser Phe Ser Leu Pro Leu Arg Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
                165                 170                 175

Ile Pro Lys Phe His Glu Thr Tyr Thr Glu Phe Phe Gly Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Asn Leu Phe Val Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Met Lys Ser Ile Ala Lys Ala Gly Val
                325                 330                 335

Asp Leu His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Cys Glu Met Leu Phe Gly Tyr Gln Pro Phe
```

```
                    405                  410                  415
Ala Thr Lys Asp Pro Lys Ile Phe Asp Arg Pro Glu Glu Phe Val Ala
                420                  425                  430

Asp Arg Phe Val Gly Glu Glu Gly Glu Lys Leu Leu Lys Tyr Val Leu
            435                  440                  445

Trp Ser Asn Gly Pro Glu Thr Glu Ser Pro Thr Val Gly Asn Lys Gln
        450                  455                  460

Cys Ala Gly Lys Asp Phe Val Val Met Val Ser Arg Leu Phe Val Thr
465                  470                  475                  480

Glu Phe Phe Leu Arg Tyr Asp Thr Phe Asn Val Asp Val Gly Lys Ser
                485                  490                  495

Ala Leu Gly Ala Ser Ile Thr Ile Thr Ser Leu Lys Lys Ala
                500                  505                  510

<210> SEQ ID NO 14
<211> LENGTH: 1533
<212> TYPE: DNA
<213> ORGANISM: Solanum tuberosum

<400> SEQUENCE: 14
atggcattaa cttcatcttt ttctcttcct cttcgttctc ttcaccaaca atttccatca      60
aaatactcca catttcgtcc tattattgtt tctttatcgg aaaagccaac aatcgtggta     120
acccaaccta caaaattacc taccaggaca atacccggcg actatgggtt gccgggtatt     180
ggtccatgga agataggct tgattacttt tacaatcaag ggaagacga atttttcgaa       240 tcaagagtag tgaaatacaa atcaactata ttcagaacga acatgccacc gggaccattc     300
atttcttcta acccgaaggt cattgttttg ctcgacggca agagtttccc agtcctttc      360 gatgtttcga agtcgaaaa aaaggacctc ttcaccggaa cttatatgcc gtcgactgaa      420
ctcaccggtg ttaccgtgt ctttcttat cttgacccat ctgaaccaaa ccatgaaaaa       480
ttgaaaaaat tgatgttctt ccttctttct tcccgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaatc cagttgaaac taaactcgga ggtgatggtc cgacattgat cggaaaatgg     720
gttttgcttc agcttcatcc tgtgctcact ctcggtcttc cgaagtttct agacgactta     780
atcctccata ctttccggtt acctccgttt ctggtgaaga agattacca gagactttac     840 gatttctttt acaccaactc cgccaattta ttcgtcgaag ctgaaaaact cggcatttct    900
aaagaagaag cttgtcataa tcttctcttc gctacttgct tcaattcctt cggcgggatg    960
aagattttct tcccgaatat gatgaaatcg atagcgaaag caggggtgga tctccatacc   1020
cgtttagcaa acgagatccg atcggaagta aaatccgccg gcgggaagat cacgatgtcg   1080
gcgatggaga aaatgccgtt aatgaaatca gtagtttatg aagctttacg agttgatcct   1140
ccggtagctt cacaatacgg aagagccaaa caggacctta agatcgaatc acacgacgcc   1200
gttttcgagg tgaaaaaatg tgaaatgcta ttcgggtacc aaccatttgc aacgaaggat   1260
ccgaaaattt ttgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg gtaagtcggc gttggggct    1500 tcaattacta taacttcttt gaaaaaagct tag                                 1533
```

<210> SEQ ID NO 15
<211> LENGTH: 510
<212> TYPE: PRT
<213> ORGANISM: Solanum tuberosum

<400> SEQUENCE: 15

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
290                 295                 300

Cys His Asn Leu Leu Phe Ala Thr Cys Phe Asn Ser Phe Gly Gly Met
305                 310                 315                 320

Lys Ile Phe Phe Pro Asn Met Met Lys Ser Ile Ala Lys Ala Gly Val
                325                 330                 335

Asp Leu His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
```

```
                370               375               380
Gln Tyr Gly Arg Ala Lys Gln Asp Leu Lys Ile Glu Ser His Asp Ala
385                 390                 395                 400

Val Phe Glu Val Lys Lys Cys Glu Met Leu Phe Gly Tyr Gln Pro Phe
                405                 410                 415

Ala Thr Lys Asp Pro Lys Ile Phe Asp Arg Pro Glu Glu Phe Val Ala
                420                 425                 430

Asp Arg Phe Val Gly Glu Gly Glu Lys Leu Leu Lys Tyr Val Leu
                435                 440                 445

Trp Ser Asn Gly Pro Glu Thr Glu Ser Pro Thr Val Gly Asn Lys Gln
450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
                500                 505                 510
```

<210> SEQ ID NO 16
<211> LENGTH: 1533
<212> TYPE: DNA
<213> ORGANISM: Solanum tuberosum

<400> SEQUENCE: 16

```
atggcattaa cttcatcttt ttctcttcct cttccttctc ttcaccaaca atttccatca    60
aaatactcta catttcgtcc tattatcgtt tctttatccg aaaaaccaac aatcgtggta   120
acccaaccta caaaattacc taccaggaca atacccggcg actatgggtt gccgggtatt   180
ggtccatgga agataggct tgattacttt acaatcaag ggaaagacga atttttcgaa    240
tcaagagtag tgaaatacaa atcaactata tcagaacga acatgccacc gggaccattc   300
atttcttcta acccgaaggt cattgttttg ctcgacggca agagtttccc agtccttttc   360
gatgtttcga agtcgaaaa aaaggacctc ttcaccggaa cttatatgcc gtcgactgaa    420
ctcaccggtg ttaccgtgt tctttcttat cttgacccat ctgaaccaaa ccatgaaaaa   480
ttgaaaaaat tgatgttctt ccttctttct tcccgtcgtg atcacgttat acccaaattc   540
catgaaactt atacagagtt ttttgaaacc ctagataagg aaatggcgga aaaaggtaca   600
gctggtttaa actccggcaa tgatcaagct gcgtttaatt tcttagctag atcgttgttc   660
ggagttaacc cagttgaaac taaactcgga ggtgatggtc cgacattgat cggaaaatgg   720
gttttgcttc agcttcatcc tgtgctcact ctcggtcttc cgaagtttct agacgactta   780
atcctccata ctttccggtt acctccgttt ctggtgaaga aagattacca gagactttac   840
gatttctttt acaccaactc cgccagttta ttcgccgaag ctgaaaaact cggcatttca   900
aaagaagaag cttgtcataa tcttctcttc gctacttgct tcaattcctt cggcgggatg   960
aagatttct tcccgaatat gatgaaatcg atagcgaaag caggggtgga tctccatacc  1020
cgtttagcaa acgagatccg atcggaagta aaatccgccg gcgggaagat cacgatgtcg  1080
gcgatggaga aaatgccgtt aatgaaatca gtagtttatg aagctttacg agttgatcct  1140
ccggtagctt cacaatacgg aagagccaaa caggaccta agatcgaatc acacgacgcc  1200
gttttcgagg tgaaaaaatg tgaaatgcta ttcgggtacc aaccatttgc aacgaaggat  1260
ccgaaaattt tgaccggcc ggaagagttc gtcgccgatc ggttcgtcgg agaagaagga  1320
gaaaagttat tgaaatatgt attatggtct aatggaccgg aaacggaaag tccgacagtg  1380
```

-continued

```
gggaataaac agtgtgctgg caaagatttt gtagtgatgg tttcgaggtt attcgtaacg   1440
gagttttttc tccgttacga tacattcaac gtcgacgttg gtaagtcggc gttgggggct   1500
tcaattacta taacttcttt gaaaaaagct tag                                1533
```

```
<210> SEQ ID NO 17
<211> LENGTH: 510
<212> TYPE: PRT
<213> ORGANISM: Solanum tuberosum

<400> SEQUENCE: 17
```

| | | | | | | | | | | | | | | | |
|---|---|---|---|---|---|---|---|---|---|---|---|---|---|---|---|
| Met | Ala | Leu | Thr | Ser | Ser | Phe | Ser | Leu | Pro | Leu | Arg | Ser | Leu | His | Gln |
| 1 | | | | 5 | | | | | 10 | | | | | 15 | |
| Gln | Phe | Pro | Ser | Lys | Tyr | Ser | Thr | Phe | Arg | Pro | Ile | Ile | Val | Ser | Leu |
| | | | 20 | | | | | 25 | | | | | 30 | | |
| Ser | Glu | Lys | Pro | Thr | Ile | Val | Val | Thr | Gln | Pro | Thr | Lys | Leu | Pro | Thr |
| | | 35 | | | | | 40 | | | | | 45 | | | |
| Arg | Thr | Ile | Pro | Gly | Asp | Tyr | Gly | Leu | Pro | Gly | Ile | Gly | Pro | Trp | Lys |
| | 50 | | | | | 55 | | | | | 60 | | | | |
| Asp | Arg | Leu | Asp | Tyr | Phe | Tyr | Asn | Gln | Gly | Lys | Asp | Glu | Phe | Phe | Glu |
| 65 | | | | | 70 | | | | | 75 | | | | | 80 |
| Ser | Arg | Val | Val | Lys | Tyr | Lys | Ser | Thr | Ile | Phe | Arg | Thr | Asn | Met | Pro |
| | | | | 85 | | | | | 90 | | | | | 95 | |
| Pro | Gly | Pro | Phe | Ile | Ser | Ser | Asn | Pro | Lys | Val | Ile | Val | Leu | Leu | Asp |
| | | | 100 | | | | | 105 | | | | | 110 | | |
| Gly | Lys | Ser | Phe | Pro | Val | Leu | Phe | Asp | Val | Ser | Lys | Val | Glu | Lys | Lys |
| | | 115 | | | | | 120 | | | | | 125 | | | |
| Asp | Leu | Phe | Thr | Gly | Thr | Tyr | Met | Pro | Ser | Thr | Glu | Leu | Thr | Gly | Gly |
| | 130 | | | | | 135 | | | | | 140 | | | | |
| Tyr | Arg | Val | Leu | Ser | Tyr | Leu | Asp | Pro | Ser | Glu | Pro | Asn | His | Glu | Lys |
| 145 | | | | | 150 | | | | | 155 | | | | | 160 |
| Leu | Lys | Lys | Leu | Met | Phe | Phe | Leu | Leu | Ser | Ser | Arg | Arg | Asp | His | Val |
| | | | | 165 | | | | | 170 | | | | | 175 | |
| Ile | Pro | Lys | Phe | His | Glu | Thr | Tyr | Thr | Glu | Phe | Phe | Glu | Thr | Leu | Asp |
| | | | 180 | | | | | 185 | | | | | 190 | | |
| Lys | Glu | Met | Ala | Glu | Lys | Gly | Thr | Ala | Gly | Leu | Asn | Ser | Gly | Asn | Asp |
| | | 195 | | | | | 200 | | | | | 205 | | | |
| Gln | Ala | Ala | Phe | Asn | Phe | Leu | Ala | Arg | Ser | Leu | Phe | Gly | Val | Asn | Pro |
| | 210 | | | | | 215 | | | | | 220 | | | | |
| Val | Glu | Thr | Lys | Leu | Gly | Gly | Asp | Gly | Pro | Thr | Leu | Ile | Gly | Lys | Trp |
| 225 | | | | | 230 | | | | | 235 | | | | | 240 |
| Val | Leu | Leu | Gln | Leu | His | Pro | Val | Leu | Thr | Leu | Gly | Leu | Pro | Lys | Phe |
| | | | | 245 | | | | | 250 | | | | | 255 | |
| Leu | Asp | Asp | Leu | Ile | Leu | His | Thr | Phe | Arg | Leu | Pro | Pro | Phe | Leu | Val |
| | | | 260 | | | | | 265 | | | | | 270 | | |
| Lys | Lys | Asp | Tyr | Gln | Arg | Leu | Tyr | Asp | Phe | Phe | Tyr | Thr | Asn | Ser | Ala |
| | | 275 | | | | | 280 | | | | | 285 | | | |
| Ser | Leu | Phe | Ala | Glu | Ala | Glu | Lys | Leu | Gly | Ile | Ser | Lys | Glu | Glu | Ala |
| | 290 | | | | | 295 | | | | | 300 | | | | |
| Cys | His | Asn | Leu | Leu | Phe | Ala | Thr | Cys | Phe | Asn | Ser | Phe | Gly | Gly | Met |
| 305 | | | | | 310 | | | | | 315 | | | | | 320 |
| Lys | Ile | Phe | Phe | Pro | Asn | Met | Leu | Lys | Ser | Ile | Ala | Lys | Ala | Gly | Val |
| | | | | 325 | | | | | 330 | | | | | 335 | |
| Glu | Val | His | Thr | Arg | Leu | Ala | Asn | Glu | Ile | Arg | Ser | Glu | Val | Lys | Ser |

```
                340                 345                 350
Ala Gly Gly Lys Ile Thr Met Ser Ala Met Glu Lys Met Pro Leu Met
                355                 360                 365

Lys Ser Val Val Tyr Glu Ala Leu Arg Val Asp Pro Pro Val Ala Ser
            370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
            420                 425                 430

Asp Arg Phe Val Gly Glu Gly Glu Lys Leu Leu Lys Tyr Val Leu
                435                 440                 445

Trp Ser Asn Gly Pro Glu Thr Glu Ser Pro Thr Val Gly Asn Lys Gln
            450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
            500                 505                 510

<210> SEQ ID NO 18
<211> LENGTH: 1533
<212> TYPE: DNA
<213> ORGANISM: Solanum tuberosum

<400> SEQUENCE: 18
atggcattaa cttcatcttt ttctcttcct cttcgttctc ttcaccaaca atttccatca      60
aaatactcca catttcgtcc tattattgtt tctttatcgg aaaagccaac aatcgtggta     120
acccaaccta caaaattacc taccaggaca atacccggcg actatgggtt gccgggtatt     180
ggtccatgga agataggct tgattacttt tacaatcaag ggaaagacga attttttcgaa     240 tcaagagtag tgaaatacaa atcaactata ttcagaacga acatgccacc gggaccattc     300
atttcttcta acccgaaggt cattgttttg ctcgacggca agagtttccc agtccttttc     360
gatgtttcga agtcgaaaaa aaaggacctc ttcaccggaa cttatatgcc gtcgactgaa     420
ctcaccggtg gttaccgtgt tctttcttat cttgacccat ctgaaccaaa ccatgaaaaa     480
ttgaaaaaat tgatgttctt ccttctttct tcccgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga ggtgatggtc cgacattgat cggaaaatgg     720
gttttgcttc agcttcatcc tgtgctcact ctcggtcttc cgaagtttct agacgactta     780
atcctccata ctttccggtt acctccgttt ctggtgaaga agattaccag agactttac      840 gatttctttt acaccaactc cgccagttta ttcgccgaag ctgaaaaact cggcatttca     900
aaagaagaag cttgtcataa tcttctcttc gctacttgct tcaattcctt cggcgggatg     960
aagattttct tcccgaatat gctgaaatcg atagcgaaag caggggtgga ggtccatacc    1020
cgtttagcaa acgagatccg atcggaagta aaatccgccg gcgggaagat cacgatgtcg    1080
gctatggaga aaatgccgtt aatgaaatca gtagtatatg aagctttgcg agttgatcct    1140
ccggtagctt cacaatacgg aagagccaaa caggaccta agatcgaatc acacgacgcc    1200
```

```
gttttcgagg tgaaaaaagg tgaaatgcta ttcgggtacc aaccatttgc aacgaaggat   1260
ccgaaaattt ttgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg gtaagtcggc gttgggggct   1500
tcaattacta taacttcttt gaaaaaagct tag                                1533
```

<210> SEQ ID NO 19
<211> LENGTH: 510
<212> TYPE: PRT
<213> ORGANISM: Solanum tuberosum
<400> SEQUENCE: 19

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Ile Phe Ala Thr Cys Phe Asn Ser Phe Gly Gly Met
```

```
          305                 310                 315                 320
Lys Ile Phe Phe Pro Asn Met Leu Lys Ser Ile Ala Lys Ala Gly Val
                    325                 330                 335

Glu Val His Thr Arg Leu Ala Asn Glu Ile Arg Ser Glu Val Lys Ser
                340                 345                 350

Ala Gly Gly Lys Ile Thr Met Ser Ala Met Glu Lys Met Pro Leu Met
            355                 360                 365

Lys Ser Val Val Tyr Glu Ala Leu Arg Val Asp Pro Pro Val Ala Ser
        370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
                420                 425                 430

Asp Arg Phe Val Gly Glu Glu Gly Lys Leu Leu Lys Tyr Val Leu
                435                 440                 445

Trp Ser Asn Gly Pro Glu Thr Glu Ser Pro Thr Val Gly Asn Lys Gln
450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
                500                 505                 510

<210> SEQ ID NO 20
<211> LENGTH: 1533
<212> TYPE: DNA
<213> ORGANISM: Solanum tuberosum

<400> SEQUENCE: 20
atggcattaa cttcatctttt ttctcttcct cttccttctc ttcaccaaca atttccatca      60
aaatactcta catttcgtcc tattatcgtt tctttatccg aaaaaccaac aatcgtggta     120
acccaaccta caaaattacc taccaggaca ataccccggcg actatgggtt gccgggtatt     180
ggtccatgga agataggct tgattacttt tacaatcagg gcaaaaacga attttttcgaa     240
tcaagagtag taaaatacaa atcaactata ttcagaacga acatgccacc gggaccattc     300
atttcttcta acccgaaggt tattgttttg ctcgacggca agagtttccc agtccttttc     360
gatgtttcga agtcgaaaa aaaggacctc ttcaccggaa cttacatgcc gtcgactgaa     420
ctcaccggtg gttaccgtgt tctttcttat cttgacccat ctgaaccaaa ccatgaaaaa     480
ttgaaaaaat tgatgttctt cctttctttcc tcccgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga ggtgatggtc cgacattgat cggaaaatgg     720
gttttgcttc agcttcatcc tgtgctcact ctcggtcttc cgaagtttct agacgactta     780
atcctccata ctttccggtt acctccgttt ctggtgaaga aagattacca gagactttac     840
gatttctttt acaccaactc cgccagttta ttcgccgaag ctgaaaaact cggcatttca     900
aaagaagaag cttgtcataa tcttatcttc gctacttgct tcaattcctt cggcgggatg     960
aagattttct tcccgaatat gctgaaatcg atagcgaaag caggggtgga ggtccatacc    1020
```

-continued

```
cgtttagcaa acgagatccg atcggaagta aaatccgctg gcgggaagat cacgatgtcg    1080
gcgatggaga aaatgccgtt aatgaaatca gtagtttatg aagctttacg agttgatcct    1140
ccggtagctt cacaatacgg aagagccaaa caggaccttc agatcgaatc acacgacgcc    1200
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaagaagga    1320
gaaaagttat tgaaatatgt attatggtct aatggaccgg aaacggaaag tccgacagtg    1380
gggaataaac agtgtgctgg caaagatttt gtagtgatgg tttcgaggtt attcgtaacg    1440
gagttttttc tccgttacga tacattcaac gtcgacgttg gtaagtcggc gttgggggct    1500
tcaattacta aacttctttg aaaaaagct tag                                  1533
```

<210> SEQ ID NO 21
<211> LENGTH: 510
<212> TYPE: PRT
<213> ORGANISM: Solanum tuberosum

<400> SEQUENCE: 21

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
```

```
                275                 280                 285
Ser Leu Phe Ala Glu Ala Glu Lys Leu Gly Ile Ser Lys Glu Glu Ala
    290                 295                 300

Cys His Asn Leu Ile Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
            420                 425                 430

Asp Arg Phe Val Gly Glu Gly Glu Lys Leu Leu Lys Tyr Val Leu
        435                 440                 445

Trp Ser Asn Gly Pro Glu Thr Glu Ser Pro Thr Val Gly Asn Lys Gln
    450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Asp Lys Ser
                485                 490                 495

Ala Leu Gly Ala Ser Ile Thr Ile Thr Ser Leu Lys Lys Ala
            500                 505                 510

<210> SEQ ID NO 22
<211> LENGTH: 1533
<212> TYPE: DNA
<213> ORGANISM: Solanum tuberosum

<400> SEQUENCE: 22
atggcattaa cttcatcttt ttctcttcct cttccttctc ttcaccaaca atttccatca      60
aaatactcta catttcgtcc tattatcgtt tctttatccg aaaaaccaac aatcgtggta     120
acccaaccta caaaattacc taccaggaca atacccggcg actatgggtt gccgggtatt     180
ggtccatgga agataggct tgattacttt tacaatcagg gcaaaaacga attttttcgaa     240 tcaagagtag taaatacaa atcaactata ttcagaacga acatgccacc gggaccattc     300
atttcttcta acccgaaggt tattgttttg ctcgacggca agagtttccc agtccttttc     360
gatgtttcga aagtcgaaaa aaaggacctc ttcaccggaa cttacatgcc gtcgactgaa     420
ctcaccggtg gttaccgtgt tctttcttat cttgacccat ctgaaccaaa ccatgaaaaa     480
ttgaaaaaat tgatgttctt ccttctttcc tcccgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga ggtgatggtc cgacattgat cggaaaatgg     720
gttttgcttc agcttcatcc tgtgctcact ctcggtcttc cgaagtttct agacgactta     780
atcctccata ctttccggtt acctccgttt ctggtgaaga aagattacca gagactttac     840
```

```
gatttctttt acaccaactc cgccagttta ttcgccgaag ctgaaaaact cggcatttca    900
aaagaagaag cttgtcataa tcttatcttc gctacttgct tcaattcctt cggcgggatg    960
aagattttct tcccgaatat gctgaaatcg atagcgaaag caggggtgga ggtccatacc   1020
cgtttagcaa acgagatccg atcggaagta aaatccgctg gcgggaagat cacgatgtcg   1080
gcgatggaga aaatgccgtt aatgaaatca gtagtttatg aagctttacg agttgatcct   1140
ccggtagctt cacaatacgg aagagccaaa caggaccta agatcgaatc acacgacgcc   1200
gttttcgagg tgaaaaaagg tgaaatgcta ttcgggtacc aaccatttgc aacgaaggat   1260
ccgaaaattt tgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg ataagtcggc gttgggggct   1500
tcaattacta taacttcttt gaaaaaagct tag                                1533
```

<210> SEQ ID NO 23
<211> LENGTH: 510
<212> TYPE: PRT
<213> ORGANISM: Solanum tuberosum

<400> SEQUENCE: 23

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Asn Val Ile Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
```

```
                    245                 250                 255
Leu Asp Asp Leu Ile Leu His Thr Phe Arg Leu Pro Pro Phe Leu Val
            260                 265                 270
Lys Lys Asp Tyr Gln Arg Leu Tyr Asp Phe Phe Tyr Thr Asn Ser Ala
            275                 280                 285
Ser Leu Phe Ala Glu Ala Glu Lys Leu Gly Ile Ser Lys Glu Glu Ala
            290                 295                 300
Cys His Asn Leu Ile Phe Ala Thr Cys Phe Asn Ser Phe Gly Gly Leu
305                 310                 315                 320
Lys Ile Phe Phe Pro Asn Met Leu Lys Ser Ile Ala Lys Ala Gly Val
                    325                 330                 335
Glu Val His Thr Arg Leu Ala Asn Glu Ile Arg Ser Glu Val Lys Ser
                340                 345                 350
Ala Gly Gly Lys Ile Thr Met Ser Ala Met Glu Lys Met Pro Leu Met
            355                 360                 365
Lys Ser Val Val Tyr Glu Ala Leu Arg Val Asp Pro Pro Val Ala Ser
            370                 375                 380
Gln Tyr Gly Arg Ala Lys Gln Asp Leu Lys Ile Glu Ser His Asp Ala
385                 390                 395                 400
Val Phe Glu Val Lys Lys Gly Glu Met Leu Phe Gly Tyr Gln Pro Phe
                    405                 410                 415
Ala Thr Lys Asp Pro Lys Ile Phe Asp Arg Pro Glu Glu Phe Val Ala
                420                 425                 430
Asp Arg Phe Val Gly Glu Gly Gly Lys Leu Leu Lys Tyr Val Leu
                435                 440                 445
Trp Ser Asn Gly Pro Glu Thr Glu Ser Pro Thr Val Gly Asn Lys Gln
            450                 455                 460
Cys Ala Gly Lys Asp Phe Val Val Met Val Ser Arg Leu Phe Val Thr
465                 470                 475                 480
Glu Phe Phe Leu Arg Tyr Asp Thr Phe Asn Val Asp Val Asp Lys Ser
                    485                 490                 495
Ala Leu Gly Ala Ser Ile Thr Ile Thr Ser Leu Lys Lys Ala
                500                 505                 510

<210> SEQ ID NO 24
<211> LENGTH: 1533
<212> TYPE: DNA
<213> ORGANISM: Solanum tuberosum

<400> SEQUENCE: 24
atggcattaa cttcatctttt tctcttcct cttccttctc ttcaccaaca atttccatca       60
aaatactcta catttcgtcc tattatcgtt tctttatccg aaaaaccaac aatcgtggta      120
acccaaccta caaaattacc taccaggaca atacccggcg actatgggtt gccgggtatt      180
ggtccatgga agataggct tgattacttt tacaatcaag caaaaacga atttttcgaa        240 tcaagagtag tgaaatacaa atcaactata ttcagaacga acatgccacc gggaccattc      300
atttcttcta acccgaatgt tattgtttttg ctcgacggca agagtttccc agtccttttc      360
gatgtttcga agtcgaaaa aaaggacctc ttcaccggaa cttacatgcc gtcgactgaa       420
ctcaccggtg gttaccgtgt tctttcttat cttgatccat ctgaaccaaa ccatgaaaaa      480
ttgaaaaaat tgatgttctt ccttctttct tctcgacgtg atcacgttat acccaaattc      540
catgaaactt atacagagtt tttcgaaacc ctagataagg aaatggcgga aaaaggtaca      600
gctggtttaa actccggcaa tgatcaagct gcgtttaatt tcttagctag atcgttgttc      660
```

```
ggagttaacc cagttgaaac taaactcgga actgatggtc cgacattgat cggaaaatgg    720
gttttgcttc agcttcatcc tgtactcact ctcggtcttc cgaagtttct agacgactta    780
atcctccata ctttccggtt acctccgttt ctggtgaaga agattacca gagactttac    840
gatttctttt acaccaactc cgccagttta ttcgccgaag ctgaaaaact cggcatttca    900
aaagaagaag cttgtcataa tcttatcttc gctacttgct tcaattcctt cggcgggttg    960
aagatttttct tcccgaatat gctgaaatcg atagcgaaag caggggtgga ggtccatacc   1020
cgtttagcaa acgagatccg atcggaagta aaatccgctg gcgggaagat cacgatgtcg   1080
gcgatggaga aaatgccgtt aatgaaatca gtagtttatg aagctttacg agttgatcct   1140
ccggtagctt cacaatacgg aagagccaaa caggaccctta agatcgaatc acgacgcc    1200
gttttcgagg tgaaaaaagg tgaaatgcta ttcgggtacc aaccatttgc aacgaaggat   1260
ccgaaaattt ttgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg ataagtcggc gttggggct    1500
tcaattacta taacttcttt gaaaaaagct tag                                1533

<210> SEQ ID NO 25
<211> LENGTH: 509
<212> TYPE: PRT
<213> ORGANISM: Solanum tuberosum

<400> SEQUENCE: 25

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
```

```
    210                 215                 220
Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
                260                 265                 270

Lys Lys Asp Tyr Gln Arg Leu Tyr Asp Phe Phe Tyr Thr Asn Ser Ala
                275                 280                 285

Ser Leu Phe Ala Glu Ala Glu Lys Leu Gly Ile Ser Lys Glu Glu Ala
                290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
                340                 345                 350

Ala Gly Gly Lys Ile Thr Met Ser Ala Met Glu Lys Met Pro Leu Met
                355                 360                 365

Lys Ser Val Val Tyr Glu Ala Leu Arg Val Asp Pro Pro Val Ala Ser
                370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
                420                 425                 430

Asp Arg Phe Val Gly Glu Gly Glu Lys Leu Leu Lys Tyr Val Leu Trp
                435                 440                 445

Ser Asn Gly Pro Glu Thr Glu Ser Pro Thr Val Gly Asn Lys Gln Cys
                450                 455                 460

Ala Gly Lys Asp Phe Val Val Met Val Ser Arg Leu Phe Val Thr Glu
465                 470                 475                 480

Phe Phe Leu Arg Tyr Asp Thr Phe Asn Val Asp Val Gly Lys Ser Ala
                485                 490                 495

Leu Gly Ala Ser Ile Thr Ile Thr Ser Leu Lys Lys Ala
                500                 505

<210> SEQ ID NO 26
<211> LENGTH: 1533
<212> TYPE: DNA
<213> ORGANISM: Solanum tuberosum

<400> SEQUENCE: 26
atggcattaa cttcatcttt ttctcttcct cttccttctc ttcaccaaca atttccatca     60
aaatactcta catttcgtcc tattatcgtt tctttatccg aaaaaccaac aatcgtggta    120
acccaaccta caaaattacc taccaggaca atacccggcg actatgggtt gccgggtatt    180
ggtccatgga agataggct tgattacttt tacaatcaag caaaaacga atttttcgaa     240 tcaagagtag tgaaatacaa atcaactata ttcagaacga acatgccacc gggaccattc    300
atttcttcta acccgaatgt tattgttttg ctcgacggca agagtttccc agtccttttc    360
gatgtttcga agtcgaaaaa aaaggacctc ttcaccggaa cttacatgcc gtcgactgaa    420
ctcaccggtg gttaccgtgt tctttcttat cttgatccat ctgaaccaaa ccatgaaaaa    480
```

```
ttgaaaaaat tgatgttctt ccttctttct tctcgacgtg atcacgttat acccaaattc    540
catgaaactt atacagagtt tttcgaaacc ctagataagg aaatggcgga aaaaggtaca    600
gctggtttaa actccggcaa tgatcaagct gcgtttaatt tcttagctag atcgttgttc    660
ggagttaacc cagttgaaac taaactcgga actgatggtc cgacattgat cggaaaatgg    720
gttttgcttc agcttcatcc tgtactcact cttggtcttc cgaagtttct agacgactta    780
atcctccata ctttccggtt acctccgttt ctggtgaaga aagattacca gagactttac    840
gatttctttt acaccaactc cgccagttta ttcgccgaag ctgaaaaact cggcatttca    900
aaagaagaag cttgtcataa tcttatcttc gctacttgct tcaattcctt cggcgggatg    960
aagattttct tcccgaatat gctgaaatcg atagcgaaag caggggtgga ggtccatacc   1020
cgtttagcaa acgagatccg atcggaagta aaatccgctg gcgggaagat cacgatgtcg   1080
gcgatggaga aaatgccgtt aatgaaatca gtagtttatg aagctttacg agttgatcct   1140
ccggtagctt cacaatacgg aagagccaaa caggacctta agatcgaatc acacgacgcc   1200
gttttcgagg tgaaaaaagg tgaaatgcta ttcgggtacc aaccatttgc aacgaaggat   1260
ccgaaatttt ttgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg gtaagtcggc gttgggggct   1500
tcaattacta aacttctttg aaaaaagct tag                                 1533
```

<210> SEQ ID NO 27
<211> LENGTH: 510
<212> TYPE: PRT
<213> ORGANISM: Solanum tuberosum

<400> SEQUENCE: 27

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Ile
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
```

|   |   |   | 180 |   |   |   |   | 185 |   |   |   |   | 190 |   |   |
|---|---|---|---|---|---|---|---|---|---|---|---|---|---|---|---|
| Lys | Glu | Met | Ala | Glu | Lys | Gly | Thr | Ala | Gly | Leu | Asn | Ser | Gly | Asn | Asp |
|   |   |   | 195 |   |   |   |   | 200 |   |   |   |   | 205 |   |   |
| Gln | Ala | Ala | Phe | Asn | Phe | Leu | Ala | Arg | Ser | Leu | Phe | Gly | Val | Asn | Pro |
|   |   |   | 210 |   |   |   |   | 215 |   |   |   |   | 220 |   |   |
| Val | Glu | Thr | Lys | Leu | Gly | Thr | Asp | Gly | Pro | Thr | Leu | Ile | Gly | Lys | Trp |
| 225 |   |   |   |   | 230 |   |   |   |   | 235 |   |   |   |   | 240 |
| Val | Leu | Leu | Gln | Leu | His | Pro | Val | Leu | Thr | Leu | Gly | Leu | Pro | Lys | Phe |
|   |   |   |   | 245 |   |   |   |   | 250 |   |   |   |   | 255 |   |
| Leu | Asp | Asp | Leu | Ile | Leu | His | Thr | Phe | Arg | Leu | Pro | Pro | Phe | Leu | Val |
|   |   |   | 260 |   |   |   |   | 265 |   |   |   |   | 270 |   |   |
| Lys | Lys | Asp | Tyr | Gln | Arg | Leu | Tyr | Asp | Phe | Phe | Tyr | Thr | Asn | Ser | Ala |
|   |   | 275 |   |   |   |   | 280 |   |   |   |   | 285 |   |   |   |
| Ser | Leu | Phe | Ala | Glu | Ala | Glu | Lys | Leu | Gly | Ile | Ser | Lys | Glu | Glu | Ala |
|   |   |   | 290 |   |   |   |   | 295 |   |   |   |   | 300 |   |   |
| Cys | His | Asn | Leu | Leu | Phe | Ala | Thr | Cys | Phe | Asn | Ser | Phe | Gly | Gly | Met |
| 305 |   |   |   |   | 310 |   |   |   |   | 315 |   |   |   |   | 320 |
| Lys | Ile | Phe | Phe | Pro | Asn | Met | Val | Lys | Ser | Ile | Ala | Lys | Ala | Gly | Val |
|   |   |   |   | 325 |   |   |   |   | 330 |   |   |   |   | 335 |   |
| Glu | Val | His | Thr | Arg | Leu | Ala | Asn | Glu | Ile | Arg | Ser | Glu | Val | Lys | Ser |
|   |   |   | 340 |   |   |   |   | 345 |   |   |   |   | 350 |   |   |
| Ala | Gly | Gly | Lys | Ile | Thr | Met | Ser | Ala | Met | Glu | Lys | Met | Pro | Leu | Met |
|   |   | 355 |   |   |   |   | 360 |   |   |   |   | 365 |   |   |   |
| Lys | Ser | Val | Val | Tyr | Glu | Ala | Leu | Arg | Val | Asp | Pro | Pro | Val | Ala | Ser |
|   | 370 |   |   |   |   | 375 |   |   |   |   | 380 |   |   |   |   |
| Gln | Tyr | Gly | Arg | Ala | Lys | Gln | Asp | Leu | Lys | Ile | Glu | Ser | His | Asp | Ala |
| 385 |   |   |   |   | 390 |   |   |   |   | 395 |   |   |   |   | 400 |
| Val | Phe | Glu | Val | Lys | Lys | Gly | Glu | Met | Leu | Phe | Gly | Tyr | Gln | Pro | Phe |
|   |   |   |   | 405 |   |   |   |   | 410 |   |   |   |   | 415 |   |
| Ala | Thr | Lys | Asp | Pro | Lys | Phe | Phe | Asp | Arg | Pro | Glu | Glu | Phe | Val | Ala |
|   |   |   | 420 |   |   |   |   | 425 |   |   |   |   | 430 |   |   |
| Asp | Arg | Phe | Val | Gly | Glu | Gly | Glu | Lys | Leu | Leu | Lys | Tyr | Val | Leu |   |
|   |   | 435 |   |   |   |   | 440 |   |   |   |   | 445 |   |   |   |
| Trp | Ser | Asn | Gly | Pro | Glu | Thr | Glu | Ser | Pro | Thr | Val | Gly | Asn | Lys | Gln |
|   | 450 |   |   |   |   | 455 |   |   |   |   | 460 |   |   |   |   |
| Cys | Ala | Gly | Lys | Asp | Phe | Val | Met | Val | Ser | Arg | Leu | Phe | Val | Thr |   |
| 465 |   |   |   |   | 470 |   |   |   |   | 475 |   |   |   |   | 480 |
| Glu | Phe | Phe | Leu | Arg | Tyr | Asp | Thr | Phe | Asn | Val | Asp | Val | Gly | Lys | Ser |
|   |   |   |   | 485 |   |   |   |   | 490 |   |   |   |   | 495 |   |
| Ala | Leu | Gly | Ala | Ser | Ile | Thr | Ile | Thr | Ser | Leu | Lys | Lys | Ala |   |   |
|   |   |   | 500 |   |   |   |   | 505 |   |   |   |   | 510 |   |   |

<210> SEQ ID NO 28
<211> LENGTH: 1533
<212> TYPE: DNA
<213> ORGANISM: Solanum tuberosum

<400> SEQUENCE: 28

| atggcattaa | cttcatcttt | ttctcttcct | cttccttctc | ttcaccaaca | atttccatca | 60 |
| aaatactcca | catttcgtcc | tattattgtt | tctttatccg | aaaaaccaac | aatcgtggta | 120 |
| acccaaccta | caaaattacc | tatcaggaca | atacccggcg | actatgggtt | gccgggtatt | 180 |
| ggtccatgga | aagataggct | tgattacttt | tacaatcaag | ggaaagacga | attttttcgaa | 240 |
| tcaagagtag | tgaaatacaa | atcaactata | ttcagaacga | acatgccacc | gggaccattc | 300 |

```
atttcttcta acccgaaggt tattgttttg ctcgacggca agagtttccc agtccttttc      360
gatgtttcga aagtcgaaaa aaaggacctc ttcaccggaa cttacatgcc gtcgactgaa      420
ctcaccggtg gttaccgtgt tctttcttat cttgacccat ctgaaccaaa ccatgaaaaa      480
ttgaaaaaat tgatgttctt ccttctttcc tcccgtcgtg atcacgttat acccaaattc      540
catgaaactt atacagagtt ttttgaaacc ctagataagg aaatggcgga aaaaggtaca      600
gctggtttaa actccggcaa tgatcaagct gcgtttaatt tcttagctag atcgttgttc      660
ggagttaacc cagttgaaac taaactcgga actgatggtc cgacattgat cggaaaatgg      720
gttttgcttc agcttcatcc tgtactcact ctcggtcttc cgaagtttct agacgactta      780
atcctccata ctttccggtt acctccgttt ctggtgaaga agattacca gagactttac      840 gatttctttt acaccaactc cgccagttta ttcgccgaag ctgaaaaact cggcatttct      900
aaagaagaag cttgtcataa tcttctcttc gctacttgct tcaattcctt cggcgggatg      960 aagatttttct tcccgaatat ggtgaaatcg atagcaaaag caggggtgga ggtccatacc     1020
cgtttagcaa acgagatccg atcggaagta aaatccgccg gcgggaagat cacgatgtcg     1080
gcgatggaga aaatgccgtt aatgaaatca gtagtttatg aagctttacg agttgatcct     1140
ccagtagctt cacaatacgg aagagccaaa caggacctta agatcgaatc acacgacgcc     1200
gttttcgagg tgaaaaaagg tgaaatgcta ttcgggtacc aaccatttgc aacgaaggat     1260
ccgaaatttt ttgaccggcc ggaagagttc gtcgccgatc ggttcgtcgg agaagaagga     1320
gaaaagttat tgaaatatgt attatggtct aatggaccgg aaacggaaag tccgacagtg     1380
gggaataaac agtgtgctgg caaagatttt gtagtgatgg tttcgaggtt attcgtaacg     1440
gagttttttc tccgttacga tacattcaac gtcgacgttg gtaagtcggc gttgggggct     1500
tcaattacta taacttcttt gaaaaaagct tag                                  1533
```

<210> SEQ ID NO 29
<211> LENGTH: 509
<212> TYPE: PRT
<213> ORGANISM: Solanum tuberosum

<400> SEQUENCE: 29

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
                20                  25                  30

Ser Glu Lys Pro Thr Ile Val Val Thr Gln Pro Thr Lys Leu Pro Thr
            35                  40                  45

Arg Thr Ile Pro Gly Asp Tyr Gly Leu Pro Gly Ile Gly Pro Trp Lys
        50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Leu Leu Asp
                100                 105                 110

Gly Lys Ser Phe Pro Val Leu Phe Asp Val Ser Lys Val Glu Lys Lys
            115                 120                 125

Asp Leu Phe Thr Gly Thr Tyr Met Pro Ser Thr Glu Leu Thr Gly Gly
        130                 135                 140

Tyr Arg Val Leu Ser Tyr Leu Asp Pro Ser Glu Pro Asn His Glu Lys
```

145                 150                 155                 160
Leu Lys Lys Leu Met Phe Phe Leu Leu Ser Ser Arg Arg Asp His Val
                165                 170                 175
Ile Pro Lys Phe His Glu Thr Tyr Thr Glu Phe Phe Glu Thr Leu Asp
            180                 185                 190
Lys Glu Met Ala Glu Lys Gly Thr Ala Gly Leu Asn Ser Gly Asn Asp
            195                 200                 205
Gln Ala Ala Phe Asn Phe Leu Ala Arg Ser Leu Phe Gly Val Asn Pro
210                 215                 220
Val Glu Thr Lys Leu Gly Gly Asp Gly Pro Thr Leu Ile Gly Lys Trp
225                 230                 235                 240
Val Leu Leu Gln Leu His Pro Val Leu Thr Leu Gly Leu Pro Lys Phe
                245                 250                 255
Leu Asp Asp Leu Ile Leu His Thr Phe Arg Leu Pro Pro Phe Leu Val
            260                 265                 270
Lys Lys Asp Tyr Gln Arg Leu Tyr Asp Phe Phe Tyr Thr Asn Ser Ala
            275                 280                 285
Ser Leu Phe Ala Glu Ala Glu Lys Leu Gly Ile Ser Lys Glu Glu Ala
            290                 295                 300
Cys His Asn Leu Leu Phe Ala Thr Cys Phe Asn Ser Phe Gly Gly Met
305                 310                 315                 320
Lys Ile Phe Phe Pro Asn Met Leu Lys Ser Ile Ala Lys Ala Gly Val
                325                 330                 335
Glu Val His Thr Arg Leu Ala Asn Glu Ile Arg Ser Glu Val Lys Ser
            340                 345                 350
Ala Gly Gly Lys Ile Thr Met Ser Ala Met Glu Lys Met Pro Leu Met
            355                 360                 365
Lys Ser Val Val Tyr Glu Ala Leu Arg Val Asp Pro Pro Val Ala Ser
370                 375                 380
Gln Tyr Gly Arg Ala Lys Gln Asp Leu Lys Ile Glu Ser His Asp Ala
385                 390                 395                 400
Val Phe Glu Val Lys Lys Gly Glu Met Leu Phe Gly Tyr Gln Pro Phe
                405                 410                 415
Ala Thr Lys Asp Pro Lys Ile Phe Asp Arg Pro Glu Glu Phe Val Ala
            420                 425                 430
Asp Arg Phe Val Gly Glu Gly Glu Lys Leu Leu Lys Tyr Val Leu Trp
            435                 440                 445
Ser Asn Gly Pro Glu Thr Glu Ser Pro Thr Val Gly Asn Lys Gln Cys
450                 455                 460
Ala Gly Lys Asp Phe Val Val Met Val Ser Arg Leu Phe Val Thr Glu
465                 470                 475                 480
Phe Phe Leu Arg Tyr Asp Thr Phe Asn Val Asp Val Gly Lys Ser Ala
                485                 490                 495
Leu Gly Ala Ser Ile Thr Ile Thr Ser Leu Lys Lys Ala
            500                 505

<210> SEQ ID NO 30
<211> LENGTH: 1530
<212> TYPE: DNA
<213> ORGANISM: Solanum tuberosum

<400> SEQUENCE: 30
atggcattaa cttcatcttt ttctcttcct cttccttctc ttcaccaaca atttccatca        60
aaatactcta catttcgtcc tattatcgtt tctttatccg aaaaaccaac aatcgtggta       120

```
acccaaccta caaaattacc taccaggaca atacccggcg actatgggtt gccgggtatt    180
ggtccatgga agataggct tgattacttt tacaatcagg gcaaaaacga attttcgaa     240
tcaagagtag taaatacaa atcaactata ttcagaacga acatgccacc gggaccattc    300
atttcttcta acccgaaggt tattgttttg ctcgacggca agagtttccc agtccttttc   360
gatgtttcga aagtcgaaaa aaaggacctc ttcaccggaa cttacatgcc gtcgactgaa    420
ctcaccggtg gttaccgtgt tcttcttat cttgacccat ctgaaccaaa ccatgaaaaa    480
ttgaaaaat tgatgttctt ccttctttcc tcccgtcgtg atcacgttat acccaaattc    540
catgaaactt atacagagtt ttttgaaacc ctagataagg aaatggcgga aaaaggtaca   600
gctggtttaa actccggcaa tgatcaagct gcgtttaatt tcttagctag atcgttgttc   660
ggagttaacc cagttgaaac taaactcgga ggtgatggtc cgacattgat cggaaaatgg   720
gttttgcttc agcttcatcc tgtgctcact ctcggtcttc cgaagtttct agacgactta   780
atcctccata ctttccggtt acctccgttt ctggtgaaga aagattacca gagactttac    840
gatttctttt acaccaactc cgccagttta ttcgccgaag ctgaaaaact cggcatttca    900
aaagaagaag cttgtcataa tcttctcttc gctacttgct tcaattcctt cggcgggatg   960
aagattttct tcccgaatat gctgaaatcg atagcgaaag caggggtgga ggtccatacc   1020
cgtttagcaa acgagatccg atcggaagta aaatccgctg gcgggaagat cacgatgtcg   1080
gcgatggaga aaatgccgtt aatgaaatca gtagtttatg aagctttacg agttgatcct   1140
ccggtagctt cacaatacgg aagagccaaa caggaccta agatcgaatc acacgacgcc    1200
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaaggagaa   1320
aagttattga aatatgtatt atggtctaat ggaccggaaa cggaaagtcc aacagtgggg   1380
aataaacagt gtgctggcaa agattttgta gtgatggttt cgaggttatt cgtaacggag   1440
tttttctcc gttacgatac attcaacgtc gacgttggta agtcggcgtt gggggcttca    1500
attactataa cttctttgaa aaagcttag                                      1530

<210> SEQ ID NO 31
<211> LENGTH: 509
<212> TYPE: PRT
<213> ORGANISM: Solanum tuberosum

<400> SEQUENCE: 31

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Leu Leu Asp
            100                 105                 110

Gly Lys Ser Phe Pro Val Leu Phe Asp Val Ser Lys Val Glu Lys Lys
```

```
            115                 120                 125
Asp Leu Phe Thr Gly Thr Tyr Met Pro Ser Thr Glu Leu Thr Gly Gly
        130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
                165                 170                 175

Ile Pro Lys Phe His Glu Thr Tyr Thr Glu Phe Phe Glu Thr Leu Asp
                180                 185                 190

Lys Glu Met Ala Glu Lys Gly Thr Ala Gly Leu Asn Ser Gly Asn Asp
                195                 200                 205

Gln Ala Ala Phe Asn Phe Leu Ala Arg Ser Leu Phe Gly Val Asn Pro
            210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
                260                 265                 270

Lys Lys Asp Tyr Gln Arg Leu Tyr Asp Phe Phe Tyr Thr Asn Ser Ala
            275                 280                 285

Ser Leu Phe Ala Glu Ala Glu Lys Leu Gly Ile Ser Lys Glu Glu Ala
            290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
                340                 345                 350

Ala Gly Gly Lys Ile Thr Met Ser Ala Met Glu Lys Met Pro Leu Met
            355                 360                 365

Lys Ser Val Val Tyr Glu Ala Leu Arg Val Asp Pro Pro Val Ala Ser
370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
                420                 425                 430

Asp Arg Phe Val Gly Glu Gly Glu Lys Leu Leu Lys Tyr Val Leu Trp
            435                 440                 445

Ser Asn Gly Pro Glu Thr Glu Ser Pro Thr Val Gly Asn Lys Gln Cys
            450                 455                 460

Ala Gly Lys Asp Phe Val Val Met Val Ser Arg Leu Phe Val Thr Glu
465                 470                 475                 480

Phe Phe Leu Arg Tyr Asp Thr Phe Asn Val Asp Val Asp Lys Ser Ala
                485                 490                 495

Leu Gly Ala Ser Ile Thr Ile Thr Ser Leu Lys Lys Ala
                500                 505

<210> SEQ ID NO 32
<211> LENGTH: 1530
<212> TYPE: DNA
<213> ORGANISM: Solanum tuberosum
```

<400> SEQUENCE: 32

```
atggcattaa cttcatctttt ttctcttcct cttccttctc ttcaccaaca atttccatca      60
aaatactcta catttcgtcc tattatcgtt tctttatccg aaaaaccaac aatcgtggta     120
acccaaccta caaaattacc taccaggaca atacccggcg actatgggtt gccgggtatt    180
ggtccatgga agataggct tgattacttt tacaatcagg gcaaaacga atttttcgaa      240
tcaagagtag taaaatacaa atcaactata ttcagaacga acatgccacc gggaccattc    300
atttcttcta acccgaaggt tattgttttg ctcgacggca agagtttccc agtcctttc    360
gatgtttcga agtcgaaaa aaaggacctc ttcaccggaa cttacatgcc gtcgactgaa    420
ctcaccggtg gttaccgtgt tctttcttat cttgacccat ctgaaccaaa ccatgaaaaa    480
ttgaaaaaat tgatgttctt ccttctttct tctcgtcgtg atcacgttat acccaaattc    540
catgaaactt atacagagtt ttttgaaacc ctagataagg aaatggcgga aaaaggtaca    600
gctggtttaa actccggcaa tgatcaagct gcgtttaatt tcttagctag atcgttgttc    660
ggagttaacc cagttgaaac taaactcgga actgatggtc cgacattgat cggaaaatgg    720
gttttgcttc agcttcatcc tgtactcact ctcggtcttc cgaagtttct agacgactta    780
atcctccata ctttccggtt acctccgttt ctggtgaaga aagattacca gagactttac    840
gatttctttt acaccaactc cgccagttta ttcgccgaag ctgaaaaact cggcatttca    900
aaagaagaag cttgtcataa tcttctcttc gctacttgct tcaattcctt cggcgggatg    960
aagattttct tcccgaatat gctgaaatcg atagcgaaag cagggtgga ggtccatacc  1020
cgtttagcaa acgagatccg atcggaagta aaatccgctg gcgggaagat cacgatgtcg   1080
gcgatggaga aaatgccgtt aatgaaatca gtagtttatg aagctttacg agttgatcct   1140
ccggtagctt cacaatacgg aagagccaaa caggaccta agatcgaatc acacgacgcc   1200
gttttcgagg tgaaaaaagg tgaaatgcta ttcgggtacc aaccatttgc aacgaaggat   1260
ccgaaaattt ttgaccggcc ggaagagttc gtcgccgatc ggttcgtcgg agaaggagaa   1320
aagttattga aatatgtatt atggtctaat ggaccggaaa cggaaagtcc aacagtgggg  1380
aataaacagt gtgctggcaa agattttgta gtgatggttt cgaggttatt cgtaacggag  1440
ttttttctcc gttacgatac attcaacgtc gacgttgata agtcggcgtt gggggcttca   1500
attactataa cttctttgaa aaaagcttag                                     1530
```

<210> SEQ ID NO 33
<211> LENGTH: 510
<212> TYPE: PRT
<213> ORGANISM: Solanum tuberosum

<400> SEQUENCE: 33

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
```

```
                85                  90                  95
Pro Gly Pro Phe Ile Ser Ser Asn Pro Lys Val Ile Val Leu Leu Asp
            100                 105                 110
Gly Lys Ser Phe Pro Val Leu Phe Asp Val Ser Lys Val Glu Lys Lys
            115                 120                 125
Asp Leu Phe Thr Gly Thr Tyr Met Pro Ser Thr Glu Leu Thr Gly Gly
            130                 135                 140
Tyr Arg Val Leu Ser Tyr Leu Asp Pro Ser Glu Pro Asn His Glu Lys
145                 150                 155                 160
Leu Lys Lys Leu Met Phe Phe Leu Leu Ser Arg Arg Asp His Val
                165                 170                 175
Ile Pro Lys Phe His Glu Thr Tyr Thr Glu Phe Phe Glu Thr Leu Asp
            180                 185                 190
Lys Glu Met Ala Glu Lys Gly Thr Ala Gly Leu Asn Ser Gly Asn Asp
            195                 200                 205
Gln Ala Ala Phe Asn Phe Leu Ala Arg Ser Leu Phe Gly Val Asn Pro
            210                 215                 220
Val Glu Thr Lys Leu Gly Thr Asp Gly Pro Thr Leu Ile Gly Lys Trp
225                 230                 235                 240
Val Leu Leu Gln Leu His Pro Val Leu Thr Leu Gly Leu Pro Lys Phe
                245                 250                 255
Leu Asp Asp Leu Ile Leu His Thr Phe Arg Leu Pro Pro Phe Leu Val
            260                 265                 270
Lys Lys Asp Tyr Gln Arg Leu Tyr Asp Phe Phe Tyr Thr Asn Ser Ala
            275                 280                 285
Ser Leu Phe Ala Glu Ala Glu Lys Leu Gly Ile Ser Lys Glu Glu Ala
            290                 295                 300
Cys His Asn Leu Leu Phe Ala Thr Cys Phe Asn Ser Phe Gly Gly Met
305                 310                 315                 320
Lys Ile Phe Phe Pro Asn Met Val Lys Ser Ile Ala Lys Ala Gly Val
                325                 330                 335
Glu Val His Thr Arg Leu Ala Asn Glu Ile Arg Ser Glu Val Lys Ser
            340                 345                 350
Ala Gly Gly Lys Ile Thr Met Ser Ala Met Glu Lys Met Pro Leu Met
            355                 360                 365
Lys Ser Val Val Tyr Glu Ala Leu Arg Val Asp Pro Pro Val Ala Ser
            370                 375                 380
Gln Tyr Gly Arg Ala Lys Gln Asp Leu Lys Ile Glu Ser His Asp Ala
385                 390                 395                 400
Val Phe Glu Val Lys Lys Gly Glu Met Leu Phe Gly Tyr Gln Pro Phe
                405                 410                 415
Ala Thr Lys Asp Pro Lys Phe Phe Asp Arg Pro Glu Glu Phe Val Ala
            420                 425                 430
Asp Arg Phe Val Gly Glu Gly Glu Lys Leu Leu Lys Tyr Val Leu
            435                 440                 445
Trp Ser Asn Gly Pro Glu Thr Glu Ser Pro Thr Val Gly Asn Lys Gln
            450                 455                 460
Cys Ala Gly Lys Asp Phe Val Met Val Ser Arg Leu Phe Val Thr
465                 470                 475                 480
Glu Phe Phe Leu Arg Tyr Asp Thr Phe Asn Val Asp Val Gly Lys Ser
                485                 490                 495
Ala Leu Gly Ala Ser Ile Thr Ile Thr Ser Leu Lys Lys Ala
            500                 505                 510
```

<210> SEQ ID NO 34
<211> LENGTH: 1533
<212> TYPE: DNA
<213> ORGANISM: Solanum tuberosum

<400> SEQUENCE: 34

```
atggcattaa cttcatcttt ttctcttcct cttccttctc ttcaccaaca atttccatca      60
aaatactcca catttcgtcc tattattgtt tctttatcgg aaaagccaac aatcgtggta     120
acccaaccta caaaattacc tactaggaca ataccggcg actatgggtt gccgggtatt     180
ggtccatgga agataggct tgattacttt tacaatcaag gaaagacga attttcgaa       240
tcaagagtag tgaaatacaa atcaactata ttcagaacga acatgccacc gggaccattc     300
atttcttcta acccgaaggt tattgtttg ctcgacggca agagtttccc agtccttttc     360
gatgtttcga agtcgaaaa aaaggacctc ttcaccggaa cttacatgcc gtcgactgaa     420
ctcaccggtg ttaccgtgt tctttcttat cttgacccat ctgaaccaaa ccatgaaaaa     480
ttgaaaaat tgatgttctt ccttctttct ctcgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga actgatggtc cgacattgat cggaaaatgg     720
gttttgcttc agcttcatcc tgtactcact ctcggtcttc cgaagtttct agacgactta     780
atcctccata ctttccggtt acctccgtt ctggtgaaga aagattacca gagacttttac    840
gatttctttt acaccaactc cgccagttta ttcgccgaag ctgaaaaact cggcattca      900
aaagaagaag cttgtcataa tcttctcttc gctacttgct tcaattcctt cggcgggatg     960
aagatttct tcccgaatat ggtgaaatcg atagcaaaag caggggtgga ggtccatacc    1020
cgtttagcaa acgagatccg atcggaagta aaatccgccg gcgggaagat cacgatgtcg    1080
gcgatggaga aaatgccgtt aatgaaatca gtagtttatg aagctttacg agttgatcct    1140
ccagtagctt cacaatacgg aagagccaaa caggaccta agatcgaatc acacgacgcc    1200
gttttcgagg tgaaaaagg tgaaatgcta ttcgggtacc aaccatttgc aacgaaggat    1260
ccgaaatttt ttgaccggcc ggaagagttc gtcgccgatc ggttcgtcgg agaagaagga    1320
gaaaagttat tgaaatatgt attatggtct aatggaccgg aaacgaaaag tccgacagtg    1380
gggaataaac agtgtgctgg caaagatttt gtagtgatgg tttcgaggtt attcgtaacg    1440
gagtttttc tccgttacga tacattcaac gtcgacgttg gtaagtcggc gttgggggct    1500
tcaattacta aacttcttt gaaaaaagct tag                                  1533
```

<210> SEQ ID NO 35
<211> LENGTH: 509
<212> TYPE: PRT
<213> ORGANISM: Solanum tuberosum

<400> SEQUENCE: 35

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys

-continued

```
                50                  55                  60
Asp Arg Leu Asp Tyr Phe Tyr Asn Gln Gly Lys Asp Glu Phe Glu
 65                  70                  75                  80

Ser Arg Val Val Lys Tyr Lys Ser Thr Ile Phe Arg Thr Asn Met Pro
                     85                  90                  95

Pro Gly Pro Phe Ile Ser Ser Asn Pro Lys Val Ile Val Leu Leu Asp
                    100                 105                 110

Gly Lys Ser Phe Pro Val Leu Phe Asp Val Ser Lys Val Glu Lys Lys
                115                 120                 125

Asp Leu Phe Thr Gly Thr Tyr Met Pro Ser Thr Glu Leu Thr Gly Gly
            130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
                180                 185                 190

Lys Glu Met Ala Glu Lys Gly Thr Ala Gly Leu Asn Ser Gly Asn Asp
                195                 200                 205

Gln Ala Ala Phe Asn Phe Leu Ala Arg Ser Leu Phe Gly Val Asn Pro
                210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
                260                 265                 270

Lys Lys Asp Tyr Gln Arg Leu Tyr Asp Phe Phe Tyr Thr Asn Ser Ala
                275                 280                 285

Ser Leu Phe Ala Glu Ala Glu Lys Leu Gly Ile Ser Lys Glu Glu Ala
                290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
                340                 345                 350

Ala Gly Gly Lys Ile Thr Met Ser Ala Met Glu Lys Met Pro Leu Met
                355                 360                 365

Lys Ser Val Val Tyr Glu Ala Leu Arg Val Asp Pro Leu Val Ala Ser
370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Ile Phe Asp Arg Pro Glu Glu Phe Val Ala
                420                 425                 430

Asp Arg Phe Val Gly Glu Gly Glu Lys Leu Leu Lys Tyr Val Leu Trp
                435                 440                 445

Ser Asn Gly Pro Glu Thr Glu Ser Pro Thr Val Gly Asn Lys Gln Cys
                450                 455                 460

Ala Gly Lys Asp Phe Val Val Met Val Ser Arg Leu Phe Val Thr Glu
465                 470                 475                 480
```

Phe Phe Leu Arg Tyr Asp Thr Phe Asn Val Asp Val Gly Lys Ser Ala
                485                 490                 495

Leu Gly Ala Ser Ile Thr Ile Thr Ser Leu Lys Lys Ala
            500                 505

<210> SEQ ID NO 36
<211> LENGTH: 1530
<212> TYPE: DNA
<213> ORGANISM: Solanum tuberosum

<400> SEQUENCE: 36

| | | | | | |
|---|---|---|---|---|---|
| atggcattaa | cttcatcttt | ttctcttcct | cttccttctc | ttcaccaaca | atttccatca | 60 |
| aaatactcca | catttcgtcc | tattattgtt | tctttatcgg | aaaagccaac | aatcgtggta | 120 |
| acccaaccta | caaaattacc | tactaggaca | atacccggcg | actatgggtt | gccgggtatt | 180 |
| ggtccatgga | agataggct | tgattacttt | tacaatcaag | ggaaagacga | atttttcgaa | 240 |
| tcaagagtag | tgaaatacaa | atcaactata | ttcagaacga | acatgccacc | gggaccattc | 300 |
| atttcttcta | acccgaaggt | tattgttttg | ctcgacggca | agagtttccc | agtccttttc | 360 |
| gatgtttcga | aagtcgaaaa | aaaggacctc | ttcaccggaa | cttacatgcc | gtcgactgaa | 420 |
| ctcaccggtg | gttaccgtgt | tctttcttat | cttgacccat | ctgaaccaaa | ccatgaaaaa | 480 |
| ttgaaaaaat | tgatgttctt | ccttctttct | tctcgtcgtg | atcatgttat | acccaaattc | 540 |
| catgaaactt | atacagagtt | ttttgaaacc | ctagataagg | aaatggcgga | aaaaggtaca | 600 |
| gctggtttaa | actccggcaa | tgatcaagct | gcgtttaatt | tcttagctag | atcgttgttc | 660 |
| ggagttaacc | cagttgaaac | taaactcgga | actgatggtc | caacattgat | cggaaaatgg | 720 |
| gttttgcttc | agcttcatcc | tgtactcact | ctcggtcttc | cgaagtttct | agacgactta | 780 |
| atcctccata | ctttccggtt | acctccgttt | ctggtgaaga | aagattacca | gagactttac | 840 |
| gatttctttt | acaccaactc | cgccagttta | ttcgccgaag | ctgaaaaact | cggcatttca | 900 |
| aaagaagaag | cttgtcataa | tcttctcttc | gctacttgct | tcaattcctt | cggcgggatg | 960 |
| aagattttct | ccccgaatat | gctgaaatcg | atagcgaaag | caggggtgga | ggtccatacc | 1020 |
| cgtttagcaa | acgagatccg | atcggaagta | aaatccgctg | gcgggaagat | cacgatgtcg | 1080 |
| gcgatggaga | aaatgccgtt | aatgaaatca | gtagtttatg | aagctttacg | agttgatcct | 1140 |
| ctggtagctt | cacaatacgg | aagagccaaa | caggacctta | gatcgaatc | acacgacgcc | 1200 |
| gttttcgagg | tgaaaaaagg | tgaaatgcta | ttcgggtacc | aaccatttgc | aacgaaggat | 1260 |
| ccgaaaattt | ttgaccggcc | ggaagagttc | gtcgccgatc | ggttcgtcgg | agaaggagaa | 1320 |
| aagttattga | aatatgtatt | atggtctaat | ggaccggaaa | cggaaagtcc | aacagtgggg | 1380 |
| aataaacagt | gtgctggcaa | agattttgta | gtgatggttt | cgaggttatt | cgtaacggag | 1440 |
| ttttttctcc | gttacgatac | attcaacgtc | gacgttggta | agtcggcgtt | gggggcttca | 1500 |
| attactataa | cttctttgaa | aaaagcttag | | | | 1530 |

<210> SEQ ID NO 37
<211> LENGTH: 509
<212> TYPE: PRT
<213> ORGANISM: Solanum tuberosum

<400> SEQUENCE: 37

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu

```
            20                  25                  30
Ser Glu Lys Pro Thr Ile Val Val Thr Gln Pro Thr Lys Leu Pro Thr
        35                  40                  45
Arg Thr Ile Pro Gly Asp Tyr Gly Leu Pro Gly Ile Gly Pro Trp Lys
    50                  55                  60
Asp Arg Leu Asp Tyr Phe Tyr Asn Gln Gly Lys Asp Glu Phe Phe Glu
65                  70                  75                  80
Ser Arg Val Val Lys Tyr Lys Ser Thr Ile Phe Arg Thr Asn Met Pro
                85                  90                  95
Pro Gly Pro Phe Ile Ser Ser Asn Pro Lys Val Ile Val Leu Leu Asp
            100                 105                 110
Gly Lys Ser Phe Pro Val Leu Phe Asp Val Ser Lys Val Glu Lys Lys
            115                 120                 125
Asp Leu Phe Thr Gly Thr Tyr Met Pro Ser Thr Glu Leu Thr Gly Gly
        130                 135                 140
Tyr Arg Val Leu Ser Tyr Leu Asp Pro Ser Glu Pro Asn His Glu Lys
145                 150                 155                 160
Leu Lys Lys Leu Met Phe Phe Leu Leu Ser Ser Arg Arg Asp His Val
                165                 170                 175
Ile Pro Lys Phe His Glu Thr Tyr Thr Glu Phe Glu Thr Leu Asp
            180                 185                 190
Lys Glu Met Ala Glu Lys Gly Thr Ala Gly Leu Asn Ser Gly Asn Asp
            195                 200                 205
Gln Ala Ala Phe Asn Phe Leu Ala Arg Ser Leu Phe Gly Val Asn Pro
            210                 215                 220
Val Glu Thr Lys Leu Gly Thr Asp Gly Pro Thr Leu Ile Gly Lys Trp
225                 230                 235                 240
Val Leu Leu Gln Leu His Pro Val Leu Thr Leu Gly Leu Pro Lys Phe
                245                 250                 255
Leu Asp Asp Leu Ile Leu His Thr Phe Arg Leu Pro Pro Phe Leu Val
            260                 265                 270
Lys Lys Asp Tyr Gln Arg Leu Tyr Asp Phe Phe Tyr Thr Asn Ser Ala
            275                 280                 285
Ser Leu Phe Ala Glu Ala Glu Lys Leu Gly Ile Ser Lys Glu Glu Ala
        290                 295                 300
Cys His Asn Leu Leu Phe Ala Thr Cys Phe Asn Ser Phe Gly Gly Met
305                 310                 315                 320
Lys Ile Phe Phe Pro Asn Met Leu Lys Ser Ile Ala Lys Ala Gly Val
                325                 330                 335
Glu Val His Thr Arg Leu Ala Asn Glu Ile Arg Ser Glu Val Lys Ser
            340                 345                 350
Ala Gly Gly Lys Ile Thr Met Ser Ala Met Glu Lys Met Pro Leu Met
        355                 360                 365
Lys Ser Val Val Tyr Glu Ala Leu Arg Val Asp Pro Pro Val Ala Ser
    370                 375                 380
Gln Tyr Gly Arg Ala Lys Gln Asp Leu Lys Ile Glu Ser His Asp Ala
385                 390                 395                 400
Val Phe Glu Val Lys Lys Gly Glu Met Leu Phe Gly Tyr Gln Pro Phe
                405                 410                 415
Ala Thr Lys Asp Pro Lys Ile Phe Asp Arg Pro Glu Glu Phe Val Ala
            420                 425                 430
Asp Arg Phe Val Gly Glu Gly Glu Lys Leu Leu Lys Tyr Val Leu Trp
        435                 440                 445
```

```
Ser Asn Gly Pro Glu Thr Glu Ser Pro Thr Val Gly Asn Lys Gln Cys
    450                 455                 460

Ala Gly Lys Asp Phe Val Val Met Val Ser Arg Leu Phe Val Thr Glu
465                 470                 475                 480

Phe Phe Leu Arg Tyr Asp Thr Phe Asn Val Asp Val Gly Lys Ser Ala
                485                 490                 495

Leu Gly Ala Ser Ile Thr Ile Thr Ser Leu Lys Lys Ala
            500                 505
```

<210> SEQ ID NO 38
<211> LENGTH: 1530
<212> TYPE: DNA
<213> ORGANISM: Solanum tuberosum

<400> SEQUENCE: 38

```
atggcattaa cttcatctttt ttctcttcct cttccttctc ttcaccaaca atttccatca      60
aaatactcca catttcgtcc tattattgtt tctttatcgg aaaagccaac aatcgtggta     120
acccaaccta caaaattacc tactaggaca atacccggcg actatgggtt gccgggtatt     180
ggtccatgga agataggct tgattacttt tacaatcaag gaaagacga atttttcgaa       240
tcaagagtag tgaaatacaa atcaactata ttcagaacga acatgccacc gggaccattc     300
atttcttcta acccgaaggt tattgttttg ctcgacggca agagtttccc agtccttttc     360
gatgtttcga agtcgaaaa aaaggacctc ttcaccggaa cttacatgcc gtcgactgaa      420
ctcaccggtg gttaccgtgt tctttcttat cttgacccat ctgaaccaaa ccatgaaaaa     480
ttgaaaaaat tgatgttctt ccttctttct tctcgtcgtg atcatgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga actgatggtc caacattgat cggaaaatgg     720
gttttgcttc agcttcatcc tgtactcact ctcggtcttc cgaagtttct agacgactta     780
atcctccata ctttccggtt acctccgttt ctggtgaaga agattacca gagacttta      840
gatttctttt acaccaactc cgccagttta ttcgccgaag ctgaaaaact cggcatttca     900
aaagaagaag cttgtcataa tcttctcttc gctacttgct tcaattcctt cggcgggatg     960
aagatttttct tcccgaatat gctgaaatcg atagcgaaag caggggtgga ggtccatacc    1020
cgtttagcaa acgagatccg atcggaagta aaatccgctg gcgggaagat cacgatgtcg    1080
gcgatggaga aaatgccgtt aatgaaatca gtagtttatg aagctttacg agttgatcct    1140
ccggtagctt cacaatacgg aagagccaaa caggacctta agatcgaatc acacgacgcc    1200
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaaggagaa    1320
aagttattga aatatgtatt atggtctaat ggaccggaaa cggaaagtcc aacagtgggg    1380
aataaacagt gtgctggcaa agattttgta gtgatggttt cgaggttatt cgtaacggag    1440
ttttttctcc gttacgatac attcaacgtc gacgttggta agtcggcgtt gggggcttca    1500
attactataa cttcctttgaa aaaagcttag                                    1530
```

<210> SEQ ID NO 39
<211> LENGTH: 510
<212> TYPE: PRT
<213> ORGANISM: Solanum tuberosum

<400> SEQUENCE: 39

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415
```

```
Ala Thr Lys Asp Pro Lys Ile Phe Asp Arg Pro Glu Glu Phe Val Ala
            420                 425                 430

Asp Arg Phe Val Gly Glu Gly Glu Lys Leu Leu Lys Tyr Val Leu
        435                 440                 445

Trp Ser Asn Gly Pro Glu Thr Glu Ser Pro Thr Val Gly Asn Lys Gln
    450                 455                 460

Cys Ala Ser Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
            500                 505                 510

<210> SEQ ID NO 40
<211> LENGTH: 1533
<212> TYPE: DNA
<213> ORGANISM: Solanum tuberosum

<400> SEQUENCE: 40
atggcattaa cttcatcttt ttctcttcct cttccttctc ttcaccaaca atttccatca      60
aaatactcca catttcgtcc tattattgtt tctttatcgg aaaaaccaac aatcgtggta     120
acccaaccta caaaattacc taccaggaca atacccggcg actatgggtt gccgggtatt     180
ggtccatgga agataggct tgattacttt tacaatcaag ggaaagacga attttttcgaa     240 tcaagagtag tgaaatacaa atcaactata ttcagaacga acatgccacc gggaccattc     300
atttcttcta acccgaaggt tattgttttg ctcgatggca agagtttccc agtcctttt     360 gatgtttcga agtcgaaaa aaaggacctc ttcaccggaa cttacatgcc gtcgactgaa     420
ctcaccggtg ttaccgtgt ctttcttat cttgacccat ctgaaccaaa ccatgaaaaa      480
ttgaaaaaat tgatgttctt ccttctttct ctcgacgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga actgatggtc cgacattgat cggaaaatgg     720
gttttgcttc agcttcatcc tgtactcact ctcggtcttc cgaagtttct agacgactta     780
atcctccata ctttccggtt acctccgttt ctggtgaaga aagattacca gagactttac     840
gatttctttt acaccaactc cgccagttta ttcgccgaag ctgaaaaact cggcatttca     900
aaagaagaag cttgtcataa tcttctcttc gctacttgct tcaattcctt cggcgggatg     960
aagattttct tcccgaatat gctgaaatcg atagcgaaag caggggtgga ggtccatacc    1020
cgtttagcaa acgagatccg atcggaagta aaatccgctg gcgggaagat cacgatgtcg    1080
gcgatggaga aaatgccgtt aatgaaatca gtagtttatg aagctttacg agttgatcct    1140
ccggtagctt cacaatacgg aagagccaaa caggaccta agatcgaatc acacgacgcc    1200
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaagaagga    1320 gaaagttat tgaaatatgt attatggtct aatggaccgg aaacggaaag tccgacagtg    1380
gggaataaac agtgtgctag caaagatttt gtagtgatgg tttcgaggtt attcgtaacg    1440
gagttttttc tccgttacga tacattcaac gtcgacgttg gtaagtcggc gttgggggct    1500
tcaattacta taacttcttt gaaaaaagct tag                                1533
```

<210> SEQ ID NO 41
<211> LENGTH: 510
<212> TYPE: PRT
<213> ORGANISM: Solanum tuberosum

<400> SEQUENCE: 41

```
Met Ala Leu Thr Ser Ser Phe Ser Leu Pro Leu Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Gly Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380
```

```
Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
            405                 410                 415

Ala Thr Lys Asp Pro Lys Ile Phe Asp Arg Pro Glu Glu Phe Val Ala
        420                 425                 430

Asp Arg Phe Val Gly Glu Gly Glu Lys Leu Leu Lys Tyr Val Leu
    435                 440                 445

Trp Ser Asn Gly Pro Glu Thr Glu Ser Pro Thr Val Gly Asn Lys Gln
450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
            500                 505                 510
```

<210> SEQ ID NO 42
<211> LENGTH: 1533
<212> TYPE: DNA
<213> ORGANISM: Solanum tuberosum

<400> SEQUENCE: 42

```
atggcattaa cttcatcttt ttctcttcct cttccttctc ttcaccaaca atttccatca      60
aaatactcca catttcgtcc tattattgtt tctttatcgg aaaaaccaac aatcgtggta     120
acccaaccta caaaattacc taccaggaca ataccggcg actatgggtt gccgggtatt     180
ggtccatgga agataggct tgattacttt acaatcaag ggaaagacga atttttcgaa      240
tcaagagtag tgaaatacaa atcaactata ttcagaacga acatgccacc gggaccattc     300
atttcttcta acccgaaggt tattgttttg ctcgatggca agagtttccc agtccttttc     360
gatgtttcga aagtcgaaaa aaaggacctc ttcaccggaa cttacatgcc gtcgactgaa     420
ctcaccggtg ttaccgtgt tctttcttat cttgacccat ctgaaccaaa ccatgaaaaa     480
ttgaaaaaat tgatgttctt ccttctttct ctcgacgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga actgatggtc cgacattgat cggaaaatgg     720
gttttgcttc agcttcatcc tgtactcact ctcggtcttc cgaagtttct agacgactta     780
atcctccata ctttccggtt acctccgttt ctggtgaaga agattacca gagactttac     840
gatttctttt acaccaactc cgccagttta ttcgccgaag ctgaaaaact cggcatttca     900
aaagaagaag cttgtcataa tcttctcttc gctacttgct tcaattcctt cggcgggatg     960
aagatttctct tcccgaatat gctgaaatcg tagcgaaag caggggtgga ggtccatacc    1020
cgtttagcaa acgagatccg atcggaagta aaatccgctg gcgggaagat cacgatgtcg    1080
gcgatggaga aaatgccgtt aatgaaatca gtagtttatg aagctttacg agttgatcct    1140
ccggtagctt cacaatacgg aagagccaaa caggacctta agatcgaatc acacgacgcc    1200
gttttcgagg tgaaaaaagg tgaaatgcta ttcgggtacc aaccatttgc aacgaaggat    1260
ccgaaaattt tgaccggcc ggaagagttc gtcgccgatc ggttcgtcgg agaagaagga    1320
gaaagttat tgaaatatgt attatggtct aatggaccgg aaacggaaag tccgacagtg    1380
```

```
gggaataaac agtgtgctgg caaagatttt gtagtgatgg tttcgaggtt attcgtaacg   1440
gagttttttc tccgttacga tacattcaac gtcgacgttg gtaagtcggc gttgggggct   1500
tcaattacta taacttcttt gaaaaaagct tag                                1533
```

<210> SEQ ID NO 43
<211> LENGTH: 510
<212> TYPE: PRT
<213> ORGANISM: Solanum tuberosum

<400> SEQUENCE: 43

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asn Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Ile Phe Ala Thr Cys Phe Asn Ser Phe Gly Gly Met
305                 310                 315                 320

Lys Ile Phe Phe Pro Asn Met Leu Lys Ser Ile Ala Lys Ala Gly Val
                325                 330                 335

Glu Val His Thr Arg Leu Ala Asn Glu Ile Arg Ser Glu Val Lys Ser
            340                 345                 350
```

```
Ala Gly Gly Lys Ile Thr Met Ser Ala Met Glu Lys Met Pro Leu Met
        355                 360                 365
Lys Ser Val Val Tyr Glu Ala Leu Arg Val Asp Pro Pro Val Ala Ser
    370                 375                 380
Gln Tyr Gly Arg Ala Lys Gln Asp Leu Lys Ile Glu Ser His Asp Ala
385                 390                 395                 400
Val Phe Glu Val Lys Lys Gly Glu Met Leu Phe Gly Tyr Gln Pro Phe
                405                 410                 415
Ala Thr Lys Asp Pro Lys Ile Phe Asp Arg Pro Glu Glu Phe Val Ala
            420                 425                 430
Asp Arg Phe Val Gly Glu Glu Gly Glu Lys Leu Leu Lys Tyr Val Leu
        435                 440                 445
Trp Ser Asn Gly Pro Glu Thr Glu Ser Pro Thr Val Gly Asn Lys Gln
    450                 455                 460
Cys Ala Gly Lys Asp Phe Val Val Met Val Ser Arg Leu Phe Val Thr
465                 470                 475                 480
Glu Phe Phe Leu Arg Tyr Asp Thr Phe Asn Val Asp Val Asp Lys Ser
                485                 490                 495
Ala Leu Gly Ala Ser Ile Thr Ile Thr Ser Leu Lys Lys Ala
            500                 505                 510

<210> SEQ ID NO 44
<211> LENGTH: 1533
<212> TYPE: DNA
<213> ORGANISM: Solanum tuberosum

<400> SEQUENCE: 44
atggcattaa cttcatcttt ttctcttcct cttccttctc ttcaccaaca atttccatca    60
aaatactcta catttcgtcc tattatcgtt tctttatccg aaaaaccaac aatcgtggta   120
acccaaccta caaaattacc taccaggaca tacccggcg actatgggtt gccgggtatt   180
ggtccatgga agataggct tgattacttt tacaatcagg gcaaaacga atttttcgaa    240
tcaagagtag taaatacaa atcaactata ttcagaacga acatgccacc gggaccattc   300
atttcttcta acccgaaggt tattgttttg ctcgacggca agagtttccc agtccttttc   360
gatgtttcga agtcgaaaa aaaggacctc ttcaccggaa cttacatgcc gtcgactgaa   420
ctcaccggtg ttaccgtgt tctttcttat cttgacccat ctgaaccaaa ccatgaaaaa   480
ttgaaaaaat tgatgttctt ccttctttcc tcccgtcgtg atcacgttat acccaaattc   540
catgaaactt atacagagtt ttttgaaacc ctagataagg aaatggcgga aaaaggtaca   600
gctggtttaa actccggcaa tgatcaagct gcgtttaatt tcttagctag atcgttgttc   660
ggagttaacc cagttgaaac taaactcgga ggtgatggtc cgacattgat cggaaaatgg   720
gttttgcttc agcttcatcc tgtgctcact ctcggtcttc gaagtttct agacgactta   780
atcctccata ctttccggtt acctccgttt ctggtgaaga agattacca gagactttac   840
gatttctttt acaccaactc cgccagttta ttcgccgaag ctgaaaaact cggcatttca   900
aaagaagaag cttgtcataa tcttatcttc gctacttgct tcaattcctt cggcgggatg   960
aagattttct tcccgaatat gctgaaatcg atagcgaaag caggggtgga ggtccatacc  1020
cgtttagcaa acgagatccg atcggaagta aaatccgctg gcgggaagat cacgatgtcg  1080
gcgatggaga aaatgccgtt aatgaaatca gtagtttatg aagctttacg agttgatcct  1140
ccggtagctt cacaatacgg aagagccaaa caggaccttaa gatcgaatc acacgacgcc  1200
```

-continued

```
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaagaagga    1320
gaaaagttat tgaaatatgt attatggtct aatggaccgg aaacggaaag tccgacagtg    1380
gggaataaac agtgtgctgg caaagatttt gtagtgatgg tttcgaggtt attcgtaacg    1440
gagttttttc tccgttacga tacattcaac gtcgacgttg ataagtcggc gttgggggct    1500
tcaattacta taacttcttt gaaaaaagct tag                                 1533
```

```
<210> SEQ ID NO 45
<211> LENGTH: 510
<212> TYPE: PRT
<213> ORGANISM: Solanum tuberosum

<400> SEQUENCE: 45

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Thr
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Gly Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320
```

Lys Ile Phe Phe Pro Asn Met Leu Lys Ser Ile Ala Lys Ala Gly Val
              325                 330                 335

Glu Val His Thr Arg Leu Ala Asn Glu Ile Arg Ser Glu Val Lys Ser
              340                 345                 350

Ala Gly Gly Lys Ile Thr Met Ser Ala Met Glu Lys Met Pro Leu Met
              355                 360                 365

Lys Ser Val Val Tyr Glu Ala Leu Arg Val Asp Pro Pro Val Ala Ser
          370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
              405                 410                 415

Ala Thr Lys Asp Pro Lys Ile Phe Asp Arg Pro Glu Glu Phe Val Ala
              420                 425                 430

Asp Arg Phe Val Gly Glu Gly Glu Lys Leu Leu Lys Tyr Val Leu
              435                 440                 445

Trp Ser Asn Gly Pro Glu Thr Glu Ser Pro Thr Val Gly Asn Lys Gln
          450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
              485                 490                 495

Ala Leu Gly Ala Ser Ile Thr Ile Thr Ser Leu Lys Lys Ala
          500                 505                 510

<210> SEQ ID NO 46
<211> LENGTH: 1533
<212> TYPE: DNA
<213> ORGANISM: Solanum tuberosum

<400> SEQUENCE: 46

```
atggcattaa cttcatcttt ttctcttcct cttccttctc ttcaccaaca atttccatca     60
aaatactcta catttcgtcc tattatcgtt tctttatccg aaaaaccaac aatcgtggta    120
acccaaccta caaaattacc taccaggaca ataccggcg actatgggtt gccgggtatt    180
ggtccatgga agataggct tgattacttt acaatcaag ggaaagacga attttcgaa     240 tcaagagtag tgaaatacaa atcaactata ttcagaacga acatgccacc gggaccattc    300
atttcttcta acccgaaggt cattgttttg ctcgacggca agagtttccc agtcctttc    360 gatgtttcga aagtcgaaaa aaaggacctc ttcaccggaa cttatatgcc gtcgactgaa    420
ctcaccggtg gttaccgtgt tcttcttat cttgacccat ctgaaccaaa ccatgaaaaa    480
ttgaaaaaat tgatgttctt ccttctttct cccgtcgtg atcacgttat acccaaattc    540
catgaaactt atacagagtt ttttgaaacc ctagataagg aaatggcgga aaaaggtaca    600
gctggtttaa actccggcaa tgatcaagct gcgtttaatt tcttagctag atcgttgttc    660
ggagttaacc cagttgaaac taaactcgga ggtgatggtc cgacattgat cggaaaatgg    720
gttttgcttc agcttcatcc tgtgctcact ctcggtcttc cgaagtttct agacgactta    780
atcctccata ctttccggtt acctccgttt ctggtgaaga aagattacca gagacttac    840 gatttctttt acaccaactc cgccagttta ttcgccgaag ctgaaaaact cggcatttca    900
aaagaagaag cttgtcataa tcttctcttc gctacttgct tcaattcctt cggcgggatg    960
aagattttct tcccgaatat gctgaaatcg atagcgaaag caggggtgga ggtccatacc   1020
```

```
cgtttagcaa acgagatccg atcggaagta aaatccgccg gcgggaagat cacgatgtcg    1080
gctatggaga aaatgccgtt aatgaaatca gtagtatatg aagctttgcg agttgatcct    1140
ccggtagctt cacaatacgg aagagccaaa caggacctta agatcgaatc acacgacgcc    1200
gttttcgagg tgaaaaaagg tgaaatgcta ttcgggtacc aaccatttgc aacgaaggat    1260
ccgaaaattt ttgaccggcc ggaagagttc gtcgccgatc ggttcgtcgg agaagaagga    1320
gaaaagttat tgaaatatgt attatggtct aatggaccgg aaacgaaaag tccgacagtg    1380
gggaataaac agtgtgctgg caaagatttt gtagtgatgg tttcgaggtt attcgtaacg    1440
gagttttttc tccgttacga tacattcaac gtcgacgttg gtaagtcggc gttgggggct    1500
tcaattacta aacttctttt gaaaaaagct tag                                 1533
```

<210> SEQ ID NO 47
<211> LENGTH: 510
<212> TYPE: PRT
<213> ORGANISM: Solanum tuberosum

<400> SEQUENCE: 47

```
Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
            20                  25                  30

Ser Glu Lys Pro Thr Ile Val Val Thr Gln Pro Thr Lys Leu Pro Ile
        35                  40                  45

Arg Thr Ile Pro Gly Asp Tyr Gly Leu Pro Gly Ile Gly Pro Trp Lys
    50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Gly Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285
```

```
Ser Leu Phe Ala Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Val Lys Ser Ile Ala Lys Ala Gly Val
                325                 330                 335

Glu Val His Thr Arg Leu Ala Asn Glu Ile Arg Ser Glu Val Lys Ser
                340                 345                 350

Ala Gly Gly Lys Ile Thr Met Ser Ala Met Glu Lys Met Pro Leu Met
                355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Phe Phe Asp Arg Pro Glu Glu Phe Val Ala
                420                 425                 430

Asp Arg Phe Val Gly Glu Glu Gly Glu Lys Leu Leu Lys Tyr Val Leu
                435                 440                 445

Trp Ser Asn Gly Pro Glu Thr Glu Ser Pro Thr Val Gly Asn Lys Gln
    450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
                500                 505                 510

<210> SEQ ID NO 48
<211> LENGTH: 1533
<212> TYPE: DNA
<213> ORGANISM: Solanum tuberosum

<400> SEQUENCE: 48
atggcattaa cttcatcttt ttctcttcct cttccttctc ttcaccaaca atttccatca      60
aaatactcca catttcgtcc tattattgtt tctttatccg aaaaaccaac aatcgtggta     120
acccaaccta caaaattacc tatcaggaca atacccggcg actatgggtt gccgggtatt     180
ggtccatgga agataggct tgattacttt tacaatcaag ggaaagacga atttttcgaa      240
tcaagagtag tgaaatacaa atcaactata ttcagaacga acatgccacc gggaccattc     300
atttcttcta acccgaaggt tattgttttg ctcgacggca agagtttccc agtccttttc     360
gatgtttcga agtcgaaaa aaaggacctc ttcaccggaa cttacatgcc gtcgactgaa     420
ctcaccggtg ttaccgtgt ctttcttat cttgacccat ctgaaccaaa ccatgaaaaa       480
ttgaaaaaat tgatgttctt ccttctttcc tcccgtcgtg atcacgttat acccaaattc     540
catgaaactt atacagagtt ttttgaaacc ctagataagg aaatggcgga aaaaggtaca     600
gctggtttaa actccggcaa tgatcaagct gcgtttaatt tcttagctag atcgttgttc     660
ggagttaacc cagttgaaac taaactcgga actgatggtc cgacattgat cggaaaatgg     720
gttttgcttc agcttcatcc tgtactcact ctcggtcttc cgaagtttct agacgactta     780
atcctccata ctttccggtt acctccgttt ctggtgaaga aagattacca gagactttac     840
```

| | | |
|---|---|---|
| gatttcttt acaccaactc cgccagttta ttcgccgaag ctgaaaaact cggcatttct | 900 | |
| aaagaagaag cttgtcataa tcttctcttc gctacttgct tcaattcctt cggcgggatg | 960 | |
| aagattttct tcccgaatat ggtgaaatcg atagcaaaag caggggtgga ggtccatacc | 1020 | |
| cgtttagcaa acgagatccg atcggaagta aaatccgccg gcgggaagat cacgatgtcg | 1080 | |
| gcgatggaga aaatgccgtt aatgaaatca gtagtttatg aagctttacg agttgatcct | 1140 | |
| ccagtagctt cacaatacgg aagagccaaa caggaccta agatcgaatc acacgacgcc | 1200 | |
| gttttcgagg tgaaaaaagg tgaaatgcta ttcgggtacc aaccatttgc aacgaaggat | 1260 | |
| ccgaaatttt ttgaccggcc ggaagagttc gtcgccgatc ggttcgtcgg agaagaagga | 1320 | |
| gaaaagttat tgaaatatgt attatggtct aatggaccgg aaacggaaag tccgacagtg | 1380 | |
| gggaataaac agtgtgctgg caaagatttt gtagtgatgg tttcgaggtt attcgtaacg | 1440 | |
| gagttttttc tccgttacga tacattcaac gtcgacgttg gtaagtcggc gttgggggct | 1500 | |
| tcaattacta aacttctttt gaaaaaagct tag | 1533 | |

<210> SEQ ID NO 49
<211> LENGTH: 510
<212> TYPE: PRT
<213> ORGANISM: Solanum tuberosum

<400> SEQUENCE: 49

Met Ala Leu Thr Ser Ser Phe Ser Leu Pro Leu Pro Ser Leu His Gln
1               5                   10                  15

Gln Phe Pro Ser Lys Tyr Ser Thr Phe Arg Pro Ile Ile Val Ser Leu
                20                  25                  30

Ser Glu Lys Pro Thr Ile Val Val Thr Gln Pro Thr Lys Leu Pro Ile
            35                  40                  45

Arg Thr Ile Pro Gly Asp Tyr Gly Leu Pro Gly Ile Gly Pro Trp Lys
        50                  55                  60

Asp Arg Leu Asp Tyr Phe Tyr Asn Gln Gly Lys Asp Glu Phe Phe Glu
65                  70                  75                  80

Ser Arg Val Val Lys Tyr Lys Ser Thr Ile Phe Arg Thr Asn Met Pro
                85                  90                  95

Pro Gly Pro Phe Ile Ser Ser Asn Pro Lys Val Ile Val Leu Leu Asp
            100                 105                 110

Asp Lys Ser Phe Pro Val Leu Phe Asp Val Ser Lys Val Glu Lys Lys
        115                 120                 125

Asp Leu Phe Thr Gly Thr Tyr Met Pro Ser Thr Glu Leu Thr Gly Gly
    130                 135                 140

Tyr Arg Val Leu Ser Tyr Leu Asp Pro Ser Glu Pro Asn His Glu Lys
145                 150                 155                 160

Leu Lys Lys Leu Met Phe Phe Leu Leu Ser Arg Arg Asp His Val
                165                 170                 175

Ile Pro Lys Phe His Glu Thr Tyr Thr Glu Phe Phe Glu Thr Leu Asp
            180                 185                 190

Lys Glu Met Ala Glu Lys Gly Thr Ala Gly Leu Asn Ser Gly Asn Asp
        195                 200                 205

Gln Ala Ala Phe Asn Phe Leu Ala Arg Ser Leu Phe Gly Val Asn Pro
    210                 215                 220

Val Glu Thr Lys Leu Gly Thr Asp Gly Pro Thr Leu Ile Gly Lys Trp
225                 230                 235                 240

Val Leu Leu Gln Leu His Pro Val Leu Thr Leu Gly Leu Pro Lys Phe
                245                 250                 255

Leu Asp Asp Leu Ile Leu His Thr Phe Arg Leu Pro Pro Phe Leu Val
            260                 265                 270

Lys Lys Asp Tyr Gln Arg Leu Tyr Asp Phe Phe Tyr Thr Asn Ser Ala
        275                 280                 285

Ser Leu Phe Ala Glu Ala Glu Lys Leu Gly Ile Ser Lys Glu Glu Ala
    290                 295                 300

Cys His Asn Leu Leu Phe Ala Thr Cys Phe Asn Ser Phe Gly Gly Met
305                 310                 315                 320

Lys Ile Phe Phe Pro Asn Met Val Lys Ser Ile Ala Lys Ala Gly Val
                325                 330                 335

Glu Val His Thr Arg Leu Ala Asn Glu Ile Arg Ser Glu Val Lys Ser
            340                 345                 350

Ala Gly Gly Lys Ile Thr Met Ser Ala Met Glu Lys Met Pro Leu Met
        355                 360                 365

Lys Ser Val Val Tyr Glu Ala Leu Arg Val Asp Pro Pro Val Ala Ser
    370                 375                 380

Gln Tyr Gly Arg Ala Lys Gln Asp Leu Lys Ile Glu Ser His Asp Ala
385                 390                 395                 400

Val Phe Glu Val Lys Lys Gly Glu Met Leu Phe Gly Tyr Gln Pro Phe
                405                 410                 415

Ala Thr Lys Asp Pro Lys Phe Phe Asp Arg Pro Glu Glu Phe Val Ala
            420                 425                 430

Asp Arg Phe Val Gly Glu Gly Glu Lys Leu Leu Lys Tyr Val Leu
        435                 440                 445

Trp Ser Asn Gly Pro Glu Thr Glu Ser Pro Thr Val Gly Asn Lys Gln
    450                 455                 460

Cys Ala Gly Lys Asp Phe Val Val Met Val Ser Arg Leu Phe Val Thr
465                 470                 475                 480

Glu Phe Phe Leu Arg Tyr Asp Thr Phe Asn Val Asp Val Gly Lys Ser
                485                 490                 495

Ala Leu Gly Ala Ser Ile Thr Ile Thr Ser Leu Lys Lys Ala
            500                 505                 510

<210> SEQ ID NO 50
<211> LENGTH: 1533
<212> TYPE: DNA
<213> ORGANISM: Solanum tuberosum

<400> SEQUENCE: 50

```
atggcattaa cttcatcttt ttctcttcct cttccttctc ttcaccaaca atttccatca        60
aaatactcca catttcgtcc tattattgtt tctttatccg aaaaaccaac aatcgtggta       120
acccaaccta caaattacc tatcaggaca atacccggcg actatgggtt gccgggtatt       180
ggtccatgga agataggct tgattacttt tacaatcaag ggaagacga atttttcgaa        240 tcaagagtag tgaaatacaa atcaactata ttcagaacga acatgccacc gggaccattc       300
atttcttcta acccgaaggt tattgttttg ctcgacgaca agagtttccc agtcctttc        360 gatgtttcga agtcgaaaa aaaggaccte ttcaccggaa cttacatgcc gtcgactgaa       420
ctcaccggtg ttaccgtgt ctttcttat cttgacccat ctgaaccaaa ccatgaaaaa        480
ttgaaaaaat tgatgttctt ccttctttcc tcccgtcgtg atcacgttat acccaaattc       540
catgaaactt atacagagtt ttttgaaacc ctagataagg aaatggcgga aaaaggtaca       600
gctggtttaa actccggcaa tgatcaagct gcgtttaatt tcttagctag atcgttgttc       660
```

```
ggagttaacc cagttgaaac taaactcgga actgatggtc cgacattgat cggaaaatgg    720
gttttgcttc agcttcatcc tgtactcact ctcggtcttc cgaagtttct agacgactta    780
atcctccata ctttccggtt acctccgttt ctggtgaaga aagattacca gagactttac    840
gatttctttt acaccaactc cgccagttta ttcgccgaag ctgaaaaact cggcatttct    900
aaagaagaag cttgtcataa tcttctcttc gctacttgct tcaattcctt cggcgggatg    960 aagatttttct tcccgaatat ggtgaaatcg atagcaaaag caggggtgga ggtccatacc   1020
cgtttagcaa acgagatccg atcggaagta aaatccgccg gcgggaagat cacgatgtcg   1080
gcgatggaga aaatgccgtt aatgaaatca gtagtttatg aagctttacg agttgatcct   1140
ccagtagctt cacaatacgg aagagccaaa caggacctta agatcgaatc acacgacgcc   1200
gttttcgagg tgaaaaaagg tgaaatgcta ttcgggtacc aaccatttgc aacgaaggat   1260
ccgaaatttt ttgaccggcc ggaagagttc gtcgccgatc ggttcgtcgg agaagaagga   1320
gaaaagttat tgaaatatgt attatggtct aatggaccgg aaacggaaag tccgacagtg   1380
gggaataaac agtgtgctgg caaagatttt gtagtgatgg tttcgaggtt attcgtaacg   1440
gagttttttc tccgttacga tacattcaac gtcgacgttg gtaagtcggc gttgggggct   1500
tcaattacta taacttcttt gaaaaaagct tag                                1533

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cacctttgta tcactaacat tacccatcc                                       29

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gcatgtgttg cttgttctta taatttcag                                       29

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaaaggcata gaaggtaga                                                  19

<210> SEQ ID NO 54
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 54
taaccgacca agtagtaaa                                                  19
```